United States Patent
Saab et al.

(10) Patent No.: US 9,782,572 B2
(45) Date of Patent: Oct. 10, 2017

(54) APPARATUS AND METHODS FOR TREATING BONE STRUCTURES, TISSUES AND DUCTS USING A NARROW GAUGE CANNULA SYSTEM

(71) Applicant: Vention Medical Advanced Components, Inc., Salem, NH (US)

(72) Inventors: Mark A. Saab, Lowell, MA (US); Michael D. Barbere, Dunstable, MA (US)

(73) Assignee: Nordson Corporation, Westlake, OH (US)

( * ) Notice: Subject to any disclaimer, the term of this patent is extended or adjusted under 35 U.S.C. 154(b) by 1174 days.

(21) Appl. No.: 13/800,197

(22) Filed: Mar. 13, 2013

(65) Prior Publication Data
US 2013/0197563 A1    Aug. 1, 2013

Related U.S. Application Data

(60) Continuation-in-part of application No. 12/322,883, filed on Feb. 9, 2009, now Pat. No. 8,454,646, which
(Continued)

(51) Int. Cl.
| | |
|---|---|
| *A61M 29/00* | (2006.01) |
| *A61M 29/02* | (2006.01) |
| *A61F 2/44* | (2006.01) |
| *A61F 2/46* | (2006.01) |
| *A61B 17/88* | (2006.01) |

(Continued)

(52) U.S. Cl.
CPC ......... *A61M 29/02* (2013.01); *A61B 17/8855* (2013.01); *A61B 17/8805* (2013.01); *A61B 2017/00539* (2013.01); *A61B 2017/00544* (2013.01); *A61B 2017/00867* (2013.01); *A61F 2/44* (2013.01); *A61F 2/4601* (2013.01); *A61F 2/4611* (2013.01); *A61F 2002/30092* (2013.01); *A61F 2002/4677* (2013.01);
(Continued)

(58) Field of Classification Search
CPC ... A61B 17/8805; A61B 17/8855; A61F 2/44; A61M 25/10; A61M 25/1025; A61M 25/1034; A61M 25/1038
See application file for complete search history.

(56) References Cited

U.S. PATENT DOCUMENTS

| | | | |
|---|---|---|---|
| 624,811 A | 5/1899 | Hunt et al. | |
| 3,779,239 A | 12/1973 | Fischer et al. | |

(Continued)

OTHER PUBLICATIONS

International Search Report from PCT application, PCT/US2012/00162 dated Jul. 27, 2012.

*Primary Examiner* — Gregory Anderson
(74) *Attorney, Agent, or Firm* — Baker & Hostetler LLP

(57) ABSTRACT

Systems, apparatus and methods are disclosed for medical treatment comprising bone access and dilatation and/or cavity creation or enlargement using a narrow gauge, preferably 11-gauge or smaller, cannula wherein a catheter/expandable element assembly meeting medical protocols for such procedures is designed, adapted and fabricated to fit through the interior of the associated 11-gauge or smaller cannula, and further including apparatus and methods for wrapping and/or folding the expandable element either before or after a procedure to reduce its profile to fit through the cannula.

64 Claims, 56 Drawing Sheets

Related U.S. Application Data is a division of application No. 10/674,031, filed on Sep. 29, 2003, now Pat. No. 7,488,337.

(60) Provisional application No. 60/414,766, filed on Sep. 30, 2002.

(51) Int. Cl.
*A61B 17/00* (2006.01)
*A61F 2/30* (2006.01)

(52) U.S. Cl.
CPC .. *A61F 2210/0014* (2013.01); *A61M 2210/02* (2013.01); *A61M 2210/1003* (2013.01)

(56) References Cited

U.S. PATENT DOCUMENTS

| | | | |
|---|---|---|---|
| 4,261,339 A * | 4/1981 | Hanson | A61M 1/1072 600/18 |
| 4,406,656 A | 9/1983 | Hattler et al. | |
| 4,846,174 A | 7/1989 | Willard et al. | |
| 4,969,888 A | 11/1990 | Scholten et al. | |
| 5,108,404 A | 4/1992 | Scholten et al. | |
| 5,163,989 A | 11/1992 | Campbell et al. | |
| 5,290,306 A | 3/1994 | Trotta et al. | |
| 5,295,994 A | 3/1994 | Bonutti | |
| 5,331,975 A | 7/1994 | Bonutti | |
| 5,342,301 A | 8/1994 | Saab | |
| 5,352,199 A | 10/1994 | Tower | |
| 5,361,752 A | 11/1994 | Moll et al. | |
| 5,411,477 A | 5/1995 | Saab | |
| 5,492,532 A | 2/1996 | Ryan et al. | |
| 5,499,973 A | 3/1996 | Saab | |
| 5,569,195 A | 10/1996 | Saab | |
| 5,624,392 A | 4/1997 | Saab | |
| 5,741,282 A | 4/1998 | Anspach, III et al. | |
| 5,766,151 A | 6/1998 | Valley et al. | |
| 5,772,681 A | 6/1998 | Leoni | |
| 5,795,325 A | 8/1998 | Valley et al. | |
| 5,797,878 A * | 8/1998 | Bleam | A61M 25/10 604/196 |
| 5,827,289 A | 10/1998 | Reiley et al. | |
| 5,972,015 A | 10/1999 | Scribner et al. | |
| 6,013,085 A | 1/2000 | Howard | |
| 6,048,346 A | 4/2000 | Reiley et al. | |
| 6,066,154 A | 5/2000 | Reiley et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,383,190 B1 | 5/2002 | Preissman | |
| 6,582,446 B1 | 6/2003 | Marchosky | |
| 6,607,544 B1 | 8/2003 | Boucher et al. | |
| 6,613,054 B2 | 9/2003 | Scribner et al. | |
| 6,719,773 B1 | 4/2004 | Boucher et al. | |
| 6,780,183 B2 | 8/2004 | Jimenez, Jr. et al. | |
| 6,979,341 B2 | 12/2005 | Scribner et al. | |
| 7,261,720 B2 | 8/2007 | Stevens et al. | |
| 7,488,337 B2 | 2/2009 | Saab et al. | |
| 7,722,624 B2 | 5/2010 | Boucher et al. | |
| 8,177,744 B2 | 5/2012 | Saab et al. | |
| 8,216,182 B2 | 7/2012 | Saab et al. | |
| 8,394,056 B2 | 3/2013 | Saab et al. | |
| 8,454,646 B2 | 6/2013 | Saab et al. | |
| 8,454,647 B2 | 6/2013 | Saab et al. | |
| 2001/0007938 A1 | 7/2001 | Long | |
| 2002/0156482 A1 | 10/2002 | Scribner et al. | |
| 2002/0161373 A1 | 10/2002 | Osorio et al. | |
| 2002/0183778 A1 | 12/2002 | Reiley et al. | |
| 2003/0045869 A1 * | 3/2003 | Ryan | A61B 18/04 606/27 |
| 2003/0050702 A1 | 3/2003 | Berger | |
| 2008/0140084 A1 | 6/2008 | Osorio et al. | |
| 2010/0298832 A1 | 11/2010 | Lau et al. | |
| 2013/0345765 A1 | 12/2013 | Brockman et al. | |

* cited by examiner

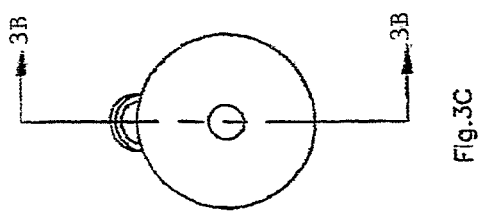
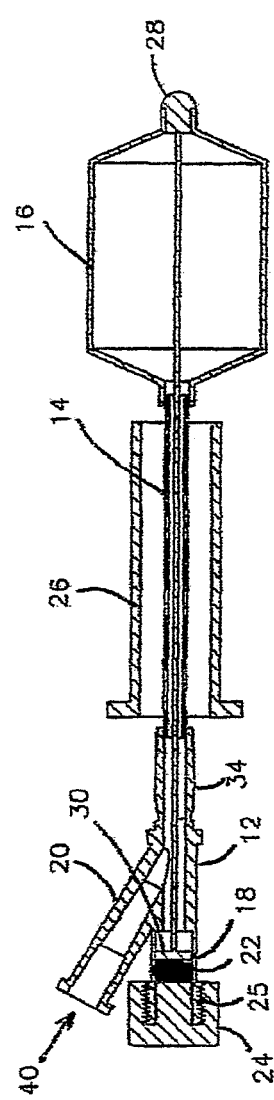
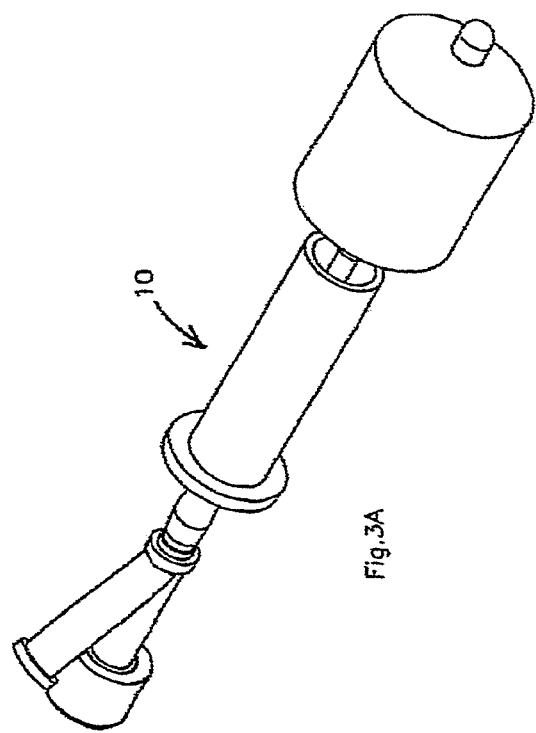

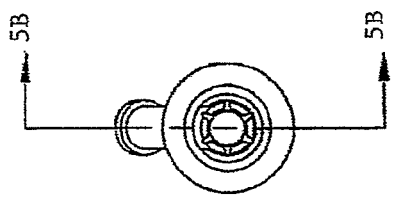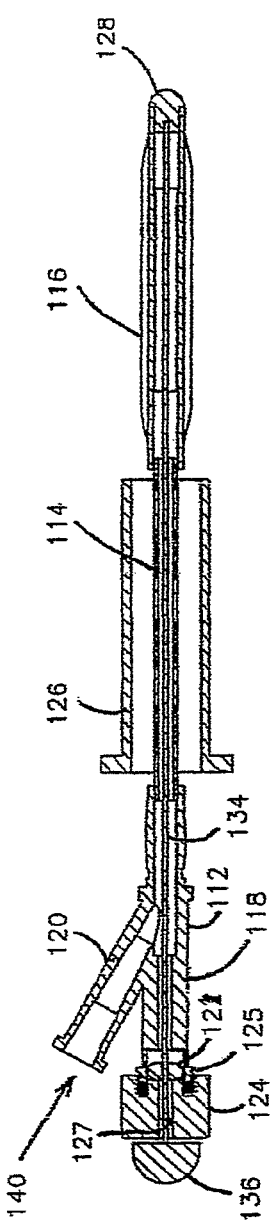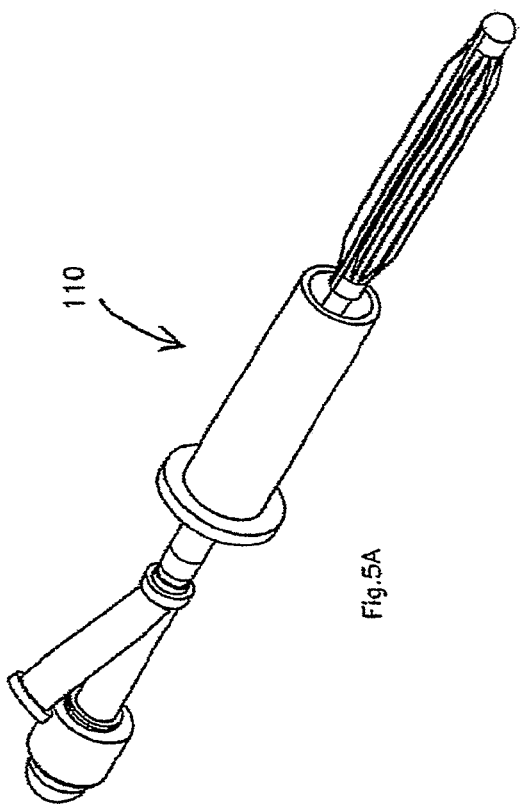

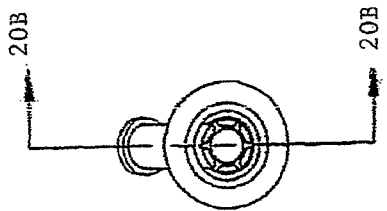
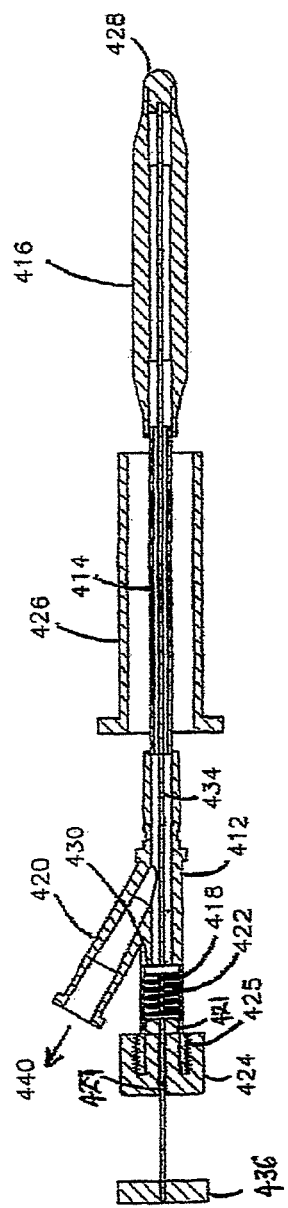
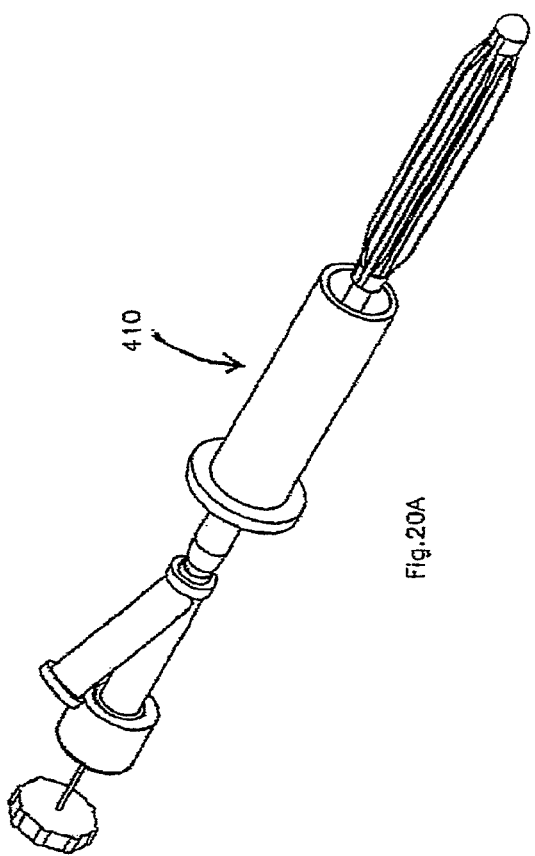

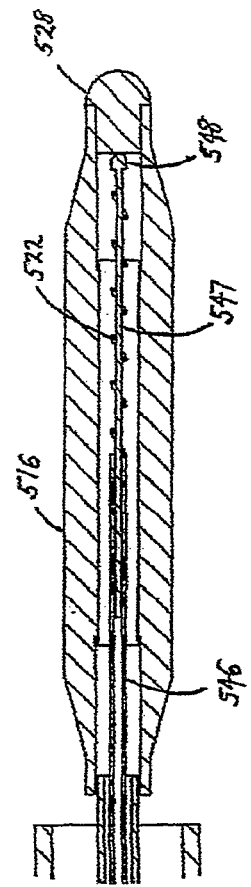
Fig.22C
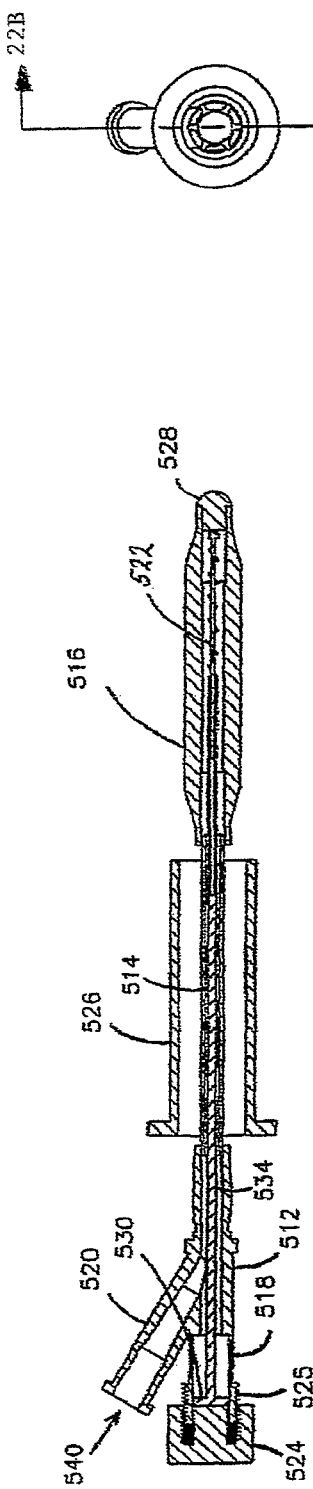
Fig.22B
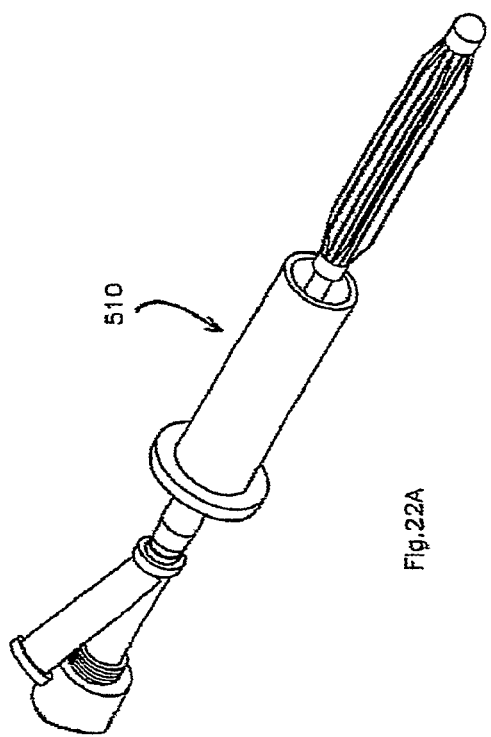
Fig.22D
Fig.22A

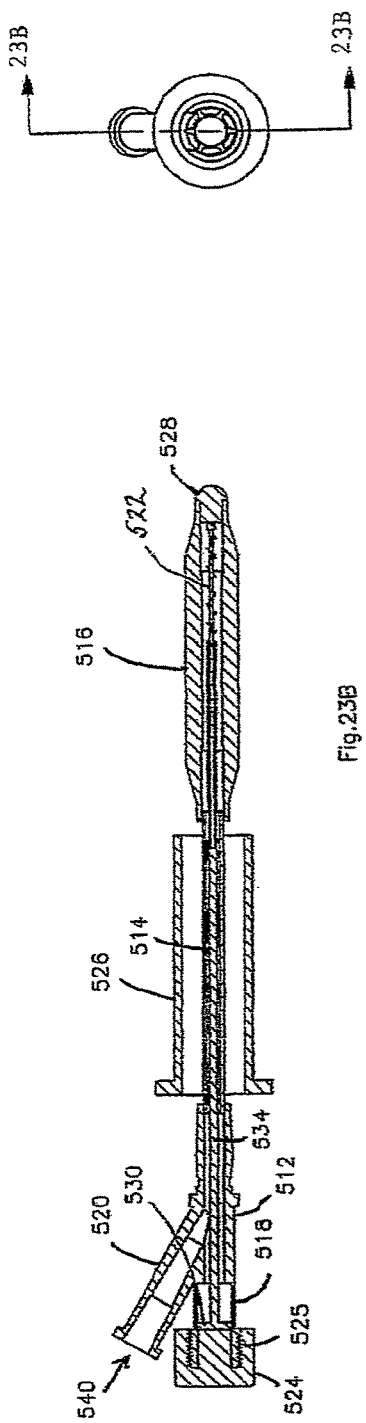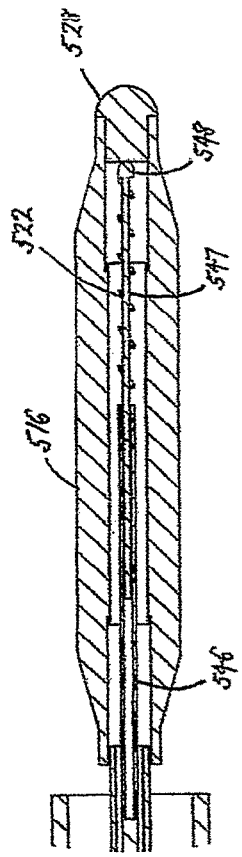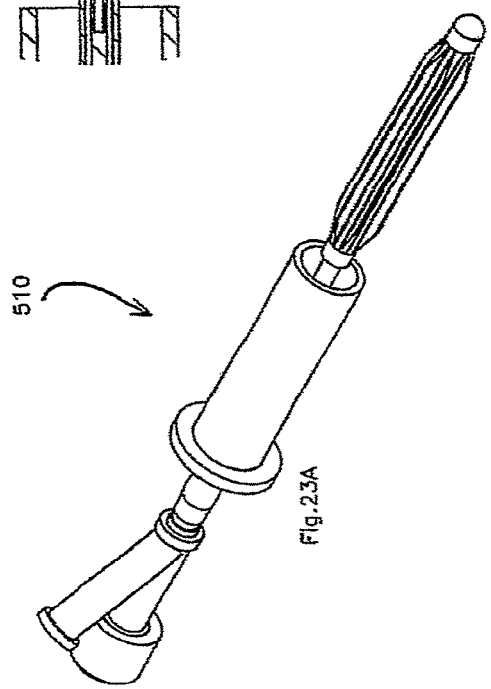

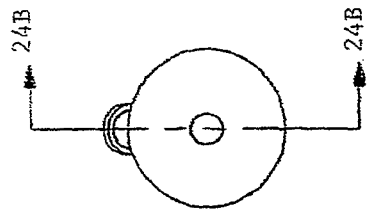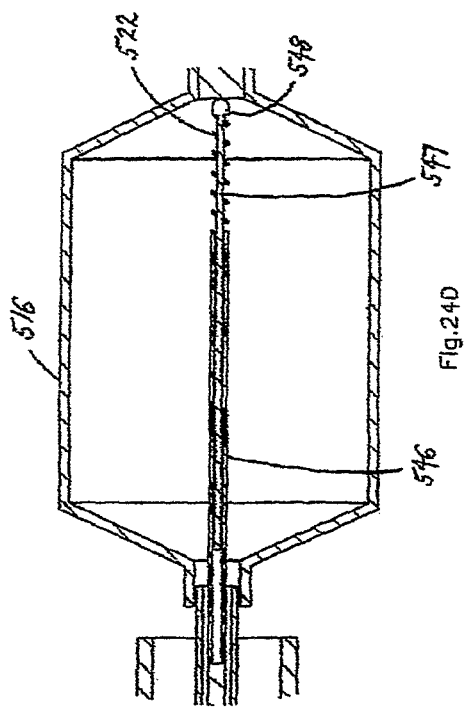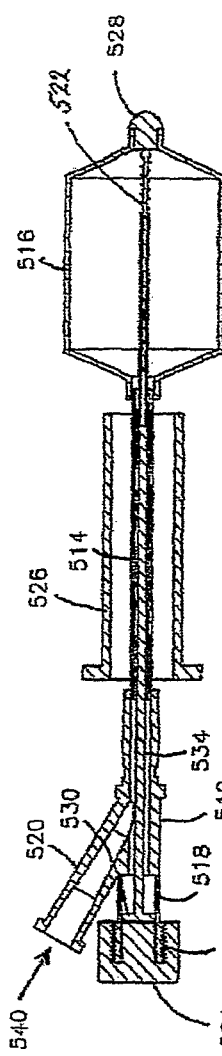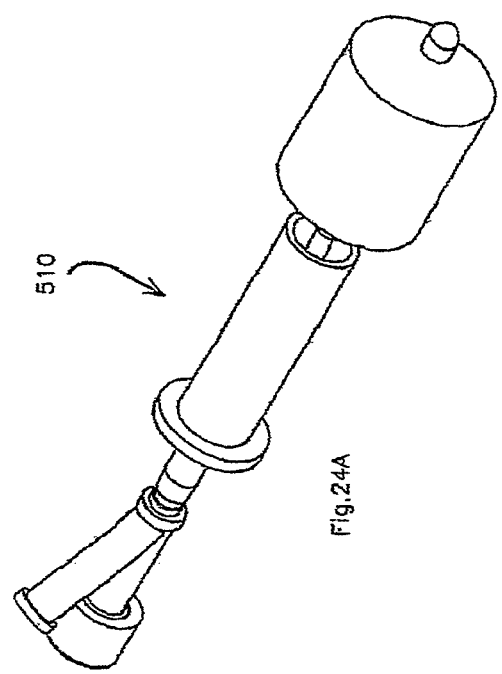

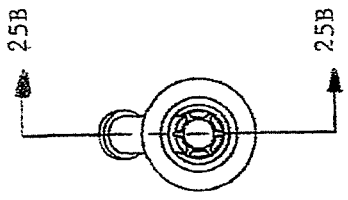
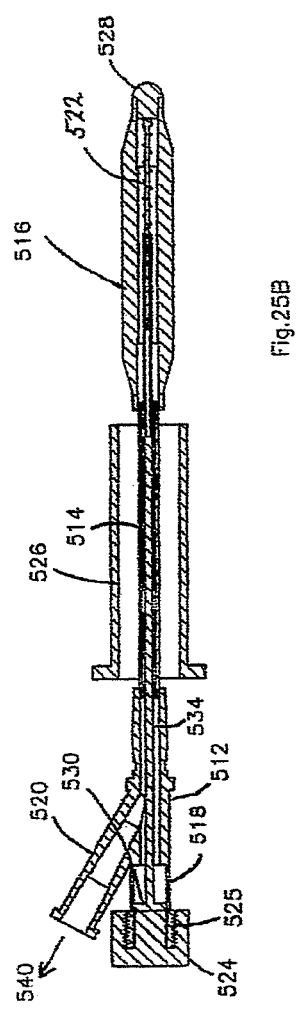
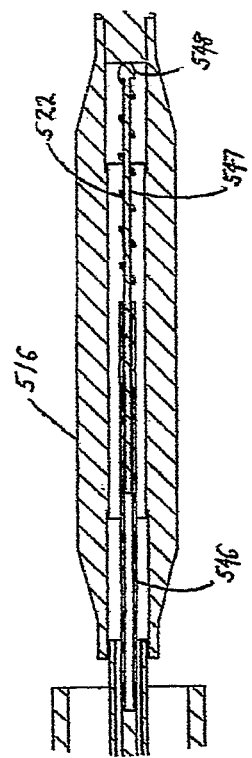
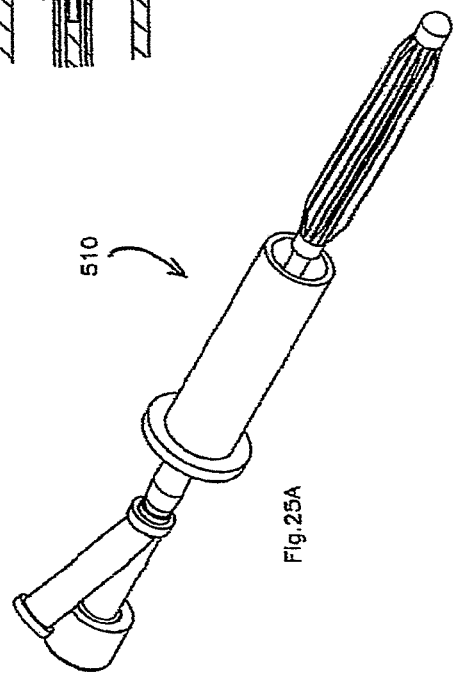

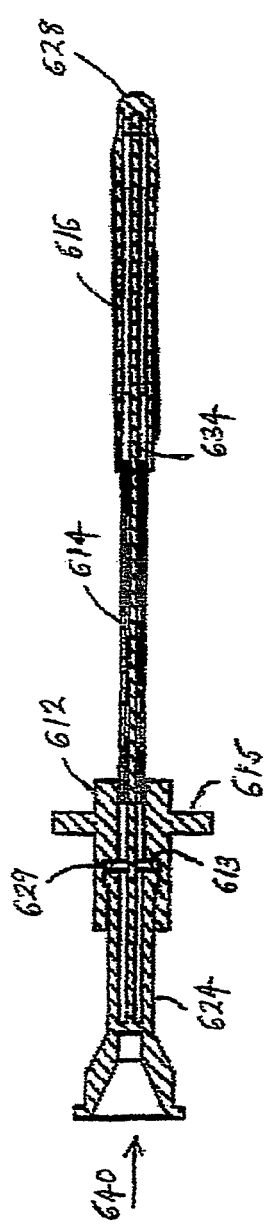
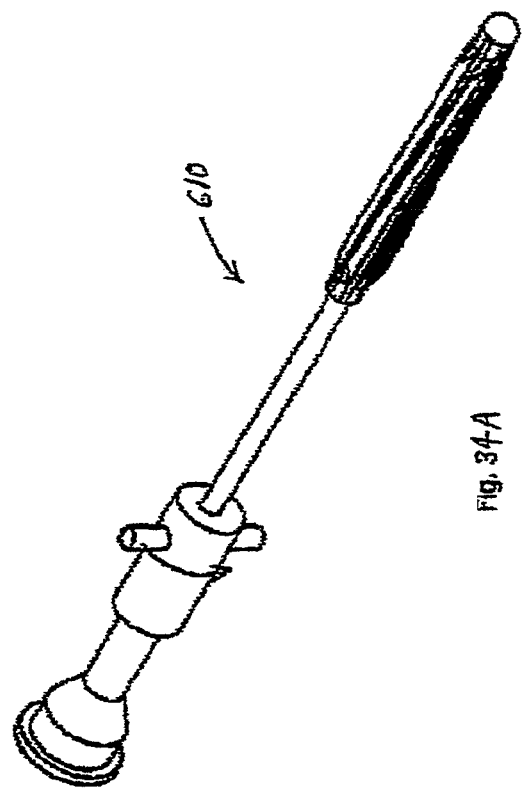
Fig. 34B
Fig. 34A

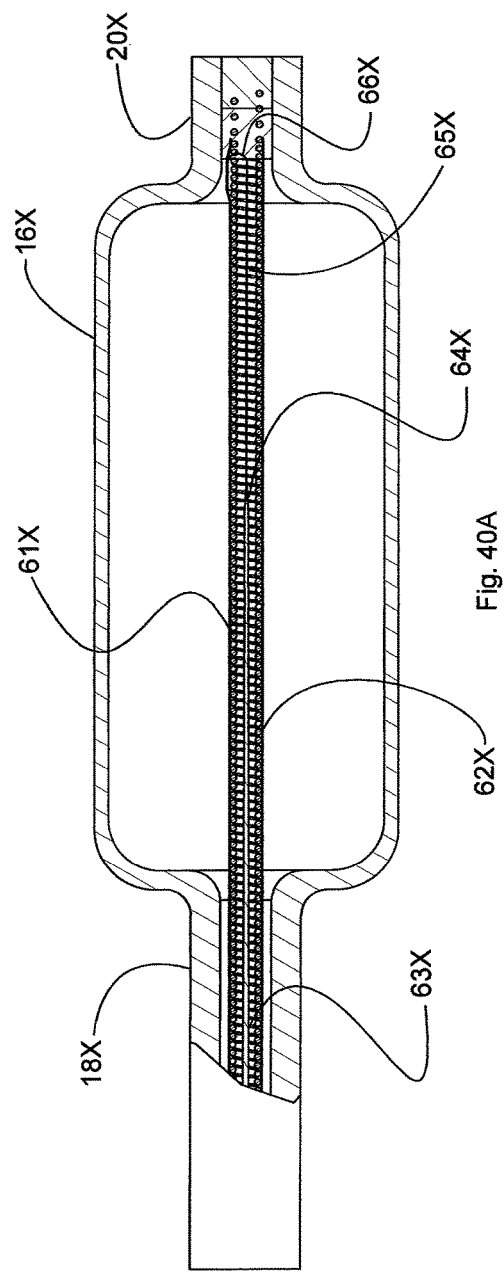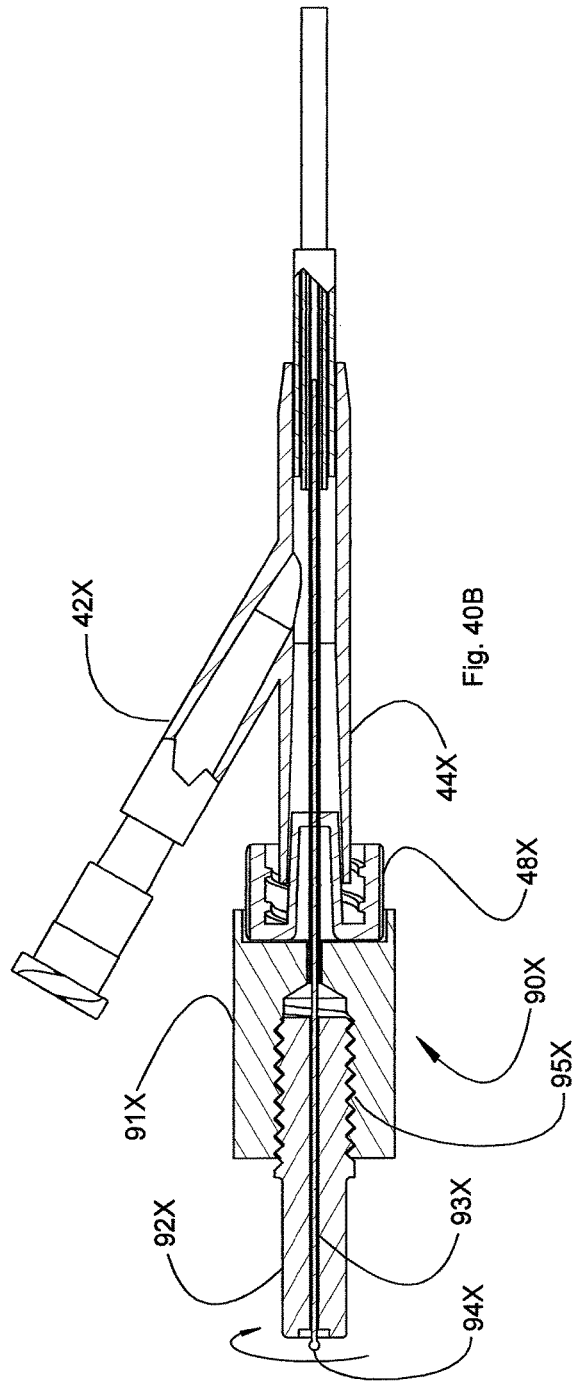

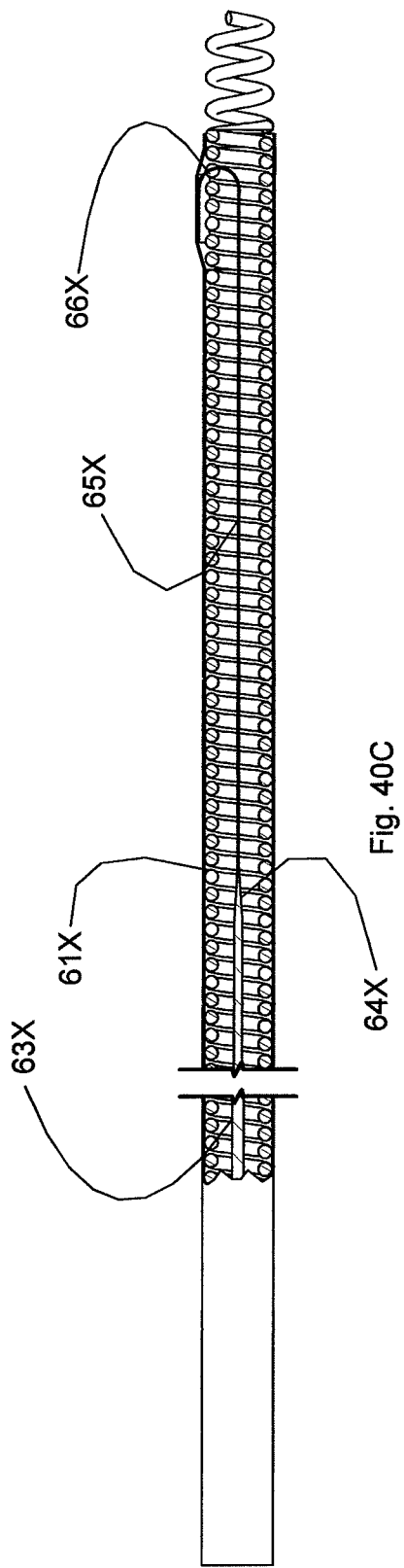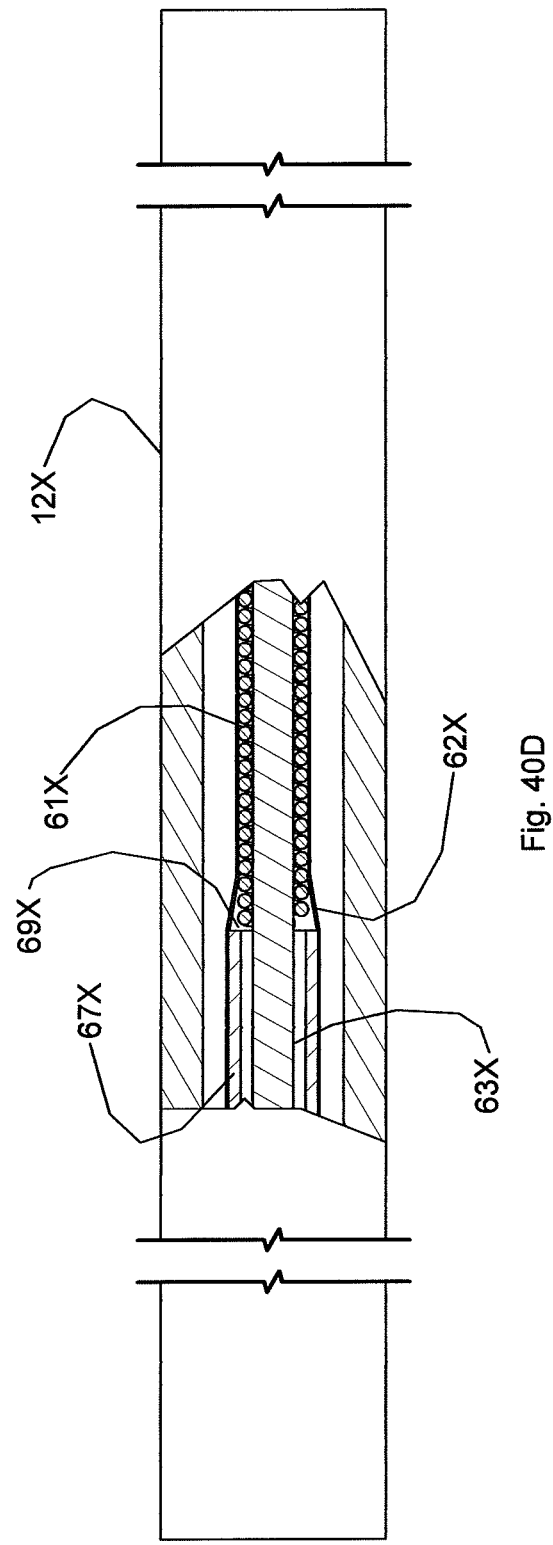

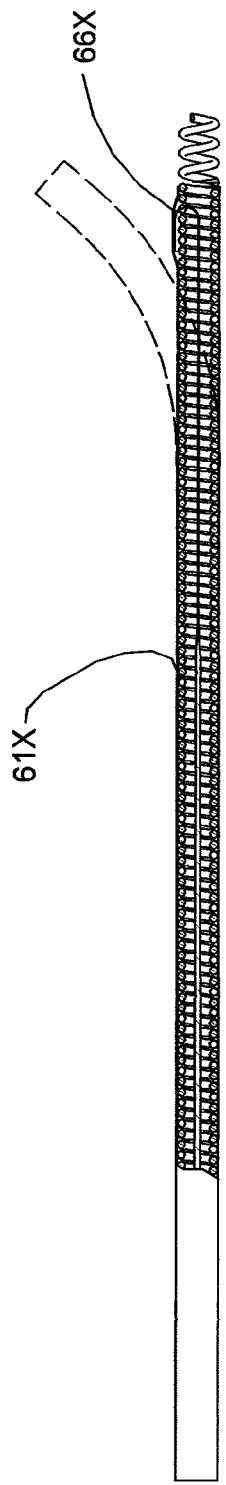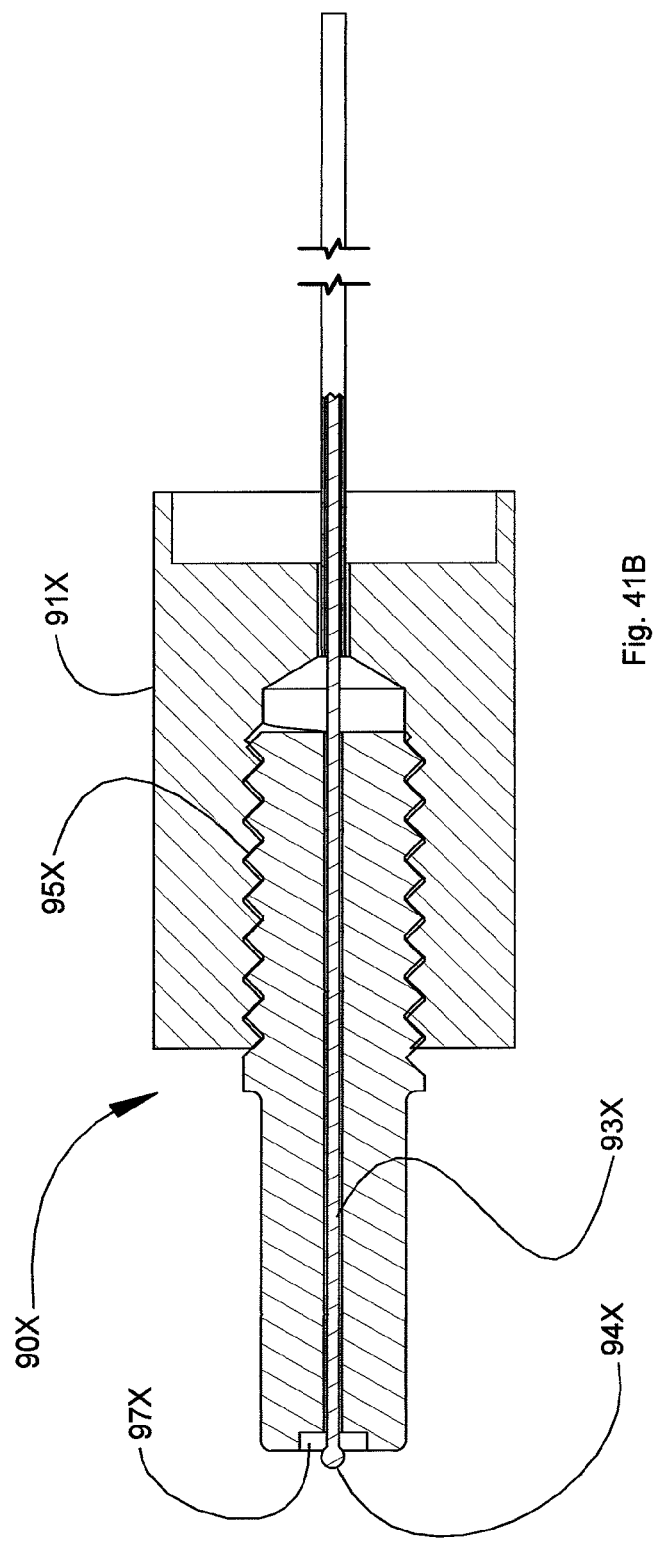
Fig. 41A
Fig. 41B

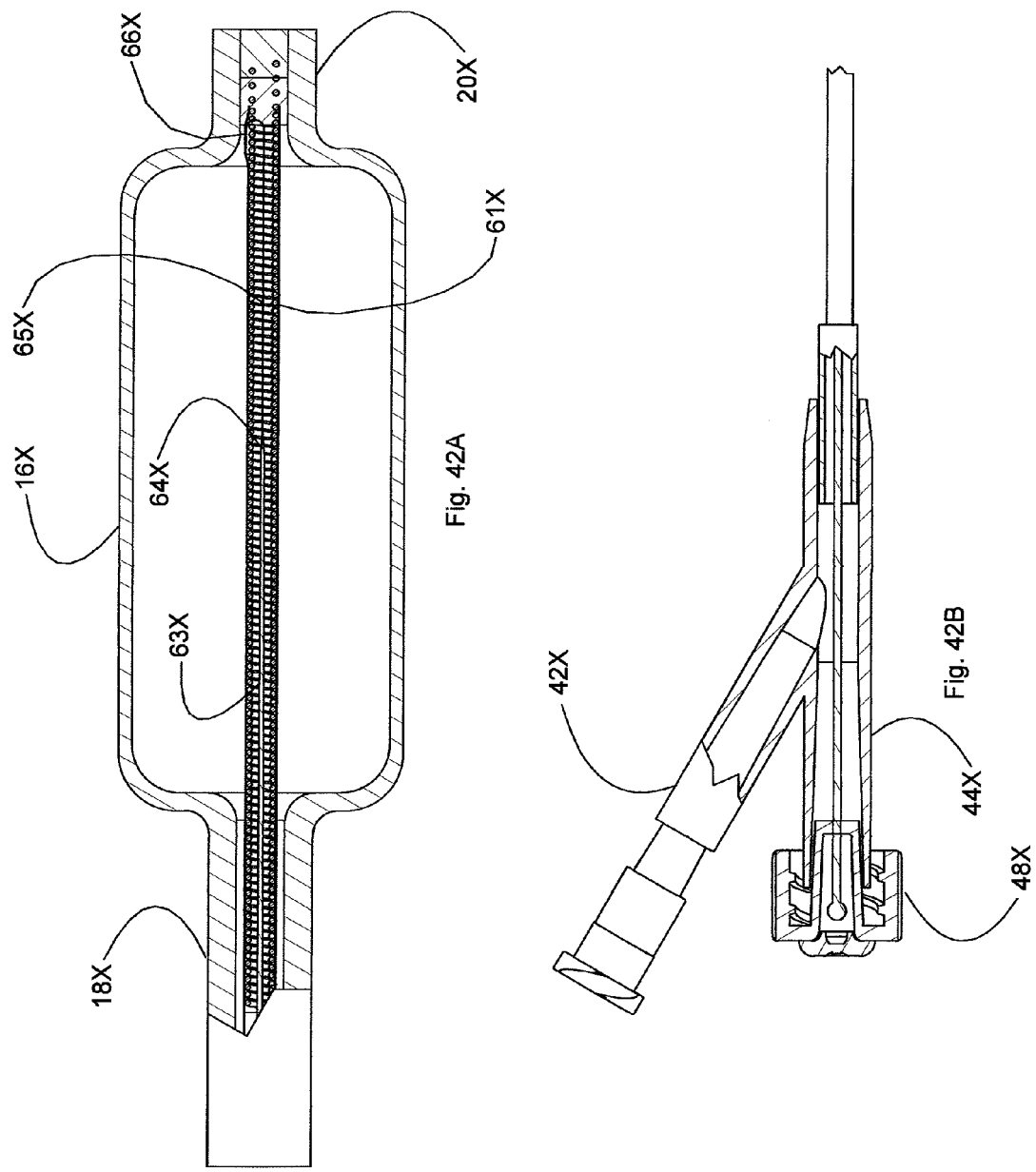

APPARATUS AND METHODS FOR TREATING BONE STRUCTURES, TISSUES AND DUCTS USING A NARROW GAUGE CANNULA SYSTEM

CROSS-REFERENCE TO RELATED APPLICATIONS

This application claims benefit of the filing dates of international application PCT/US2012/000162 filed Mar. 24, 2012, now pending, which claims the benefit of the filing date of U.S. Provisional Application Ser. No. 61/465,893 filed Mar. 25, 2011, and also of U.S. patent application Ser. No. 12/322,883, filed Feb. 9, 2009, now pending. The complete contents of the preceding earlier applications are incorporated herein by reference.

FIELD OF THE INVENTION

The present invention relates generally to systems, apparatus and methods for stabilizing bone structures (and, in some embodiments, for treating other body regions) by accessing and dilating such bone structures using a narrow gauge cannula, for example in surgically treating bone deformities and bones suffering from or predisposed to fracture or to collapse, particularly spinal fractures such as those commonly resulting from osteoporosis. The present invention further relates to systems, apparatus and methods for delivering a curable, stabilizing material into a bone structure, such as a vertebral body, through a narrow gauge cannula.

In some invention embodiments, an inflatable element is inserted into an interior region, cavity or passage of a damaged, collapsed, or deformed bone segment using a narrow gauge cannula; and, thereafter the inflatable element is inflated to form, enlarge or support the interior bone region thereby to effect a desirable realignment of the damaged bone segment with adjacent bone portions and to create a cavity. In at least some embodiments of this invention, following the dilatation step, the inflatable element may be collapsed and withdrawn from the interior bone region. A suitable bone support material may then be introduced into the dilated bone cavity. In some embodiments, the inflatable element may be left in place, and the cavity or the interior of the element may be filled with a suitable support material. The present invention has particular application in, but is not limited to, treatment of vertebral body compression fractures.

GENERAL BACKGROUND OF THE INVENTION

A number of diseases, illnesses and other medical conditions are treatable at least in part by dilatation of a bone, tissue or duct. For example, medical conditions and/or physical injuries can lead to or predispose a bone to deformity, such as a fracture. A familiar example is osteoporosis, in which bones lose calcium and break more easily. The human spinal column, comprised of interconnected vertebrae or vertebral bodies, has proven to be especially susceptible to the effects of osteoporosis. A vertebral body weakened by osteoporosis can fracture from a fall, or simply during routine activities. When a vertebral body fractures, it can collapse and change the shape of the spine. The damaged portion of the spine becomes shorter, and the rest of the spine above the broken vertebral body bends forward. As additional vertebral fractures occur, the spine shortens further, increasingly forcing the individual into a hunched-over posture.

As taught by U.S. Pat. No. 6,248,110 (Reiley et al.), U.S. Pat. No. 6,235,043 (Reiley et al.) and U.S. Pat. No. 6,066,154 (Reiley et al.), each of which is incorporated herein in its entirety by reference, it is known in the art to use expandable bodies, such as a balloon element, to treat certain bone conditions, resulting from osteoporosis, avascular necrosis, bone cancer and the like, that predispose a bone to, or lead to, fracture or collapse. A particularly common application is in the treatment of vertebral body compression fractures resulting from osteoporosis, as taught for example by U.S. Pat. No. 6,719,773 (Boucher et al.) and U.S. Pat. Publ. No. 2008/0140084 (Osorio et al.), each of which is incorporated herein in its entirety by reference.

Typical treatment of such conditions includes a series of steps which a surgeon or health care provider can perform to form a cavity in an interior region of pathological bone, including but not limited to osteoporotic bone, osteoporotic fractured metaphyseal and epiphyseal bone, osteoporotic vertebral bodies, fractured osteoporotic vertebral bodies, fractures of vertebral bodies due to tumors especially round cell tumors, avascular necrosis of the epiphyses of long bones, especially avascular necrosis of the proximal femur, distal femur and proximal humerus and defects arising from endocrine conditions.

The method typically further includes the steps of making an incision in the skin (usually one incision, but a second small incision may also be required if a suction egress is used) followed by the placement of a guide pin which is passed through the soft tissue down to and into the bone.

The method of the Reiley '154 patent, for example, further includes the steps of drilling the bone to be treated to form a cavity or passage in the bone, following which an inflatable balloon-like device is inserted into the cavity or passage where it is inflated. The inflation of the inflatable device causes a compacting of the cancellous bone and bone marrow against the inner surface of the cortical wall of the bone to further enlarge the cavity or passage. The inflatable device is then deflated and then is completely removed from the bone. The art further teaches that a smaller inflatable device (a starter balloon) can be used initially, if needed, to initiate the compacting of the bone marrow and to commence the formation of the cavity or passage in the cancellous bone and marrow. After this has occurred, a larger, inflatable device can be inserted into the cavity or passage to further compact the bone marrow in all directions.

Next in accordance with Reiley '154, a flowable biocompatible filling material, such as methylmethacrylate cement or a synthetic bone substitute, is directed into the bone cavity or passage that has been formed and enlarged, and the filling material is allowed to set to a hardened condition to provide ongoing structural support for the bone. Following this latter step, the insertion instruments are removed from the body and the incision in the skin is covered with a bandage.

A related U.S. Pat. No. 6,048,346 (Reiley et al.), which is also incorporated herein in its entirety by reference, teaches an improved mechanical bone cement injection assembly, which is described as constituting an improvement over prior art devices that operated "similar to a household caulking gun" in that it facilitates greater control over the placement of cement and other flowable liquids into an interior region of a bone.

Another inflatable apparatus intended for deployment into interior body regions is described in U.S. Pat. No. 5,972,015 (Scribner et al.), which is also incorporated herein in its entirety by reference. The Scribner '015 patent describes a catheter tube extending along a first axis in conjunction with an expandable structure having an expanded geometry oriented about a second axis, not aligned with the first axis, so as to treat an asymmetrically-shaped interior body region or where the access channel cannot be aligned with the body region to be treated. A particular application of this technology is stated to be for the fixation of fractures or other osteoporotic and non-osteoporotic conditions of human and animal bones, specifically for treating a human lumbar vertebra.

Two somewhat earlier patents describing similar apparatus and methods for treating vertebral body compression fractures and the like using an inflatable balloon-like element inserted into the bone cavity are U.S. Pat. No. 5,108,404 (Scholten et al.) and U.S. Pat. No. 4,969,888 (Scholten et al.), each of which is also incorporated herein in its entirety by reference.

In additional embodiments of known technologies for treating bone structures, U.S. Pat. No. 6,613,054 (Scribner et al.) and U.S. Pat. No. 6,241,734 (Scribner et al.), each of which is incorporated herein in its entirety by reference, describe systems and methods for advancing a tamping instrument through a cannula that has been deployed to establish a subcutaneous channel into bone. Material is introduced into the bone through the cannula, and the tamping instrument is used to move material in the cannula into the bone.

Numerous problems remain, however, with the prior art systems and methods. For successful expansion of a fractured vertebral body, an expandable element inserted into the vertebral cavity must be capable of being inflated to a relatively large working diameter of about 12 mm-25 mm, starting with a relatively short balloon working length, e.g., about 10 mm-25 mm, sized to fit inside the vertebral cavity, at very high working pressures on the order of 200-450 psi or higher. Use of lower inflation pressure in such applications may result in only a partial, incomplete expansion of a fractured vertebral body. When that partially-expanded vertebral body is subsequently filled with cement or comparable material, which then hardens, there is a permanent remaining spinal deformity at that vertebral body. Not only must the expandable/inflatable element in the vertebral cavity be capable of inflation to very high pressure without rupture in order to fully expand a collapsed/fractured vertebral body, in addition the inflated element must resist puncture by hard, sharp cancellous bone and surface irregularities around the outer edges of the vertebral cavity. Medical protocols have been developed for this type of vertebral fracture treatment, including specifying standards for the minimum recommended thickness of the balloon or expandable element in order to provide a safeguard and a margin of error against puncture/rupture of the balloon during a treatment procedure.

The following detailed description of the expandable structure for a preferred assembly for medical procedures to compact cancellous bone for the fixation of bone fractures appears in U.S. Pat. No. 6,719,773 (Boucher '773) at col. 8, line 64 to col. 12, line 17:

A. The Expandable Structure. The material from which the structure 56 is made should possess various physical and mechanical properties to optimize its functional capabilities to compact cancellous bone. Important properties for the structure include one or more of the following: (1) the ability to expand in volume; (2) the ability to deform in a desired way when expanding and assume a desired shape inside bone; and/or (3) the ability to withstand abrasion, tearing, and puncture when in contact with cancellous and/or cortical bone.

1. Expansion Property. A first desired property for the structure material is the ability to expand or otherwise increase in volume without failure. This property enables the structure 56 to be deployed in a collapsed, low profile condition subcutaneously, e.g., through a cannula, into the targeted bone region. This property also enables the expansion of the structure 56 inside the targeted bone region to press against and compress surrounding cancellous bone, or move cortical bone to a prefracture or other desired condition, or both.

The desired expansion property for the structure material can be characterized in one way by ultimate elongation properties, which indicate the degree of expansion that the material can accommodate prior to failure. Sufficient ultimate elongation permits the structure 56 to compact cortical bone, as well as lift contiguous cortical bone, if necessary, prior to wall failure. Desirably, the structure 56 will comprise material able to undergo an ultimate elongation of at least 50%, prior to wall failure, when expanded outside of bone. More desirably, the structure will comprise material able to undergo an ultimate elongation of at least 150%, prior to wall failure, when expanded outside of bone. Most desirably, the structure will comprise material able to undergo an ultimate elongation of at least 300%, prior to wall failure, when expanded outside of bone.

Alternatively, the structure material can comprise one or more non-compliant or partially compliant materials having substantially lower ultimate elongation properties, including, but not limited to, kevlar, aluminum, nylon, polyethylene, polyethyiene-terephthalate (PET) or mylar. Such a structure would desirably be initially formed to a desired shape and volume, and then contracted to a collapsed, low profile condition for introduction through a cannula into the targeted bone region. The structure could then be expanded to the desired shape and volume to press against and compress surrounding cancellous bone and/or move cortical bone to a prefracture or desired condition, or both. As another alternative, the structure could comprise a combination of non-compliant, partially compliant and/or compliant materials.

2. Shape Property. A second desired property for the material of the structure 56, either alone or in combination with the other described properties, is the ability to predictably deform during expansion, so that the structure 56 consistently achieves a desired shape inside bone.

The shape of the structure 56, when expanded in bone, is desirably selected by the physician, taking into account the morphology and geometry of the site to be treated. The shape of the cancellous bone to be compressed and/or cortical bone to be displaced, and the local structures that could be harmed if bone were moved inappropriately, are generally understood by medical professionals using textbooks of human skeletal anatomy along with their knowledge of the site and its disease or injury, and also taking into account the teachings of U.S. patent application Ser. No. 08/788,786, filed Jan. 23, 1997, and entitled "Improved Inflatable Device for Use in Surgical Protocol Relating to Fixation of Bone," which is incorporated herein by reference. The physician is also desirably able to select the desired expanded shape inside bone based upon prior analysis of the morphology of the targeted bone using, for example, plain film x-ray, fluoroscopic x-ray, or MRI or CT scanning.

Where compression of cancellous bone and/or cavity creation is desired, the expanded shape inside bone is selected to optimize the formation of a cavity that, when filled with a selected material, provides support across the region of the bone being treated. The selected expanded shape is made by evaluation of the predicted deformation that will occur with increased volume due to the shape and physiology of the targeted bone region.

Where displacement of cortical bone is desired, the expanded shape can be selected to optimize displacement of the cortical bone in the desired direction(s), as well as to distribute forces in a desired manner across the targeted cortical bone region. If desired, the structure can be designed to distribute forces evenly and/or uniformly across the targeted cortical bone region. Alternatively, the structure can be designed to impart a maximum force on a specific area of the cortical bone so as to cause desired fracture and/or maximum displacement of specific cortical bone regions.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 56 results in a worsening of the overall condition of the bone and surrounding anatomic structures, for example, by injury to surrounding tissue or causing a permanent adverse change in bone biomechanics.

As one general consideration, in cases where the bone disease causing fracture (or the risk of fracture) is the loss of cancellous bone mass (as in osteoporosis), the selection of the expanded shape of the structure 56 inside bone should take into account the cancellous bone volume which should be compacted to achieve the desired therapeutic result. An exemplary range is about 30% to 90% of the cancellous bone volume, but the range can vary depending upon the targeted bone region. Generally speaking, compacting less of the cancellous bone volume leaves more uncompacted, diseased cancellous bone at the treatment site.

Another general guideline for the selection of the expanded shape of the structure 56 inside bone is the amount that the targeted fractured bone region has been displaced or depressed. The expansion of the structure 56 inside a bone can elevate or push the fractured cortical wall back to or near its anatomic position occupied before fracture occurred.

For practical reasons, it is often desired that the expanded shape of the structure 56 inside bone, when in contact with cancellous bone, substantially conforms to the shape of the structure 56 outside bone, when in an open air environment. This allows the physician to select in an open air environment a structure having an expanded shape desired to meet the targeted therapeutic result, with the confidence that the expanded shape inside bone will be similar in important respects.

An optimal degree of shaping can be achieved by material selection and by special manufacturing techniques, e.g., thermoforming or blow molding, as will be described in greater detail later.

In some instances, it may not be necessary or desired for the structure to predictably deform and/or assume a desired shape during expansion inside bone. Rather, it may be preferred that the structure expand in a substantially uncontrolled manner, rather than being constrained in its expansion. For example, where compaction of weaker sections of the cancellous bone is desired, it may be preferred that the structure initially expand towards weaker areas within the bone. In such cases, the structure can be formed without the previously-described shape and/or size, and the expanded shape and/or size of the structure can be predominantly determined by the morphology and geometry of the treated bone.

3. Toughness Property. A third desired property for the structure 56, either alone or in combination with one or more of the other described properties, is the ability to resist surface abrasion, tearing, and puncture when in contact with cancellous bone. This property can be characterized in various ways.

One way of measuring a material's resistance to abrasion, tearing and/or puncture is by a Taber Abrasion test. A Taber Abrasion test evaluates the resistance of a material to abrasive wear. For example, in a Taber Abrasion test configured with an H-18 abrasive wheel and a 1 kg load for 1000 cycles (ASTM Test Method D 3489), Texin® 5270 material exhibits a Taber Abrasion value of approximately 75 mg loss. As another example, under the same conditions Texin® 5286 material exhibits a Taber Abrasion value of approximately 30 mg loss. Typically, a lower Taber Abrasion value indicates a greater resistance to abrasion. Desirably, one embodiment of the structure will comprise material having a Taber Abrasion value under these conditions of less than approximately 200 mg loss. More desirably, the structure will comprise material having a Taber Abrasion value under these conditions of less than approximately 145 mg loss. Most desirably, the structure will comprise material having a Taber Abrasion value under these conditions of less than approximately 90 mg loss. Of course, materials having a Taber Abrasion value of greater than or equal to 200 mg loss may be utilized to accomplish some or all of the objectives of the present invention.

Another way of measuring a material's resistance to abrasion, tearing and/or puncture is by Elmendorf Tear Strength. For example, under ASTM Test Method D 624, Texin® 5270 material exhibits a Tear Strength of 1,100 lb-ft/in. As another example, under the same conditions, Texin® 5286 exhibits a Tear Strength of 500 lb-ft/in. Typically, a higher Tear Strength indicates a greater resistance to tearing. Desirably, an alternate embodiment of the structure will comprise material having a Tear Strength under these conditions of at least approximately 150 lb-ft/in. More desirably, the structure will comprise material having a Tear Strength under these conditions of at least approximately 220 lb-ft/in. Most desirably, the structure will comprise material having a Tear Strength under these conditions of at least approximately 280 lb-ft/in. Of course, materials having a Tear Strength of less than or equal to 150 lb-ft/in may be utilized to accomplish some or all of the objectives of the present invention.

Another way of measuring a material's resistance to abrasion, tearing and/or puncture is by Shore Hardness. For example, under ASTM Test Method D 2240, Texin® 5270 material exhibits a Shore Hardness of 70 D. As another example, under the same conditions, Texin® 5286 material exhibits a Shore Hardness of 86 A. Typically, a lower Shore Hardness number on a given scale indicates a greater degree of elasticity, flexibility and ductility. Desirably, another alternate embodiment of the structure will comprise material having a Shore Hardness under these conditions of less than approximately 75 D. More desirably, the structure will comprise material having a Shore Hardness under these conditions of less than approximately 65 D. Most desirably, the structure will comprise material having a Shore Hardness under these conditions of less than approximately 100 A. Of course, materials having a Shore Hardness of greater than or equal to 75 D may be utilized to accomplish some or all of the objectives of the present invention.

It should also be noted that another alternate embodiment of a structure incorporating a plurality of materials, such as layered materials and/or composites, may possess significant resistance to surface abrasion, tearing and puncture. For example, a layered expandable structure incorporating an inner body formed of material having a Taber Abrasion value of greater than 200 mg loss and an outer body having a shore hardness of greater than 75 D might possess significant resistance to surface abrasion, tearing and puncture. Similarly, other combinations of materials could possess the desired toughness to accomplish the desired goal of compressing cancellous bone and/or moving cortical bone prior to material failure.

One possible approach to improve the strength of the balloon-like elements to make them better able to withstand very high inflation pressures would be to use thicker balloon walls and/or to make these elements out of stiffer, stronger materials. There are several reasons, however, why these seemingly straightforward solutions have not proven successful in practice. One is the need to limit the balloon wall thickness and the need to maintain balloon wall flexibility to facilitate access to, and withdrawal from, a bone cavity.

In treating a vertebral fracture, for example, the vertebral cavity is typically accessed by drilling a small hole and locating a short, hollow, metallic tubular element (i.e., a hollow sleeve or cannula) through the left or right pedicle portion (or sometimes both) of the vertebral arch (see, e.g., FIG. 2 of U.S. Pat. No. 5,972,015, which shows the left and right pedicle portions 42 of vertebral arch 40, and FIG. 6 of the same patent which shows an access hole for catheter tube 50 and expandable structure 56 through one pedicle portion 42 into the interior volume 30 of reticulated cancellous, or spongy, bone 32). Because pedicle portion 42 shown in FIGS. 2 and 6 of the Scribner '015 patent is relatively small and is itself readily susceptible to fracture if its structural integrity is impaired by too large a hole, it is crucial to keep the diameter of the hole, therefore also of the cannula, to a minimum, typically no larger than about 4-5 mm. Indeed, as taught hereinafter, it has become desirable based on current medical practice to use an opening made by an 11-gauge needle with a diameter of only about 0.121 inches (about 3.06 mm) or less, thereby requiring the use of an 11-gauge needle cannula. The cannula helps to protect surrounding bone portions from abrasion and from expansion forces while inserting or removing the catheter shaft or while inflating the balloon element that is bonded to the distal end of the catheter shaft.

Because of the narrow interior diameter of the cannula used in these applications, it was typical to fold or wrap the balloon-like element relatively tightly at the distal end of an associated catheter shaft in order to keep the maximum diameter of the unit at the balloon end small enough to fit through the cannula of a small-diameter pedicle hole. An expandable element fabricated with relatively thick walls and/or made from a relatively stiff, less flexible material might be inflatable to a higher pressure, but these characteristics could impede folding or wrapping the element tightly enough to fit through the cannula of a narrow-diameter pedicle opening. For these reasons, balloon elements for bone dilatation procedures would typically have thicker walls compared, for example, to the balloon elements commonly used for angioplasty procedures, but the bone dilatation balloons would generally be fabricated from more flexible, elastic materials than those used in angioplasty procedures.

Even if a balloon element can be wrapped or folded sufficiently tightly for insertion through the cannula of a narrow-diameter pedicle hole, it can later be difficult to remove or withdraw that balloon element through the same cannula following a dilatation procedure because, after a cycle of inflation and deflation inside a vertebral cavity, a balloon element may not be able to be refolded or rewrapped in-situ to its previously folded size or to a size sufficiently small to be withdrawn through the cannula without the use of excessive force which might crack or break the pedicle or tear the balloon from the catheter.

These problems were addressed, at least in part, by U.S. Pat. No. 7,488,337 (Saab et al.), which is incorporated herein in its entirety by reference. Saab '337 describes techniques for tensioning, stretching, folding and/or wrapping the expandable elements of devices designed for bone dilatation procedures to better facilitate insertion of the expandable elements into and, after an inflation procedure, withdrawal of the expandable elements from a bone structure through a narrow diameter cannula.

As noted above, however, the trend in medical practice in this field has been to utilize the smallest possible diameter hole or holes through the exterior portion of the bone to access the bone interior region. Current practice is to use an 11-gauge needle in order to perform a vertebral treatment, if possible, using bone openings that are so small (about 0.120 inches) that they can only accommodate an eleven (11) gauge cannula. Currently available catheter/expandable element apparatus for such bone treatment procedures, however, cannot be inserted into and later, following a treatment procedure, withdrawn from a bone dilatation site through a standard wall 11-gauge cannula (which typically has an inside diameter of only 0.094 inches±0.002 inches). For example, the Osorio '084 patent publication cited above contemplates use of an 11-gauge needle for performing a vertebral fracture treatment. But, in Osorio '084, after dilating the bone structure, the expandable structure is left in place and filled with cement or comparable material. Thus, Osorio '084 does not contemplate or address the problem of removing the expandable structure through the very small interior of an 11-gauge cannula following an inflation/deflation cycle.

By contrast with an 11-gauge cannula, a thin-walled 10-gauge needle cannula (having a thinner wall thickness than a "standard" 10G cannula), which has become the industry standard for Kyphoplasty procedures, has an inside diameter of 0.114 inches (2.89 mm). The thin-walled 10-gauge cannula and its 0.114 inch inside diameter can accommodate current catheter assemblies used in these procedures, but it also has a larger outside diameter of about 0.134 inches that cannot fit inside a bone opening of only about 0.121 inches, which is the size of the opening made with an 11-gauge needle.

But, adapting the technology in this field to a smaller 11-gauge cannula, having an inside diameter (ID) of about 0.094 inches (2.39 mm)±0.002 inches and an outside diameter (OD) of about 0.120 inches (3.05 mm)±0.001 inches involves many substantial technological challenges. Much more is involved in this adaptation than just slightly shrinking all of the standard apparatus components.

First, because the volume of the bone interior that needs expanding remains unchanged, the expandable element must still be capable of expanding to that necessary bone interior volume, but that expandable element also needs to fit through the smaller interior diameter of an 11-gauge cannula. One approach to facilitate the insertion and removal steps with the larger, conventional 8-gauge and 10-gauge cannulas is to provide a slippery, friction-reducing coating or lubricating fluid (such as a silicone material) along the interior of the cannula, on the exterior of the expandable element, or both, to reduce friction and facilitate sliding the expandable element through the cannula.

A potential problem with this lubricant coating approach, however, is that at least a portion of such a lubricant would be transferred via the expandable element into the interior of the bone, where it would remain as a foreign contaminant. The presence of such a contaminant might cause irritation or an adverse body reaction at the interior bone site. In addition, the presence of a lubricating substance coating the walls of the expanded cavity of the bone following a dilatation procedure can possibly prevent a subsequently injected cement material from solidly and effectively bonding to the bone interior.

It also is not currently feasible to facilitate the use of an 11-gauge cannula in these procedures by reducing the wall thickness of the expandable element. As discussed above, the expandable element needs to withstand inflation to relatively high pressure without being punctured by irregularities or projecting portions of the bone interior. Furthermore, current medical protocols for bone dilatation procedures using an expandable balloon prescribe the minimum acceptable wall thickness for the expandable element, and those protocols must be met whether the balloon element needs to fit through the interior of a conventional 8-gauge or 10-gauge cannula, or through a very narrow diameter 11-gauge cannula.

Structural integrity and materials issues for the cannula create another significant design constraint. A "standard" 11-gauge cannula has an interior diameter (ID) of 0.094 inches with a tolerance of ±0.002 inches (i.e., an interior diameter that may range from 0.092 to 0.096 inches) and an outer diameter (OD) ranging from 0.119 to 0.121 inches (about 3.05 mm). In theory, one could make an ultra-thin walled 11-gauge cannula with an interior diameter of about 0.114 inches (i.e., comparable to a thin-walled 10-gauge cannula) but with a very thin wall such that the outer diameter was only about 0.120 inches. But, such an ultra-thin wall of only about 0.003 inches would compromise the structural integrity of the cannula which must function under demanding operating conditions. Such a modification would therefore raise numerous patient safety issues.

Another performance issue in this field is being able to accurately monitor the location of the expandable element as it is slid through the cannula and into the interior region of the bone that is being treated. This is an important issue because the length (along the catheter axis) of the expandable element (before inflation) is carefully selected to correspond to the size of the bone interior when the element is fully inflated.

Because of these narrow tolerances, it is important that the expandable element be properly situated in the bone interior before an inflation procedure is initiated. If the expandable element is pushed too hard and too far into the bone interior region, the distal tip of the catheter/expandable element may damage or even rupture the distal wall of the bone interior region. On the other hand, if the proximal portion of the expandable element is still located inside the cannula when the inflation procedure is started, the expandable element will be unable to fully inflate and, thus, unable to fully dilate the bone interior.

One approach to addressing the expandable element positioning problem has been to place radiopaque markings at one or more locations inside the expandable element and, using appropriate fluoroscopy equipment, to monitor the location of the expandable element by means of those markings as it is slid through the cannula and into the interior of the bone structure. Although the thickness of such radiopaque markings is generally very small, even that small added thickness becomes a significant factor in the context of wrapping or folding a full-sized bone dilatation expandable element to fit through the very small inside diameter of an 11-gauge cannula.

Yet another factor that becomes significant in the context of fitting a full-sized bone dilatation expandable element through the interior of an 11-gauge cannula is the juncture where the proximal end of the expandable element is secured to the distal end of the catheter shaft on which the expandable element is carried. Typically, the opening at the proximal end of the expandable element is formed slightly larger than the exterior diameter of the distal end of the catheter shaft. Thus, the proximal end of the expandable element can be slid over the distal end of the catheter shaft, and the expandable element can then be sealed to the end of the shaft by gluing, thermal bonding, or using similar sealing techniques. The result of this bonding procedure, however, is typically a small section of enlarged diameter at the juncture between the two components, and such an enlarged diameter section of the combined apparatus can inhibit passage of the expandable element through the interior of an 11-gauge cannula.

Still another design constraint of conventional expandable element bone dilatation systems is the use of a catheter shaft having an annular configuration with concentric inner and outer lumens. This coaxial, dual-lumen structure permits the outer lumen to be used for flowing a fluid (such as air, water or contrast fluid) to or from the expandable element for inflating or deflating the element once it is in place inside the bone, while using the separate inner lumen (which extends to the interior distal end of the expandable element) to contain a mandrel, rod or similar component. The mandrel may be moveable and slidable axially along the axis of the catheter assembly and may extend the length of the inner lumen into and to the distal end of the inner lumen and the expandable element.

At the same time, however, the separate, concentric lumen structure of such a catheter shaft takes up additional space and requires a larger diameter catheter shaft to achieve a given degree of cross-sectional area for fluid flow to/from the expandable element. In addition, this design generally increases the size of the wrapped or folded expandable element because in these configurations the inner catheter lumen typically extends through the interior of the expandable element.

These and other deficiencies in and limitations of the above-described prior art approaches to treating bone deformities, such as vertebral body compression fractures, and other medical treatments involving inserting and inflating an expandable element through a narrow cannula are overcome in whole or in part with the systems, apparatus and methods of this invention.

SPECIFIC INVENTION
BACKGROUND—STANDARD IBT DEVICES
AND PROCEDURES AND THEIR LIMITATIONS

As discussed above, surgical intervention at damaged or compromised bone sites has proven highly beneficial for patients, for example patients with back pain associated with vertebral damage.

Bones of the human skeletal system include mineralized tissue that can be generally categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone-related procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement or bone curable material). In other procedures, percutaneous injection of stabilization material into vertebral compression fractures, by, for example, transpedicular or parapedicular approaches, has proven beneficial in relieving pain and stabilizing damaged bone sites. Such techniques are commonly referred to in this art as vertebroplasty. Other skeletal bones (e.g., the femur) can be treated in a similar fashion. Bone in general, and cancellous bone in particular, can be strengthened and stabilized by palliative insertion or injection of bone-compatible material.

Using vertebroplasty as a non-limiting example, a conventional technique for delivering the bone stabilizing material entails placing a cannula using an internal stylet into the targeted delivery site. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone. Once positioned in the cancellous bone, the stylet is then removed, leaving the cannula in the appropriate position for delivery of curable material to the trabecular space of the vertebra that in turn reinforces and solidifies the target site.

In some instances, an effectiveness of the procedure can be enhanced by forming a cavity or void within the cancellous bone, and then depositing the curable material in the cavity. The cavity can be formed in various manners (e.g., mechanical cutting or shearing of cancellous tissue, expansion of a balloon or other expandable device to compress cancellous bone and also cause a "height" of the bone to increase, etc.). To minimize the duration of the procedure and number of tools required, it is desirable to use the same cannula to first guide delivery of the cavity-forming device and subsequently to deliver the curable material. One such procedure entails initially locating a distal end of the access cannula immediately adjacent the target site. The cavity-forming device is then delivered through the cannula to the target site and operated to form the cavity. The cavity will have an enlarged width (e.g., diameter) as compared to a diameter of the cannula. The cavity-forming device is then removed from the cannula, and curable material can be delivered to the target site via the cannula.

To get the curable material to fill the cavity, the surgeon can either inject the curable material through the cannula and any intervening space (between the distal end of the cannula and the cavity) to reach the cavity or else push the cannula through the intervening space until the distal end is suitably located in the cavity before delivering the curable material. Under the first approach, curable material is deposited into the intervening space and may undesirably solidify or attach to the cannula. Further, the intervening space represents an uncontrolled volume that may negatively affect the surgeon's evaluation of whether a necessary volume has been delivered to the cavity. With the second approach, it may be difficult for the surgeon to accurately re-position the cannula within the cavity and/or may cause unintended damage to the tissue surrounding the cavity and/or to the cannula.

The access cannula is normally a metal tube rigidly defining a central axis. Conventional cavity forming devices typically include a longitudinally linear shaft carrying the expandable body. With this linear configuration, the shaft/expandable body progresses from the access cannula into the bone structure along a relatively straight or linear path that is coaxial with the access cannula's central axis. This linear configuration, however, may inhibit the surgeon's ability to form the cavity at a desired location. For example, with Kyphoplasty the confined nature of the inner vertebral body and surrounding anatomy may necessitate insertion of the access cannula immediately adjacent to one of the vertebra's pedicles. This access site, in combination with the linear configuration of the access cannula and the shaft carrying the expandable body, dictates that the expandable body can only be located in a relatively limited area in line with the access cannula's central axis. In some instances, this restricted spatial positioning of the expandable body relative to the desired target site may not be optimal.

The standard design of an Inflatable Balloon Tamp (IBT) device (presently available from many sources) used for vertebral bone dilatation/treatment procedures consists of an inflatable, relatively thick-walled, elastomeric balloon connected to the outer lumen of a concentric lumen catheter shaft which, in turn, is connected to a bifurcation assembly at the proximal end of the device. The bifurcation assembly consists of two arms, one of which arms connects to the outer concentric lumen of the catheter shaft and is used for supplying an inflation fluid to the balloon, while the other arm is axially aligned with the catheter shaft and connects to the inner lumen of the catheter shaft of the device. This conventional arrangement allows access to the balloon's interior through the outer lumen to allow inflation and deflation of the balloon, and it also allows access to the balloon interior through the inner lumen of the catheter shaft. The inner lumen of the catheter shaft generally holds a 0.035 inch diameter stainless steel mandrel. The mandrel typically can be positioned so as to extend for the length of the interior of the inner lumen, but it can also be fully removed from the inner catheter lumen at the proximal end of the device. The mandrel also typically has a male luer bonded on its proximal end to allow a secure connection of the mandrel assembly to the luer lock on the straight arm of the bifurcation fitting. Radiopaque marker bands are located inside the balloon along the exterior of the inner shaft and are used to mark the proximal and distal ends of the balloon to assist the physician in positioning the balloon under fluoroscopy prior to inflation of the balloon.

The conventional IBT device is delivered to the vertebral body of a patient by means of a needle cannula. The standard for use in such procedures was originally a standard wall 8-gauge (0.135 inch or 3.4 mm inside diameter) needle together with a suitably sized IBT instrument. A smaller, thin-walled 10-gauge (0.114 inch or 2.89 mm inside diameter) needle was later introduced and has since gained favor because of its smaller size, which makes a smaller opening in the patient, and which in turn creates less trauma and aids in a quicker recovery time for the patient. The smaller size opening created with the 10-gauge needle also reduces the chances of fracture of the pedicle and provides the ability to treat smaller vertebrae that might not be able to accommodate an 8-gauge needle.

In the bone dilatation form of a vertebral treatment procedure that uses an expandable element, an IBT device sized to accommodate the inner diameter of the cannula is introduced into the interior of the vertebral body of a patient. The expandable element of the device is then inflated inside the fractured vertebra. For a compression fracture, the procedure is intended to substantially restore the bone to its pre-fractured dimensions and, on withdrawal of the balloon, the space created by the inflated balloon can be filled with bone cement that hardens in place to stabilize the fracture.

A second, alternative form of a vertebral treatment procedure (one that is generally known in this art as "vertebroplasty"), however, can be performed without the use of an IBT device and without an expandable element. This alternative "vertebroplasty" procedure presently uses a standard eleven (11) gauge (0.094 inch or 2.4 mm inside diameter) needle cannula. But, rather than using an IBT device to first create a cavity to restore the vertebrae dimensions, in this alternative procedure the cement is injected directly into the vertebral body to stabilize the fracture. The medical decision about which of the two procedures should be performed in a particular case is best decided after the physician has fluoroscopically assessed the condition of the patient's vertebra.

The ability of a physician to decide between the two procedures at or shortly after the start of a procedure is currently limited, however, by the size of the opening into the bone interior. If the opening was created using an 11-gauge needle in anticipation of performing a vertebroplasty (no balloon element) procedure, that opening will not accommodate a cannula that is large enough to pass a conventional 10-gauge IBT assembly if the physician decides instead on the bone dilatation procedure. Accordingly, it would be highly desirable to have an IBT catheter assembly (including a conforming expandable element meeting current medical protocols) that is capable of fitting through the smaller interior opening of an 11-gauge needle cannula. This would allow the physician to start a procedure with a smaller entry opening in the skin and bone, use an 11-gauge cannula, and then still be able to select either type of bone treatment procedure, depending on which procedure is deemed best suited to the patient's condition. The ability to use an 11-gauge cannula in such procedures also would substantially reduce the chance of fracturing the pedicle (because a much reduced area of the pedicle would need to be opened to accommodate the smaller cannula), and it would also allow for the treatment of smaller vertebra as described above.

Accordingly, there is a currently unfilled need in this art for a system, apparatus and method wherein a narrow gauge (e.g., an 11-gauge) cannula can be utilized in combination with a specially designed catheter/expandable element apparatus adapted and sized to slide through the interior of the associated narrow gauge (e.g., an 11-gauge) cannula.

OBJECTS OF THE INVENTION

A first set of invention objectives relates to providing improved apparatus and methods for bone, tissue and/or duct dilatation. These invention embodiments include:

Providing improved inflatable balloon-like elements for dilatation of interior bone regions, tissue portions, or duct segments in combination with balloon withdrawal systems and methods of using the same.

Providing inflatable balloon-like elements able to expand to relatively large diameters, to withstand relatively high inflation pressures, and to resist damage by hard, sharp cancellous bone for use in dilating an interior region of a damaged bone.

Providing apparatus and methods for more effectively treating vertebral body compression fractures.

Providing apparatus and methods for removing congenital obstructions of the nasal lacrimal duct.

Providing inflatable balloon-like elements for dilatation of an interior region of a damaged bone capable of expansion to inflated working diameters of about 12 mm-25 mm, starting with relatively short balloon working lengths sized to fit inside a vertebral or other bone or body cavity, at working pressures of about 200-400 psi or higher.

Providing inflatable balloon structures, capable of inflation to high working pressures, which are relatively easily introduced into the interior region of a bone, tissue or duct through a small diameter opening, on the order of about 4 to about 5 mm or less in diameter or width, and which balloon structures are capable of being collapsed to a very small diameter following inflation to facilitate withdrawal after use.

Providing active or passive balloon wrapping or tensioning assemblies, or both for use in conjunction with inflatable balloon structures according to the present invention to facilitate insertion of a balloon structure through a narrow diameter opening or passageway and/or withdrawal of a balloon structure through a narrow diameter opening or passageway following an inflation-deflation cycle.

Providing assemblies comprising in combination an inflatable balloon element, a catheter shaft connected to the balloon element to provide a working fluid for inflating the balloon element and for withdrawing the fluid to deflate the balloon element, and at least a balloon tensioning and/or wrapping device or both for stretching the balloon element and/or folding, pleating or wrapping the balloon element to facilitate insertion and/or removal of the balloon element through a narrow diameter duct, access channel or cannula typically having an opening of about 4 to 5 mm or less.

A second set of invention objectives relates to providing improved apparatus and methods for using a narrow gauge cannula for a bone dilatation and/or treatment procedure carried out with an inflatable balloon element. These invention objectives include:

Providing a combined system for a bone dilatation and treatment procedure, the system comprising a narrow gauge cannula sized to fit in a subcutaneous channel formed using an 11-gauge or smaller needle, in combination with a catheter shaft and expandable element assembly designed and sized for insertion into a bone/body location through the associated cannula.

Providing systems, apparatus and methods that enable a physician to utilize an 11-gauge or smaller cannula, positioned in a body/bone opening formed using an 11-gauge needle, to perform either a vertebroplasty procedure (with no balloon element) or, alternatively, a bone dilatation and/or treatment procedure using an expandable element positioned in the bone interior, using the same 11-gauge or smaller cannula depending on the physician's choice according to an assessment of the patient's condition.

Providing a catheter shaft and expandable element assembly (using a medically conforming expandable element according to current medical protocols), the assembly being designed and sized to fit through the interior of an 11-gauge cannula.

Providing a catheter shaft and expandable element assembly (using a medically conforming expandable element), wherein the expandable element (when properly folded or wrapped), the adjacent portion of the catheter shaft, and the juncture between the catheter shaft and the expandable element are adapted and sized: (1) to pass through the interior of an 11-gauge cannula to position the expandable element in the interior of a bone structure to be treated; and then, (2) following the steps of inflating, subsequently deflating, and re-wrapping/re-folding the expandable element, to also withdraw the expandable element through the interior of the same 11-gauge cannula.

Providing a catheter shaft and expandable element assembly (using a medically conforming expandable element) designed and sized to fit through the interior of an 11-gauge cannula in the absence of any lubricant or other friction-reducing coating.

Providing a catheter shaft and expandable element assembly (using a medically conforming expandable element) designed and sized to fit through the interior of an 11-gauge cannula with radiopaque markings at the distal tip of the expandable element but at no other location along the expandable element.

Providing a catheter shaft and expandable element assembly (using a medically conforming expandable element) designed and sized to fit through the interior of an 11-gauge cannula with at least a radiopaque marking at or near the proximal end of the interior of the expandable element, with or without a radiopaque marking at or near the distal end of the interior of the expandable element, and with or without another such marking at or near the distal tip.

Providing a catheter shaft and expandable element assembly (using a medically conforming expandable element) designed and sized to fit through the interior of an 11-gauge cannula in which the outside diameter of the assembly at the juncture between the catheter shaft and the expandable element is substantially the same as the outside diameter of the distal end of the catheter shaft.

Providing a catheter shaft and expandable element assembly (using a medically conforming expandable element) designed and sized to fit through the interior of an 11-gauge cannula in which the interior of the catheter shaft comprises a single lumen.

Providing a catheter shaft and expandable element assembly (using a medically conforming expandable element) designed and sized to fit through the interior of an 11-gauge cannula in which the assembly comprises a "floating" mandrel capable of limited axial movement along or parallel to the catheter axis in a direction toward or away from the distal end of the assembly by bonding the distal end of the mandrel and providing an enclosed channel or sleeve of limited length in which the unbonded proximal end of the mandrel can slide.

Providing a catheter shaft and expandable element assembly (using a medically conforming expandable element) designed and sized to fit through the interior of an 11-gauge cannula in which the assembly comprises a mandrel with a distal end bonded at the distal end of the assembly and with an unbounded, axial moveable proximal end that may, in some cases, extend externally of the proximal end of the catheter shaft.

Providing a catheter shaft and expandable element assembly (using a medically conforming expandable element) designed and sized to fit through the interior of an 11-gauge cannula in which the assembly additionally comprises one or more features in accordance with U.S. Pat. No. 7,488,337 for actively or passively tensioning, stretching, folding and/or wrapping the expandable element, especially to facilitate removal of the expandable element through a narrow gauge cannula following an inflation/bone dilatation and/or treatment procedure.

Providing a medical device system comprising in combination a narrow gauge cannula (as defined hereinafter) and a catheter shaft/expandable element assembly (using a medically conforming expandable element) wherein the catheter/expandable element assembly is designed and sized to fit through the interior of the narrow gauge cannula both prior to and subsequent to an inflation procedure.

Providing a medical device system comprising in combination an 11-gauge cannula (as defined hereinafter) and a catheter shaft/expandable element assembly (using a medically conforming expandable element) wherein the catheter/expandable element assembly is designed and sized to fit through the interior of the 11-gauge cannula both prior to and subsequent to an inflation procedure.

Providing a catheter shaft and expandable element assembly including a mandrel.

Providing a catheter shaft and expandable element assembly including a mandrel wherein the mandrel is bonded at its distal end to the expandable element.

Providing a catheter shaft and expandable element assembly including a mandrel wherein the mandrel is bonded at its distal end to the expandable element using a spring element to improve the bonding between the distal end of the mandrel and the distal end of the expandable element.

Providing a catheter shaft and expandable element assembly including a mandrel wherein the mandrel is bonded at its distal end to the expandable element wherein the distal end of the mandrel and the distal portion of the assembly are configured to facilitate active or passive deflection of the distal tip portion of the mandrel or core wire and of the distal end of the assembly.

Providing a catheter shaft and expandable element assembly including a mandrel wherein the mandrel is bonded at its distal end to the expandable element wherein the distal end of the mandrel and the distal portion of the assembly are configured to facilitate active or passive deflection of the distal tip portion of the mandrel or core wire and of the distal end of the assembly and further wherein the proximal end of the catheter assembly is configured to apply axial force when desired to the proximal end of the mandrel to cause active deflection of the distal tip.

Providing a catheter shaft and expandable element assembly including a mandrel wherein a distal portion of the mandrel or core wire and the distal portion of the assembly are configured to improve the flexibility of the distal end of the assembly to facilitate better navigating curves or bends during placement of the expandable element at a desired treatment site.

Other objects and advantages of the present invention will in part be obvious and will in part appear hereinafter. The invention accordingly comprises, but is not limited to, the apparatus and related methods, involving the several steps and the various components, and the relation and order of one or more such steps and components with respect to each of the others, as exemplified by the following description and the accompanying drawings. Various modifications of and variations on the apparatus and methods as herein described will be apparent to those skilled in the art, and all such modifications and variations are considered to be within the scope of the invention.

SUMMARY OF THE INVENTION

The following definitions will apply to terms of art as used in this application:

The term "11-gauge needle" as used in this application refers to a needle that creates an opening about 0.120 inches in diameter, preferably ranging from 0.119 to 0.121 inches, in diameter.

The terms "narrow gauge cannula" or "narrow diameter cannula" are used interchangeably in this application to broadly refer to a cannula having an outside diameter that is less than the diameter of an opening made by a 10-gauge needle, in other words less than about 0.134 inches. For purposes of this application, a cannula that fits into the opening made by an 11-gauge needle or smaller, namely an opening with a diameter of about 0.121 inches or less, is regarded as a "narrow gauge cannula" or a "narrow diameter cannula."

The term "11-gauge cannula" as used in this application refers to a cannula or a needle cannula having an outside diameter of about 0.120 inches, preferably plus or minus 0.001 inches (i.e., ranging from 0.119 to 0.121 inches).

The term "standard 11-gauge cannula" as used in this application refers to a cannula or a needle cannula having an outside diameter of about 0.120 inches, preferably plus or minus 0.001 inches (i.e., ranging from 0.119 to 0.121 inches), and having an open interior diameter of about 0.094 inches, preferably plus or minus 0.002 inches (i.e., ranging from 0.092 to 0.096 inches).

The terms "medically conforming catheter" or "medically conforming catheter shaft" or "conforming catheter shaft" are used interchangeably in this application to refer to a catheter that satisfies current (2012) medical protocols for performing a vertebral fracture or similar type of bone dilatation or treatment procedure.

The terms "medically conforming expandable element" or "conforming balloon" or "balloon element suitable for treating vertebral fractures" are used interchangeably in this application to refer to a balloon element having at least a wall thickness that satisfies current (2012) medical protocols for performing a vertebral fracture or similar type of bone dilatation or treatment procedure.

The present invention provides systems, apparatus and methods for treating and stabilizing bone structures by accessing and dilating such bone structures using an 11-gauge or smaller cannula, followed by deflating the balloon element, stretching, folding and/or wrapping the deflated balloon element to reduce its profile, and withdrawing the deflated balloon element through the cannula. The treatment may also include filling the interior of the bone structure with a bone-compatible cement or similar material. The present invention provides a catheter shaft and expandable element assembly (using a wrapped or folded expandable element that meets current medical protocols in this field, especially with regard to minimum wall thickness) that can be slid through the interior of an 11-gauge or smaller cannula before and, especially, after a dilatation or treatment procedure.

The present invention also provides a medical device system comprising a catheter assembly in accordance with this invention in combination with an 11-gauge cannula that has been specially prepared to adapt it for use with the catheter assembly of this invention by not applying any friction-reducing coatings to the interior of the cannula or to any exterior portion of the catheter shaft or expandable element. Additionally, the present invention also comprises methods for fabricating and configuring the catheter assembly and the cannula of this invention and methods for utilizing the several component elements that comprise this invention in conjunction with one another.

The distal end of the catheter assembly of this invention will enter and exit the interior of an 11-gauge needle cannula without any added lubrication, which is unique compared with other similar products currently available. As described below, this functionality is accomplished by a number of novel design and fabrication innovations. Among the novel design and fabrication innovations of some embodiments of this invention are the elimination of the inner catheter shaft and the modification of moving the radiopaque markings from inside the balloon, where they can interfere with and enlarge the wrapped profile of the balloon and thus compromise its ability to pass through the cannula easily, to the distal end of the device. As discussed hereinafter, however, in other invention embodiments it has been found possible to place one or two very thin radiopaque bands under the balloon and still wrap or fold it tightly enough to fit through the interior of an 11-gauge cannula.

In still another invention embodiment, eliminating the inner shaft and fixing the distal tip of a novel "floating" mandrel provides a configuration having the needed axial stiffness to properly place the device in a vertebral body while also allowing movement of the elastomeric polymer structures during balloon inflation without placing undue stress on the distal balloon bond. This invention embodiment also allows the balloon to stretch in length instead of bunching up during a removal step following an inflation/bone treatment procedure, and in this way this design feature further facilitates withdrawal of the deflated balloon through the interior of an 11-gauge cannula.

More particularly, the catheter/expandable element assembly of the present invention is specially designed and adapted to fit through an eleven (11) gauge cannula or needle cannula (both for insertion and for removal following an inflation/treatment procedure) while still providing an expandable element having a suitable balloon wall thickness (i.e., a 0.010 inch double wall thickness (DWT) or greater) to resist puncture by bone fragments during an inflation/bone dilatation and/or treatment procedure and to meet existing medical protocols. The several novel and unique cooperating synergistic design adaptations of this invention that make it possible to fabricate a catheter/expandable element assembly that can be slid through the interior of an 11-gauge cannula (for insertion or for removal following an inflation procedure) are described in greater detail below.

A first design change that characterizes the present invention is the substitution of a single lumen catheter shaft for the dual concentric lumen configuration found on conventional IBT devices.

A second design change that characterizes the present invention is the replacement of the conventional fully removable mandrel (which is ordinarily located in the inner catheter lumen of the concentric, dual-lumen catheter shaft) with a redesigned mandrel and a novel structure at the proximal end of the assembly. The redesigned mandrel of the present invention is not removable, but rather is a relatively permanent, integral part of the catheter/expandable element assembly. In the mandrel design of the present invention, the mandrel is capable of only limited, constrained axial movement (along or parallel to the axis of the catheter assembly) toward or away from the distal end of the assembly, and the extent of such movement is defined by a sleeve or channel at the proximal end of the assembly in which the free proximal end of the mandrel can slide.

These design modifications eliminate a large volume of material from the distal structure of the device, which in turn allows the balloon to be wrapped or folded into a smaller diameter (i.e., a reduced-diameter wrapped balloon profile), which in turn facilitates passage of the assembly through a smaller diameter needle cannula. In addition, the present invention incorporates a unique and completely novel "floating mandrel" design in which the mandrel is attached at the distal balloon bond but is nevertheless able to slide parallel to the long axis of the catheter shaft because the mandrel is not bonded at the proximal end of the device. This novel configuration allows the polymer body of the catheter assembly to shrink slightly during the pre-use sterilization and storage steps without causing severe distortion of the device. Such distortion could occur over time if both the proximal and distal ends of the mandrel were fixed at the respective ends of the device.

Providing for constrained axial movement of the mandrel also allows the elastomeric portion (expandable element) of the device to expand in length during an inflation procedure to very high pressures while the mandrel exerts little or no force on the distal balloon bond because the mandrel is allowed to move axially with the expanding elastomeric portion of the device as it grows in length during inflation. By contrast, if the mandrel were fixed at both ends within the device, the stretching of the balloon and outer shaft during an inflation procedure could result in peeling away the distal end of the elastomeric element from its bond to the mandrel and causing detachment of the mandrel from the distal bond. If the mandrel were to detach and the balloon were to fail, the mandrel could then puncture the balloon and exit the device into the bone interior through the failed section of the balloon.

To maintain the mandrel inside the catheter assembly at the proximal end of the assembly, while permitting constrained axial movement, a ball or other enlarged geometric feature is provided at the proximal end of the mandrel such that the ball or geometric feature can be captured by a suitable mandrel retaining structure provided within the bifurcation assembly portion located at the proximal end of the device. This ball or enlarged proximal end of the mandrel is captured at the proximal end of the device where the mandrel passes through a male fitting which has a hole drilled in its luer stem, such hole being smaller in diameter than the size of the ball or other enlarged geometric feature, thereby preventing the geometric feature (and the proximal end of the mandrel) from passing through the luer lock. The proximal end of the mandrel is thus able to slide within a sleeve portion of the proximal assembly end, but that axial movement is limited, for example to about 8 mm, of longitudinal (axial) motion.

At its distal end, the mandrel is preferably embedded in the balloon bond at the distal tip of the balloon to prevent the mandrel from exiting the interior of the balloon if the balloon should fail. In a preferred invention embodiment, this is achieved by using a stainless steel, helically coiled mandrel bonding spring element, typically about 2 mm in length, attached to the distal end of the mandrel. The mandrel bonding spring element preferably comprises a coil of stainless steel wire at least about 0.007 inches in diameter for structural integrity. Approximately 1 mm of the approximately 2 mm long spring element extends from the distal end of the mandrel. This 1 mm length of spring section extending from the distal end of the mandrel is encapsulated with a suitable material, such as a high durometer (e.g., 75 D) polyurethane polymer which fills the spring's interior and covers the exterior of its most distal 1 mm length of coils in polyurethane.

The use of high durometer polyurethane provides a strong anchor for the balloon bond to the mandrel bonding spring coil interior so that this bond will resist deformation and failure during inflation of the balloon. This polyurethane encapsulation is then also preferably bonded to the interior of the distal balloon neck. With the distal end of the mandrel bonding spring thus encapsulated, the distal tip of the mandrel stays within the balloon bond even if the balloon should split through the distal neck of the balloon during a balloon failure.

In another preferred embodiment design feature of this invention, a radiopaque distal tip may also be incorporated into the polyurethane encapsulation at the distal tip of the device. The radiopaque marker used in the distal tip of an 11-gauge IBT catheter assembly in accordance with an embodiment of this invention can be formed using the following multi-step process. The first step is mixing a tungsten filler, which is made into a fine powder, with a suitable polymer. Polyurethane is a preferred polymer for this application. The polymer is blended and pelletized in preparation for the next fabrication step. The second step is an extrusion process. In this step, the pellets are fed into an extruder where they are melted and formed into a solid radiopaque marker rod (beading) typically about 1 mm in diameter. The last step is to cut the radiopaque marker rod into small lengths, e.g., 2 to 3 mm long, and those short lengths are bonded inside the distal balloon neck portion of the expandable element by thermal or adhesive means. Once the length of radiopaque marker rod is bonded, the distal tip is trimmed to a suitable length leaving about 1 mm of radiopaque marker rod in the distal tip of the catheter assembly.

Alternatively, the spring element itself used to secure the distal end of the mandrel could be fashioned from a radiopaque metal (e.g., platinum) or from an alloy of a radiopaque metal, which could be easily viewed under fluoroscopy. It would be necessary, however, for the radiopaque metal or alloy used for this mandrel bonding spring fabrication to have the necessary tensile strength sufficient for reliable operation in this capacity.

The design of the proximal and distal ends of the mandrel can be varied and still function effectively substantially as described herein. In alternative invention embodiments, the distal end of the mandrel could be in the form of braided wires, a hypotube with holes or slots, slots or holes made in the distal end of the mandrel, or other means of establishing the passages where a material, such as a polymer, can be flowed or otherwise applied during assembly to fill in open spaces and to form a strong mechanical bond to the distal end of the mandrel when the polymer hardens. In still other embodiments, a distal portion of the mandrel may comprise a reduced diameter section, or a spring section, or a flattened section to provide increased flexibility of the mandrel, at least for a mandrel portion located inside the expandable element. In some embodiments, the distal end of the mandrel may comprise a core wire with a hooked or angled end that can engage a distal portion of a spring element located inside the expandable element to provide active deflection of the distal tip of the expandable element.

In other alternative invention embodiments, the proximal ball end of the mandrel could be substituted by a hooked or angled proximal mandrel end, for example with the end folded over on itself, or by any other means to make it larger in diameter such that the proximal mandrel end is retained by a male cap or other mandrel proximal end retaining structure to provide comparable retention functionality to the ball proximal end design. In other alternative invention embodiments, proximal end of mandrel may extend beyond the proximal end of the catheter shaft and be axially moveable to apply tensioning to the distal end.

In still another important aspect of this invention, the bond juncture (where the expandable element and the catheter shaft are joined and sealed) is formed such that the maximum diameter of the catheter assembly at this juncture is less than the smallest possible inside diameter of a standard 11-gauge cannula (i.e., 0.092 inches based on an ID of 0.094 inches with a tolerance of ±0.002 inches). This sizing allows the passage of the catheter assembly through the 11-gauge cannula without the need for any lubricating fluids. Currently available catheter assemblies for these bone dilatation applications employ a lap joint as a means to attach the proximal balloon neck of the expandable element to the catheter shaft. This means that the balloon proximal neck must be placed over the distal end of the catheter shaft prior to bonding these components, and this approach requires that the balloon neck ID must be greater than the shaft outside diameter at this juncture. This type of construction (i.e., balloon neck over the shaft) creates a juncture that would typically be slightly smaller than the original outer diameter of the balloon neck prior to bonding if a thermal bonding procedure is used (because there is some melting that occurs with the thermal bonding). Alternatively, the juncture would be about the same diameter as the outer diameter of the balloon neck if an adhesive bonding procedure is used. In either of these cases, however, the juncture between the catheter shaft and the balloon neck for the balloon-neck-over-the-catheter-shaft configuration would necessarily be significantly larger than the outside diameter of the distal end of the catheter shaft because of the added thickness of the balloon neck.

By contrast, the catheter assembly of this invention preferably utilizes a butt-joint bonding procedure in which the distal end of the catheter shaft is butt up against the proximal balloon neck (which can be substantially the same outer diameter as the catheter shaft), and the two components are bonded by an adhesive bonding, solvent bonding, thermal bonding or equivalent bonding procedure. In this fabrication procedure, the juncture between the catheter shaft and the balloon neck can have substantially the same diameter as the catheter shaft and the balloon neck. The resulting bond is very close or identical in diameter to the original catheter shaft diameter. This fabrication approach, which is novel in this field, reduces the maximum outer diameter of the catheter assembly at this critical juncture location by as much as 25% compared with conventional catheter assemblies being used for this procedure.

Additionally, as discussed above, catheters currently available employ lubricating fluids to a great extent, coating these devices quite heavily in order to facilitate sliding a catheter that has a marginal interference fit with the inside diameter of the cannula through the interior of the cannula and without damage to the catheter assembly. Without the heavy use of such lubrication, these conventional catheter assemblies would be unable to pass through the cannula or would do so only with force and great difficulty. However, these lubricating fluids are generally silicone-based oils which can cause contamination of the interior bone site and also interfere with adhesion when they are transferred to the interior of a bone structure that is being treated. These lubricating fluids can be carried by the expandable element and transferred to the interior of the vertebra, thereby compromising the adhesion of cement to the bone in a subsequent treatment step. The advantages of employing the butt-joined shaft/balloon bond as described above, in combination with one or more of the other novel design and fabrication innovations of this invention, make it possible to completely eliminate the use of lubricating fluids which can contaminate the interior of the vertebral cavity, cause interference with complete adhesion of cement to the bone, and also expose the patient's bone interior to these substances.

In addition, in other embodiments, the design and fabrication features of this invention as herein described may be used in combination with the features taught by U.S. Pat. No. 7,488,337 for tensioning, stretching, folding and/or wrapping the expandable element, especially to facilitate removal of the expandable element through an 11-gauge cannula following an inflation/bone dilatation procedure.

In one embodiment, the distal end of the balloon is sealed off either by integral manufacturing of a sealed end balloon, for example in accordance with U.S. Pat. No. 5,411,477, which is incorporated herein by reference, or by sealing or potting the distal balloon neck. This end is left unattached and an axially-oriented push rod is used to push against the sealed end of the balloon causing tension and axial elongation or movement of the balloon during deflation, which causes the balloon to form a number of longitudinal pleats or folds which substantially reduces the profile of the deflated balloon allowing it to be more easily withdrawn. The fact that the distal end is not attached makes this embodiment easier to manufacture and reduces the chance of a leak point by eliminating a glue or bond joint.

In an alternative embodiment, the distal end of the balloon can be attached to the push rod by adhesive or thermal bonding if desired. The push rod can be rotated and pushed to produce an even tighter re-wrap of the balloon. Both active and passive rotation of the push rod can be used.

The push rod can be spring loaded anywhere along the shaft, preferably at the back (proximal) end of the catheter inside a suitable manifold where the force, distance and other important parameters can be easily controlled, permanently set, or be made adjustable by the device user. The force can be active or passive, it can be adjusted so that there is always an axial load on the balloon or only a load when the balloon is inflated and deflated. Once the balloon is stretched a predetermined amount the tension is released. The removal of constant tension during sterilization, storage, etc. can be important to prevent creep or weakening of the balloon and at the bond areas. A method of passive tension, but with an active preparation before using it, may be the most desirable approach for many applications.

The push rod itself can be a compressive spring or a spring can be incorporated anywhere along the length of the push rod or machined as part of the rod. Alternatively, the design can be fabricated such that there is no push rod, but the hollow tube has a spring section either attached or integrally formed somewhere along its length inside the balloon, and the balloon is attached to this rod at one or both ends. The tension can also be provided by hydraulic or pneumatic actuation on the back end of the device, or a pneumatic bladder can be inflated in the back.

An adjustable position/tension rod may be preferred in some applications in which the balloon may be inflated to very high pressure beyond its elastic limit where permanent axial and radial deformation may occur. Such deformation would require the catheter design to accommodate this growth to insure that enough tension and axial displacement takes place to fold the balloon down.

In all of these designs, inflation of the balloon will cause the balloon to fill up in diameter while causing the overall length of the balloon to shorten, which will push or compress the shaft. The tension is designed to allow the balloon to fully expand. As the balloon is deflated, the tension in the shaft pushes the distal end in the distal direction and begins folding or collapsing the balloon and may also assist in more rapid deflation of the balloon. In another embodiment, elastomeric tubing can be placed over the balloon to help it refold and to protect the balloon from damage. The balloon can also be coated to help improve its puncture and abrasion resistance.

In still another embodiment of the present invention, a balloon that is longer than the length necessary to fill a bone or similar body cavity can be used, and the cannula can be designed so as to restrict any expansion thereby creating an absolute maximal dilation region for each and every application without wasting space for the balloon transitions or requiring multiple length balloons for treating various size vertebral or other bone or body cavities. All that would be necessary is to have available several balloon diameters or a more compliant balloon, but of only one length. In this embodiment, it is also envisioned to size or position the cannula such that the distal end may extend partially into the cavity to be dilated so as to further control balloon length and area of dilation.

In still another embodiment, after dilating a balloon or inflation element in accordance with this invention, the rod structure is removed, the balloon is filled with cement or a cement-like material that cures and hardens in situ and left in place as an implant. After removing the cannula, the long proximal neck can be cut off to separate the proximal end of the catheter from the filled balloon element. In another variation, a hollow push rod could be left in place during cement filling of the balloon to act as a vent tube, which would be removed after the balloon is full of cement.

In yet another embodiment of this invention, multi-lumen balloon elements, for example as described in my U.S. Pat. Nos. 5,342,301; 5,569,195; and 5,624,392, which are incorporated herein by reference, may be used as the balloon elements for the catheters of this invention.

The following are particularly preferred embodiments of the present invention:

1. A catheter/expandable element assembly for medical applications comprising a conforming catheter shaft having proximal and distal ends, an expandable element having an expandable balloon portion bonded at the distal end of the catheter shaft, and a fluid passageway extending from a proximal end of the catheter shaft to the interior of the balloon portion of the expandable element, the assembly being characterized by one or more of the following features:
 (a) the expandable element comprises a conforming balloon which can be folded or wrapped to a maximum diameter of less than 0.092 inches;
 (b) the assembly including both a wrapped/folded balloon portion and a juncture between the catheter shaft and a proximal balloon neck portion will fit through the interior of a standard 11-gauge medical cannula;
 (c) the assembly including both a wrapped/folded balloon portion and a juncture between the catheter shaft and a proximal balloon neck portion will fit through the interior of a standard 11-gauge medical cannula without the use of any lubricant or similar friction-reducing substance;
 (d) the expandable element can be folded or wrapped to sufficiently reduce the cross-sectional profile of the assembly to be compatible with the use of a narrow gauge cannula;
 (e) the expandable element can be folded or wrapped to sufficiently reduce the cross-sectional profile of the assembly to be compatible with the use of an 11-gauge or smaller-diameter cannula;
 (f) the catheter shaft is a single lumen catheter shaft and the assembly including both a wrapped/folded balloon portion and a juncture between the catheter shaft and a proximal balloon neck portion fits through the interior of a standard 11-gauge medical cannula;
 (g) the expandable element comprises a proximal neck portion that is butt-jointed by an adhesive bonding procedure, a solvent bonding procedure or a thermal bonding procedure to the distal end of the catheter shaft;
 (h) the expandable element comprises a distal neck portion having a sealed tip, and the sealed tip contains the only radiopaque marker along the expandable element;
 (i) the expandable element comprises one or more bands of a radiopaque material under a balloon portion of the element with or without radiopaque material at a distal tip of the expandable element;
 (j) the assembly additionally comprises a mandrel element that extends from a proximal end of the assembly, through the catheter shaft, and through the expandable element to an interior distal end of the assembly;
 (k) the assembly additionally comprises a mandrel element that extends from an interior proximal end of the assembly, through the catheter shaft, and through the expandable element to an interior distal end of the assembly and further wherein a distal end of the mandrel is bonded to the interior distal end of the assembly;
 (l) the assembly additionally comprises a catheter bifurcation assembly at the proximal end of the catheter shaft;
 (m) the assembly additionally comprises a catheter bifurcation assembly at a proximal end having an inflation arm portion and a mandrel arm portion, where the mandrel arm portion is substantially in axial alignment with the catheter shaft;
 (n) the assembly additionally comprises a catheter bifurcation assembly at a proximal end having an inflation arm portion and a mandrel arm portion, where the mandrel arm portion is substantially in axial alignment with the catheter shaft and further wherein the proximal end of the mandrel arm portion provides an enclosed sleeve for limited axial movement of the mandrel and the proximal end of the mandrel is of an enlarged size such that the proximal end of the mandrel is retained in the sleeve;
 (o) the assembly additionally comprises a mandrel element and a balloon-wrapping and/or tensioning device for actively or passively applying axial and/or rotational forces to the balloon portion following a balloon inflation and treatment procedure and subsequent deflation but prior to the withdrawal step causing the balloon portion to stretch axially and/or to wrap at least in part around a mandrel element to reduce the profile of the balloon portion and thereby facilitate the withdrawal step;
 (p) the assembly additionally comprises a mandrel element that extends from an interior proximal end of the assembly, through the catheter shaft, and through the expandable element to an interior distal end of the assembly, and further wherein a distal end of the mandrel is bonded to the distal end of the assembly and an unbonded proximal end of the mandrel has an enlarged geometrical feature that can move axially along or parallel to the axis of the catheter shaft but only within an enclosed sleeve that is bounded at its proximal end by the interior proximal end of the assembly and is bounded at its distal end by a mandrel retaining structure;

(q) the assembly additionally comprises a mandrel element that extends from a proximal end of the assembly, through the catheter shaft, and through the expandable element to an interior distal end of the assembly, wherein a distal portion of the mandrel is of a reduced diameter relative to a more proximal portion of the mandrel;

(r) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion;

(s) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils;

(t) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein there is greater spacing between adjacent spring coils along a distal portion of the spring than along a more proximal spring portion;

(u) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein the spring is covered by a polymeric sleeve;

(v) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein the proximal end of the mandrel extends proximally of the assembly and terminates in an enlarged geometrical feature whereby the mandrel can be axially tensioned by pulling on that proximal mandrel end so as to compress the spring where the hooked mandrel tip engages the spring coils and thereby causing the distal end of the expandable element to temporarily deflect from an axial orientation for as long as the mandrel is axially tensioned; and, (w) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements at the proximal end of the catheter/expandable element assembly whereby the threadably-engaged tensioning elements provide an axial channel in which the proximal end of the mandrel can slide such that rotating one tensioning element relative to the other causes one of the tensioning elements to move in a proximal direction relative to the second element thereby applying axial tensioning to the mandrel and causing deflection of the hooked mandrel tip and the distal tip of the expandable element as long as the axial tensioning is applied.

2. A system for carrying out a medical dilatation and/or a cavity creation, enlargement or treatment procedure at an internal body site comprising a catheter/expandable element assembly according to any combination of characterizing features of the invention as described in paragraph 1 above, in combination with an 11-gauge cannula capable of delivering the expandable element from outside the body to the desired internal body site.

3. A system for carrying out a medical dilatation and/or a cavity creation, enlargement or treatment procedure at an internal body site comprising a catheter/expandable element assembly according to any combination of characterizing features of the invention as described in paragraph 1 above, in combination with a narrow gauge cannula capable of delivering the expandable element from outside the body to the desired internal body site.

4. A system according to either of paragraphs 2 or 3 above, wherein the interior of the cannula is free of any lubricant and also wherein no lubricant is applied to the catheter/expandable element assembly.

5. A method for carrying out a medical treatment that includes a dilatation and/or a cavity creation, enlargement or treatment procedure using a catheter/expandable element assembly according to any combination of characterizing features of the invention as described in paragraph 1 above, the method comprising the steps of: (a) inserting at least the expandable element portion of the assembly through an 11-gauge cannula to position the expandable element in the interior of a bone or body site; (b) inflating the expandable element inside the interior of the bone or body site to a size and/or inflation pressure and for a time sufficient to complete the treatment; (c) deflating the expandable element; and (d) withdrawing the expandable element portion of the assembly through the cannula.

6. A method for carrying out a medical treatment that includes a dilatation and/or a cavity creation, enlargement or treatment procedure using a catheter/expandable element assembly according to any combination of characterizing features of the invention as described in paragraph 1 above, the method comprising the steps of: (a) inserting at least the expandable element portion of the assembly through a narrow gauge cannula to position the expandable element in the interior of a bone or body site; (b) inflating the expandable element inside the interior of the bone or body site to a size and/or inflation pressure and for a time sufficient to complete the treatment; (c) deflating the expandable element; and, (d) withdrawing the expandable element portion of the assembly through the cannula.

7. A method according to either of paragraphs 5 or 6 above, additionally comprising a step of stretching, folding and/or wrapping the expandable element following step (c) and prior to step (d).

8. A method for carrying out a medical treatment that includes a dilatation and/or a cavity creation, enlargement or treatment procedure using a system according to either of paragraphs 2 or 3 above, the method comprising the steps of: (a) positioning the cannula in a body location so that a distal end of the cannula is proximate to the intended treatment site; (b) inserting at least the expandable element portion of the assembly through the cannula to position the expandable element in the interior of a bone or body site without the use of any lubricants; (c) inflating the expandable element inside the interior of the bone or body site to a size and/or inflation pressure and for a time sufficient to complete the treatment; (d) deflating the expandable element; and, (e) withdrawing the expandable element portion of the assembly through the cannula without the use of any lubricants.

9. A method of manufacturing the assembly of the invention as described in paragraph 1 above, by bonding the catheter shaft to the expandable element, the method comprising the steps of butting an end of the catheter shaft against a similarly-sized open end of the expandable element followed by an adhesive bonding procedure, a solvent bonding procedure or a thermal bonding procedure for securing the two abutting ends to one another thereby creating a fluid passageway through the interior of the catheter shaft and into the balloon portion of the expandable element.

10. A method of manufacturing the assembly of the invention as described in paragraph 1 above, including positioning a mandrel inside the assembly for restricted axial movement of the mandrel, the method comprising the steps of bonding the distal end of the mandrel to the inside distal end of the expandable element and positioning the proximal end of the mandrel inside an enclosed sleeve at the proximal end of the assembly.

11. The method of manufacturing the assembly of the invention as described in paragraph 10 above, wherein the mandrel has an enlarged proximal end that cannot pass through an aperture in a mandrel retention structure at the proximal end of the catheter/expandable element assembly that thereby retains the enlarged proximal end of the mandrel in the sleeve.

12. A method of practicing the invention according to either of paragraphs 5 or 6 above, additionally comprising a step, between steps (a) and (c), of temporarily deflecting the distal tip of the expandable element out of axial alignment by applying axial tensioning to the slidable proximal end of a mandrel having a hooked mandrel distal tip that engages at least some of the coils of a coiled spring element surrounding the mandrel inside the expandable element, where the distal end of the spring element is bonded to the distal tip of the expandable element.

13. A method of practicing the invention according to paragraph 12 above, further comprising a step, before step (d), of relaxing the axial tensioning of the mandrel and allowing the expandable element to return to axial alignment by action of the spring element.

14. A method of practicing the invention according to either of paragraphs 5 or 6 above, additionally comprising a step, between steps (a) and (c), of rotating one of two threadably engaged mandrel tensioning elements at a proximal end of the assembly in a first rotation direction so as to move the rotating element in a proximal direction thereby axially tensioning the mandrel of the assembly, which engages at its distal end a spring element located inside and fixed to the end of the expandable element, causing deflection of the tip of the expandable element out of axial alignment.

15. A method of practicing the invention according to paragraph 1 above, further comprising a step, before step (d), of rotating the rotatable threaded tensioning element in a second rotation direction so as to relax the axial tensioning of the mandrel and to permit the spring element to return the expandable element to axial alignment.

16. An assembly adapted for bone, tissue and/or duct dilatation of a living being comprising in combination: a hollow tube; an inflatable and deflatable balloon element having proximal and distal ends in fluid communication with the hollow tube; and, balloon tensioning and/or balloon wrapping device(s) for stretching the balloon element and/or folding, pleating or wrapping the balloon element to facilitate insertion and/or removal of the balloon element through a narrow diameter duct, access channel or cannula.

17. An assembly according to paragraph 16 above in which said balloon element is capable of being inflated to a working diameter of about 12 mm to about 25 mm.

18. An assembly according to paragraph 16 above in which said balloon element is capable of being inflated to a working pressure of about 200-400 psi over a relatively short balloon working length.

19. An assembly according to paragraph 16 above in which said balloon element is stretched and/or folded, pleated or wrapped to a diameter of about 4-5 mm or less for insertion through and/or removal from said duct, access channel or cannula.

20. An assembly according to paragraph 16 above in which said balloon tensioning and/or balloon wrapping device(s) is/are selected from the group consisting of active and passive tensioning and wrapping devices.

21. An assembly according to paragraph 16 above in which, upon inflation to its working pressure, the balloon element maintains a high degree of puncture and abrasion resistance.

22. An assembly according to paragraph 16 above in which the balloon element is mounted on the distal end of the hollow tube, and the proximal end of the balloon element is bonded to or integrally connected with an end of the tube to create a passage through the tube to the interior of the balloon element.

23. An assembly according to paragraph 22 above in which the distal end of the balloon element is sealed, and the assembly further comprises a rod element running through the passage of the tube and the interior of the balloon element to the sealed distal end of the balloon element.

24. An assembly according to paragraph 23 above in which axial force can be applied manually or automatically to push the rod element against the sealed distal end of the balloon element causing tension and axial elongation of the balloon element.

25. An assembly according to paragraph 24 above in which the rod element is not attached to the balloon element.

26. An assembly according to paragraph 24 above in which the rod element is attached to or otherwise engages the balloon element.

27. An assembly according to paragraph 26 above in which wherein rotational force can be applied manually or automatically to rotate the rod element from its free-standing position causing the balloon element at least in part to wrap around the rod element.

28. An assembly according to paragraph 24 above in which wherein said rod element is spring loaded to apply axial tensioning and elongation to the balloon element.

29. An assembly according to paragraph 26 above in which said rod element is spring loaded to apply rotational tensioning to the balloon element.

30. An assembly according to paragraph 26 above in which said rod element is spring loaded to apply both automatic axial and rotational tensioning to the balloon element.

31. An assembly according to paragraph 24 above in which said rod element comprises a compressive or rotational spring element.

32. An assembly according to paragraph 22 above in which said hollow tube comprises a compressive spring element.

33. An assembly according to paragraph 16 above in which the balloon tensioning and/or wrapping device is hydraulically or pneumatically actuated.

34. An assembly according to paragraph 23 above in which said rod element is adjustable in length.

35. An assembly according to paragraph 16 above including elastomeric tubing placed over said balloon element.

36. An assembly according to paragraph 16 above in which wherein the exterior of said balloon element is coated with a material to improve puncture and abrasion resistance.

37. An assembly according to paragraph 26 above including at least a cannula element wherein at least one end of the balloon element extends into or completely through said cannula element when the balloon element is positioned in a cavity to be dilated.

38. An assembly according to paragraph 37 above in which said cannula element is adapted to restrict expansion forces of the balloon element during inflation.

39. An assembly according to paragraph 23 above in which, after the balloon element is inserted in a cavity to be dilated and inflated to working pressure for a sufficient period of time, the interior of the inflated balloon element is filled in situ with a cement material.

40. An assembly according to paragraph 39 above in which the rod element is removed before the balloon element is filled with a cement material.

41. An assembly according to paragraph 39 above in which the rod element has a hollow interior to act as a vent for working fluid while the balloon element is filled with a cement material, and is removed before the cement hardens.

42. An assembly according to paragraph 39 above in which the hollow tube is detached from the balloon element after the balloon element is filled with the cement material.

43. An assembly according to paragraph 16 above in which said balloon element comprises a multi-lumen balloon.

44. An assembly according to paragraph 26 above in which said rod element is spring loaded to apply automatic axial tensioning to the balloon element and is adapted for optional manual rotational tensioning of the balloon element.

45. An assembly according to paragraph 16 above including a pre-curved guidewire in the interior of the balloon element.

46. An assembly according to paragraph 23 above in which said rod element comprises concentric inner and outer tubular members which are rotatable relative to one another and said balloon element is attached to or engages one of said tubular members whereby rotational forces can be applied to cause the balloon element at least in part to wrap around one of said tubular members.

47. An assembly according to paragraph 23 above in which wherein said rod element is pre-curved and consists essentially of a material having memory properties.

48. An assembly according to paragraph 16 above in which said balloon element is pre-curved.

49. An assembly according to paragraph 16 above in which said balloon element consists essentially of a non-elastomeric material.

50. A method for treating a living being for bone, tissue and/or body duct dilatation comprising the sequential steps of: inserting an inflatable balloon element in an uninflated state into an interior region, cavity or passage of a damaged, collapsed or deformed bone, tissue or duct through a first narrow diameter opening or passageway to position the balloon element at a body location requiring dilatation; inflating the balloon element with a working fluid to a working pressure and for a time period sufficient to substantially completely dilate the interior region, cavity or passage to substantially restore its normal size, shape and/or alignment; deflating the balloon element by withdrawing the working fluid; during and/or subsequent to said deflating step, stretching and/or folding, pleating or wrapping the balloon element to reduce its profile; and, withdrawing the previously-inflated balloon element through a narrow diameter opening or passageway, which may be the same as or different than said first narrow diameter opening or passageway.

51. A method according to paragraph 50 above in which said balloon element is inflated to a working diameter of about 12 mm to about 25 mm during the inflating step.

52. A method according to paragraph 50 above in which said balloon element is inflated to a working pressure of about 200-400 psi over a relatively short balloon working length during the inflating step.

53. A method according to paragraph 16 above in which said balloon element is stretched and/or folded, pleated or wrapped to a diameter of about 4-5 mm or less for the steps of inserting and/or withdrawing the balloon element.

54. A method according to paragraph 50 above in which said balloon element is stretched and/or folded, pleated or wrapped using at least a balloon tensioning and/or balloon wrapping device selected from the group consisting of active and passive tensioning and wrapping devices.

55. A method according to paragraph 50 above in which, following inflation to its working pressure, the balloon element maintains a high degree of puncture and abrasion resistance.

56. A method according to paragraph 50 above including the step of applying a vacuum to the inflated balloon element during the deflating step to assist with drawal of the working fluid.

57. A method according to paragraph 50 above in which the balloon element is mounted on the distal end of a hollow tube, and the proximal end of the balloon element is bonded to or integrally connected with an end of the tube to create a passage through the tube to the interior of the balloon element.

58. A method according to paragraph 57 above in which the distal end of the balloon element is sealed.

59. A method according to paragraph 58 above in which a rod element passes through the tube and the interior of the balloon element to the sealed end of the balloon element.

60. A method according to paragraph 59 above including the step of applying axial force manually or automatically to said sealed end of the balloon element through said rod element during and/or subsequent to the deflating step causing tension and axial elongation of the balloon element.

61. A method according to paragraph 60 above in which the rod element is not attached to the balloon element.

62. A method according to paragraph 60 above in which the rod element is attached to or otherwise engages the balloon element.

63. A method according to paragraph 62 above including the step of applying rotational force manually or automatically to said rod element during and/or subsequent to the deflating step causing the balloon element at least in part to wrap around the rod element.

64. A method according to paragraph 60 above in which said rod element is spring loaded to apply axial tensioning and elongation to the balloon element.

65. A method according to paragraph 63 above in which said rod element is spring loaded to apply rotational tensioning to the balloon element.

66. A method according to paragraph 50 above in which the balloon tensioning and/or wrapping device is hydraulically or pneumatically actuated.

67. A method according to paragraph 59 above in which said rod element is adjustable in length, said method further comprising the step of adjusting the length of said rod element such that said rod element applies an axial tensioning to the balloon element during the deflating step.

68. A method according to paragraph 50 above including the step of coating the exterior of the balloon element with a coating to improve puncture and abrasion resistance.

69. A method according to paragraph 50 above in which, upon inserting the balloon element into an interior region, cavity or passage, at least one end of the balloon element extends into or completely through a cannula element positioned in one of the narrow diameter openings or passageways.

70. A method according to paragraph 50 above in which said balloon element comprises a multi-lumen balloon.

71. A method according to paragraph 62 above in which said rod element is spring loaded to automatically apply axial tensioning to the balloon element during the deflating step, said method further comprising the step of applying manual rotational tensioning to the balloon element during and/or subsequent to the deflating step.

72. A method according to paragraph 50 above including the steps of positioning a guidewire through the interior region, cavity or passage to be dilated, and using the guidewire to position the balloon element during the inserting step.

73. A method according to paragraph 72 above in which said guidewire is pre-curved.

74. A method according to paragraph 59 above in which said rod element is pre-curved and fabricated from a material having memory properties.

75. A method according to paragraph 50 above in which said balloon element is pre-curved.

76. A method according to paragraph 50 above in which said balloon element consists essentially of a non-elastomeric material.

77. A method for treating a living being for bone or tissue dilatation comprising the sequential steps of: providing a dilatation apparatus able to fit through a narrow opening, said dilatation apparatus comprising an inflatable balloon element in fluid communication with a hollow tube, and a rod element running through the interior of the hollow tube and the inflatable balloon element, wherein said balloon element is uninflated and is wrapped, folded, pleated or stretched at least in part about said rod element to reduce the profile of the balloon portion of the dilatation apparatus; inserting the dilatation apparatus into an interior region, cavity or passage of a damaged, collapsed or deformed bone or tissue region through a first narrow diameter opening or passageway to position the balloon element at a body location requiring dilatation; inflating the balloon element through the hollow tube with a working fluid to a working pressure and for a time period sufficient to substantially completely dilate the interior region, cavity or passage to substantially its normal size, shape and/or alignment; and, filling the inflated balloon element in situ through the hollow tube with a cement material.

78. A method according to paragraph 77 above including the further steps of removing the rod element before filling the balloon element with cement material and detaching the hollow tube from the balloon element after it is filled with cement.

79. A method according to paragraph 77 above in which the rod element has a hollow interior which is used for venting working fluid from the balloon element while it is being filled with cement material.

80. A method according to paragraph 79 above including the steps of removing the rod element and detaching the hollow tube from the balloon element after it is filled with cement.

81. A method according to paragraph 77 above in which said balloon element is inflated to a working diameter of about 12 mm to about 25 mm during the inflating step.

82. A method according to paragraph 77 above in which said balloon element is inflated to a working pressure of about 200-400 psi over a relatively short balloon working length during the inflating step.

83. A method according to paragraph 77 above in which said balloon element is wrapped, folded, stretched and/or pleated about said rod element such that the balloon portion of the dilatation apparatus has a diameter of about 4-5 mm or less for the inserting step.

84. A method according to paragraph 77 above in which said balloon element comprises a multi-lumen balloon.

85. A method according to paragraph 77 above including the steps of positioning a guidewire through the interior region, cavity or passage to be dilated, and using the guidewire to position the balloon element during the inserting step.

86. A method according to paragraph 77 above in which said guidewire is pre-curved.

87. A method according to paragraph 77 above in which said rod element is pre-curved and fabricated from a material having memory properties.

88. A method according to paragraph 77 above in which said rod element is pre-curved and fabricated from a material having memory properties.

89. A method according to paragraph 77 above in which said balloon element consists essentially of a non-elastomeric material.

90. A method for treating a living being for dilatation of a section of a body duct to relieve a collapse or blockage condition comprising the sequential steps of: providing a dilatation apparatus able to fit through a narrow opening, said dilatation apparatus comprising an inflatable balloon element in fluid communication with a hollow tube, and a rod element running through the interior of the hollow tube and the inflatable balloon element, wherein said balloon element is uninflated and is wrapped, folded, pleated or stretched at least in part about said rod element to reduce the profile of the balloon portion of the dilatation apparatus; inserting the dilatation apparatus into a body duct to be dilated to position the balloon element at a duct section requiring dilatation; inflating the balloon element through the hollow tube with a working fluid to a working pressure and for a time period sufficient to substantially completely dilate the duct section to substantially its normal size; deflating the balloon element by withdrawing the working fluid; during and/or subsequent to said deflating step, stretching and/or folding, pleating or wrapping the balloon element to reduce its profile; and, withdrawing the dilatation apparatus including the previously-inflated balloon element from the treated duct.

91. A method according to paragraph 90 above in which said balloon element is inflated to a working diameter of about 12 mm to about 25 mm during the inflating step.

92. A method according to paragraph 90 above in which said balloon element is inflated to a working pressure of about 200-400 psi over a relatively short balloon working length during the inflating step.

93. A method according to paragraph 90 above in which said balloon element is stretched and/or folded, pleated or wrapped to a diameter of about 4-5 mm or less for the steps of inserting and/or withdrawing the balloon element.

94. A method according to paragraph 90 above in which said balloon element is stretched and/or folded, pleated or wrapped using at least a balloon tensioning and/or balloon wrapping device selected from the group consisting of active and passive tensioning and wrapping devices.

95. A method according to paragraph 90 above including the step of applying a vacuum to the inflated balloon element during the deflating step to assist with drawal of the working fluid.

96. A method according to paragraph 90 above in which the distal end of the balloon element is sealed, said method further comprising the step of applying axial force manually or automatically to said sealed end of the balloon element through said rod element during and/or subsequent to the deflating step causing tension and axial elongation of the balloon element.

97. A method according to paragraph 96 above in which the rod element is not attached to the balloon element.

98. A method according to paragraph 96 above in which the rod element is attached to or otherwise engages the balloon element.

99. A method according to paragraph 98 above including the step of applying rotational force manually or automatically to said rod element during and/or subsequent to the deflating step causing the balloon element at least in part to wrap around the rod element.

100. A method according to paragraph 96 above in which said rod element is spring loaded to apply axial tensioning and elongation to the balloon element.

101. A method according to paragraph 99 above in which said rod element is spring loaded to apply rotational tensioning to the balloon element.

102. A method according to paragraph 90 above in which the balloon tensioning and/or wrapping device is hydraulically or pneumatically actuated.

103. A method according to paragraph 90 above in which said rod element is adjustable in length, said method further comprising the step of adjusting the length of said rod element such that said rod element applies an axial tensioning to the balloon element during the deflating step.

104. A method according to paragraph 99 above in which said rod element is spring loaded to automatically apply axial tensioning to the balloon element during the deflating step, said method further comprising the step of applying manual rotational tensioning to the balloon element during and/or subsequent to the deflating step.

105. A method according to paragraph 90 above in which said rod element comprises concentric inner and outer tubular members which are rotatable relative to one another, and said balloon element is attached to or engages one of said tubular members, said method further comprising the step of rotating said tubular members relative to one another during an/or subsequent to the deflating step to cause the balloon element to wrap at least in part around one of said tubular members.

106. An assembly with proximal and distal ends for bone, tissue and/or duct dilatation of a living being comprising in combination: (a) a tube having a fluid inlet at a tube proximal end, a fluid outlet at a tube distal end, and a tube lumen extending between the fluid inlet and the fluid outlet; (b) an inflatable and deflatable balloon element having a balloon interior and balloon proximal and distal ends in fluid communication with the tube lumen, said balloon element being suitable for treating vertebral fractures and capable of being folded and/or wrapped to a sufficiently small diameter to fit through the interior of a narrow diameter cannula; and, (c) balloon tensioning and/or balloon wrapping device(s) for stretching the balloon element and/or folding, pleating or wrapping the balloon element before and/or after inflation to facilitate insertion and/or removal of the balloon element through a narrow diameter cannula, said balloon tensioning and/or balloon wrapping device(s) comprising at least a spring element, located at the proximal end of the assembly proximal of the fluid inlet and fluidically isolated from the tube lumen, which spring element can alternately be compressed or decompressed, said spring activating an associated rod extending through at least a part of said tube lumen and said balloon interior such that compression of the spring element toward the distal end applies an axial stretching force to the balloon and decompression of the spring element away from the distal end releases the axial stretching force.

107. An assembly according to paragraph 106 wherein said narrow diameter cannula is an 11-gauge or smaller cannula.

108. An assembly according to paragraph 106 wherein said balloon element is stretched and/or folded, pleated or wrapped to a diameter of about 4-5 mm or less for insertion through and/or removal from said duct, access channel or cannula.

109. An assembly according to paragraph 106 wherein said balloon tensioning and/or balloon wrapping device(s) is/are selected from the group consisting of active and passive tensioning and wrapping devices.

110. An assembly with proximal and distal ends for bone, tissue and/or duct dilatation of a living being comprising in combination:
(a) an inflatable and deflatable medical balloon having a balloon interior, said balloon being suitable for treating vertebral fractures and capable of being folded and/or wrapped to a sufficiently small diameter to fit through the interior of a narrow diameter cannula;
(b) a conduit defining a channel for accessing the balloon interior from a location outside a living body when the balloon is positioned inside the living body;
(c) a rod having proximal and distal ends extending through the channel to the balloon at the distal end of the rod;
(d) a spring element capable of temporarily applying axial and/or rotational forces to the balloon by means of the rod causing the balloon to elongate, or to wrap around the rod, or both, said spring element being housed in a spring housing section located at the proximal end of the assembly and fluidically isolated from the channel; and,
(e) a knob element connected to the proximal end of the rod for manual manipulation of the rod.

111. An assembly according to paragraph 110 wherein said balloon is stretched and/or folded, pleated or wrapped to a diameter of about 4-5 mm or less for insertion through and/or removal from a duct, access channel or cannula.

112. An assembly according to paragraph 110 further comprising an 11-gauge or smaller cannula wherein at least one end of the balloon extends into or completely through said cannula when the balloon is positioned in a cavity to be dilated.

113. An assembly with proximal and distal ends for bone, tissue and/or duct dilatation of a living being comprising in combination: (a) a tube having a fluid inlet at a tube proximal end, a fluid outlet at a tube distal end, and a tube lumen extending between the fluid inlet and the fluid outlet; (b) an inflatable and deflatable balloon element having a balloon interior and balloon proximal and distal ends in fluid communication with the tube lumen, said balloon element being suitable for treating vertebral fractures and capable of being folded and/or wrapped to a sufficiently small diameter to fit through the interior of a narrow diameter cannula; and, (c) balloon tensioning and/or balloon wrapping device(s) for stretching the balloon element and/or folding, pleating or wrapping the balloon element before and/or after inflation to facilitate insertion and/or removal of the balloon element through a narrow diameter cannula, said balloon tensioning and/or balloon wrapping device(s) comprising at least a spring element, located at the proximal end of the assembly proximal of the fluid inlet and fluidically isolated from the tube lumen, which spring element can alternately be compressed or decompressed, said spring activating an associated rod extending through at least a part of said tube lumen and said balloon interior such that compression of the spring element toward the distal end applies an axial stretching force to the balloon and decompression of the spring element away from the distal end releases the axial stretching force;
the assembly further comprising a spring housing section having proximal and distal ends for housing the spring element, the spring housing including a threaded portion at its proximal end and also comprising a threaded cap element sized to mate with the threaded portion of the spring housing, wherein the cap element includes a centrally-located axial bore to accommodate the rod, the rod including a section that extends through and beyond the cap element; and,
the assembly further comprising a sealing gasket between the spring element and the threaded portion of the spring housing, said gasket having a centrally located aperture in alignment with the axial bore to accommodate the rod.

114. An assembly with proximal and distal ends for bone, tissue and/or duct dilatation of a living being comprising in combination:
(a) an inflatable and deflatable medical balloon having a balloon interior, said balloon being suitable for treating vertebral fractures and capable of being folded and/or wrapped to a sufficiently small diameter to fit through the interior of a narrow diameter cannula;
(b) a conduit defining a channel for accessing the balloon interior from a location outside a living body when the balloon is positioned inside the living body;
(c) a rod having proximal and distal ends extending through the channel to the balloon at the distal end of the rod;
(d) a spring element capable of temporarily applying axial and/or rotational forces to the balloon by means of the rod causing the balloon to elongate, or to wrap around the rod, or both, said spring element being housed in a spring housing section located at the proximal end of the assembly and fluidically isolated from the channel; and,
(e) a knob element connected to the proximal end of the rod for manual manipulation of the rod; and,
further comprising a spring housing section having proximal and distal ends for housing the spring element, the spring housing including a threaded portion at its proximal end and also comprising a threaded cap element sized to mate with the threaded portion of the spring housing, wherein the cap element includes a centrally-located axial bore to accommodate the rod, the rod including a section that extends through and beyond the cap element; and,
further comprising a sealing gasket between the spring element and the threaded portion of the spring housing, said gasket having a centrally located aperture in alignment with the axial bore to accommodate the rod.

115. An assembly with proximal and distal ends for bone, tissue and/or duct dilatation of a living being comprising in combination:
(a) an inflatable and deflatable balloon element having a balloon interior, said balloon element being suitable for treating vertebral fractures and capable of being folded and/or wrapped to a sufficiently small diameter to fit through the interior of a narrow diameter cannula;

(b) a conduit defining a channel for accessing the balloon interior from a location outside a living body when the balloon is positioned inside the living body;

(c) a balloon tensioning and/or balloon wrapping device for stretching the balloon element and/or folding, pleating or wrapping the balloon element to facilitate insertion and/or removal of the balloon element through the narrow diameter cannula comprising a rod having proximal and distal ends extending through the channel to the balloon at the distal end of the rod;

(d) a sealing gasket inside the proximal end of the channel having a centrally-located aperture to accommodate the rod, whereby under compression the sealing gasket forms a fluid-tight seal of the channel; and, (e) a rod control element connected to the proximal end of the rod whereby the rod can be moved in a proximal or distal direction and/or rotated from a location outside the conduit.

116. An assembly according to paragraph 115 wherein active and/or passive forces can be applied to the rod for tensioning and/or wrapping the balloon element.

117. An assembly according to paragraph 115 wherein the distal end of the balloon element is sealed, and the rod extends to the sealed distal end of the balloon element.

118. An assembly according to paragraph 115 wherein the rod is not attached to the balloon element.

119. An assembly according to paragraph 115 wherein the rod is attached to or otherwise engages the balloon element.

120. An assembly according to paragraph 115 further wherein rotational force can be applied manually or automatically to rotate the rod from its free-standing position causing the balloon element at least in part to wrap around the rod.

121. An assembly according to paragraph 115 wherein said rod is positioned sufficiently in a distal direction to cause axial tensioning and elongation of the balloon element.

122. An assembly according to paragraph 115 wherein said rod is rotated sufficiently to cause wrapping and rotational tensioning of the balloon element.

123. An assembly according to paragraph 115 wherein said rod is positioned sufficiently in a distal direction and is rotated sufficiently to cause both axial and rotational tensioning of the balloon element.

124. An assembly according to paragraph 115 wherein said rod control element comprises a knob at the proximal end of the rod.

125. An assembly according to paragraph 115 wherein the rod is hydraulically or pneumatically actuated.

126. An assembly according to paragraph 115 wherein said rod is adjustable in length.

127. An assembly according to paragraph 115 further comprising at least a cannula element wherein at least one end of the balloon element extends into or completely through said cannula element when the balloon element is positioned in a cavity to be dilated.

128. An assembly according to paragraph 115 wherein said rod comprises concentric inner and outer tubular members which are rotatable relative to one another and said balloon element is attached to or engages one of said tubular members whereby rotational forces can be applied to cause the balloon element at least in part to wrap around one of said tubular members.

129. A balloon dilatation catheter apparatus having the following configuration: a proximal end catheter sleeve portion, a middle sleeve portion, and a balloon or inflation element at or near the distal end of the catheter apparatus, said balloon element being suitable for treating vertebral fractures and capable of being folded and/or wrapped to a sufficiently small diameter to fit through the interior of a narrow diameter cannula; the proximal end catheter sleeve portion comprises a branched or Y-shaped element, of which a first arm or branch comprises a tubular shell with external threads at its proximal end, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region housing a sealing gasket or a similar compressible sealing element having a centrally-located aperture; a cap element, that includes a centrally-located axial bore to accommodate a rod, and internal threads sized to mate with the external threads at the proximal end of the first branch, whereby the cap element engages the proximal end of the first branch; the rod also has a knob portion at its proximal end, and is slidably positioned inside the catheter and sized to extend axially the full length of the catheter, extending through the central bore of the cap, through the sealing gasket, which acts like a bushing for supporting and centering the rod, through the interiors of the proximal and middle catheter sleeves, and through the interior of the balloon to a sealed tip portion of the apparatus.

130. An assembly with proximal and distal ends for bone, tissue and/or duct dilatation of a living being comprising in combination: (a) a tube having a fluid inlet at a tube proximal end, a fluid outlet at a tube distal end, and a tube lumen extending between the fluid inlet and the fluid outlet; (b) an inflatable and deflatable balloon element having a balloon interior and balloon proximal and distal ends in fluid communication with the tube lumen, said balloon element being suitable for treating vertebral fractures and capable of being folded and/or wrapped to a sufficiently small diameter to fit through the interior of a narrow diameter cannula; and, (c) a balloon tensioning and/or balloon wrapping device for stretching the balloon element and/or folding, pleating or wrapping the balloon element before and/or after inflation to facilitate insertion and/or removal of the balloon element through a narrow diameter cannula, said balloon tensioning and/or balloon wrapping device comprising at least a rod slidably extending through at least a part of said tube lumen and said balloon interior such that the rod can be externally manipulated by moving it in a distal direction to apply an axial stretching force to the balloon and/or it can be externally rotated to at least partly wrap the balloon element and apply rotational tensioning to the balloon element;

said assembly further comprising: a threaded portion at the proximal end of the assembly; a threaded cap element sized to mate with the threaded portion, wherein the cap element includes a centrally-located axial bore to accommodate the rod, and the rod includes a section that extends through the axial bore of the cap element; and a sealing gasket in the interior of the threaded portion, said gasket having a centrally-located aperture in alignment with the axial bore of the cap element to accommodate the rod, whereby the cap element engages the threaded portion such that by turning the cap element the sealing gasket is compressed to form a fluid-tight seal at the proximal end of the assembly.

131. An assembly with proximal and distal ends for bone, tissue and/or duct dilatation of a living being comprising in combination:

an inflatable and deflatable medical balloon having a balloon interior, said balloon element being suitable for treating vertebral fractures and capable of being folded and/or wrapped to a sufficiently small diameter to fit through the interior of a narrow diameter cannula;

a conduit defining a channel for accessing the balloon interior from a location outside a living body when the balloon is positioned inside the living body;

a rod having proximal and distal ends extending through the channel to the balloon; and, a knob element connected to the proximal end of the rod for manual manipulation of the rod;

further wherein the assembly comprises: a threaded portion at a proximal end; a threaded cap element sized to mate with the threaded portion, wherein the cap element includes a centrally-located axial bore to accommodate a rod, and the rod includes a section that extends through the axial bore of the cap element; and a sealing gasket in the interior of the threaded portion, said gasket having a centrally-located aperture in alignment with the axial bore of the cap element to accommodate the rod, whereby the cap element engages the threaded portion such that by turning the cap element the sealing gasket is compressed to form a fluid-tight seal at the proximal end of the assembly.

132. An assembly with proximal and distal ends for bone, tissue and/or duct dilatation of a living being comprising in combination:
(a) an inflatable and deflatable balloon element having a balloon interior, said balloon element being suitable for treating vertebral fractures and capable of being folded and/or wrapped to a sufficiently small diameter to fit through the interior of a narrow diameter cannula;
(b) a conduit defining a channel for accessing the balloon interior from a location outside a living body when the balloon is positioned inside the living body;
(c) a balloon tensioning and/or balloon wrapping device for stretching the balloon element and/or folding, pleating or wrapping the balloon element to facilitate insertion and/or removal of the balloon element through the narrow diameter cannula, the device comprising a rod having proximal and distal ends and extending through the channel to or into the balloon element at the distal end of the rod in combination with a spring adjacent the proximal end of the rod, whereby compression of the spring applies an axial force to the rod tending to move it in a distal direction so as to apply axial tensioning to the balloon element; and,
(d) a rotatable cap at the proximal end of the assembly whereby rotating the cap in a first direction compresses the spring and rotating the cap in a second direction decompresses the spring.

133. An assembly according to paragraph 132 wherein active and/or passive forces can be applied to the rod for tensioning and/or wrapping the balloon element.

134. An assembly according to paragraph 132 wherein the distal end of the balloon element is sealed, and the rod extends to the sealed distal end of the balloon element.

135. An assembly according to paragraph 134 wherein the cap can be rotated manually or automatically to compress the spring and push the rod against the sealed distal end of the balloon element causing tension and axial elongation of the balloon element.

136. An assembly according to paragraph 132 wherein the rod is attached to or otherwise engages the balloon element.

137. An assembly according to paragraph 132 further wherein compression of the spring also applies rotational force to rotate the rod from its free-standing position causing the balloon element at least in part to wrap around the rod.

138. An assembly according to paragraph 132 wherein the spring has been at least partly compressed and said rod has been moved in a distal direction causing axial tensioning and elongation of the balloon element.

139. An assembly according to paragraph 132 wherein the spring has been at least partly compressed and said rod has been rotated causing wrapping and rotational tensioning of the balloon element.

140. An assembly according to paragraph 132 wherein the spring has been at least partly compressed and said rod has been moved in a distal direction and rotated causing both axial and rotational tensioning of the balloon element.

141. An assembly according to paragraph 132 wherein the balloon tensioning and/or wrapping device is hydraulically or pneumatically actuated.

142. An assembly according to paragraph 132 wherein said rod is adjustable in length.

143. An assembly according to paragraph 132 further comprising a cannula wherein at least one end of the balloon element extends into or completely through said cannula when the balloon element is positioned in a cavity to be dilated.

144. An assembly according to paragraph 132 wherein said rod is spring loaded to apply axial tensioning to the balloon element and is also adapted for rotational tensioning of the balloon element.

145. A dilatation apparatus able to fit through a narrow cannula, said dilatation apparatus comprising an inflatable balloon element at a distal apparatus end in fluid communication with a hollow tube, said balloon element being suitable for treating vertebral fractures and capable of being folded and/or wrapped to a sufficiently small diameter to fit through the interior of a narrow diameter cannula, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus.

146. A dilatation apparatus according to paragraph 145 wherein said balloon element is stretched and/or folded, pleated or wrapped to a diameter of about 4-5 mm or less.

147. A dilatation apparatus able to fit through a narrow cannula, said dilatation apparatus comprising an inflatable balloon element at a distal apparatus end in fluid communication with a hollow tube, said balloon element being suitable for treating vertebral fractures and capable of being folded and/or wrapped to a sufficiently small diameter to fit through the interior of a narrow diameter cannula, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein the distal end of the balloon element is sealed and the rod element is not attached to the balloon element.

148. A dilatation apparatus according to paragraph 146 wherein the rod element is attached to or otherwise engages the balloon element.

149. A dilatation apparatus according to paragraph 148 further wherein the balloon element is at least in part wrapped around the rod element.

150. A dilatation apparatus according to paragraph 148 wherein said rod element is applying rotational tensioning to the balloon element.

151. A dilatation apparatus according to paragraph 145 further comprising a hydraulic or pneumatic spring actuation system.

152. A dilatation apparatus according to paragraph 145 wherein said rod element is adjustable in length.

153. A dilatation apparatus able to fit through a narrow cannula, said dilatation apparatus comprising an inflatable balloon element at a distal apparatus end in fluid communication with a hollow tube, said balloon element being suitable for treating vertebral fractures and capable of being folded and/or wrapped to a sufficiently small diameter to fit through the interior of a narrow diameter cannula, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein said rod element is spring loaded to automatically apply axial tensioning to the balloon element during a balloon deflation.

154. A dilatation apparatus able to fit through a narrow cannula, said dilatation apparatus comprising an inflatable balloon element at a distal apparatus end in fluid communication with a hollow tube, said balloon element being suitable for treating vertebral fractures and capable of being folded and/or wrapped to a sufficiently small diameter to fit through the interior of a narrow diameter cannula, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein said rod element comprises concentric inner and outer tubular members.

155. A dilatation apparatus able to fit through a narrow cannula, said dilatation apparatus comprising an inflatable balloon element at a distal apparatus end in fluid communication with a hollow tube, said balloon element being suitable for treating vertebral fractures and capable of being folded and/or wrapped to a sufficiently small diameter to fit through the interior of a narrow diameter cannula, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein the cannula threadably engages external threads along a portion of the dilatation apparatus such that the cannula annularly surrounds a portion of the balloon element.

156. A dilatation apparatus having the following configuration: a proximal end catheter sleeve portion, a middle sleeve portion, and a balloon or inflation element at or near the distal end of the catheter that can be folded and/or wrapped to fit through the interior of a narrow diameter cannula, said balloon element being suitable for treating vertebral fractures; the proximal end catheter sleeve portion comprises a branched or Y-shaped element, of which a first arm or branch comprises a tubular shell with external threads at its proximal end and a spring inside the tubular shell, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region for housing the spring; a cap element with internal threads sized to mate with the external threads at the proximal end of the first branch engages the proximal end of the first branch; at the distal end of the region housing the spring element, a disc element or circular fitting is sized to slide inside the region housing the spring element so as to compress the spring element by displacement in the proximal direction or to decompress the spring element by displacement in the distal direction; associated with the disc element is an axially moveable rod element which runs axially through the interior of the catheter from the distal side of the disc element to a sealed tip portion of the balloon and thus can act like a piston to alternately compress and allow decompression of the spring element.

157. A medical dilatation apparatus having proximal and distal ends and adapted to fit through a narrow cannula into a body location, said dilatation apparatus comprising an inflatable balloon having a balloon interior in fluid communication with a hollow tube, said balloon element being suitable for treating vertebral fractures and capable of being folded and/or wrapped to a sufficiently small diameter to fit through the interior of a narrow diameter cannula, a rod element running through the interiors of the hollow tube and the inflatable balloon, and a spring element which, when compressed, applies axial and/or rotational forces to the balloon by means of the rod element, said spring element being housed in a spring housing section located at the proximal end of the apparatus, wherein said balloon is initially uninflated and is wrapped, folded, pleated or stretched at least in part about said rod element to reduce the profile of the balloon portion of the dilatation apparatus.

158. A method for treating a living being for bone, tissue and/or duct dilatation comprising the sequential steps of:
  (a) using an assembly for inserting an inflatable balloon element, said balloon element being suitable for treating vertebral fractures and capable of being folded and/or wrapped to a sufficiently small diameter to fit through the interior of a narrow diameter cannula into an interior region, cavity or passage of a damaged, collapsed or deformed bone, tissue or duct through a narrow-diameter cannula to position the balloon element at a body location requiring dilatation, the assembly comprising proximal and distal ends and the balloon element having a balloon interior;
  (b) positioning the balloon element in an uninflated state at the body location;
  (c) inflating the balloon element with a working fluid supplied through a fluid inlet/outlet to a working pressure and/or volume and for a time period sufficient to dilate the interior region, cavity or passage;
  (d) deflating the balloon element by withdrawing the working fluid through the fluid inlet/outlet; during and/or subsequent to said deflating step, stretching and/or folding, pleating or wrapping the balloon element to reduce its profile using a spring element capable of temporarily applying at least axial force to the balloon by means of a rod causing the balloon to elongate, or to wrap about the rod, or both, said spring element being housed in a spring housing section located at the proximal end of the assembly; and,
  (e) withdrawing the previously-inflated balloon element through the narrow-diameter cannula.

159. A method according to paragraph 158 wherein said narrow diameter cannula is an 11-gauge or smaller cannula.

160. A method according to paragraph 158 wherein said balloon element is stretched and/or folded, pleated or wrapped to a diameter of about 4-5 mm or less for the steps of inserting and/or withdrawing the balloon element.

161. A method according to paragraph 158 wherein the balloon element is mounted on the distal end of a hollow tube, and the proximal end of the balloon element is bonded to or integrally connected with an end of the tube to create a passage through the tube to the interior of the balloon element.

162. A method according to paragraph 161 wherein the distal end of the balloon element is sealed.

163. A method according to paragraph 162 further wherein said rod passes through the tube and the interior of the balloon element to the sealed end of the balloon element.

164. A method according to paragraph 163 wherein the rod is not attached to the balloon element.

165. A method according to paragraph 163 wherein the rod is attached to or otherwise engages the balloon element.

166. A method according to paragraph 165 wherein the force applied to said rod during and/or subsequent to the deflating step causes the balloon element at least in part to wrap around the rod.

167. A method according to paragraph 166 wherein said rod is spring-loaded to apply rotational tensioning to the balloon element.

168. A method according to paragraph 158 wherein the balloon tensioning and/or wrapping device is hydraulically or pneumatically actuated.

169. A method according to paragraph 163 further wherein said rod is adjustable in length, said method further comprising the step of adjusting the length of said rod such that said rod applies an axial tensioning to the balloon element during the deflating step.

170. A method according to paragraph 158 further wherein, upon inserting the balloon element into an interior region, cavity or passage, at least one end of the balloon element extends into or completely through an 11-gauge or smaller cannula.

171. A method according to paragraph 165 wherein said rod is spring-loaded to automatically apply axial tensioning to the balloon element during the deflating step, said method further comprising the step of applying manual rotational tensioning to the balloon element during and/or subsequent to the deflating step.

172. A method for treating a living being for dilatation of a section of a body to relieve a compression fracture or blockage condition comprising the sequential steps of:
  (a) providing a dilatation apparatus having proximal and distal ends and able to fit through a narrow diameter cannula, said dilatation apparatus comprising an inflatable balloon element having a balloon interior in fluid communication with a hollow tube, a rod element running through the interiors of the hollow tube and the inflatable balloon element, and a spring element capable of temporarily applying at least axial force to the balloon by means of the rod element, said spring element being housed in a spring housing section located at the proximal end of the apparatus, wherein said balloon element is initially uninflated and is wrapped, folded, pleated or stretched at least in part about said rod element to reduce the profile of the balloon portion of the dilatation apparatus;
  (b) inserting at least the balloon portion of the dilatation apparatus into the body section to be treated through the cannula to position the balloon element at a location requiring dilatation;
  (c) inflating the balloon element through the hollow tube with a working fluid to a working pressure and/or volume and for a time period sufficient to dilate the body section;
  (d) deflating the balloon element by withdrawing the working fluid; during and/or subsequent to said deflating step, stretching and/or folding, pleating or wrapping the balloon element using the spring element to apply the at least axial force to the balloon to reduce its profile; and,
  (e) withdrawing the dilatation apparatus including the previously-inflated balloon element from the treated location through the cannula.

173. A method according to paragraph 172 wherein said narrow diameter cannula is an 11-gauge or smaller cannula.

174. A method according to paragraph 172 wherein said balloon element is stretched and/or folded, pleated or wrapped to a diameter of about 4-5 mm or less for the steps of inserting and/or withdrawing the balloon element.

175. A method according to paragraph 172 wherein the distal end of the balloon element is sealed, said method further comprising the step of applying axial force manually or automatically to said sealed end of the balloon element through said rod element during and/or subsequent to the deflating step causing tension and axial elongation of the balloon element.

176. A method according to paragraph 175 wherein the rod element is not attached to the balloon element.

177. A method according to paragraph 175 wherein the rod element is attached to or otherwise engages the balloon element.

178. A method according to paragraph 177 wherein the force applied to said rod element during and/or subsequent to the deflating step causes the balloon element at least in part to wrap around the rod element.

179. A method according to paragraph 178 wherein said rod element is spring-loaded to apply rotational tensioning to the balloon element.

180. A method according to paragraph 172 wherein the balloon tensioning and/or wrapping device is hydraulically or pneumatically actuated.

181. A method according to paragraph 172 wherein said rod element is adjustable in length, said method further comprising the step of adjusting the length of said rod element such that said rod element applies an axial tensioning to the balloon element during the deflating step.

182. A method according to paragraph 178 wherein said rod element is spring-loaded to automatically apply axial tensioning to the balloon element during the deflating step, said method further comprising the step of applying manual rotational tensioning to the balloon element during and/or subsequent to the deflating step.

183. A method according to paragraph 172 wherein said rod element comprises concentric inner and outer tubular members which are rotatable relative to one another, and said balloon element is attached to or engages one of said tubular members, said method further comprising the step of rotating said tubular members relative to one another during and/or subsequent to the deflating step to cause the balloon element to wrap at least in part around one of said tubular members.

184. A method according to paragraph 158 wherein the cannula threadably engages external threads along a portion of the assembly such that the cannula annularly surrounds a portion of the balloon element, the method further comprising the step of adjusting the portion of the balloon contained inside the cannula by axially moving the cannula along the external threads in either the proximal or the distal direction.

185. A method according to paragraph 172 wherein the cannula threadably engages external threads along a portion of the dilatation apparatus such that the cannula annularly surrounds a portion of the balloon element, the method further comprising the step of adjusting the portion of the balloon contained inside the cannula by axially moving the cannula along the external threads in either the proximal or the distal direction.

186. A dilatation procedure for treating the body of a living being by dilating an internal body part or region using a balloon dilatation catheter apparatus, wherein the procedure comprises the following steps:
  (a) providing a balloon dilatation catheter apparatus having the following configuration: a proximal end catheter sleeve portion, a middle sleeve portion, and a balloon or inflation element at or near the distal end of the catheter; the proximal end catheter sleeve portion comprises a branched or Y-shaped element, of which a first arm or branch comprises a tubular shell with external threads at its proximal end, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region for housing a spring element; a cap element with internal threads sized to mate with the external threads at the proximal end of the first branch engages the proximal end of the first branch; at the distal end of the region housing the spring element, a disc element or circular fitting is sized to slide inside the region housing the spring element so as to compress the spring element by displacement in the proximal direction or to decompress the spring element by displacement in the distal direction; associated with the disc element is an axially moveable rod element which runs axially through the interior of the catheter from the distal side of the disc element to a sealed tip portion of the balloon and thus can act like a piston to alternately compress and allow decompression of the spring element;
  (b) inserting the catheter apparatus into the body through a narrow diameter cannula and positioning the balloon in the region to be dilated;
  (c) turning the cap element and at least partially advancing it in a distal direction and at least partially compressing the spring element;
  (d) introducing fluid through the inlet/outlet conduit of the second arm, and through the interiors of the proximal and middle sleeve portions, thereby inflating the balloon, and in turn displacing the disc element in a proximal direction and further compressing the spring element; and,
  (e) after completing the dilatation procedure, withdrawing the fluid from the balloon and from the interior of the catheter through the inlet/outlet conduit of the second arm and deflating the balloon, thereby decompressing the spring element, displacing the disc element in a distal direction, and causing the rod element to also move in a distal direction thereby stretching and tensioning the balloon in preparation for withdrawing it from the body through the cannula.

187. A method for treating a living being for bone, tissue and/or duct dilatation comprising the sequential steps of: inserting an inflatable balloon element in an uninflated state into an interior region, cavity or passage of a damaged, collapsed or deformed bone, tissue or duct through a narrow diameter cannula to position the balloon element at a body location requiring dilatation; inflating the balloon element with a working fluid to a working pressure and/or volume and for a time period sufficient to dilate the interior region, cavity or passage; deflating the balloon element by withdrawing the working fluid; during and/or subsequent to said deflating step, stretching and/or folding, pleating or wrapping the balloon element to reduce its profile using a rod that is not attached to the balloon element to apply axial force, and/or using a rod that is not attached to the balloon element but is capable of engaging the balloon element to apply rotational force, manually or automatically to the balloon element; and, withdrawing the previously-inflated balloon element through said narrow diameter cannula.

188. A method according to paragraph 187 wherein said narrow diameter cannula is an 11-gauge or smaller cannula.

189. A method according to paragraph 187 wherein said balloon element is stretched and/or folded, pleated or wrapped to a diameter of less than about 4 mm for the steps of inserting and/or withdrawing the balloon element.

190. A method according to paragraph 187 wherein said balloon element is stretched and/or folded, pleated or wrapped using a rod actuated by active and/or passive tensioning and wrapping forces.

191. A method for treating a living being for bone, tissue and/or duct dilatation comprising the sequential steps of: inserting an inflatable balloon element having a sealed distal end and mounted on the distal end of a hollow tube, the balloon element initially in an uninflated state, into an interior region, cavity or passage of a damaged, collapsed or deformed bone, tissue or duct through a narrow diameter cannula to position the balloon element at a body location requiring dilatation; inflating the balloon element with a working fluid to a working pressure and/or volume and for a time period sufficient to dilate the interior region, cavity or passage; deflating the balloon element by withdrawing the working fluid; during and/or subsequent to said deflating step, stretching and/or folding, pleating or wrapping the balloon element to reduce its profile using a rod that is not attached to the balloon element to apply axial force, and/or using a rod that is not attached to the balloon element but is capable of engaging the balloon element to apply rotational force, manually or automatically to the balloon element; and, withdrawing the previously-inflated balloon element through said narrow diameter cannula.

192. A method according to paragraph 187 further wherein said rod is adjustable in length, said method further comprising the step of adjusting the length of said rod such that said rod applies an axial tensioning to the balloon element during the deflating step.

193. A method according to paragraph 187 further wherein, upon inserting the balloon element into an interior region, cavity or passage, at least one end of the balloon element extends into or completely through the cannula.

194. A method according to paragraph 187 wherein said rod applies axial tensioning to the balloon element during the deflating step, said method further comprising the step of applying manual rotational tensioning to the balloon element during and/or subsequent to the deflating step.

195. A method according to paragraph 187 wherein the body part to be treated is a vertebral segment, said method further comprising the step of forming a passageway including at least one opening from outside the vertebral segment into an interior region of the vertebral segment.

196. A method according to paragraph 195 further comprising the steps of inserting the balloon element through the cannula such that a portion of the balloon element is inside the cannula during the inflation step.

197. A method for treating a living being for bone, tissue and/or duct dilatation comprising the sequential steps of: inserting an inflatable balloon element in an uninflated state into an interior region, cavity or passage of a damaged, collapsed or deformed bone, tissue or duct through a narrow diameter cannula to position the balloon element at a body location requiring dilatation; inflating the balloon element with a working fluid to a working pressure and/or volume and for a time period sufficient to dilate the interior region, cavity or passage; deflating the balloon element by withdrawing the working fluid; during and/or subsequent to said deflating step, stretching and/or folding, pleating or wrapping the balloon element to reduce its profile; and, withdrawing the previously-inflated balloon element through said narrow diameter cannula, wherein the body location to be treated is a vertebral segment and the method further comprises the step of forming a passageway including at least one opening from outside the vertebral segment into an interior region of the vertebral segment.

198. A dilatation procedure for treating the body of a living being by dilating an internal body part or region using a balloon dilatation catheter apparatus, wherein the procedure comprises the following steps:

(a) providing a balloon dilatation catheter apparatus having the following configuration: a proximal end catheter sleeve portion, a middle sleeve portion, and a balloon or inflation element at or near the distal end of the catheter; the proximal end catheter sleeve portion comprises a branched or Y-shaped element, of which a first arm or branch comprises a tubular shell with external threads at its proximal end, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region for housing a sealing gasket or a similar compressible sealing element having a centrally located aperture; a cap element, that includes a centrally-located axial bore to accommodate a rod element and internal threads sized to mate with the external threads at the proximal end of the first branch, engages the proximal end of the first branch; the rod element also has a knob portion at its proximal end, and is slidably positioned inside the catheter and sized to extend axially the full length of the catheter, extending through the central bore of the cap, through the sealing gasket, which acts like a bushing for supporting and centering the rod, through the interiors of the proximal and middle catheter sleeves, and through the interior of the balloon to a sealed tip portion of the apparatus;

(b) inserting the catheter apparatus into the body through a narrow diameter cannula and positioning the balloon in the region to be dilated;

(c) turning the cap element at least partially advancing it in a distal direction and at least partially compressing the sealing gasket forming a fluid-tight seal at the sealing gasket and around the rod;

(d) introducing fluid through the inlet/outlet conduit of the second arm, and through the interiors of the proximal and middle sleeve portions, inflating the balloon, and causing the rod to slide in a proximal direction;

(e) after completing the dilatation procedure, withdrawing the fluid from the balloon and from the interior of the catheter through the inlet/outlet conduit of the second arm and deflating the balloon, while manually applying axial force to the proximal end of the rod pushing it toward the distal end of the catheter thereby stretching and tensioning the balloon; and, (f) applying a rotational force to the knob of the rod, rotating the rod, and causing the balloon to wrap around the rod in preparation for withdrawing the balloon from the body through the cannula.

199. A dilatation procedure according to paragraph 198 wherein said balloon is stretched and/or folded, pleated or wrapped to a diameter of less than about 4 mm for the steps of inserting and/or withdrawing the balloon.

200. A method according to paragraph 191 wherein said balloon is stretched and/or folded, pleated or wrapped to a diameter of less than about 4 mm for the steps of inserting and/or withdrawing the balloon.

201. A method according to paragraph 191 further comprising the step of stretching and/or folding, pleating or wrapping the previously-inflated balloon element to a diameter less than the interior diameter of the cannula prior to the step of withdrawing the balloon element.

202. A method according to paragraph 191 wherein said balloon element is stretched and/or folded, pleated or wrapped using a rod actuated by active and/or passive tensioning and wrapping forces.

203. A method according to paragraph 191 further wherein said rod is adjustable in length, said method further comprising the step of adjusting the length of said rod such that said rod applies an axial tensioning to the balloon element during the deflating step.

204. A method according to paragraph 191 wherein said rod applies axial tensioning to the balloon element during the deflating step, said method further comprising the step of applying manual rotational tensioning to the balloon element during and/or subsequent to the deflating step.

205. A method for treating a living being for dilatation of a section of a body part having an interior region to relieve a compression fracture or blockage condition, said method comprising the sequential steps of: providing dilatation apparatus able to fit through narrow diameter cannula into the interior region, said dilatation apparatus comprising an inflatable balloon element in fluid communication with a hollow tube, and a slidable and rotatable rod running through the interior of the hollow tube to or into the inflatable balloon element, wherein said balloon element is initially uninflated and further wherein the rod is not attached to the balloon element but is still capable of engaging the balloon element to apply rotational force; inserting the dilatation apparatus through said cannula into the interior region of a body part to be dilated using a guidewire, that may be the same as or different from the rod, to position the balloon element in the interior region; inflating the balloon element through the hollow tube with a working fluid to a working pressure and/or volume and for a time period sufficient to dilate the interior region; deflating the balloon element by withdrawing the working fluid; during and/or subsequent to said deflating step, stretching and/or folding, pleating or wrapping the balloon element at least in part by means of the rod to reduce the profile of the balloon; and, withdrawing the dilatation apparatus including the previously-inflated balloon element from the treated region through the cannula.

206. A method according to paragraph 205 wherein said narrow diameter cannula is an 11-gauge or smaller cannula.

207. A method according to paragraph 205 wherein said balloon element is stretched and/or folded, pleated or wrapped to a diameter of less than about 4 mm for the steps of inserting and/or withdrawing the balloon element.

208. A method according to paragraph 205 wherein the distal end of the balloon element is sealed, said method further comprising the step of applying axial force manually or automatically to said sealed end of the balloon element through the rod during and/or subsequent to the deflating step causing tension and axial elongation of the balloon element.

209. A method according to paragraph 205 further comprising the step of applying rotational force manually or automatically to said rod during and/or subsequent to the deflating step causing the balloon element at least in part to wrap around the rod.

210. A method according to paragraph 205 wherein said rod is adjustable in length, said method further comprising the step of adjusting the length of said rod such that said rod applies an axial tensioning to the balloon element during the deflating step.

211. A method according to paragraph 205 wherein said rod applies axial tensioning to the balloon element during the deflating step, said method further comprising the step of manually rotating the rod to apply rotational tensioning to the balloon element during and/or subsequent to the deflating step.

212. A method according to paragraph 205 wherein said rod comprises concentric inner and outer tubular members which are rotatable relative to one another, and said balloon element is attached to or engages one of said tubular members, said method further comprising the step of rotating said tubular members relative to one another during an/or subsequent to the deflating step to cause the balloon element to wrap at least in part around one of said tubular members.

213. A method according to paragraph 205 further comprising the step of inserting the balloon element through the cannula such that a portion of the balloon element is inside the cannula during the inflation step.

214. A method for treating a living being for dilatation of a section of a body part having an interior region to relieve a compression fracture or blockage condition, said method comprising the sequential steps of: providing dilatation apparatus able to fit through a narrow diameter cannula into the interior region, said dilatation apparatus comprising an inflatable balloon element in fluid communication with a hollow tube, and a slidable and rotatable rod running through the interior of the hollow tube to or into the inflatable balloon element, wherein said balloon element is initially uninflated; inserting the dilatation apparatus through said cannula into the interior region of a body part to be dilated using a guidewire, that may be the same as or different from the rod, to position the balloon element in the interior region; inflating the balloon element through the hollow tube with a working fluid to a working pressure and/or volume and for a time period sufficient to dilate the interior region; deflating the balloon element by withdrawing the working fluid; during and/or subsequent to said deflating step, stretching and/or folding, pleating or wrapping the balloon element at least in part by means of the rod to reduce the profile of the balloon; and, withdrawing the dilatation apparatus including the previously-inflated balloon element from the treated region through the cannula.

215. A method for treating a living being for dilatation of a section of a body part having an interior region to relieve a compression fracture or blockage condition, said method comprising the sequential steps of: providing dilatation apparatus able to fit through a narrow diameter cannula into the interior region, said dilatation apparatus comprising an inflatable balloon element in fluid communication with a hollow tube, and a slidable and rotatable rod running through the interior of the hollow tube to or into the inflatable balloon element, wherein said balloon element is initially uninflated; inserting the dilatation apparatus through said cannula into the interior region of a body part to be dilated using a guidewire, that may be the same as or different from the rod, to position the balloon element in the interior region; inflating the balloon element through the hollow tube with a working fluid to a working pressure and/or volume and for a time period sufficient to dilate the interior region; deflating the balloon element by withdrawing the working fluid; during and/or subsequent to said deflating step, stretching and/or folding, pleating or wrapping the balloon element at least in part by means of the rod to reduce the profile of the balloon; and, withdrawing the dilatation apparatus including the previously-inflated balloon element from the treated region through the cannula,
wherein said rod comprises concentric inner and outer tubular members which are rotatable relative to one another, and said balloon element is attached to or engages one of said tubular members, said method further comprising the step of rotating said tubular members relative to one another during an/or subsequent to the deflating step to cause the balloon element to wrap at least in part around one of said tubular members; and also wherein the guidewire runs through the inner tubular member of the rod.

216. A dilatation procedure for treating the body of a living being by dilating an internal body part or region using a balloon dilatation catheter apparatus, wherein the procedure comprises the following steps:
(a) providing a balloon dilatation catheter apparatus having the following configuration: a proximal end catheter sleeve portion, a middle sleeve portion, and a balloon or inflation element at or near the distal end of the catheter; the proximal end catheter sleeve portion comprises a branched or Y-shaped element, of which a first arm or branch comprises a tubular shell with external threads at its proximal end, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region for housing a sealing gasket or a similar compressible sealing element having a centrally located aperture; a cap element, that includes a centrally-located axial bore to accommodate a rod and internal threads sized to mate with the external threads at the proximal end of the first branch, engages the proximal end of the first branch; the rod also has a knob portion at its proximal end, and is slidably positioned inside the catheter and sized to extend axially the full length of the catheter, extending through the central bore of the cap, through the sealing gasket, which acts like a bushing for supporting and centering the rod, through the interiors of the proximal and middle catheter sleeves, and through the interior of the balloon to a sealed tip portion of the apparatus;
(b) inserting the catheter apparatus into the body through a narrow diameter cannula and positioning the balloon in the region to be dilated using a guidewire that may be the same as or different from the rod;
(c) turning the cap element at least partially advancing it in a distal direction and at least partially compressing the sealing gasket forming a fluid-tight seal at the sealing gasket and around the rod;
(d) introducing fluid through the inlet/outlet conduit of the second arm, and through the interiors of the proximal and middle sleeve portions, inflating the balloon, and causing the rod to slide in a proximal direction;

(e) after completing the dilatation procedure, withdrawing the fluid from the balloon and from the interior of the catheter through the inlet/outlet conduit of the second arm and deflating the balloon, while manually applying axial force to the proximal end of the rod pushing it toward the distal end of the catheter thereby stretching and tensioning the balloon; and, (f) applying a rotational force to the knob of the rod, rotating the rod, and causing the balloon to wrap around the rod in preparation for withdrawing the balloon from the body through the cannula.

217. A method according to paragraph 214 wherein said balloon element is stretched and/or folded, pleated or wrapped to a diameter of less than about 4 mm for the steps of inserting and/or withdrawing the balloon element.

218. A method according to paragraph 216 wherein said balloon element is stretched and/or folded, pleated or wrapped to a diameter of less than about 4 mm for the steps of inserting and/or withdrawing the balloon element.

These and other variations and embodiments of the systems and apparatus of this invention, and different applications for and methods of fabricating and using such apparatus, will be apparent from the accompanying drawings and the following descriptions of the drawings.

BRIEF DESCRIPTION OF THE DRAWINGS

In FIG. 1A, the catheter is shown in a neutral position as it would be for shipping and storage prior to use. The cap portion is loose, and there is no compression of the spring element. The balloon element is shown extended, pleated and/or folded for compactness.

FIG. 3A (sheet 3/56) is a schematic elevation view of the same apparatus shown in FIGS. 1A and 2A, except that in FIG. 3A pressurized fluid has been introduced to fully inflate the balloon element. As a consequence of the balloon being inflated, it expands in diameter and shortens in length causing the rod/disc elements to be displaced toward the proximal end of the apparatus thereby further compressing the spring element.

FIG. 3C (sheet 3/56) is an end view of the apparatus of FIG. 3A as seen from the distal end.

FIG. 3B (sheet 3/56) is a cross-sectional view of the device as shown in FIG. 3C taken along line 3B-3B.

FIG. 5A (sheet 5/56) is a schematic elevation view of apparatus according to a second embodiment of the present invention designed for manual tensioning and optional rotation (twisting and wrapping) of a balloon element to facilitate withdrawal through a small diameter cannula from a bone cavity following dilatation and subsequent deflation. In FIG. 5A, the catheter is shown in a neutral position as it would be for shipping and storage prior to use. The cap is loose, the balloon element is prefolded and/or pleated, and, optionally, wrapped around a push rod extending along the longitudinal axis of the device. The sealing gasket is not compressed, and the push rod is in a forward position (toward the distal end of the device). In one variation of this embodiment of the invention, the push rod may be attached to the distal tip of the balloon element or otherwise capable of engaging the balloon element to enable twisting the balloon element to wrap it around the push rod as described further below.

FIG. 5C (sheet 5/56) is an end view of the apparatus of FIG. 5A as seen from the distal end.

FIG. 5B (sheet 5/56) is a cross-sectional view of the device as shown in FIG. 5C taken along line 5B-5B.

In FIG. 13A, the cap portion is loose, and there is no compression of the spring element.

In FIG. 17A, the catheter is shown in a neutral position as it would be for shipping and storage prior to use. The cap portion is loose, and there is no compression of the spring element. The balloon element is shown extended, pleated and/or folded for compactness.

FIG. 20A (sheet 20/56) is a schematic elevation view of the same apparatus shown in FIGS. 17A, 18A and 19A, except that in FIG. 20A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

FIG. 20C (sheet 20/56) is an end view of the apparatus of FIG. 20A as seen from the distal end.

FIG. 20B (sheet 20/56) is a cross-sectional view of the device as shown in FIG. 20C taken along line 20B-20B.

FIG. 22A (sheet 22/56) is a schematic elevation view of apparatus according to a sixth embodiment of the present invention designed for automatic tensioning of a balloon element using a spring tensioning system located at the distal (internal) end of the device to facilitate withdrawal through a small diameter cannula from a bone cavity following dilatation and subsequent deflation. In FIG. 22A, the catheter is shown in a neutral position as it would be for shipping and storage prior to use. The cap portion is loose, and there is little or no compression of the spring element. The balloon element is shown extended, pleated and/or folded for compactness.

FIG. 22C (sheet 22/56) is an end view of the apparatus of FIG. 22A as seen from the distal end.

FIG. 22B (sheet 22/56) is a cross-sectional view of the device as shown in FIG. 22C taken along line 22B-22B.

FIG. 22D (sheet 22/56) is an enlarged cross-sectional view of the distal end of the device as shown in FIG. 22B to better illustrate details of the spring tensioning system at the balloon end of the apparatus.

FIG. 23A (sheet 23/56) is a schematic elevation view of the same apparatus shown in FIG. 22A, except that in FIG. 23A the cap has been screwed down resulting in at least partially compressing the spring element and applying axial tension to the balloon in preparation for using the device. The balloon element remains extended and folded and/or pleated.

FIG. 23C (sheet 23/56) is an end view of the apparatus of FIG. 23A as seen from the distal end.

FIG. 23B (sheet 23/56) is a cross-sectional view of the device as shown in FIG. 23C taken along line 23B-23B.

FIG. 23D (sheet 23/56) is an enlarged cross-sectional view of the distal end of the device as shown in FIG. 23B to better illustrate details of the spring tensioning system at the balloon end of the apparatus.

FIG. 24A (sheet 24/56) is a schematic elevation view of the same apparatus shown in FIGS. 22A and 23A, except that in FIG. 24A pressurized fluid has been introduced to fully inflate the balloon element. As a consequence of the balloon being inflated, it expands in diameter and shortens in length thereby further compressing the spring element.

FIG. 24C (sheet 24/56) is an end view of the apparatus of FIG. 24A as seen from the distal end.

FIG. 24B (sheet 24/56) is a cross-sectional view of the device as shown in FIG. 24C taken along line 24B-24B.

FIG. 24D (sheet 24/56) is an enlarged cross-sectional view of the distal end of the device as shown in FIG. 24B to better illustrate details of the spring tensioning system at the balloon end of the apparatus.

FIG. 25A (sheet 25/56) is a schematic elevation view of the same apparatus shown in FIGS. 22A, 23A and 24A, except that in FIG. 25A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the rod pushing it axially toward the distal end of the apparatus. This results in stretching and tensioning the balloon element thereby assisting in collapsing, folding and/or pleating the balloon element for easier withdrawal from the dilated bone cavity.

FIG. 25C (sheet 25/56) is an end view of the apparatus of FIG. 25A as seen from the distal end.

FIG. 25B (sheet 25/56) is a cross-sectional view of the device as shown in FIG. 25C taken along line 25B-25B.

FIG. 25D (sheet 25/56) is an enlarged cross-sectional view of the distal end of the device as shown in FIG. 25B to better illustrate details of the spring tensioning system at the balloon end of the apparatus.

Similar to the embodiments of FIGS. 5-9 and 17-21, the embodiment of FIGS. 22-25 can readily be adapted to add a rod rotation/balloon wrapping capability if the rod is equipped with a rotation-resisting element and the rod engages or can engage the end of the balloon.

FIGS. 26A-26D (sheets 26/56 to 29/56) show schematic cross-sectional views of a vertebral segment with a V-shaped catheter access channel formed through both pedicle portions and the cancellous bone being treated in accordance with one embodiment of the present invention.

FIGS. 27A-27D (sheet 30/56 to 33/56) show schematic cross-sectional views of a vertebral segment with a V-shaped catheter access channel formed through both pedicle portions and the cancellous bone being treated in accordance with another embodiment of the present invention.

FIGS. 28A-28E (sheet 34/56 to 38/56) show schematic cross-sectional views of a vertebral segment with a U-shaped catheter access channel formed through both pedicle portions and the cancellous bone being treated in accordance with still another embodiment of the present invention.

Figure 29:
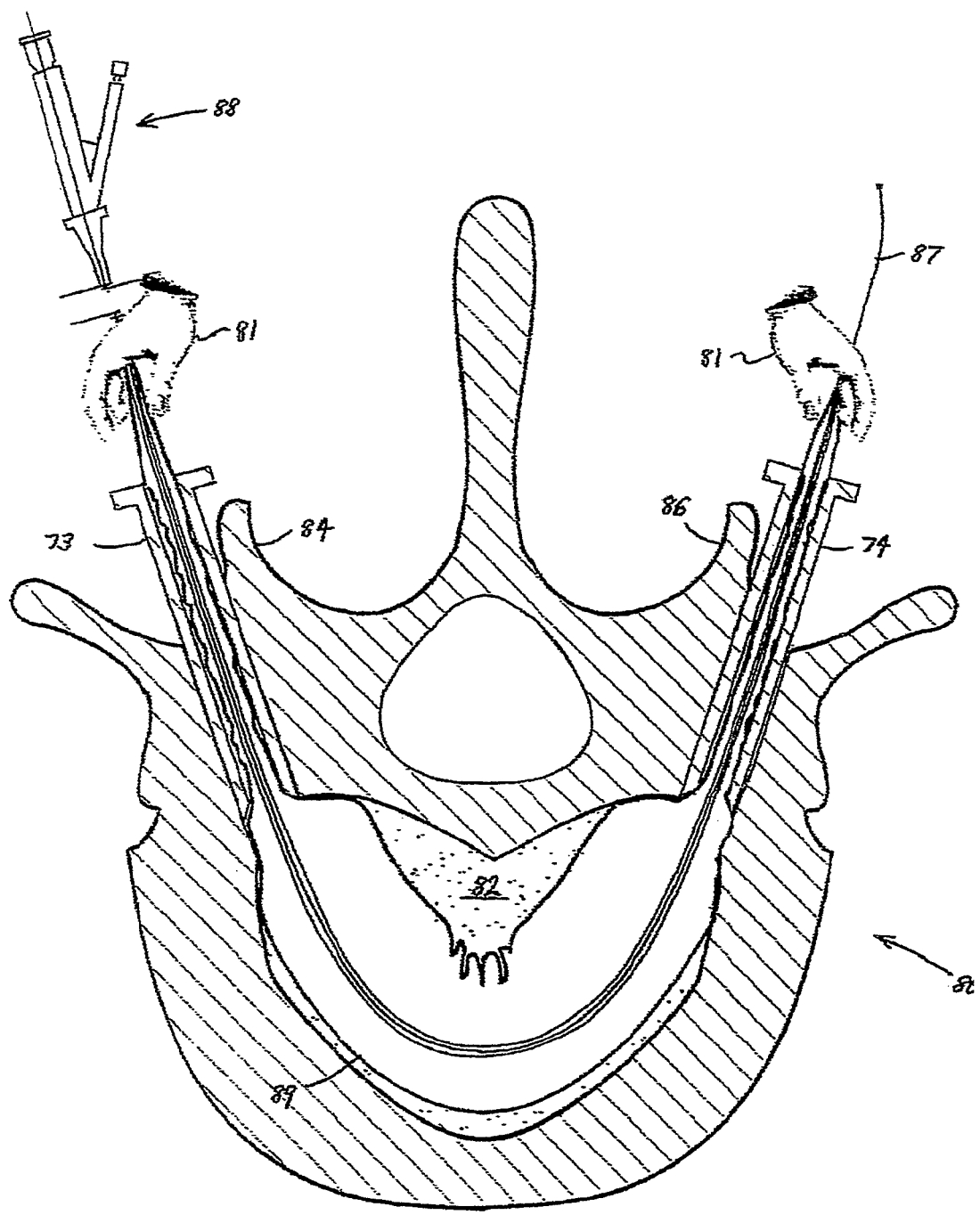

FIG. 29 (sheet 39/56) shows a schematic cross-sectional view of a vertebral segment with a U-shaped catheter access channel formed through both pedicle portions and the cancellous bone being treated in accordance with still another embodiment of the present invention.

Figure 30:
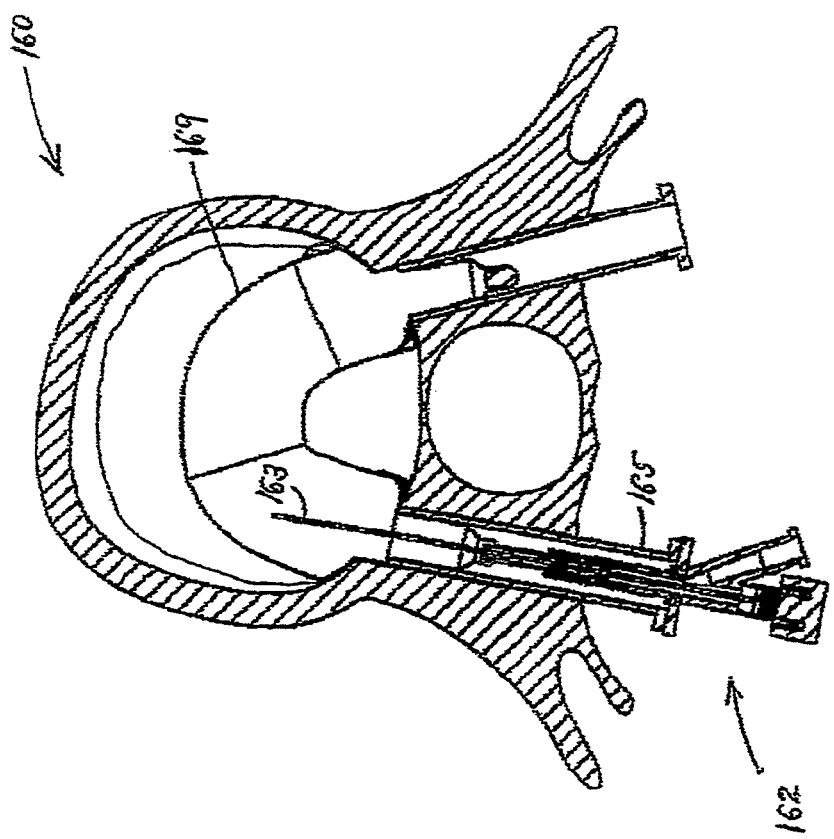

FIG. 30 (sheet 40/56) shows a schematic cross-sectional view of a vertebral segment with a U-shaped catheter access channel formed through both pedicle portions and the cancellous bone being treated with a catheter apparatus using a pre-curved guidewire in accordance with another embodiment of the present invention.

Figure 31:
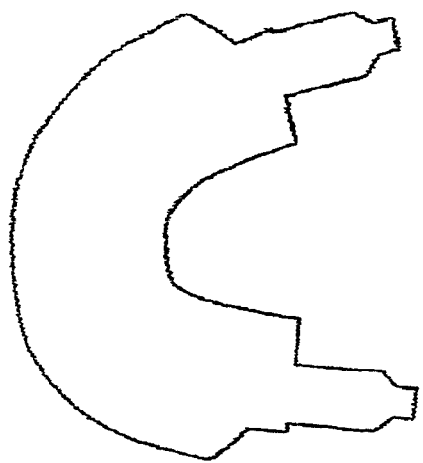

FIG. 31 (sheet 40/56) is a schematic side view of a pre-curved balloon element designed for use in some embodiments of the present invention.

Figure 32:
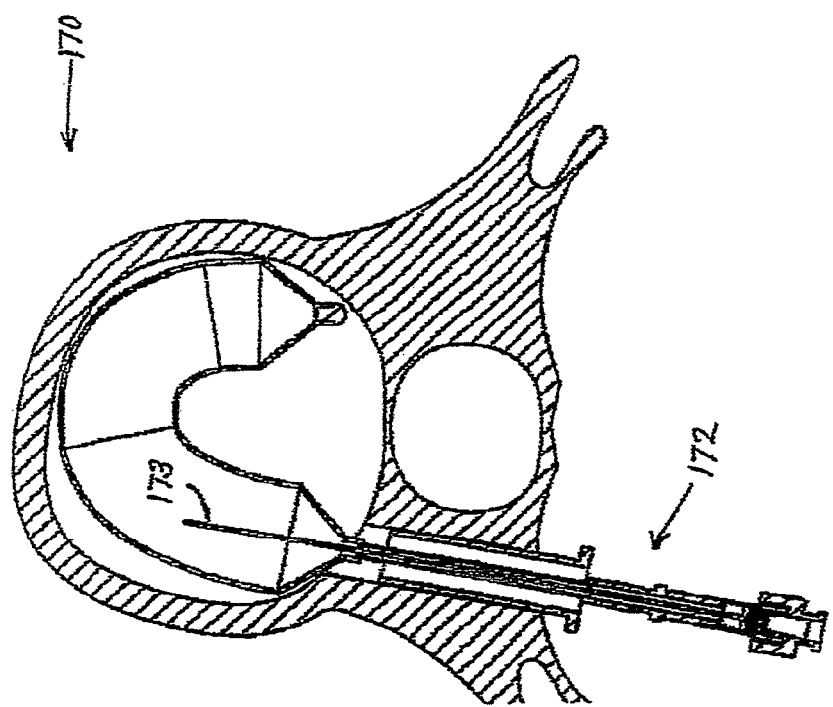

FIG. 32 (sheet 41/56) is a schematic cross-sectional view of a vertebral segment with a catheter access channel formed through only one pedicle portion being treated with a catheter apparatus using a pre-curved guidewire in accordance with another embodiment of the present invention.

Figure 33:
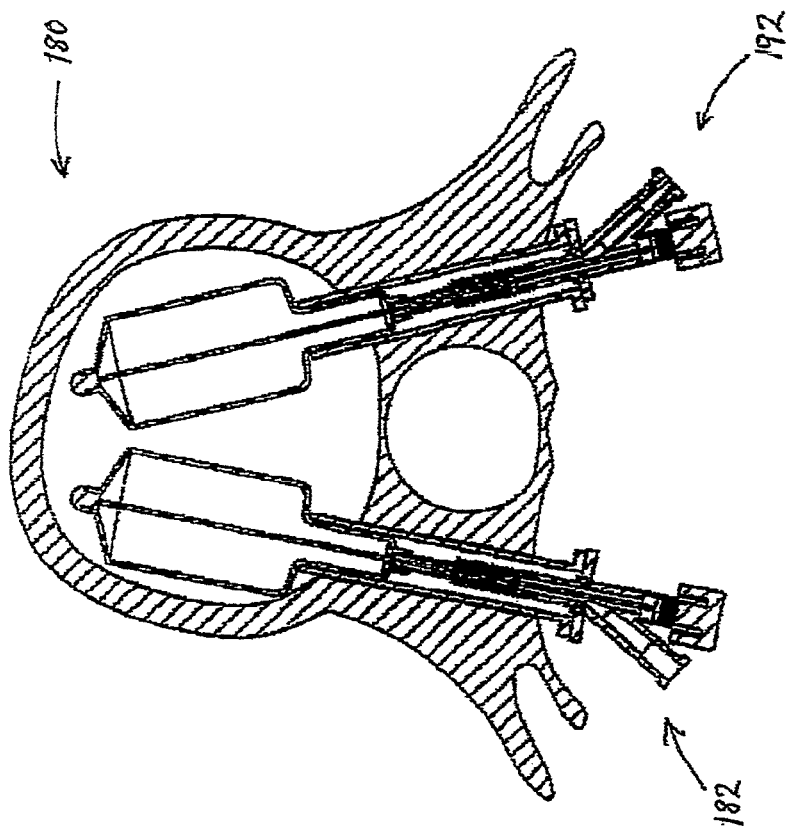

FIG. 33 (sheet 41/56) is a schematic cross-sectional view of a vertebral segment with catheter access channels formed through both pedicle portions for treatment with two catheter apparatuses in accordance with still another embodiment of the present invention.

FIG. 34A (sheet 42/56) is a schematic elevation view of apparatus according to still another embodiment of the present invention designed for wrapping a balloon or inflation element to facilitate withdrawal through a small diameter cannula from a bone cavity or through a small diameter duct following dilatation and subsequent deflation. The apparatus of FIG. 34A is configured somewhat similar to that shown in FIG. 10A except that in FIG. 34A there is a fixed inner shaft and the balloon is wrapped by rotating the outer shaft. This can be accomplished with or without tensioning of the balloon or inflation element.

FIG. 34C (sheet 42/56) is an end view of the apparatus of FIG. 34A as seen from the distal end.

FIG. 34B (sheet 42/56) is a cross-sectional view of the device as shown in FIG. 34C taken along line 34B-34B.

Figure 35A:
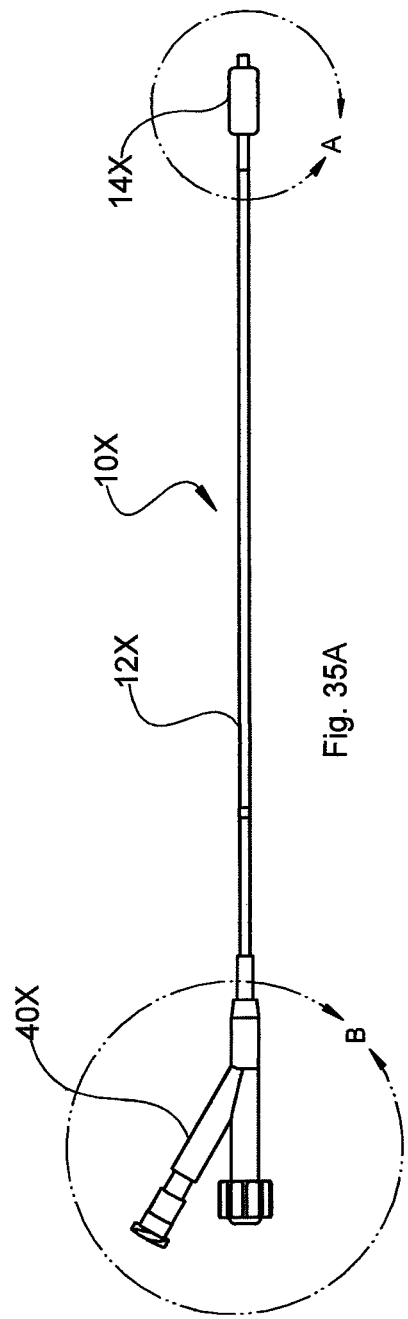

FIG. 35A (sheet 43/56) is a schematic elevational view of a catheter/expandable element apparatus according to an embodiment of the invention.

Figure 35B:
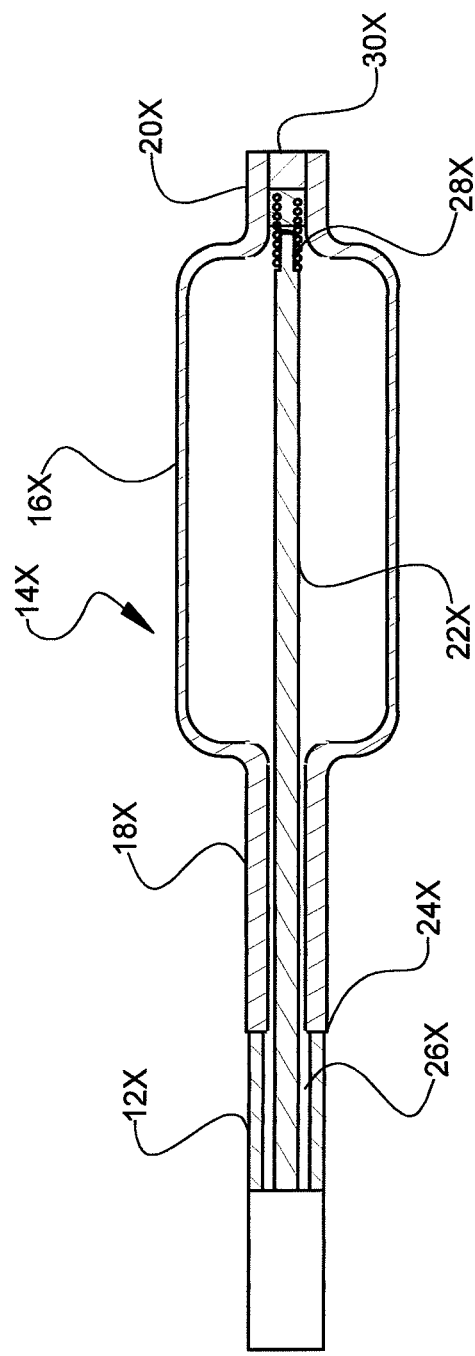

FIG. 35B (sheet 44/56) is an exploded, schematic sectional view of the distal end (i.e., that portion inside the circle A) of the apparatus illustrated in FIG. 35A.

Figure 35C:
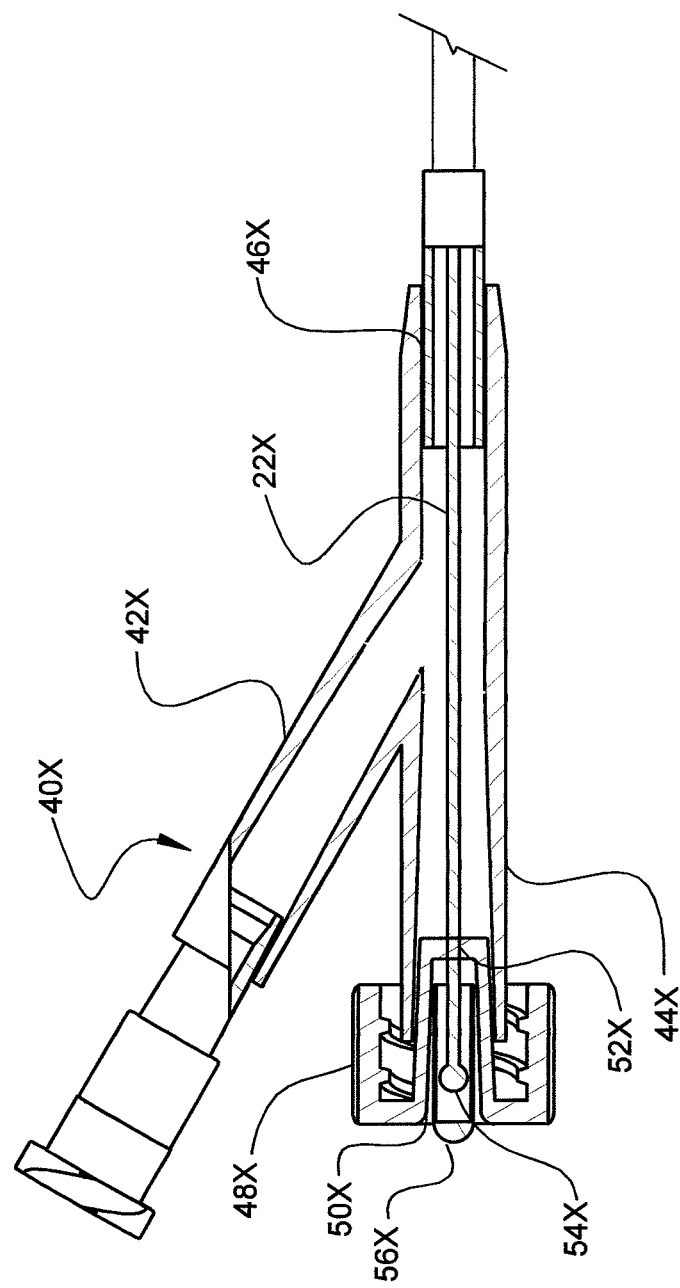

FIG. 35C (sheet 45/56) is an exploded, schematic sectional view of the proximal end (i.e., that portion inside the circle B) of an embodiment of the apparatus illustrated in FIG. 35A.

Figure 35D:
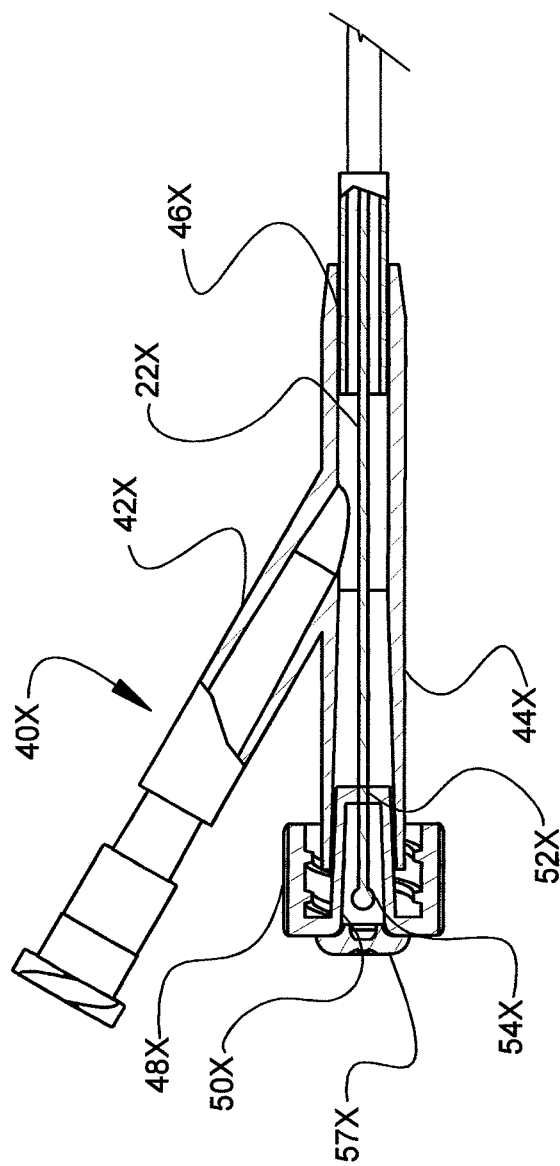

FIG. 35D (sheet 46/56) is an exploded, schematic sectional view of the proximal end (i.e., that portion inside the circle B) of an alternative embodiment of the apparatus illustrated in FIG. 35A.

Figure 35E:
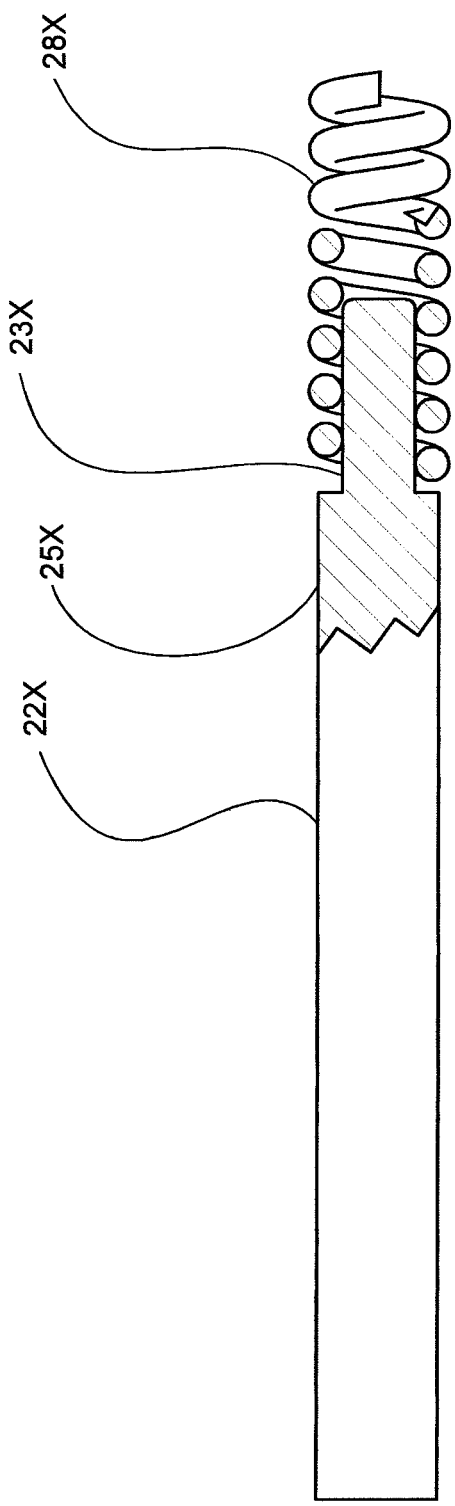

FIG. 35E (sheet 47/56) is another exploded, schematic partial sectional view of a portion of the distal end of the apparatus illustrated in FIG. 35A, specifically showing additional details of an invention embodiment wherein a spring element is bonded to a reduced-diameter distal end of the mandrel.

Figure 36A:
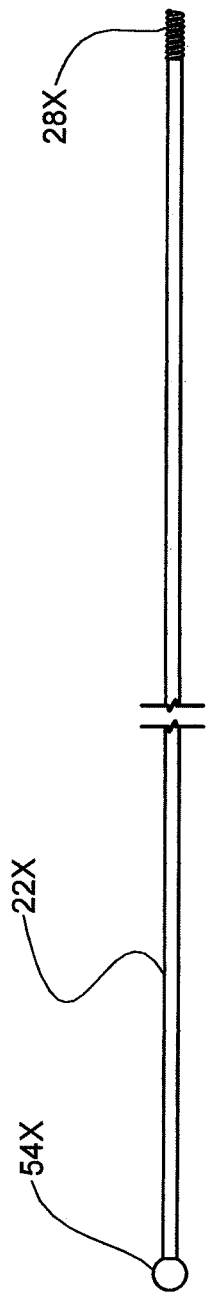
Figure 36B:
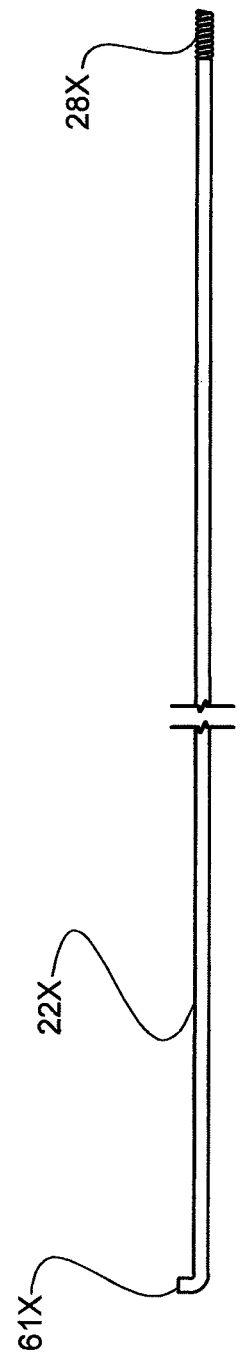

FIGS. 36A and 36B (sheet 48/56) are schematic elevational views of alternative embodiments of a mandrel according to the present invention showing alternative enlarged proximal end configurations.

Figure 37:
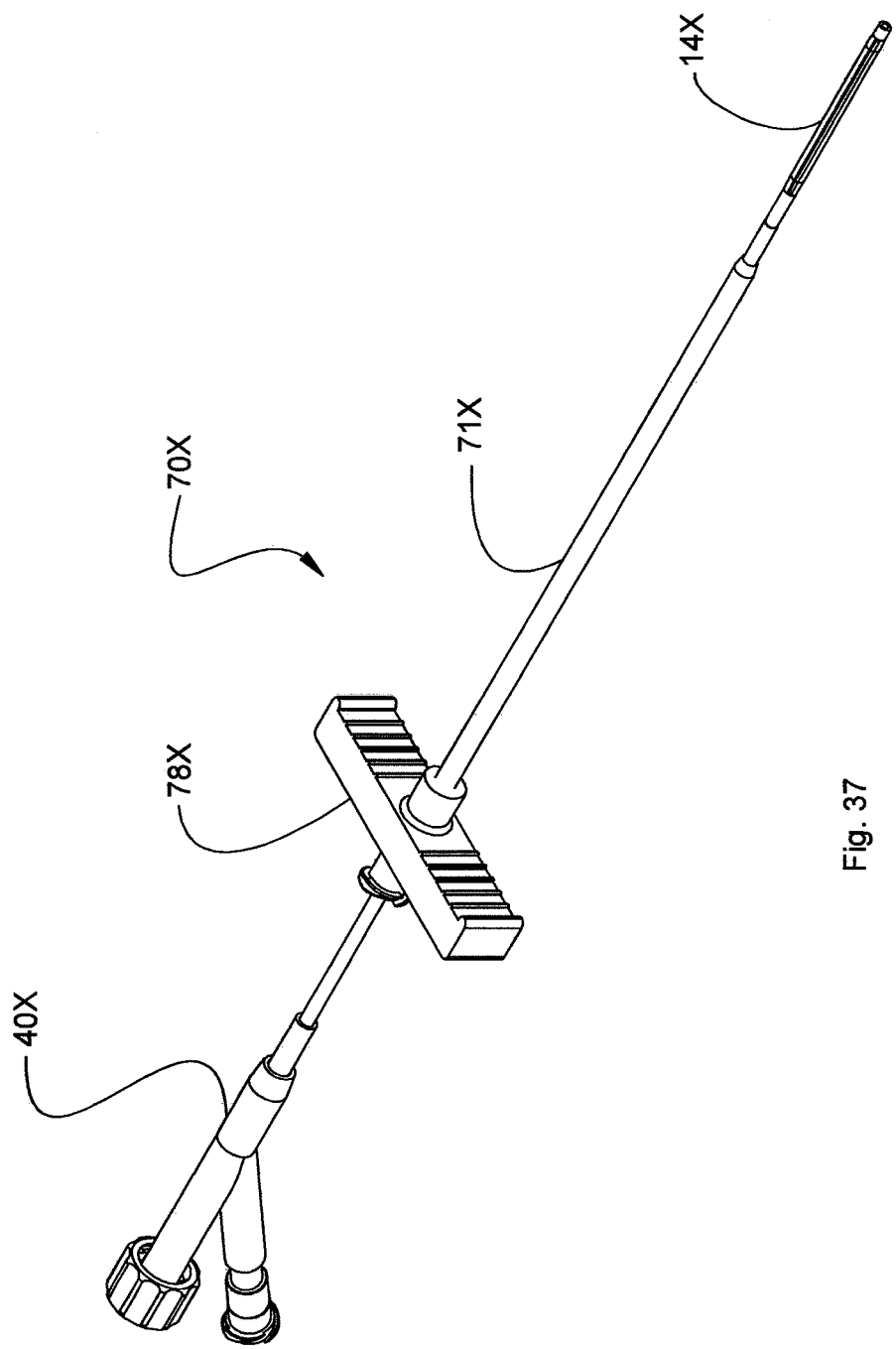

FIG. 37 (sheet 49/56) is a schematic isometric view of a medical device system comprising a narrow gauge (e.g., an 11-gauge) cannula in combination with a catheter/expandable element assembly, each of the components being specially adapted for use with one another in accordance with embodiments of this invention.

Figure 38:
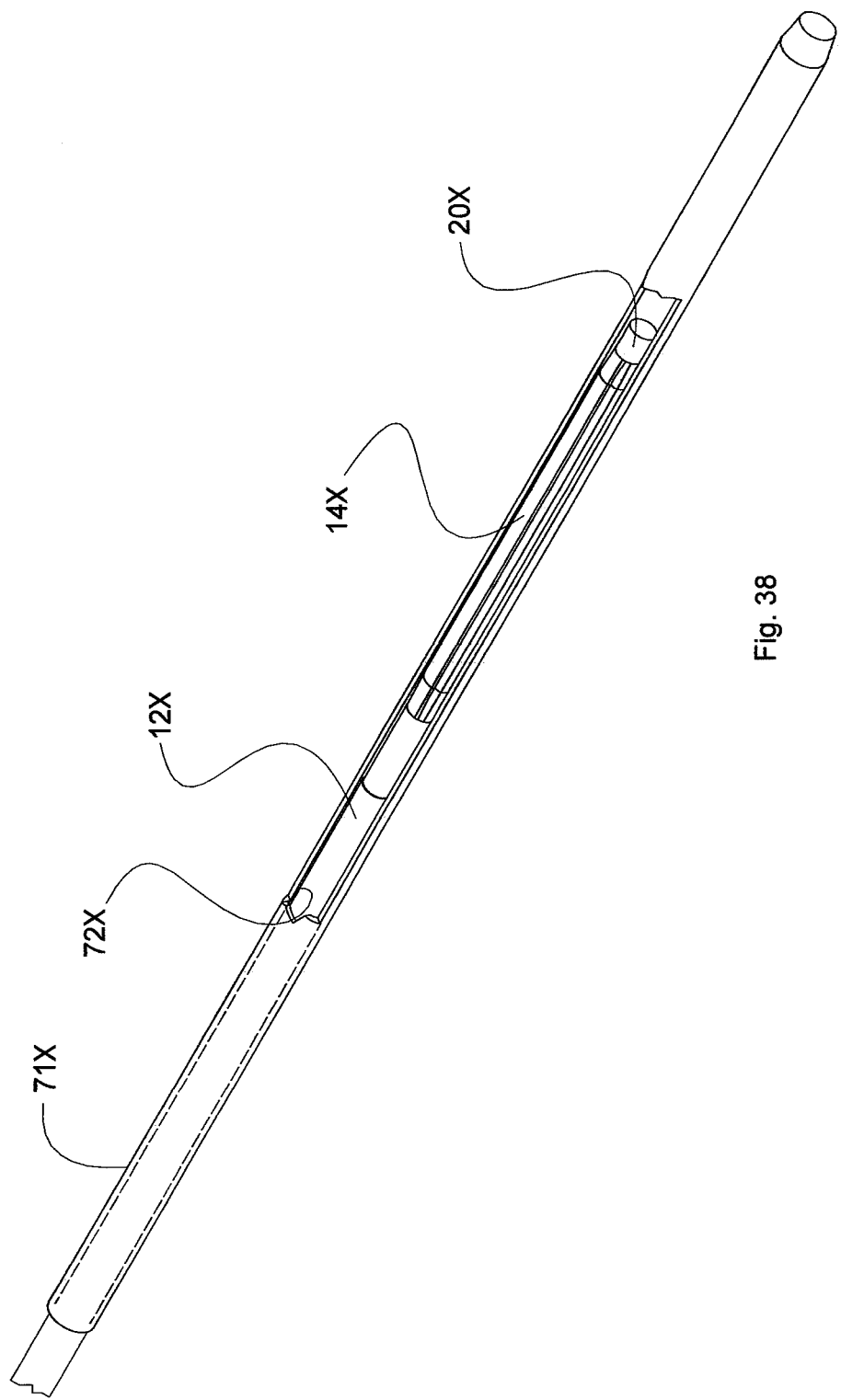

FIG. 38 (sheet 50/56) is a schematic, partially cutaway view illustrating the expandable element component of the medical device system of FIG. 37 located inside the narrow gauge cannula component of the system.

Figure 39:
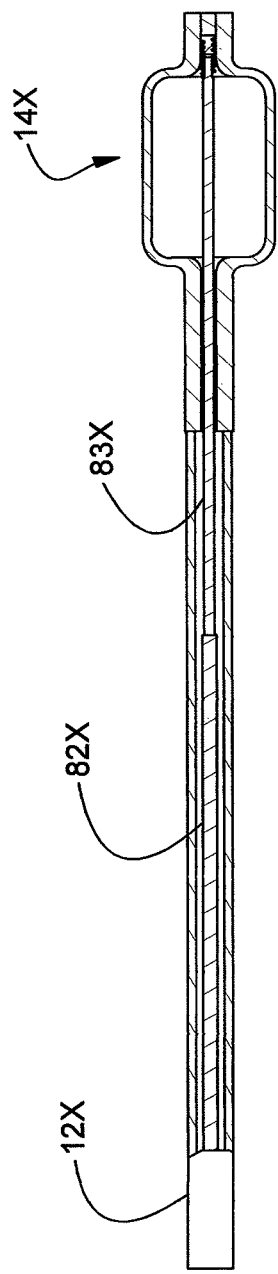

FIG. 39 (sheet 51/56) is an exploded, schematic sectional view of the distal end (i.e., that portion inside the circle A) of an assembly comparable to that illustrated in FIG. 35A showing an alternative invention embodiment for configuring the distal portion of the mandrel.

FIG. 40A (sheet 52/56) is an exploded, schematic sectional view of the distal end (i.e., that portion inside the circle A) of an assembly comparable to that illustrated in FIG. 35A showing an alternative invention embodiment for providing an actively deflectable mandrel/expandable element configuration.

FIG. 40B (sheet 52/56) is an exploded, schematic sectional view of the proximal end (i.e., that portion inside the circle B) of an assembly comparable to that illustrated in FIG. 35A showing an alternative proximal end invention embodiment for providing the actively deflectable mandrel/expandable element configuration as seen in FIG. 40A.

FIG. 40C (sheet 53/56) is a blow-up sectional view of the apparatus components inside the distal portion of the catheter shaft and inside the expandable element showing additional details of the actively deflectable mandrel invention embodiment of FIGS. 40A and 40B.

FIG. 40D (sheet 53/56) is a blow-up sectional view of the apparatus components inside the catheter shaft showing details of the juncture between a tube element and a deflectable spring element for the invention embodiment of FIGS. 40A, 40B and 40C.

FIG. 41A (sheet 54/56) shows a schematic view of the distal end of the mandrel and spring element components of FIGS. 40A and 40C being actively deflected using a mandrel deflection mechanism as seen in FIG. 40B at the proximal end of the assembly.

FIG. 41B (sheet 54/56) is a blow-up of the mandrel deflection mechanism seen in FIG. 40B at the proximal portion of the catheter assembly showing additional details of a proximal end configuration adapted for practicing the actively deflectable invention embodiment of FIGS. 40A to 40D.

Figure 41C:
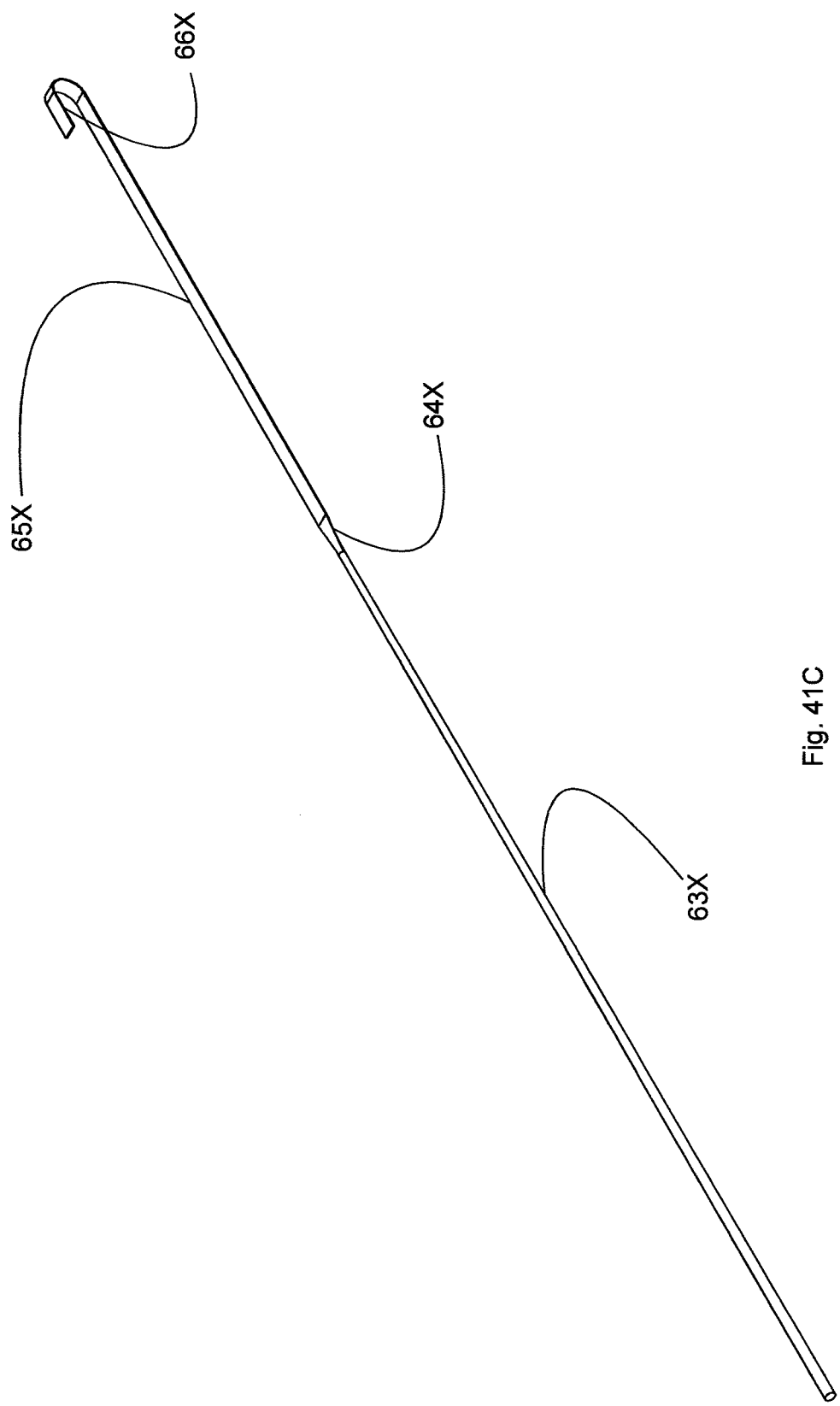

FIG. 41C (sheet 55/56) is an isolated isometric view of the distal portion of the mandrel/core wire as seen in FIG. 40C showing certain configuration details with greater clarity.

FIG. 42A (sheet 56/56) is an exploded, schematic sectional view of the distal end (i.e., that portion inside the circle A) of the assembly illustrated in FIG. 35A showing another alternative invention embodiment for configuring the distal end of the assembly to provide a passively deflectable expandable element configuration.

FIG. 42B (sheet 56/56) is an exploded, schematic sectional view of the proximal end (i.e., that portion inside the circle B) of the assembly illustrated in FIG. 35A showing a proximal end configuration consistent with the passively deflectable configuration of FIG. 42A.

DETAILED DESCRIPTION OF PREFERRED EMBODIMENTS

FIGS. 1-4 illustrate a dilatation balloon tensioning apparatus according to a first embodiment of the present invention. The balloon dilatation catheter apparatus 10 in FIGS. 1A-1C generally comprises a proximal end catheter sleeve portion 12, a middle sleeve portion 14, and a balloon or inflation element 16 at or near the distal end of the catheter. As best seen in FIG. 1B, proximal end catheter sleeve portion 12 comprises a branched or Y-shaped element, of which one arm or branch 18 comprises a tubular shell with external threads 25 at its proximal end, and the second arm or branch 20 comprises a fluid inlet/outlet conduit for introducing pressurized fluid 40 into catheter 10 for inflating balloon 16 or for withdrawing fluid 40 after a dilatation procedure.

Figure 1C:
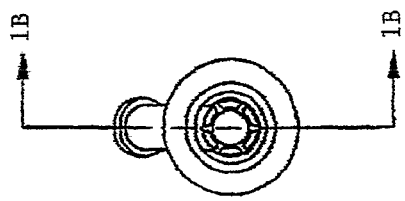
FIG. 1C (sheet 1/56) is an end view of the apparatus of FIG. 1A as seen from the distal end.
Figure 1B:
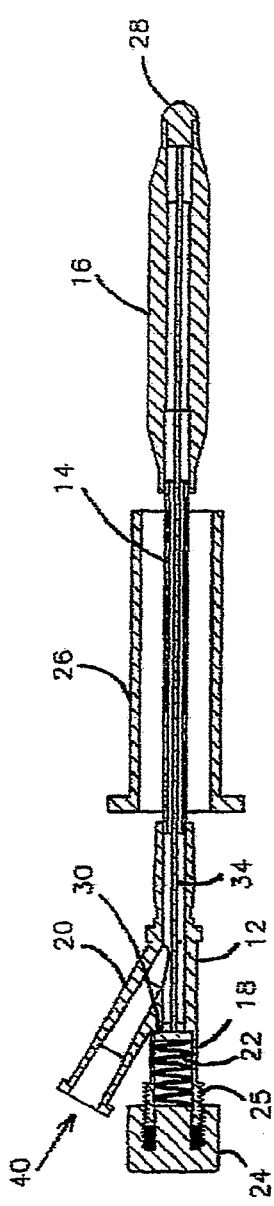
FIG. 1B (sheet 1/56) is a cross-sectional view of the device as shown in FIG. 1C taken along line 1B-1B.
Figure 1A:
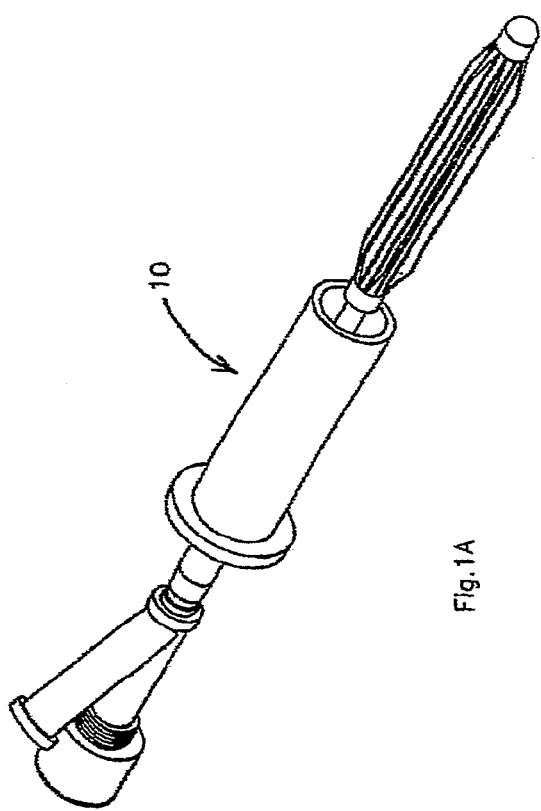
FIG. 1A (sheet 1/56) is a schematic elevation view of apparatus according to a first embodiment of the present invention designed for automatic tensioning of a balloon element using a spring tensioning system located at the proximal (external) end of the device to facilitate withdrawal through a small diameter cannula from a bone cavity following dilatation and subsequent deflation.

The tubular shell of branch 18 comprises a region adjacent to the threaded region for housing a spring element 22. Cap element 24 has internal threads and is sized to mate with the external threads 25 at the proximal end of branch 18. As seen in FIGS. 1A-1C, the cap element 24 is loosely threaded onto branch 18, and there is no compression of spring element 22, the condition in which catheter 10 would ordinarily be shipped and stored. Balloon element 16 is shown extended, and, as seen in FIGS. 1A and 1C, is preferably pleated or folded for compactness.

Balloon elements suitable for use with the various catheter designs described herein may be elastomeric or non-elastomeric, depending on the particular application, and may be fabricated from various conventional balloon catheter materials, for example the various catheter and balloon materials taught by U.S. Pat. No. 5,499,973, which is incorporated herein by reference. It is also within the scope of this invention to coat the exterior of the balloon elements to prevent or minimize damage or rupture from sharp bones. It is also within the scope of this invention to cover the balloon elements with elastomeric tubes both to help squeeze and deflate the balloons during deflation and to resist damage from surrounding bone.

At the distal end of the region for housing spring element 22 (i.e., at the end opposite from where the cap 24 is threaded onto branch 18), a disc element or circular fitting 30 is sized to slide inside the region housing spring element 22 so as to compress the spring element by displacement in the proximal direction or to decompress the spring element by displacement in the distal direction. Associated with disc element 30 is axially moveable rod element 34 (which may or may not be physically connected to disc element 30) which runs axially through the interior of the catheter from the distal side of disc element 30 to the sealed tip portion 28 of balloon 16. Rod element 34 may or may not be physically connected to or may or may not engage balloon tip portion 28. Rod element 34 operating in conjunction with disc element 30 thus can act like a piston to alternately compress and allow decompression of spring element 22.

Also shown in FIGS. 1A-1C, although it is typically not attached to catheter apparatus 10, is a small diameter cannula 26 which provides a channel for the catheter apparatus through a bone portion into the bone interior. Balloon element 16 must be able to slide through the hollow interior of cannula 26 during insertion of the catheter and, more importantly, during removal of the catheter after the balloon has undergone an inflation/deflation cycle.

Figure 2C:
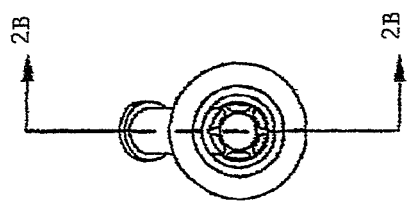
FIG. 2C (sheet 2/56) is an end view of the apparatus of FIG. 2A as seen from the distal end.
Figure 2B:
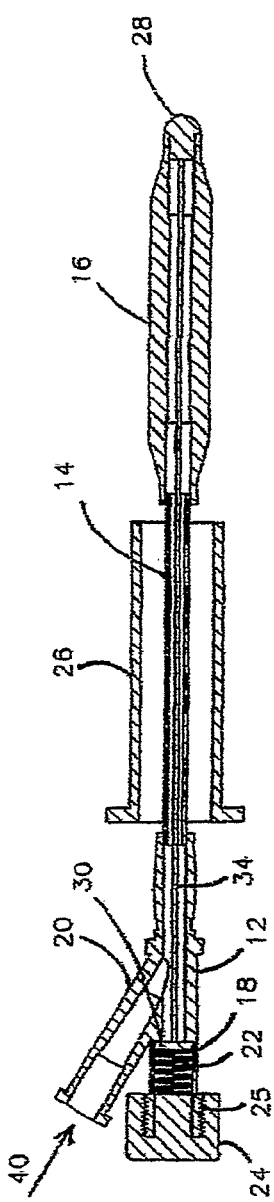
FIG. 2B (sheet 2/56) is a cross-sectional view of the device as shown in FIG. 2C taken along line 2B-2B.
Figure 2A:
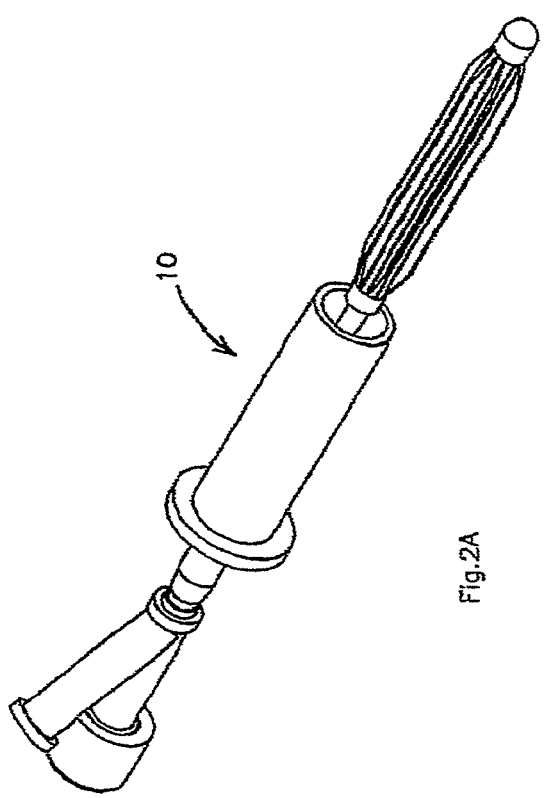
FIG. 2A (sheet 2/56) is a schematic elevation view of the same apparatus shown in FIG. 1A, except that in FIG. 2A the cap has been screwed down resulting in at least partially compressing the spring element in preparation for using the device. The balloon element remains extended and folded and/or pleated.

In FIGS. 2A-2C, catheter apparatus 10 of FIGS. 1A-1C is shown with cap element 24 screwed down resulting in at least partially compressing spring element 22 in preparation for use. In FIGS. 3A-3C, pressurized fluid 40 has been introduced through branch 20, through a part of the interior of proximal sleeve portion 12, and through the interior of middle sleeve portion 14 to fully inflate balloon 16. As balloon 16 is inflated, it expands in diameter and shortens in length causing rod 34 to move in a proximal direction, thereby displacing disc element 30 in a proximal direction and further compressing spring element 22.

Figure 4C:
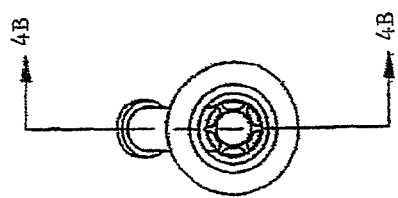
FIG. 4C (sheet 4/56) is an end view of the apparatus of FIG. 4A as seen from the distal end.
Figure 4B:
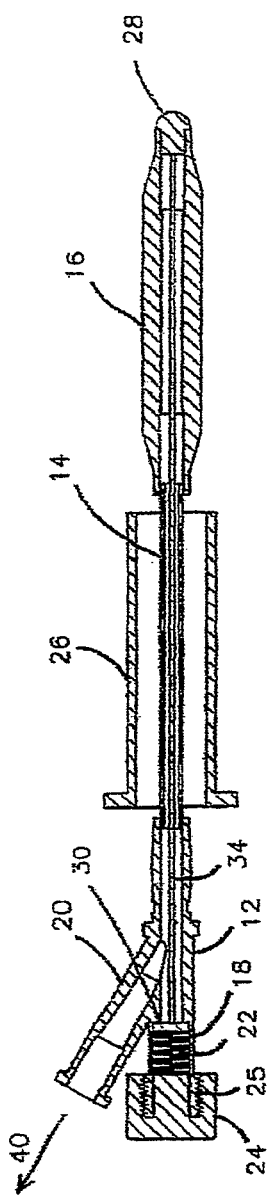
FIG. 4B (sheet 4/56) is a cross-sectional view of the device as shown in FIG. 4C taken along line 4B-4B.
Figure 4A:
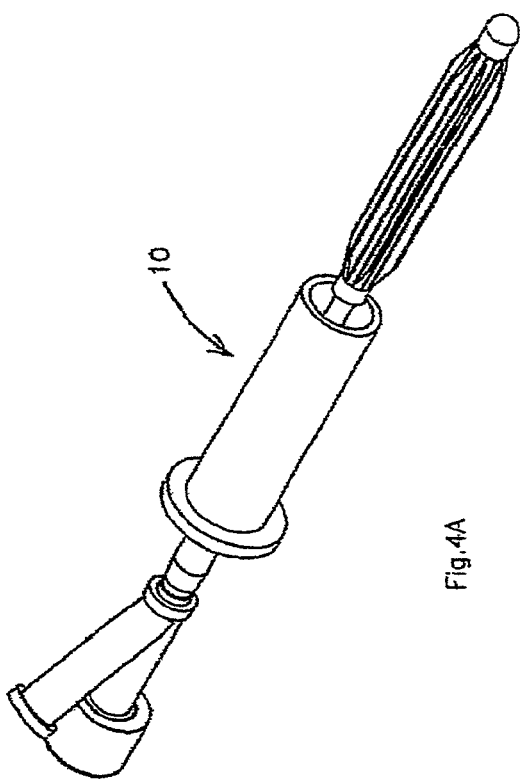
FIG. 4A (sheet 4/56) is a schematic elevation view of the same apparatus shown in FIGS. 1A, 2A and 3A, except that in FIG. 4A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 4A-4C, dilatation pressure is removed and fluid is withdrawn from balloon 16 and from the interior of catheter 10 through fluid inlet/outlet branch 20. In a preferred embodiment, a vacuum may be applied to the proximal end of branch 20 to assist in withdrawing fluid and fully collapsing balloon 16. As balloon 16 becomes deflated, the force exerted by the compressed spring element 22 becomes greater than the force exerted by the collapsing balloon. Eventually this results in displacing disc element 30 toward the distal end of the catheter, in turn driving rod 34 in the distal direction, and thereby stretching and tensioning balloon 16. This automatic tensioning of the balloon element upon deflation assists in collapsing, folding and/or pleating the balloon to minimize its lateral profile for easier withdrawal through the small diameter interior channel of cannula 26.

FIGS. 5-9 illustrate a dilatation balloon tensioning apparatus according to a second embodiment of the present invention. The balloon dilatation catheter apparatus 110 in FIGS. 5A-5C generally comprises a proximal end catheter sleeve portion 112, a middle sleeve portion 114, and a balloon or inflation element 116 at the distal end of the catheter. As best seen in FIG. 5B, proximal end catheter sleeve portion 112 comprises a branched or Y-shaped element, of which one arm or branch 118 comprises a tubular shell with external threads 125 at its proximal end, and the second arm or branch 120 comprises a fluid inlet/outlet conduit for introducing pressurized fluid 140 into catheter 110 for inflating balloon 116 or for withdrawing fluid 140 after a dilatation procedure.

The tubular shell of branch 118 comprises a region adjacent to the threaded region for housing a sealing gasket 122 or similar compressible sealing element having a centrally located aperture. Cap element 124 includes a centrally-located axial bore 127 to accommodate a push rod 134, and also has internal threads sized to mate with the external threads 125 at the proximal end of branch 118. As seen in FIGS. 5A-5C, cap element 124 is loosely threaded onto branch 118, rod 134 is forward (toward the distal end of the catheter), and there is no compression of sealing gasket 121, the condition in which catheter 110 would ordinarily be shipped and stored. Balloon element 116 is shown extended, as best seen in FIG. 5C, and is preferably pleated or folded for compactness.

Push rod 134, having a knob portion 136 at its proximal end, is slidably positioned inside the catheter and is sized to extend axially the full length of catheter 110. Push rod 134 extends through the central bore 127 of cap 124, through the sealing gasket 121, which acts like a bushing for supporting and centering rod 134, through the interior of sleeves 112 and 114, and through the interior of balloon 116 to the sealed tip portion 128. In one variation of this invention embodiment, rod 134 may be connected to or capable of engaging tip portion 128 to facilitate twisting or wrapping balloon element 116 about rod 134 following a dilatation and deflation cycle.

Figure 6C:
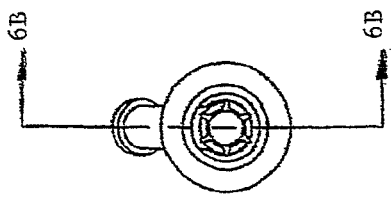
FIG. 6C (sheet 6/56) is an end view of the apparatus of FIG. 6A as seen from the distal end.
Figure 6B:
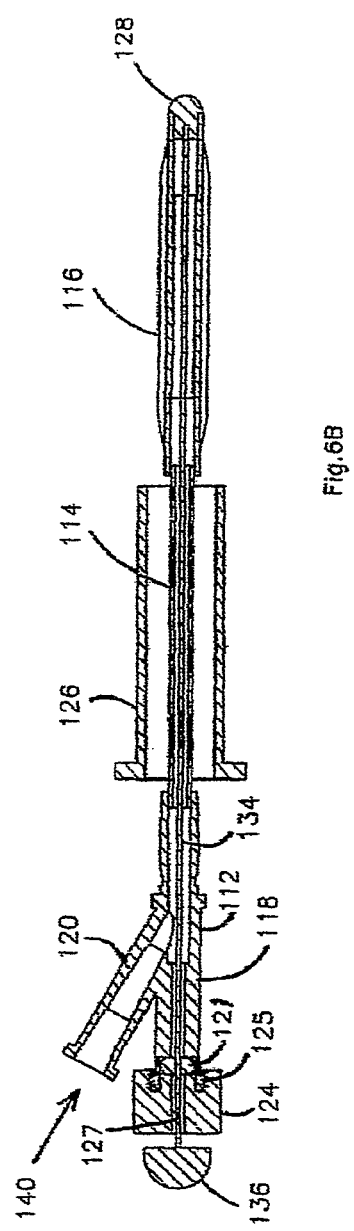
FIG. 6B (sheet 6/56) is a cross-sectional view of the device as shown in FIG. 6C taken along line 6B-6B.
Figure 6A:
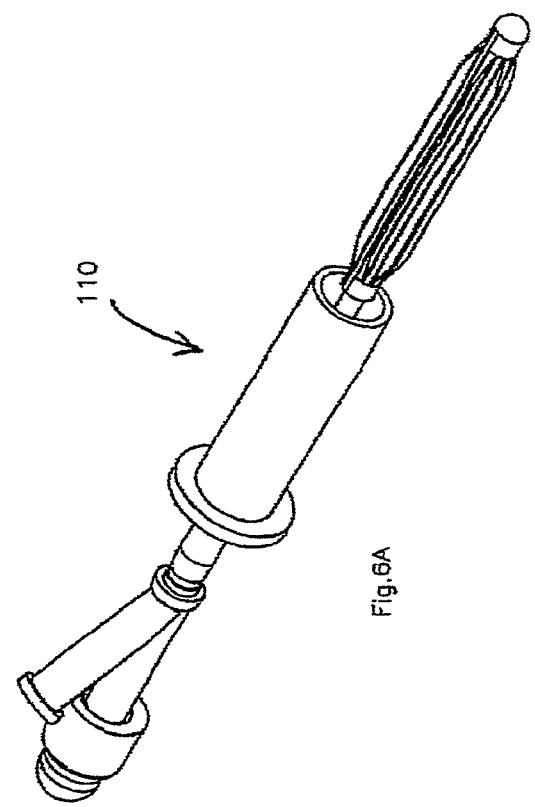
FIG. 6A (sheet 6/56) is a schematic elevation view of the same apparatus shown in FIG. 5A, except that in FIG. 6A the cap has been tightened and the sealing gasket compressed in preparation for use to prevent pressurized inflation fluid from leaking out of the proximal end of the device.
Figure 7C:
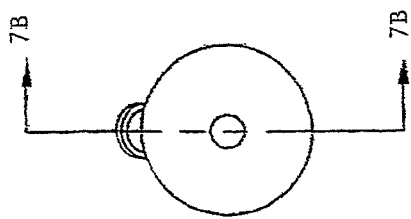
FIG. 7C (sheet 7/56) is an end view of the apparatus of FIG. 7A as seen from the distal end.
Figure 7B:
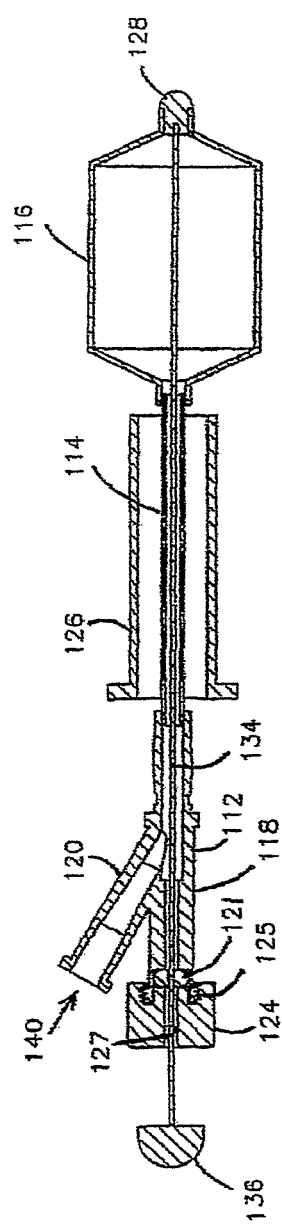
FIG. 7B (sheet 7/56) is a cross-sectional view of the device as shown in FIG. 7C taken along line 7B-7B.
Figure 7A:
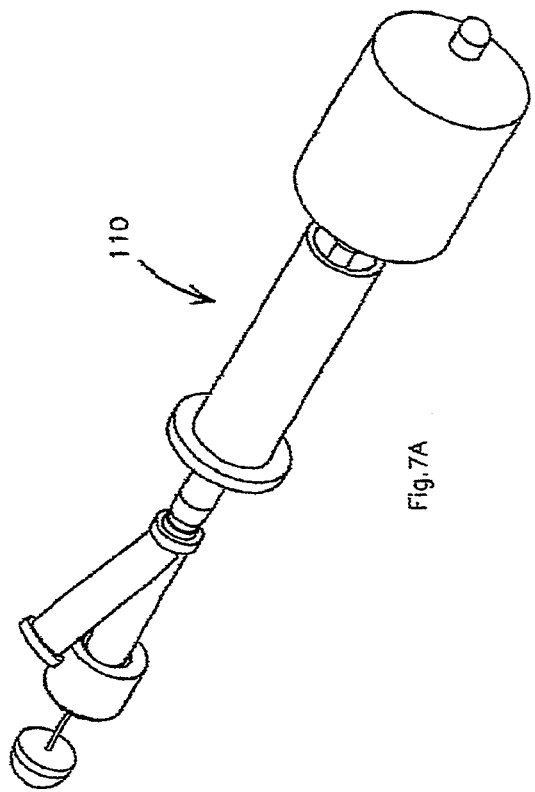
FIG. 7A (sheet 7/56) is a schematic elevation view of the same apparatus shown in FIGS. 5A and 6A, except that in FIG. 7A pressurized fluid has been used to fully inflate the balloon element. As a consequence of the balloon being inflated, it expands in diameter and shortens in length causing the push rod to be displaced toward the proximal end of the apparatus.

In FIGS. 6A-6C, catheter apparatus 110 of FIGS. 5A-5C is shown with cap element 124 screwed down and tightened thereby compressing sealing gasket 121 to form a fluid-tight seal at the sealing gasket and around rod 134 in preparation for using the catheter, while still permitting rod 134 to slide through the gasket aperture. In FIGS. 7A-7C, pressurized fluid 140 has been introduced through branch 120 to fully inflate balloon 116. As balloon 116 is inflated, it expands in diameter and shortens in length causing rod 134 to slide in a proximal direction.

Figure 8C:
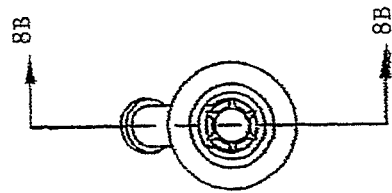
FIG. 8C (sheet 8/56) is an end view of the apparatus of FIG. 8A as seen from the distal end.
Figure 8B:
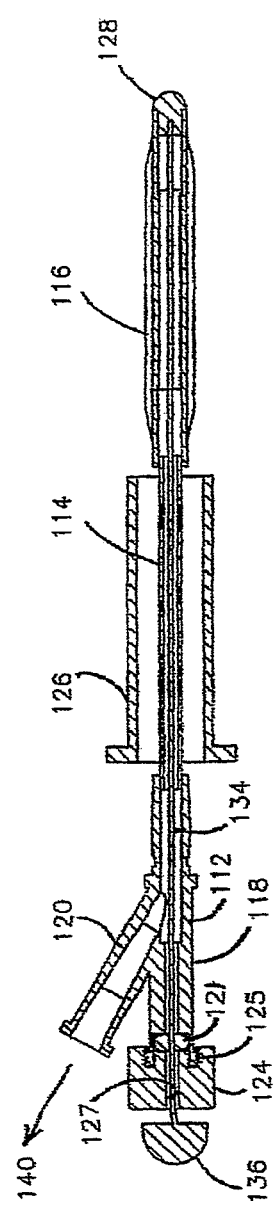
FIG. 8B (sheet 8/56) is a cross-sectional view of the device as shown in FIG. 8C taken along line 8B-8B.
Figure 8A:
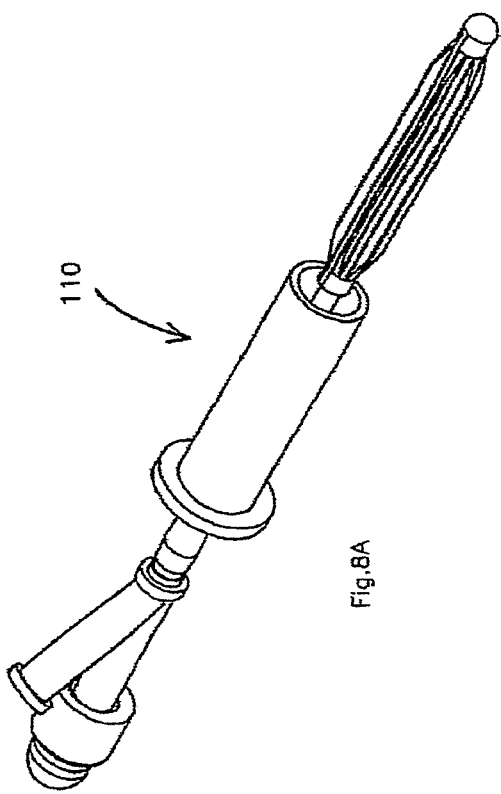
FIG. 8A (sheet 8/56) is a schematic elevation view of the same apparatus shown in FIGS. 5A, 6A and 7A, except that in FIG. 8A dilatation pressure has been removed and, optionally, a vacuum may be applied to the fluid inlet/outlet conduit to withdraw fluid from the formerly inflated balloon element thereby collapsing it. As the balloon is being deflated, or after deflation, axial force is manually applied to the proximal end of the push rod to push it toward the distal end of the device thereby assisting with stretching and refolding or repleating the balloon for easier withdrawal through the cannula from a dilated bone cavity.
Figure 9C:
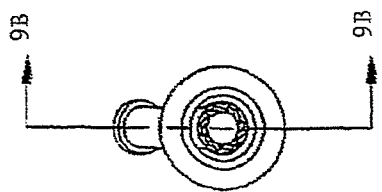
FIG. 9C (sheet 9/56) is an end view of the apparatus of FIG. 9A as seen from the distal end.
Figure 9B:
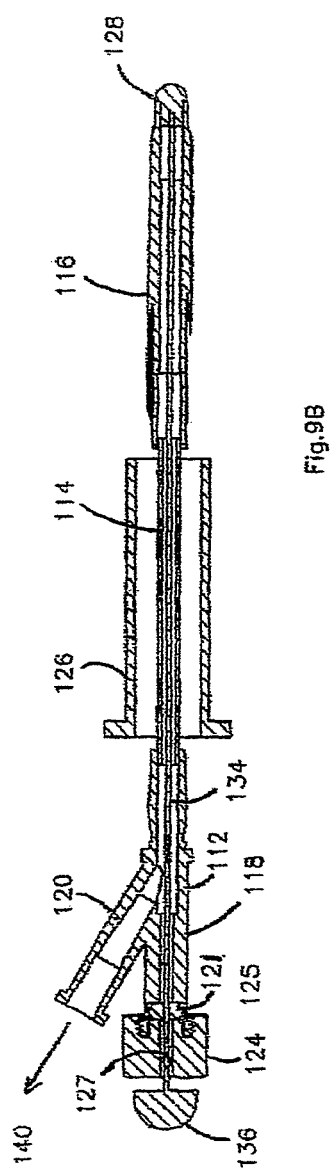
FIG. 9B (sheet 9/56) is a cross-sectional view of the device as shown in FIG. 9C taken along line 9B-9B.
Figure 9A:
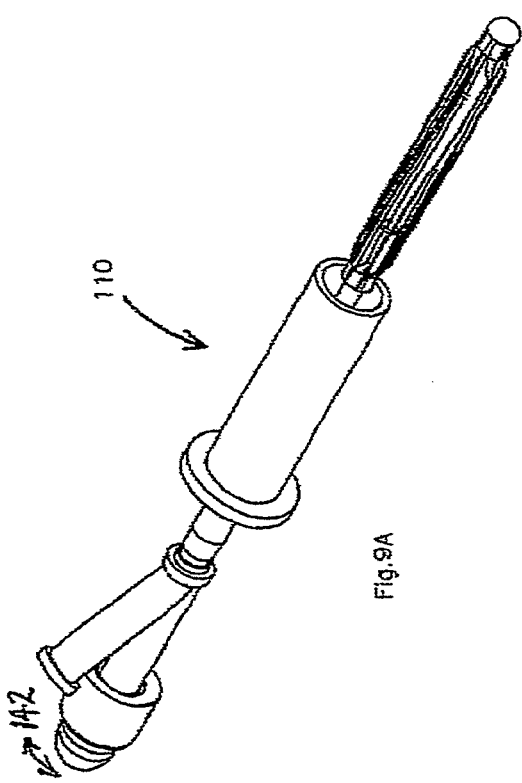
FIG. 9A (sheet 9/56) is a schematic elevation view of the same apparatus shown in FIGS. 5A, 6A and 7A, except that in FIG. 9A the push rod is attached to or engages the balloon and, as the formerly inflated balloon is being deflated, or after deflation, rotational force is manually applied to the proximal end of the push rod to rotate the push rod resulting in wrapping the deflated balloon around the push rod to further reduce the balloon profile for easier withdrawal through the cannula from a dilated bone cavity.

In FIGS. 8A-8C, dilatation pressure is removed and fluid is withdrawn from balloon 116 and from the interior of catheter 110 through branch 120. In a preferred embodiment, a vacuum may be applied to the proximal end of branch 20 to assist in withdrawing fluid and in fully collapsing balloon 116. As balloon 116 becomes deflated, axial force is manually applied to the proximal end of rod 134 to push it toward the distal end of the catheter thereby assisting with stretching and refolding or repleating the balloon into a set of small folds or pleats to create a smaller diameter profile for easier withdrawal of the deflated balloon through cannula 126. In FIGS. 9A-9C, in addition to using rod 134 to stretch the deflated balloon 116, a rotational force (as indicated by arrows 142) is applied to knob 136 to rotate rod 134 causing balloon element 116 to be wrapped around rod 134, as best seen in FIG. 9C, thereby further reducing the profile of the deflated balloon.

Figure 10C:
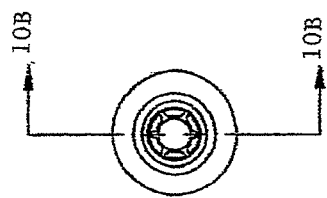
FIG. 10C (sheet 10/56) is an end view of the apparatus of FIG. 10A as seen from the distal end.
Figure 10B:
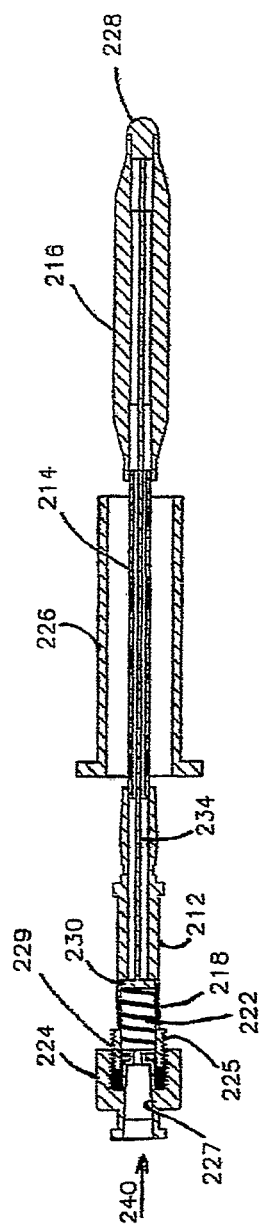
FIG. 10B (sheet 10/56) is a cross-sectional view of the device as shown in FIG. 10C taken along line 10B-10B.
Figure 10A:
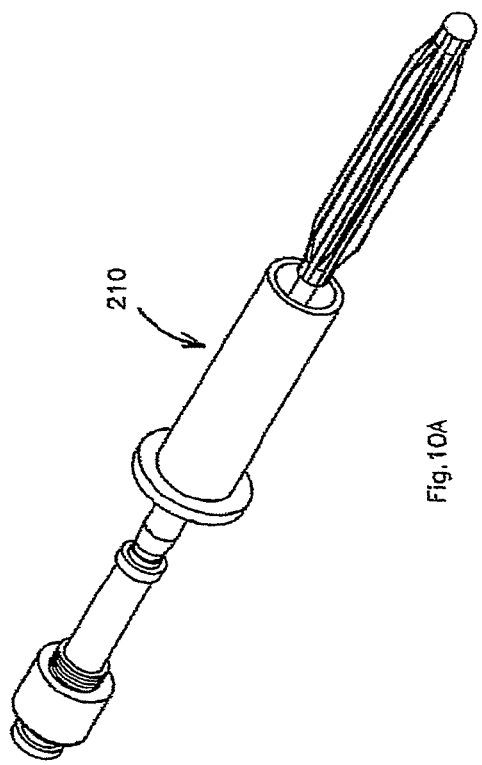
FIG. 10A (sheet 10/56) is a schematic elevation view of apparatus according to a third embodiment of the present invention designed for automatic tensioning of a balloon element to facilitate withdrawal through a small diameter cannula from a bone cavity following dilatation and subsequent deflation. The apparatus of FIG. 10A is configured substantially similar to that shown in FIG. 1A except that the inflation/deflation port in FIG. 10A has been integrated into the cap/proximal end structure thereby eliminating the Y-element or side branch in FIG. 1A which served as the fluid inlet/outlet conduit.

FIGS. 10-12 illustrate a dilatation balloon tensioning apparatus according to a third embodiment of the present invention. The balloon dilatation catheter apparatus 210 in FIGS. 10A-10C generally comprises a proximal end catheter sleeve portion 212, a middle sleeve portion 214, and a balloon or inflation element 216 at the distal end of the catheter. As best seen in FIG. 10B, proximal end catheter sleeve portion 212 comprises a tubular shell portion 218 with external threads 225 at its proximal end and a region adjacent to the threaded region for housing a spring element 222.

Cap element 224 includes a centrally-located axial bore 227 through which fluid 240 can be introduced to or withdrawn from catheter 210, and also has internal threads sized to mate with the external threads 225 at the proximal end of the shell portion 218. A gasket, seal, or O-ring 229, or a similar fluid-sealing element, having a centrally-located aperture, is disposed at the proximal end of the region of shell portion 218 which houses spring 222. As seen in FIGS. 10A-10C, cap element 224 is loosely threaded onto shell portion 218, and there is no compression of spring 222, the condition in which catheter 220 would ordinarily be shipped and stored. Balloon element 216 is shown extended, as best seen in FIG. 10C, and is preferably pleated or folded for compactness.

At the distal end of the region for housing spring element 222 (i.e., at the end opposite from where the cap 224 is threaded onto branch 218), a disc element or circular fitting 230 is sized to slide inside the region housing spring element 222 so as to compress the spring element by displacement in the proximal direction or to decompress the spring element by displacement in the distal direction. Associated with disc element 230 is axially moveable rod element 234 (which may or may not be physically connected to disc element 230) which runs axially through the interior of the catheter from the distal side of disc element 230 to the sealed tip portion 228 of balloon 216. Rod element 234 may or may not be physically connected to or may or may not engage balloon tip portion 228. Rod element 234 operating in conjunction with disc element 230 thus can act like a piston to alternately compress and allow decompression of spring element 222.

Also shown in FIGS. 10A-10C, although it is typically not attached to catheter apparatus 210, is a small diameter cannula 226 which provides a channel for the catheter apparatus through a bone portion into the bone interior. Balloon element 216 must be able to slide through the hollow interior of cannula 226 during insertion of the catheter and, more importantly, during removal of the catheter after the balloon has undergone an inflation/deflation cycle.

Figure 11C:
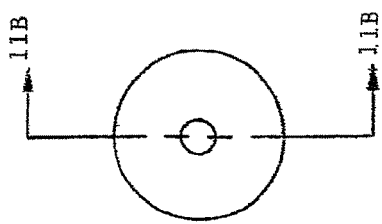
FIG. 11C (sheet 11/56) is an end view of the apparatus of FIG. 11A as seen from the distal end.
Figure 11B:
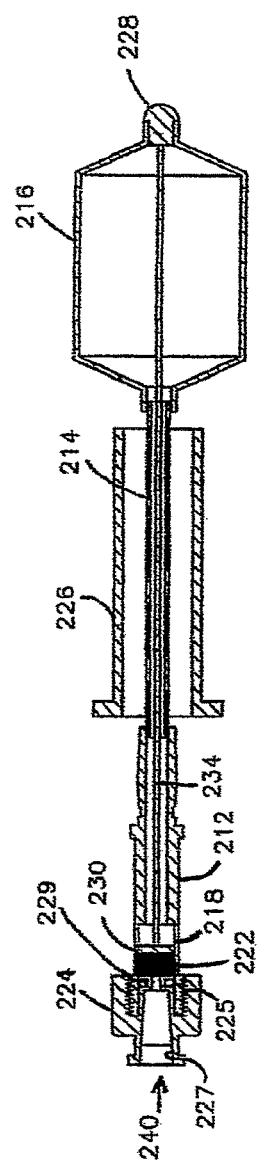
FIG. 11B (sheet 11/56) is a cross-sectional view of the device as shown in FIG. 11C taken along line 11B-11B.
Figure 11A:
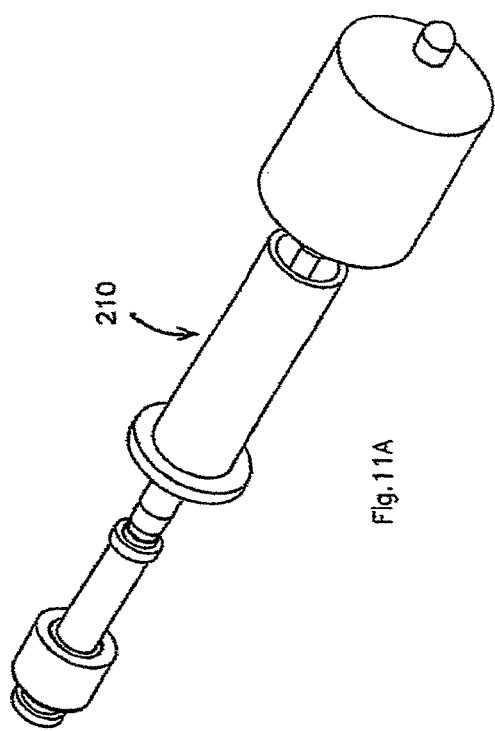
FIG. 11A (sheet 11/56) is a schematic elevation view of the same apparatus shown in FIG. 10A, except that in FIG. 11A the cap has been screwed down and pressurized fluid has been introduced to fully inflate the balloon element. As a consequence of screwing down the cap and inflating the balloon, the spring element has been compressed.

In FIGS. 11A-11C, catheter apparatus 210 of FIGS. 10A-10C is shown with cap element 224 screwed down resulting in at least partially compressing spring element 222 in preparation for use. Also in FIGS. 11A-11C, pressurized fluid 240 has been introduced through axial bore 227, through the interior of proximal sleeve portion 212, and through the interior of middle sleeve portion 214 to fully inflate balloon 216. As balloon 216 is inflated, it expands in diameter and shortens in length causing rod 234 to move in a proximal direction, thereby displacing disc element 230 in a proximal direction and further compressing spring element 222.

Figure 12C:
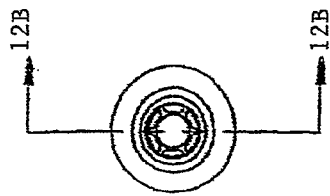
FIG. 12C (sheet 12/56) is an end view of the apparatus of FIG. 12A as seen from the distal end.
Figure 12B:
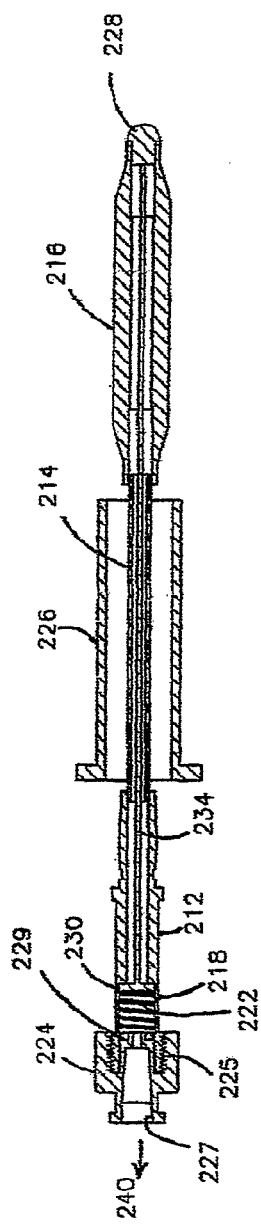
FIG. 12B (sheet 12/56) is a cross-sectional view of the device as shown in FIG. 12C taken along line 12B-12B.
Figure 12A:
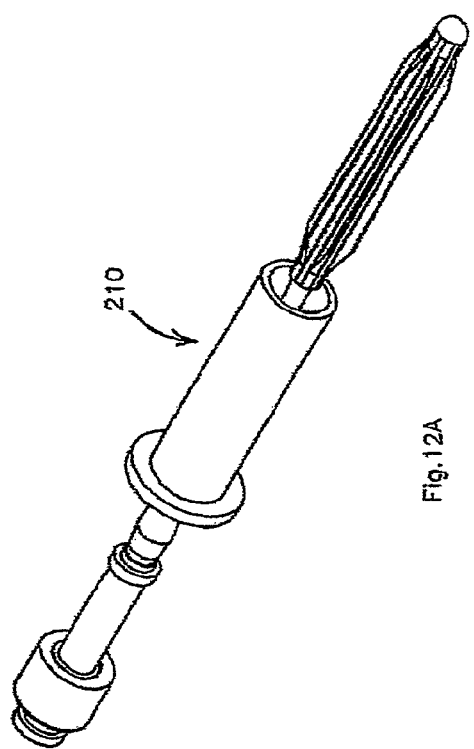
FIG. 12A (sheet 12/56) is a schematic elevation view of the same apparatus shown in FIGS. 10A and 11A, except that in FIG. 12A dilatation pressure has been removed and, optionally, a vacuum may be applied to the inflation/deflation port to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 12A-12C, dilatation pressure is removed and fluid 240 is withdrawn from balloon 216 and from the interior of catheter 210 through axial bore 227. In a preferred embodiment, a vacuum may be applied to the proximal end of axial bore 227 to assist in withdrawing fluid and fully collapsing balloon 216. As balloon 216 becomes deflated, the force exerted by the compressed spring element 222 becomes greater than the force exerted by the collapsing balloon. Eventually this results in displacing disc element 230 toward the distal end of the catheter, in turn driving rod 234 in the distal direction, and thereby stretching and tensioning balloon 216. This automatic tensioning of the balloon element upon deflation assists in collapsing, folding and/or pleating the balloon to minimize its lateral profile for easier withdrawal through the small diameter interior channel of cannula 226.

FIGS. 13-16 illustrate a dilatation balloon tensioning apparatus according to a fourth embodiment of the present invention. The balloon dilatation catheter apparatus 310 in FIGS. 13A-13C generally comprises a proximal end catheter sleeve portion 312, a middle sleeve portion 314, and a balloon or inflation element 316 at or near the distal end of the catheter. As best seen in FIG. 13B, proximal end catheter sleeve portion 312 comprises a branched or Y-shaped element, of which one arm or branch 318 comprises a tubular shell with external threads 325 at its proximal end, and the second arm or branch 320 comprises a fluid inlet/outlet conduit for introducing pressurized fluid 340 into catheter 310 for inflating balloon 316 or for withdrawing fluid 340 after a dilatation procedure.

Figure 13C:
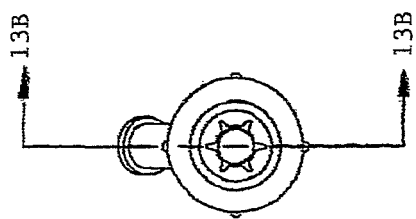
FIG. 13C (sheet 13/56) is an end view of the apparatus of FIG. 13A as seen from the distal end.
Figure 13B:
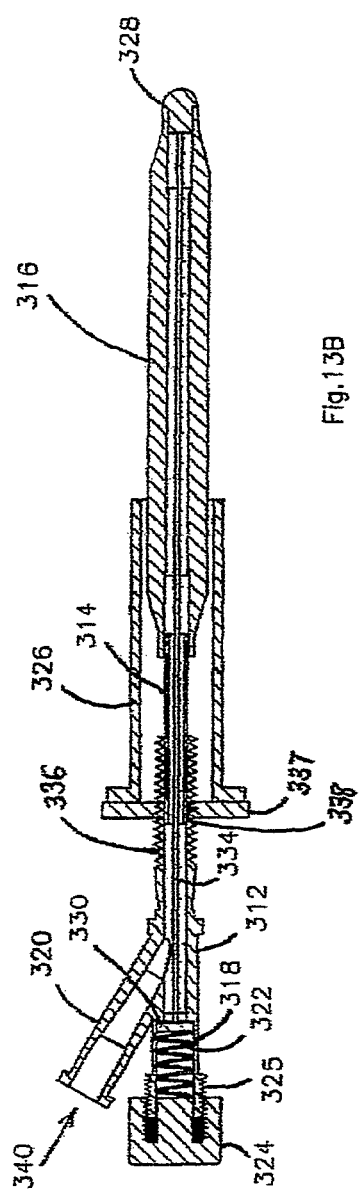
FIG. 13B (sheet 13/56) is a cross-sectional view of the device as shown in FIG. 13C taken along line 13B-13B.
Figure 13A:
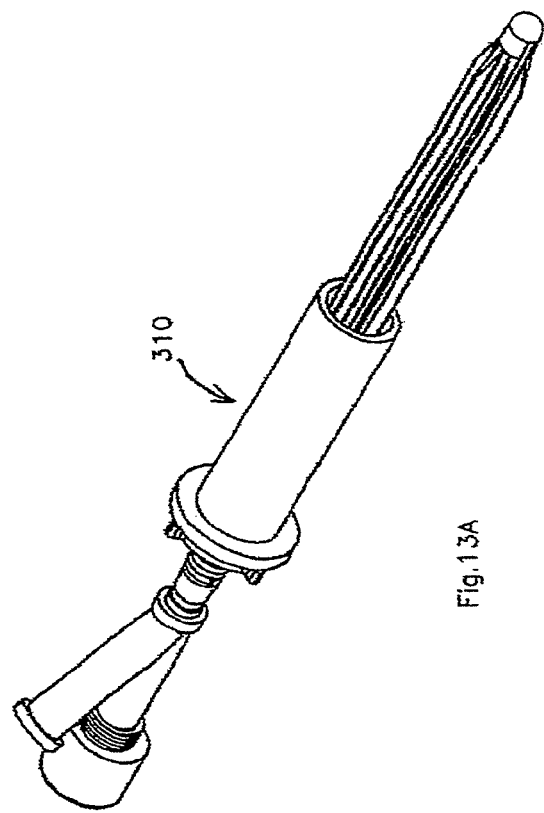
FIG. 13A (sheet 13/56) is a schematic elevation view of apparatus according to a fourth embodiment of the present invention for automatic tensioning of an adjustable length balloon element to facilitate withdrawal through a small diameter cannula from a bone cavity following dilatation and subsequent deflation. In this embodiment, the balloon element is designed longer than necessary to fill the bone cavity being treated, and an adjustable clamp, nut, collar or similar element is used to help maintain a precise balloon length and to resist expansion forces during balloon inflation. The apparatus of FIG. 13A is otherwise shown configured substantially similar to that of FIG. 1A with cap and spring elements to effect automatic tensioning of the balloon element upon deflation.

The tubular shell of branch 318 comprises a region adjacent to the threaded region for housing a spring element 322. Cap element 324 has internal threads and is sized to mate with the external threads 325 at the proximal end of branch 318. As seen in FIGS. 13A-13C, the cap element 324 is loosely threaded onto branch 318, and there is no compression of spring element 322, the condition in which catheter 310 would ordinarily be shipped and stored. Balloon element 316 is shown extended, and, as seen in FIGS. 13A and 13C, is preferably pleated or folded for compactness.

At the distal end of the region for housing spring element 322 (i.e., at the end opposite from where the cap 324 is threaded onto branch 318), a disc element or circular fitting 330 is sized to slide inside the region housing spring element 322 so as to compress the spring element by displacement in the proximal direction or to decompress the spring element by displacement in the distal direction. Associated with disc element 330 is axially moveable rod element 334 (which may or may not be physically connected to disc element 330) which runs axially through the interior of the catheter from the distal side of disc element 330 to the sealed tip portion 328 of balloon 316. Rod element 334 may or may not be physically connected to or may or may not engage balloon tip portion 328. Rod element 334 operating in conjunction with disc element 330 thus can act like a piston to alternately compress and allow decompression of spring element 322.

Also shown in FIGS. 13A-13C is a cannula element 326. In this embodiment of the invention, however, the cannula element 326 does more than just provide a channel through a bone for inserting or removing the catheter apparatus. In this embodiment, the distal section of catheter sleeve portion 312 includes external threads 336. The proximal end of cannula 326 is not open, as was the case for the previously described invention embodiments. Instead, cannula 326 is sealed at its proximal end by a plate member 337 having a threaded central bore 338, the threads being sized to mate with external threads 336. Thus, by turning cannula 326 around the axis of sleeve portion 312, the position of cannula 326 can be adjusted relative to balloon 316 by axial movement along the threaded portion of sleeve 312.

In this embodiment of the present invention, balloon element 316 is designed to be longer than the maximum length needed to fill the bone cavity being treated. By adjusting the position of cannula 326 along the distal threaded portion of sleeve 312, a surgeon can expose a length of balloon element 316 just sufficient to fill a given bone cavity before inserting the balloon into the bone cavity and inflating it. In this way, a standard catheter apparatus with a standardized balloon element in accordance with the present invention can be easily customized for each application thereby avoiding the need to prepare and stock a multiplicity of balloon lengths.

Figure 14C:
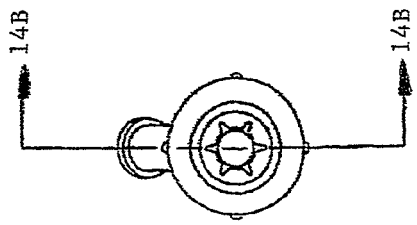
FIG. 14C (sheet 14/56) is an end view of the apparatus of FIG. 14A as seen from the distal end.
Figure 14B:
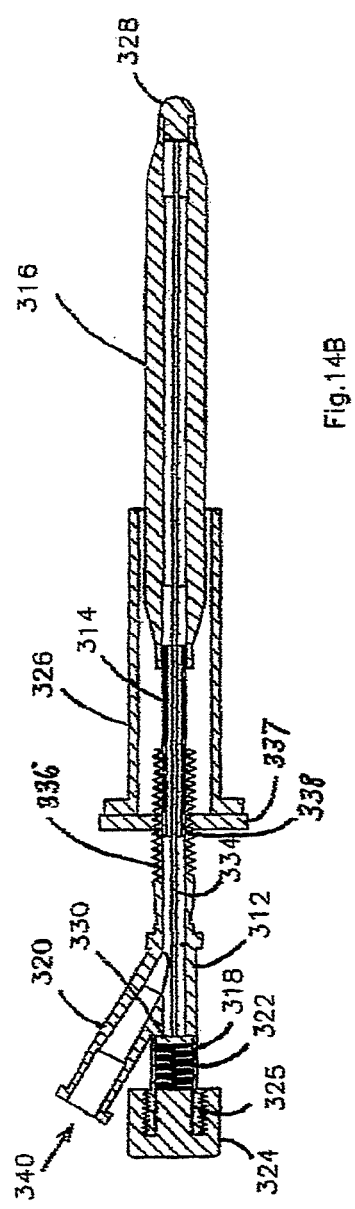
FIG. 14B (sheet 14/56) is a cross-sectional view of the device as shown in FIG. 14C taken along line 14B-14B.
Figure 14A:
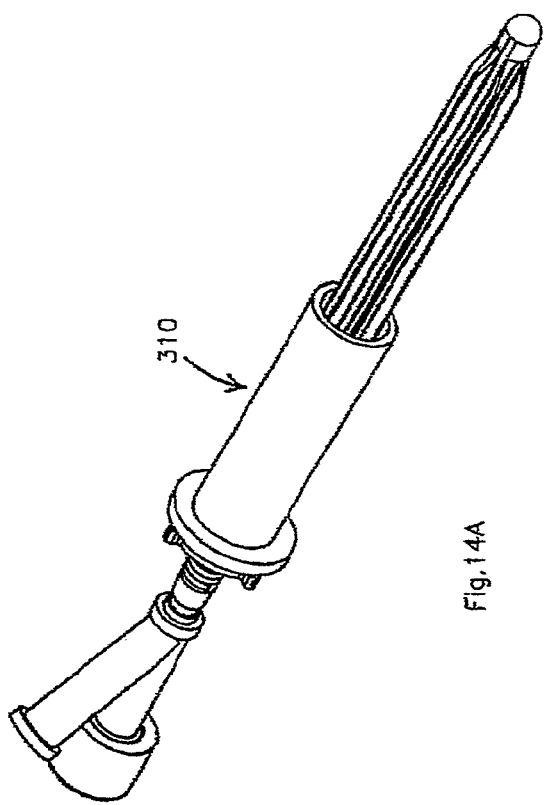
FIG. 14A (sheet 14/56) is a schematic elevation view of the same apparatus shown in FIG. 13A, except that in FIG. 14A the cap has been screwed down resulting in at least partially compressing the spring element in preparation for using the device. The balloon element remains extended and folded and/or pleated.
Figure 15C:
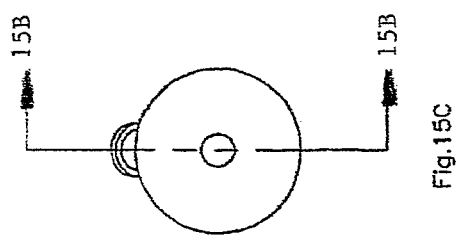
FIG. 15C (sheet 15/56) is an end view of the apparatus of FIG. 15A as seen from the distal end.
Figure 15B:
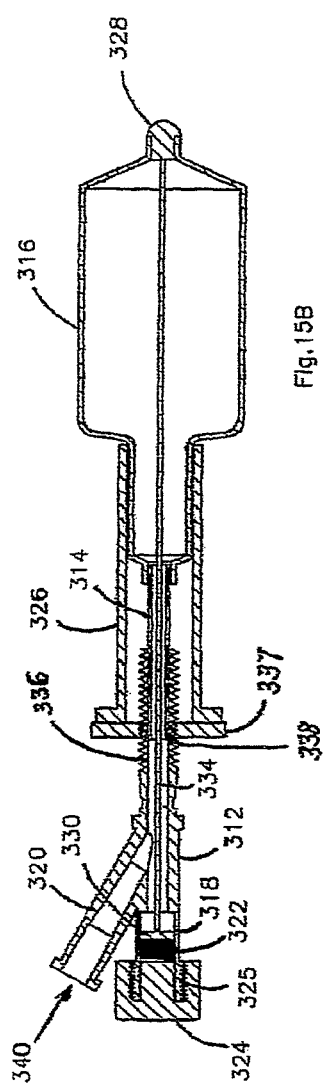
FIG. 15B (sheet 15/56) is a cross-sectional view of the device as shown in FIG. 15C taken along line 15B-15B.
Figure 15A:
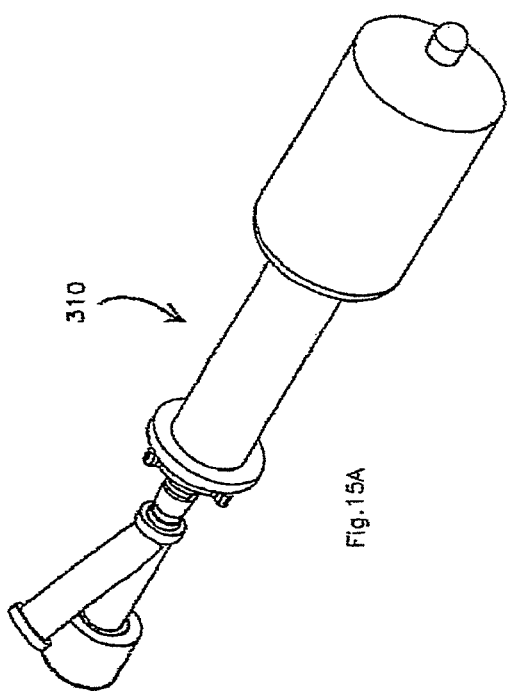
FIG. 15A (sheet 15/56) is a schematic elevation view of the same apparatus shown in FIGS. 13A and 14A, except that in FIG. 15A pressurized fluid has been introduced to inflate the distal end balloon element. As a consequence of the balloon being inflated, inflation forces try to push the cannula backward (toward the proximal end) and/or to pull the catheter out. The adjustable nut or comparable element prevents such undesirable movements.

In FIGS. 14A-14C, catheter apparatus 310 of FIGS. 13A-13C is shown with cap element 324 screwed down resulting in at least partially compressing spring element 322 in preparation for use. In FIGS. 15A-15C, pressurized fluid 340 has been introduced through branch 320, through a part of the interior of proximal sleeve portion 312, and through the interior of middle sleeve portion 314 to fully inflate the exposed portion of balloon 316. As seen best in FIG. 15B, the proximal end of balloon 316 is constrained from expanding beyond the internal diameter of cannula 326 by the walls of cannula 326. As balloon 316 is inflated, at least in part, it expands in diameter and shortens in length causing rod 334 to move in a proximal direction, thereby displacing disc element 330 in a proximal direction and further compressing spring element 322.

Figure 16C:
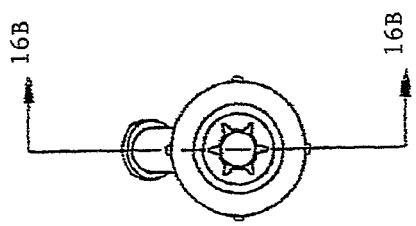
FIG. 16C (sheet 16/56) is an end view of the apparatus of FIG. 16A as seen from the distal end.
Figure 16B:
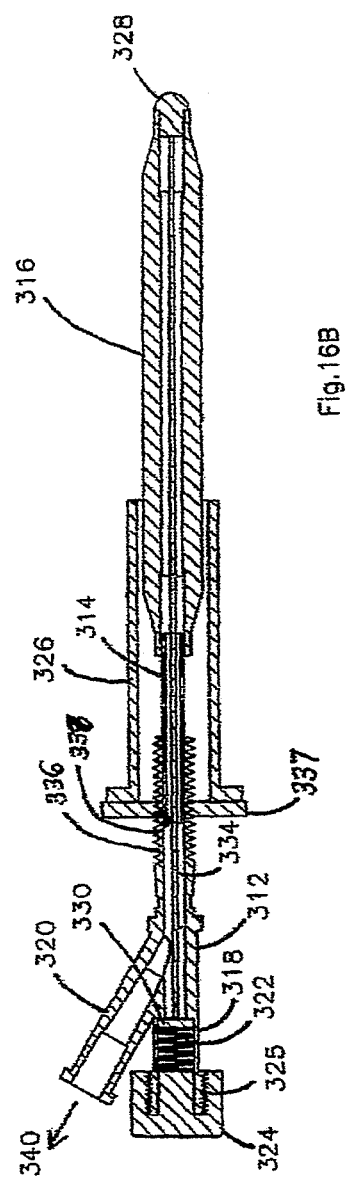
FIG. 16B (sheet 16/56) is a cross-sectional view of the device as shown in FIG. 16C taken along line 16B-16B.
Figure 16A:
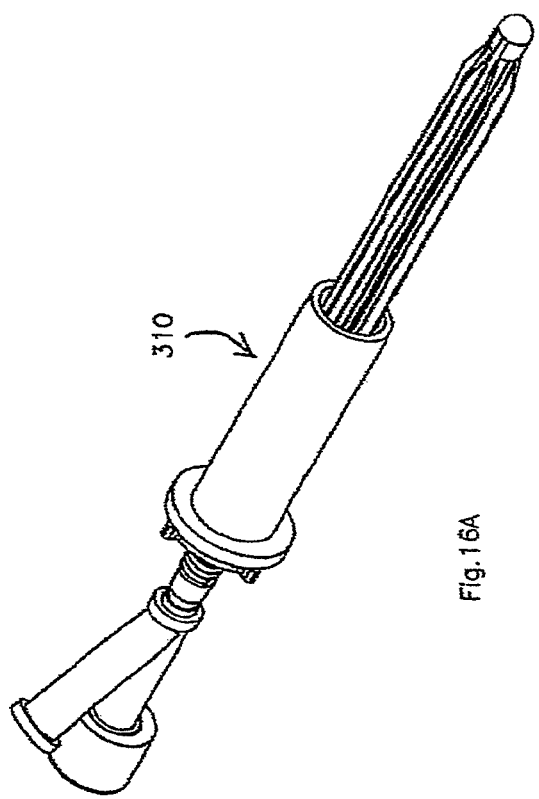
FIG. 16A (sheet 16/56) is a schematic elevation view of the same apparatus shown in FIGS. 13A, 14A and 15A, except that in FIG. 16A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 16A-16C, dilatation pressure is removed and fluid is withdrawn from balloon 316 and from the interior of catheter 310 through fluid inlet/outlet branch 320. In a preferred embodiment, a vacuum may be applied to the proximal end of branch 320 to assist in withdrawing fluid and fully collapsing balloon 316. As balloon 316 becomes deflated, the force exerted by the compressed spring element 322 becomes greater than the force exerted by the collapsing balloon. Eventually this results in displacing disc element 330 toward the distal end of the catheter, in turn driving rod 334 in the distal direction, and thereby stretching and tensioning balloon 316. This automatic tensioning of the balloon element upon deflation assists in collapsing, folding and/or pleating the balloon to minimize its lateral profile for easier withdrawal.

FIGS. 17-21 illustrate a dilatation balloon tensioning apparatus according to a fifth embodiment of the present invention. The balloon dilatation catheter apparatus 410 in FIGS. 17A-17C generally comprises a proximal end catheter sleeve portion 412, a middle sleeve portion 414, and a balloon or inflation element 416 at or near the distal end of the catheter. As best seen in FIG. 17B, proximal end catheter sleeve portion 412 comprises a branched or Y-shaped element, of which one arm or branch 418 comprises a tubular shell with external threads 425 at its proximal end, and the second arm or branch 420 comprises a fluid inlet/outlet conduit for introducing pressurized fluid 440 into catheter 410 for inflating balloon 416 or for withdrawing fluid 440 after a dilatation procedure.

Figure 17C:
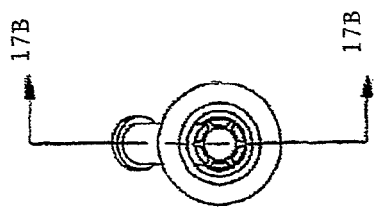
FIG. 17C (sheet 17/56) is an end view of the apparatus of FIG. 17A as seen from the distal end.
Figure 17B:
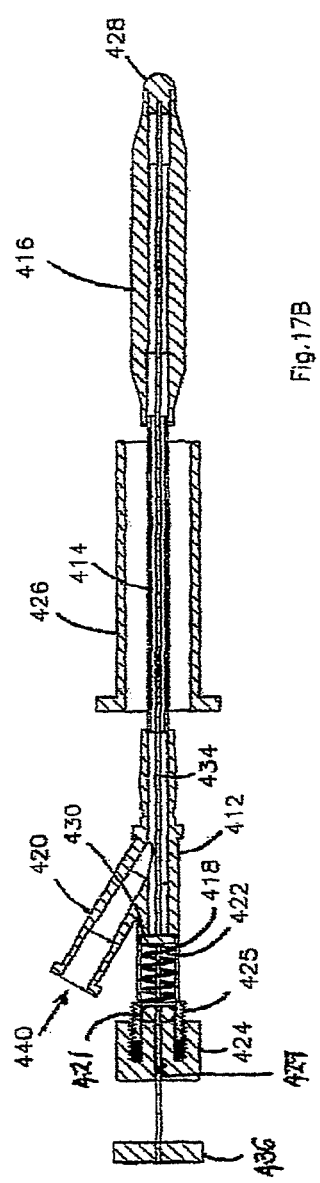
FIG. 17B (sheet 17/56) is a cross-sectional view of the device as shown in FIG. 17C taken along line 17B-17B.
Figure 17A:
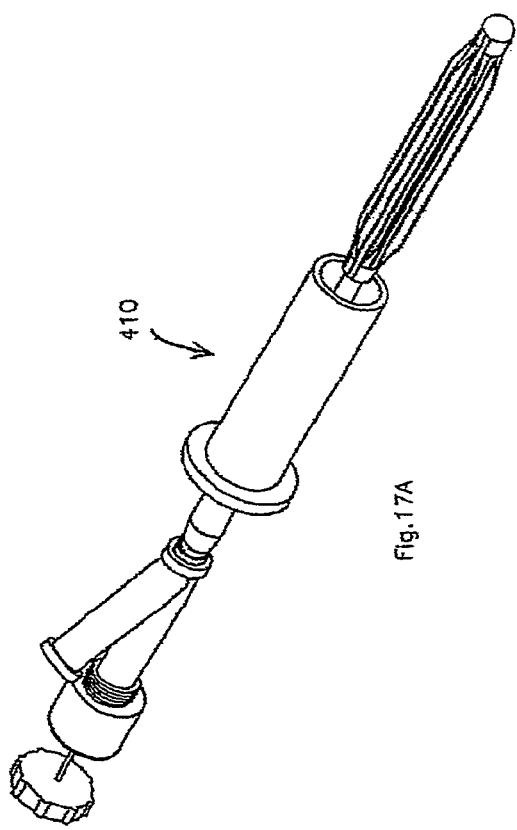
FIG. 17A (sheet 17/56) is a schematic elevation view of apparatus according to a fifth embodiment of the present invention designed for automatic tensioning and optional manual rotation (twisting and wrapping) of a balloon element to facilitate withdrawal through a small diameter cannula from a bone cavity following dilatation and subsequent deflation. In this configuration, the rod passes through the disc and is attached to the disc and to the balloon element.

The tubular shell of branch 418 comprises a region adjacent to the threaded region for housing a spring element 422. Cap element 424 has internal threads and is sized to mate with the external threads 425 at the proximal end of branch 418. As seen in FIGS. 17A-17C, the cap element 424 is loosely threaded onto branch 418, and there is no compression of spring element 422, the condition in which catheter 410 would ordinarily be shipped and stored. Cap element 424 further includes a centrally-located axial bore 427 to accommodate a rod element 434 as hereinafter described. Balloon element 416 is shown extended, and, as seen in FIGS. 17A and 17C, is preferably pleated or folded for compactness.

Push rod 434, having a knob portion 436 at its proximal end, is slidably positioned inside the catheter and is sized to extend axially the full length of catheter 410. Push rod 434 extends through the central bore 427 of cap 424, through a sealing gasket 421, which acts like a bushing for supporting and centering rod 434, through the center of spring element 422 and the interior of sleeves 412 and 414, and through the interior of balloon 416 to the sealed tip portion 428. In one variation of this invention embodiment, rod 434 may be connected to or capable of engaging tip portion 428 to facilitate twisting or wrapping balloon element 416 about rod 434 following a dilatation and deflation cycle.

At the distal end of the region for housing spring element 422 (i.e., at the end opposite from where the cap 424 is threaded onto branch 418), a disc element or circular fitting 430 is sized to slide inside the region housing spring element 422 so as to compress the spring element by displacement in the proximal direction or to decompress the spring element by displacement in the distal direction. Disc element 430 has a centrally-located axial bore to accommodate axially moveable rod element 434. Rod element 434 may or may not be physically connected to balloon tip portion 428. Rod element 434 operating in conjunction with disc element 430 thus can act like a piston to alternately compress and allow decompression of spring element 422.

Also shown in FIGS. 17A-17C, although it is typically not attached to catheter apparatus 410, is a small diameter cannula 426 which provides a channel for the catheter apparatus through a bone portion into the bone interior. Balloon element 416 must be able to slide through the hollow interior of cannula 426 during insertion of the catheter and, more importantly, during removal of the catheter after the balloon has undergone an inflation/deflation cycle.

Figure 18C:
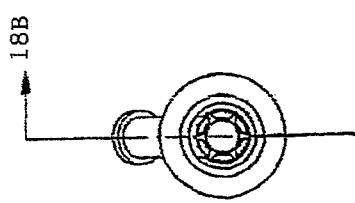
FIG. 18C (sheet 18/56) is an end view of the apparatus of FIG. 18A as seen from the distal end.
Figure 18B:
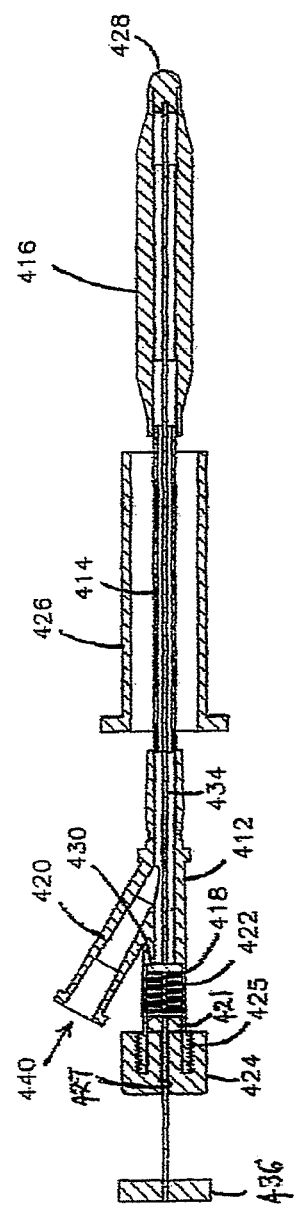
FIG. 18B (sheet 18/56) is a cross-sectional view of the device as shown in FIG. 18C taken along line 18B-18B.
Figure 18A:
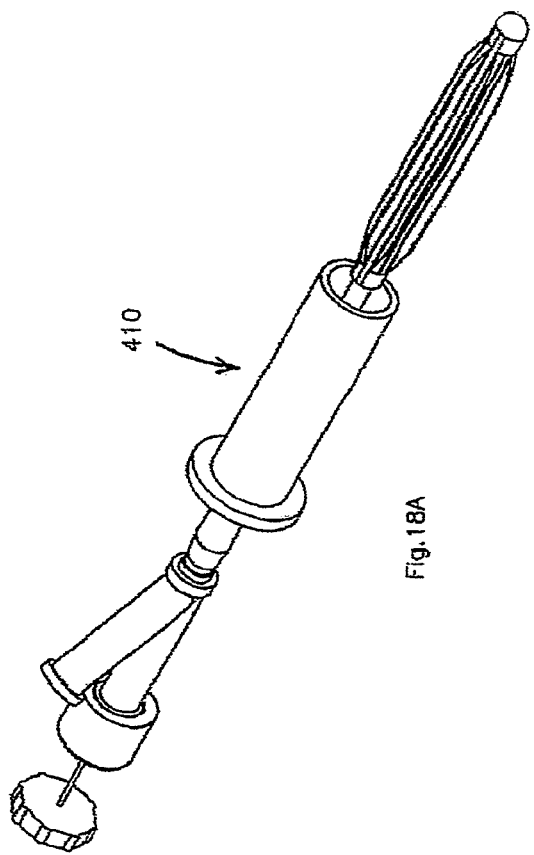
FIG. 18A (sheet 18/56) is a schematic elevation view of the same apparatus shown in FIG. 17A, except that in FIG. 18A the cap has been screwed down resulting in at least partially compressing the spring element in preparation for using the device. The balloon element remains extended and folded and/or pleated.
Figure 19C:
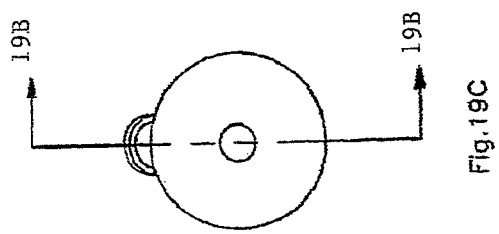
FIG. 19C (sheet 19/56) is an end view of the apparatus of FIG. 19A as seen from the distal end.
Figure 19B:
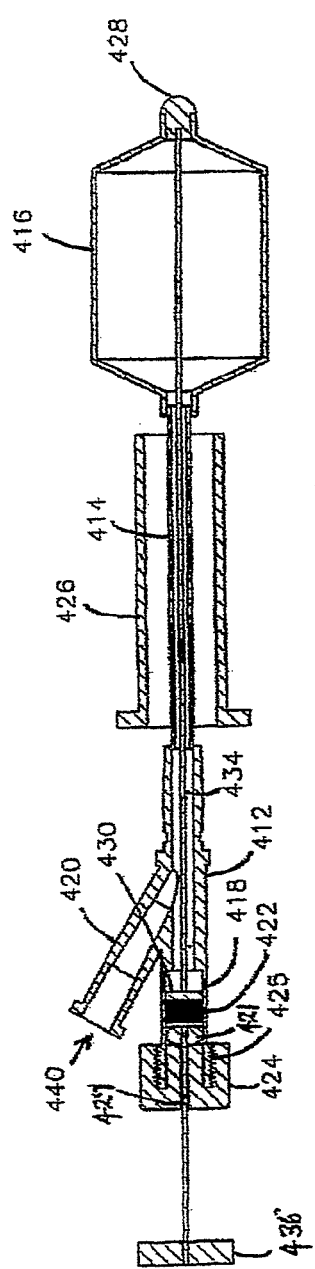
FIG. 19B (sheet 19/56) is a cross-sectional view of the device as shown in FIG. 19C taken along line 19B-19B.
Figure 19A:
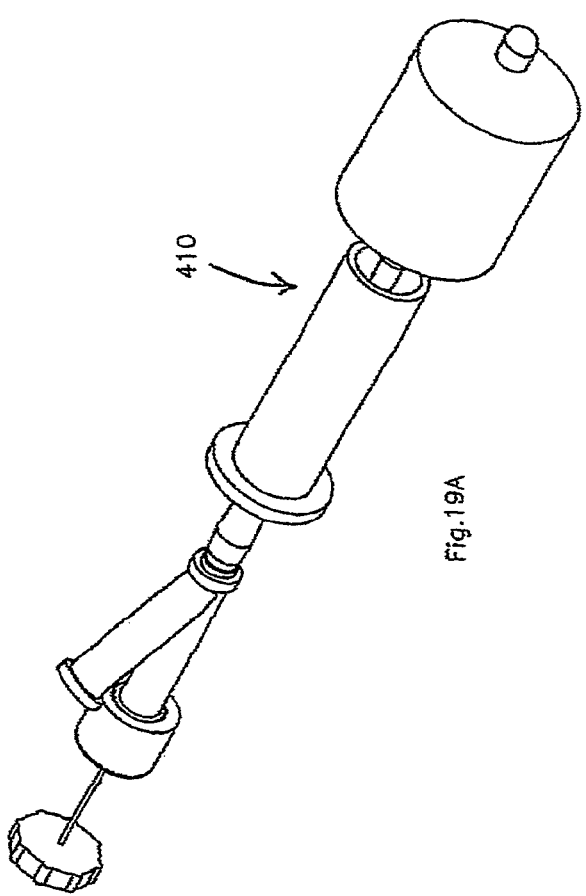
FIG. 19A (sheet 19/56) is a schematic elevation view of the same apparatus shown in FIGS. 17A and 18A, except that in FIG. 19A pressurized fluid has been introduced to fully inflate the balloon element. As a consequence of the balloon being inflated, it expands in diameter and shortens in length causing the rod/disc elements to be displaced toward the proximal end of the apparatus thereby further compressing the spring element.

In FIGS. 18A-18C, catheter apparatus 410 of FIGS. 17A-17C is shown with cap element 424 screwed down resulting in at least partially compressing spring element 422 in preparation for use. In FIGS. 19A-19C, pressurized fluid 440 has been introduced through branch 420, through a part of the interior of proximal sleeve portion 412, and through the interior of middle sleeve portion 414 to fully inflate balloon 416. As balloon 416 is inflated, it expands in diameter and shortens in length causing rod 434 to move in a proximal direction, thereby displacing disc element 430 in a proximal direction and further compressing spring element 422.

Figure 21C:
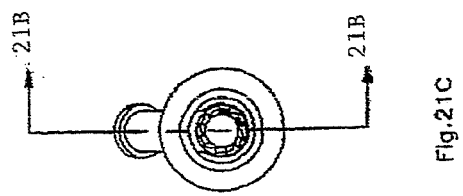
FIG. 21C (sheet 21/56) is an end view of the apparatus of FIG. 21A as seen from the distal end.
Figure 21B:
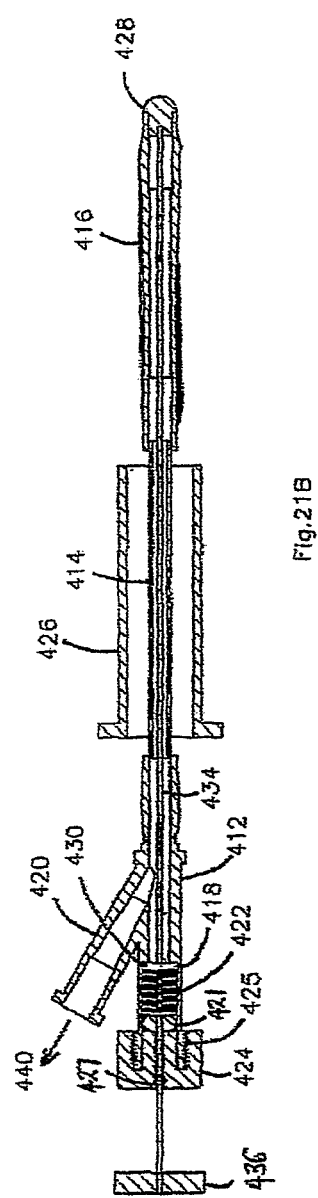
FIG. 21B (sheet 21/56) is a cross-sectional view of the device as shown in FIG. 21C taken along line 21B-21B.
Figure 21A:
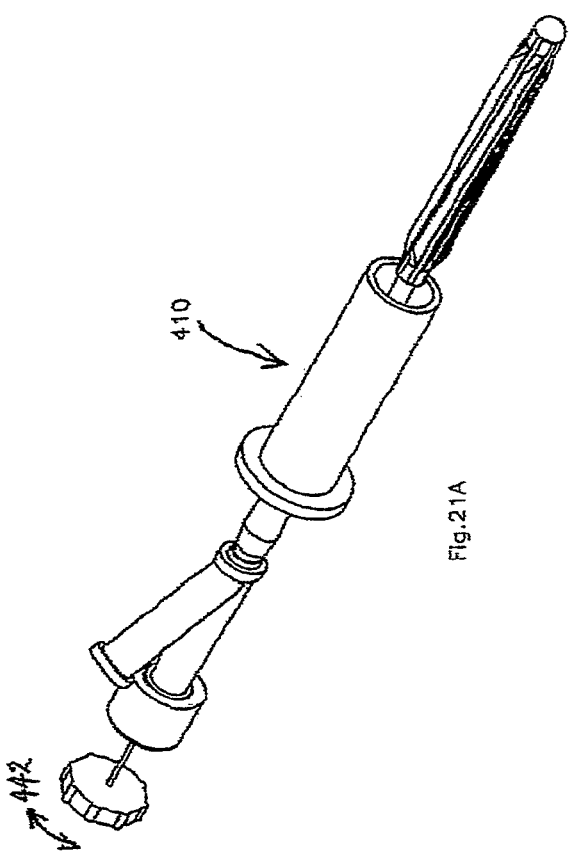
FIG. 21A (sheet 21/56) is a schematic elevation view of the same apparatus shown in FIGS. 17A, 18A, 19A and 20A, except that in FIG. 21A the rod is attached to or engages the balloon and, as the formerly inflated balloon is being deflated, or after deflation, rotational force is manually applied to the proximal end of the rod to rotate the rod resulting in wrapping the deflated balloon around the rod to further reduce the balloon profile for easier withdrawal through the cannula from a dilated bone cavity.

In FIGS. 20A-20C, dilatation pressure is removed and fluid is withdrawn from balloon 416 and from the interior of catheter 410 through fluid inlet/outlet branch 420. In a preferred embodiment, a vacuum may be applied to the proximal end of branch 420 to assist in withdrawing fluid and fully collapsing balloon 416. As balloon 416 becomes deflated, the force exerted by the compressed spring element 422 becomes greater than the force exerted by the collapsing balloon. Eventually this results in displacing disc element 430 toward the distal end of the catheter, in turn driving rod 434 in the distal direction, and thereby stretching and tensioning balloon 416. This automatic tensioning of the balloon element upon deflation assists in collapsing, folding and/or pleating the balloon to minimize its lateral profile for easier withdrawal through the small diameter interior channel of cannula 426. In FIGS. 21A-21C, in addition to using rod 434 to stretch the deflated balloon 416, a rotational force (as indicated by arrows 442) is applied to knob 436 to rotate rod 434 causing balloon element 416 to be wrapped around rod 434, as best seen in FIG. 21C, thereby further reducing the profile of the deflated balloon.

FIGS. 22-25 illustrate a dilatation balloon tensioning apparatus according to a sixth embodiment of the present invention. The balloon dilatation catheter apparatus 510 in FIGS. 22A-22D generally comprises a proximal end catheter sleeve portion 512, a middle sleeve portion 514, and a balloon or inflation element 516 at or near the distal end of the catheter. As best seen in FIG. 22B, proximal end catheter sleeve portion 512 comprises a branched or Y-shaped element, of which one arm or branch 518 comprises a tubular shell with external threads 525 at its proximal end, and the second arm or branch 520 comprises a fluid inlet/outlet conduit for introducing pressurized fluid 540 into catheter 510 for inflating balloon 516 or for withdrawing fluid 540 after a dilatation procedure.

Cap element 524 has internal threads and is sized to mate with the external threads 525 at the proximal end of branch 518. As seen in FIGS. 22A-22D, the cap element 524 is loosely threaded onto branch 518, and there is no compression of a spring element 522, located inside balloon 516, the condition in which catheter 510 would ordinarily be shipped and stored. Balloon element 516 is shown extended, and, as seen in FIGS. 22A and 22C, is preferably pleated or folded for compactness.

An axially moveable rod element 534 having a head portion 530 at its proximal end runs axially through the interior of the catheter from the distal side of cap element 524 to the sealed tip portion 528 of balloon 516. Rod element 534 may or may not be physically connected to balloon tip portion 528. The head portion 530 of rod 534 moves axially within a region in the interior of branch 518 as rod 534 slides toward or away from tip portion 528.

At the distal end of rod 534 and located inside balloon 516 is a spring tensioning system comprising a spiral spring element 522 wrapped around at least a portion of rod 534. FIG. 22D is an enlarged view of the balloon end of the catheter which better shows spring element 522 spiraling around the distal end of rod 534. As best seen in FIG. 22D, the distal end of rod 534 in one embodiment may comprise two telescoping rod sections consisting of a hollow tubular section 546 and a smaller-diameter section 547 sized to slidably fit inside the hollow interior of section 546 and terminating in a bulbous rod tip 548. Spring element 522 is a spiral spring having a diameter smaller than the outer diameter of rod section 546 but larger than the outer diameter of rod section 547. Spring element 522 is not secured at either end but occupies a region bounded at the proximal end by the distal end of rod section 546 and at the distal end by the proximal surface of rod tip 548.

In FIGS. 23A-23D, catheter apparatus 510 of FIGS. 22A-22D is shown with cap element 524 screwed down resulting in at least partially compressing spring element 522 by the distal movement of rod section 546 relative to rod section 547, in preparation for use. In FIGS. 24A-24D, pressurized fluid 540 has been introduced through branch 520, through a part of the interior of proximal sleeve portion 512, and through the interior of middle sleeve portion 514 to fully inflate balloon 516. As balloon 516 is inflated, it expands in diameter and shortens in length causing further inward telescoping of rod section 547 into rod section 546 (as best seen in FIG. 24D), thereby further compressing spring element 522.

In FIGS. 25A-25D, dilatation pressure is removed and fluid is withdrawn from balloon 516 and from the interior catheter 510 through fluid inlet/outlet branch 520. In a preferred embodiment, a vacuum may be applied to the proximal end of branch 520 to assist in withdrawing fluid and fully collapsing balloon 516. As balloon 516 becomes deflated, the force exerted by the compressed spring element 522 becomes greater than the force exerted by the collapsing balloon. Eventually this results in an outward telescoping of rod section 547 out of rod section 546 driven by the decompression of spring element 522, and thereby stretching and tensioning balloon 516. This automatic tensioning of the balloon element upon deflation assists in collapsing, folding and/or pleating the balloon to minimize its lateral profile for easier withdrawal through the small diameter interior channel of cannula 526.

Apparatus according to the present invention can be utilized in a variety of ways. As previously discussed, a principal intended application for the apparatus and methods of this invention is in treating vertebral fractures by dilating the interior of a vertebral element using a balloon catheter. FIGS. 26-33 illustrate various specific applications of apparatus and methods according to this invention in treating vertebral fractures.

Figure 26A:
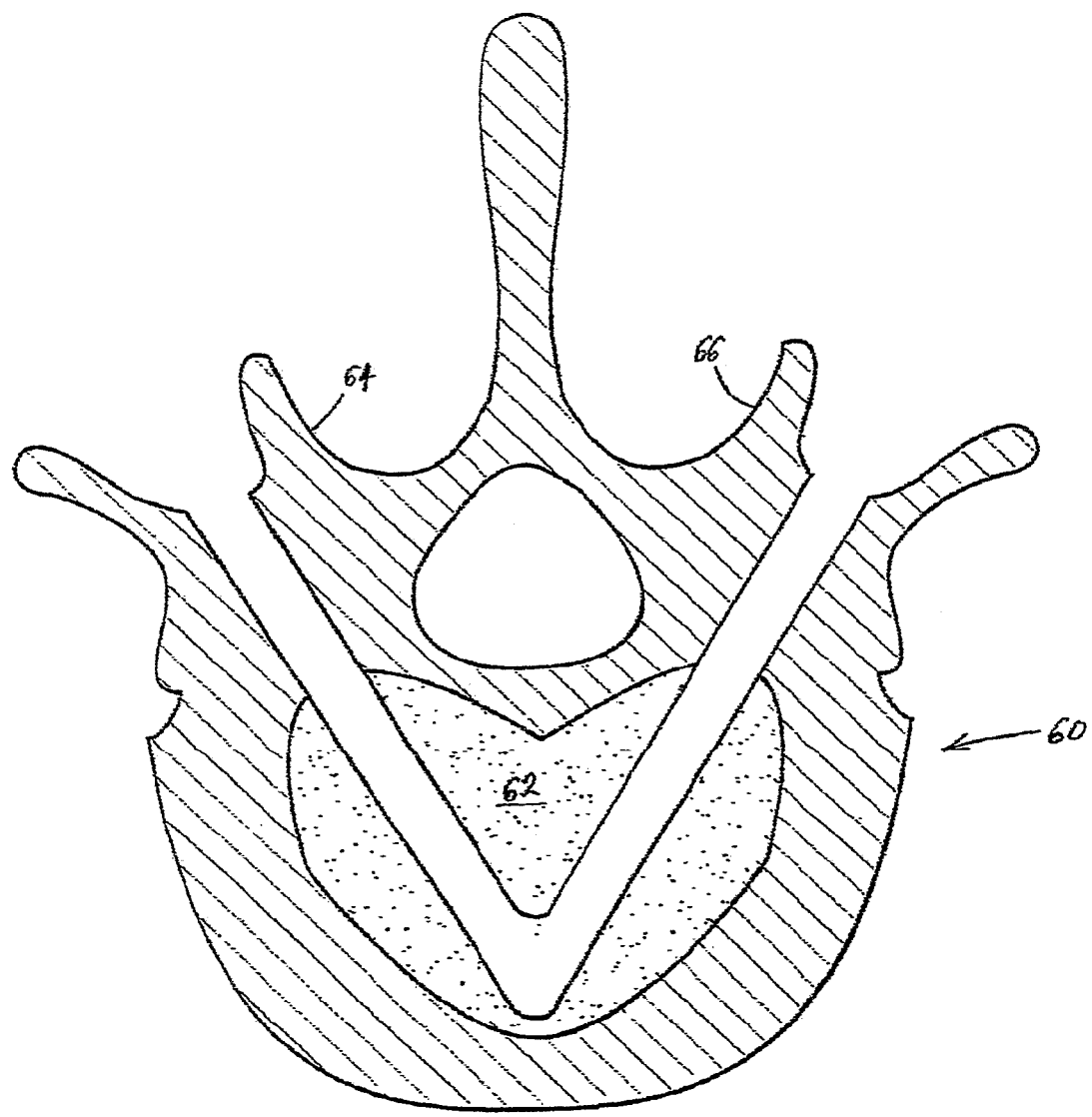

For example, FIGS. 26A-26D schematically illustrate the treatment of a partially collapsed vertebral segment with an apparatus according to one embodiment of this invention. FIG. 26A schematically illustrates a cross-section of a vertebral segment 60 comprising an interior region 62 filled with cancellous, or spongy, bone, and left and right pedicle portions 64 and 66 respectively. As seen in FIG. 26A, straight-line access holes have been drilled or otherwise created through pedicle portions 64 and 66 and into the adjacent cancellous bone in interior region 62 so as to meet and form a V-shaped passageway from the exterior of vertebral segment 60 through interior region 62.

Figure 26B:
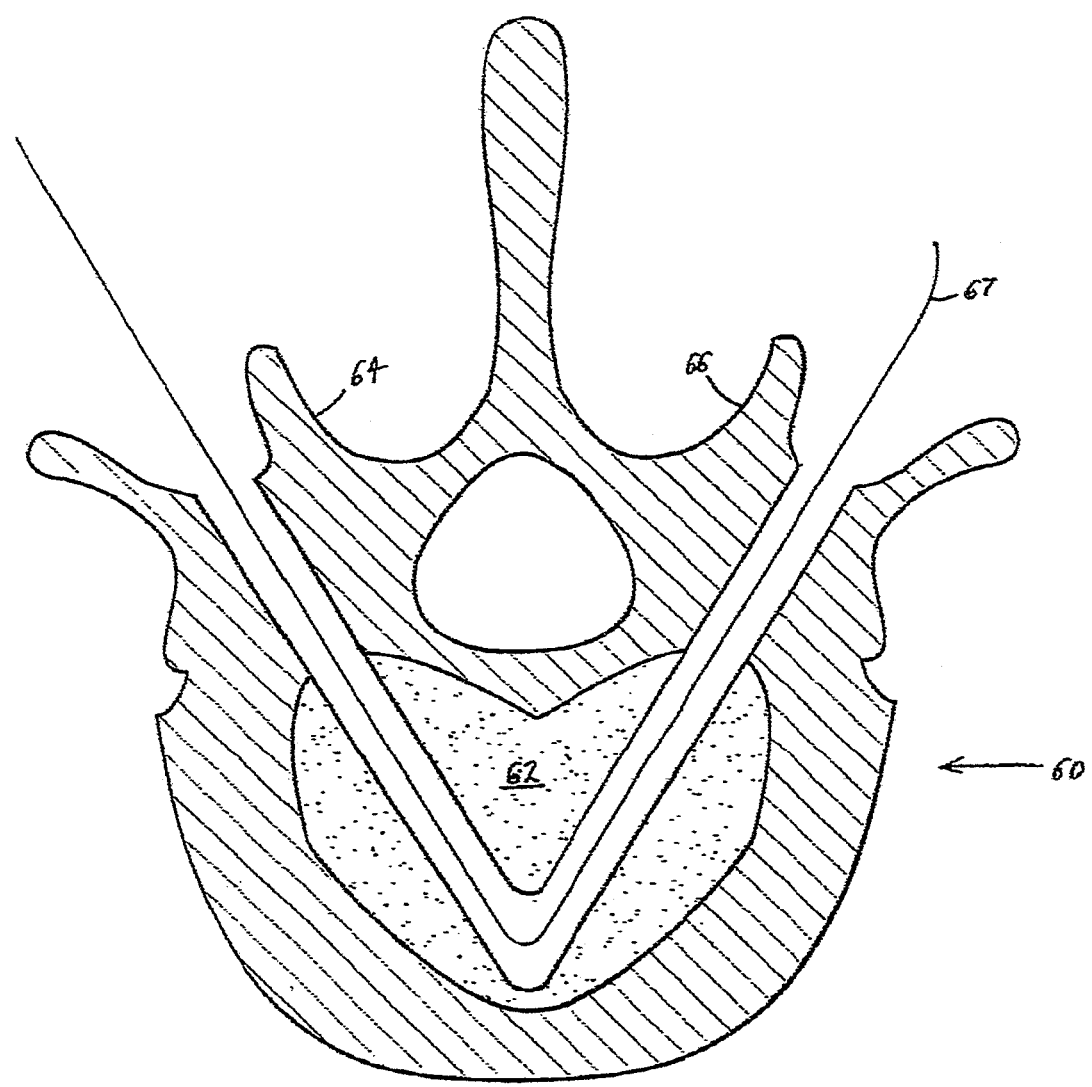
Figure 26C:
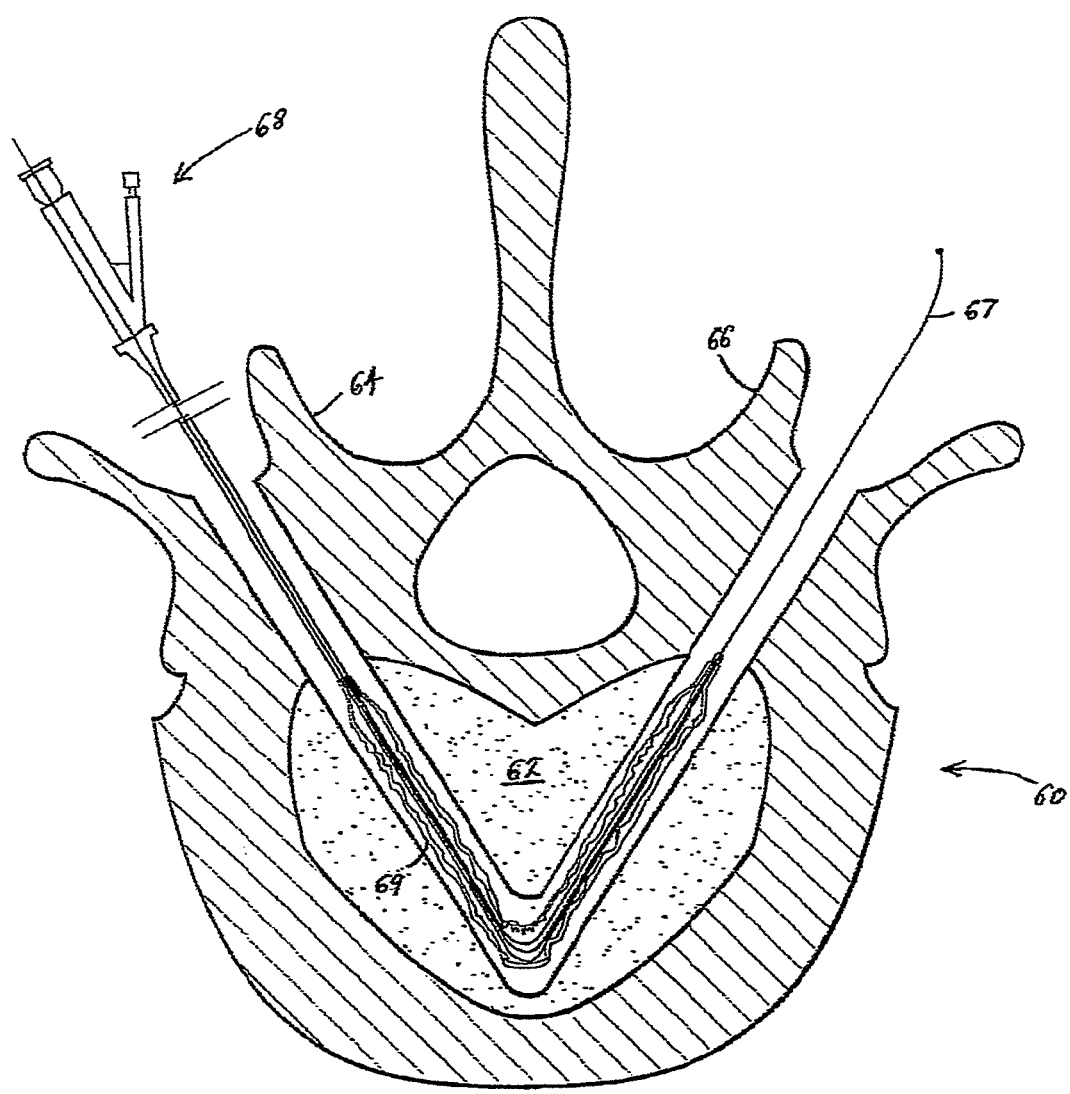
Figure 26D:
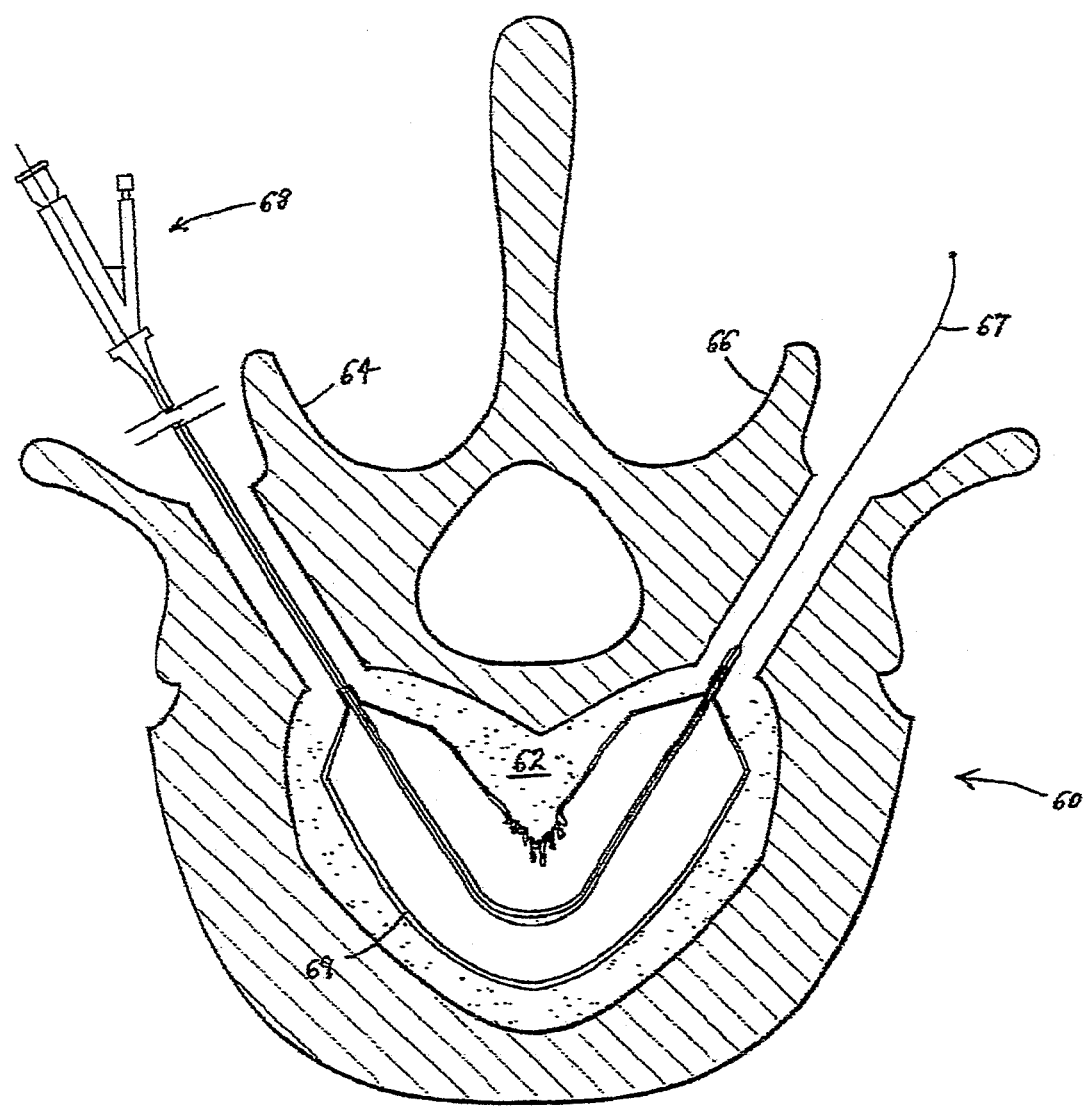

As shown in FIG. 26B, a catheter guidewire 67 may then be threaded through the V-shaped passageway. As shown in FIG. 26C, a catheter apparatus 68 according to the present invention is introduced into the V-shaped passageway along guidewire 67 so as to position all of the uninflated balloon element 69 of the catheter apparatus inside interior region 62. As shown in FIG. 26D, once balloon element 69 is properly positioned in region 62, the balloon element can be inflated, expanding against the surrounding cancellous bone and thereby restoring the shape and size of the vertebral segment close if not identical to its pre-injury configuration. Following this procedure, balloon element 69 is deflated and its lateral profile is reduced by stretching, tensioning, folding or pleating the balloon element utilizing the automatic or manual tensioning and/or twisting techniques previously described for a catheter apparatus in accordance with this invention. Once the lateral profile of balloon element 69 is sufficiently reduced, catheter apparatus 68, including balloon element 69, can be easily withdrawn from the vertebral segment.

Figure 27A:
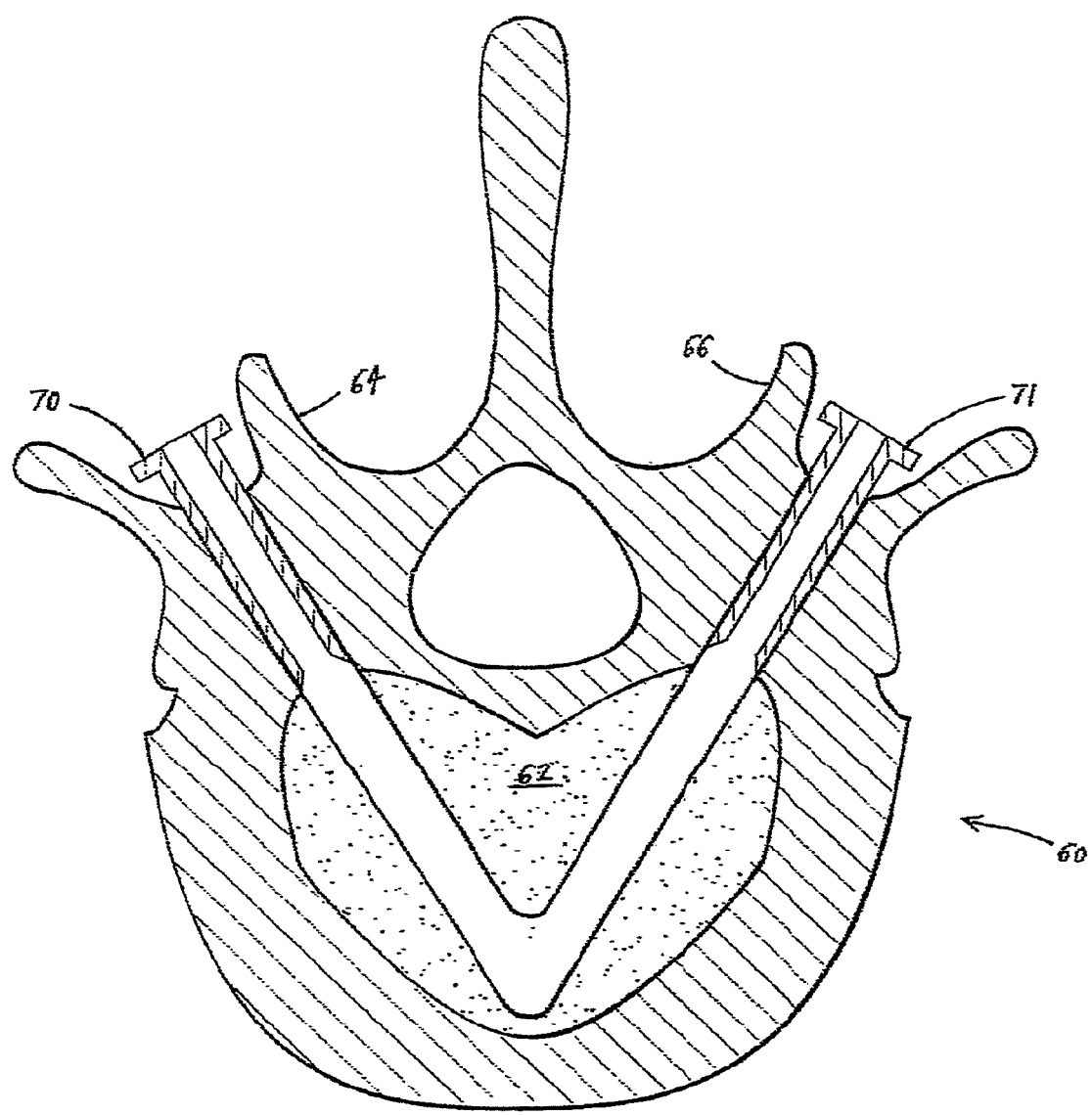
Figure 27B:
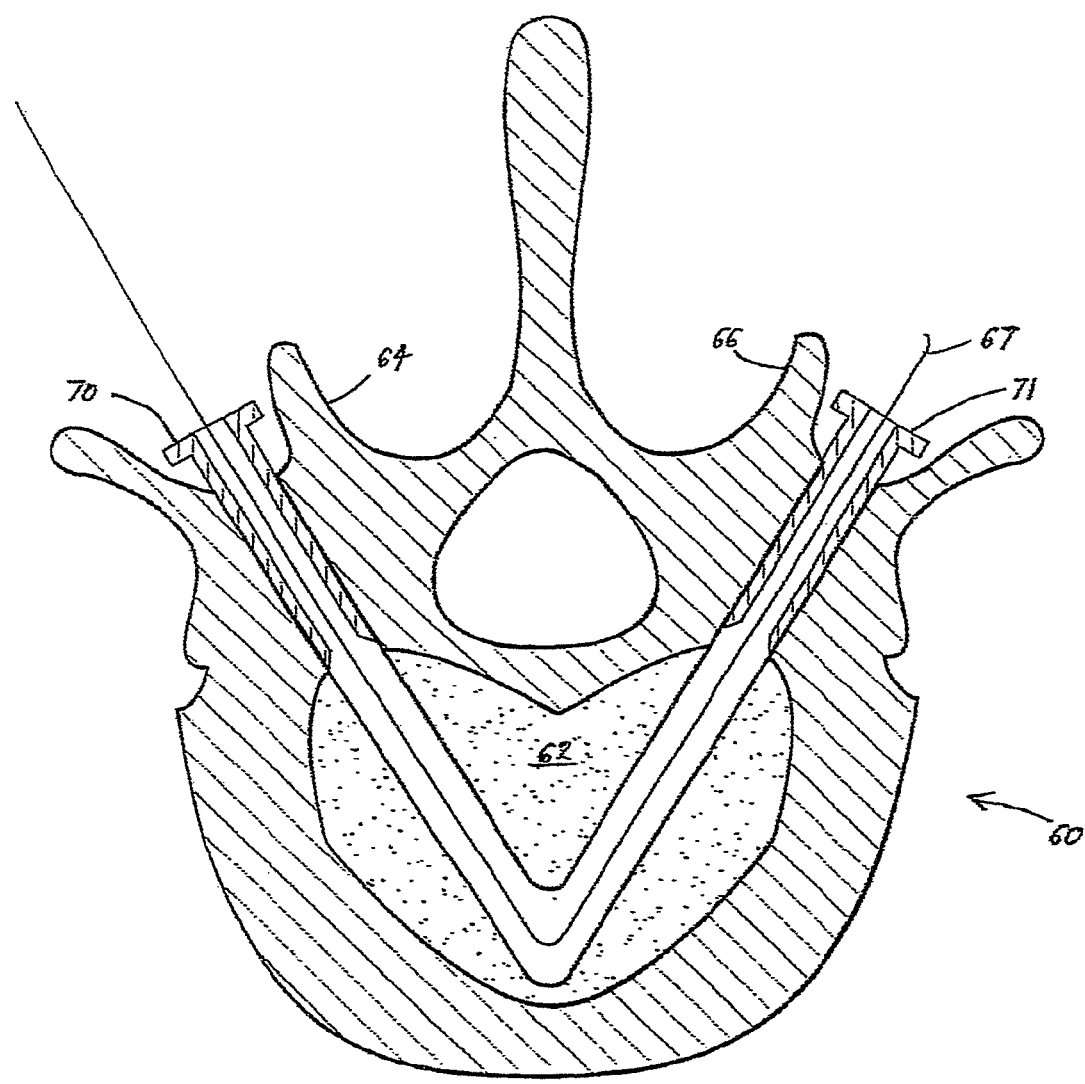
Figure 27C:
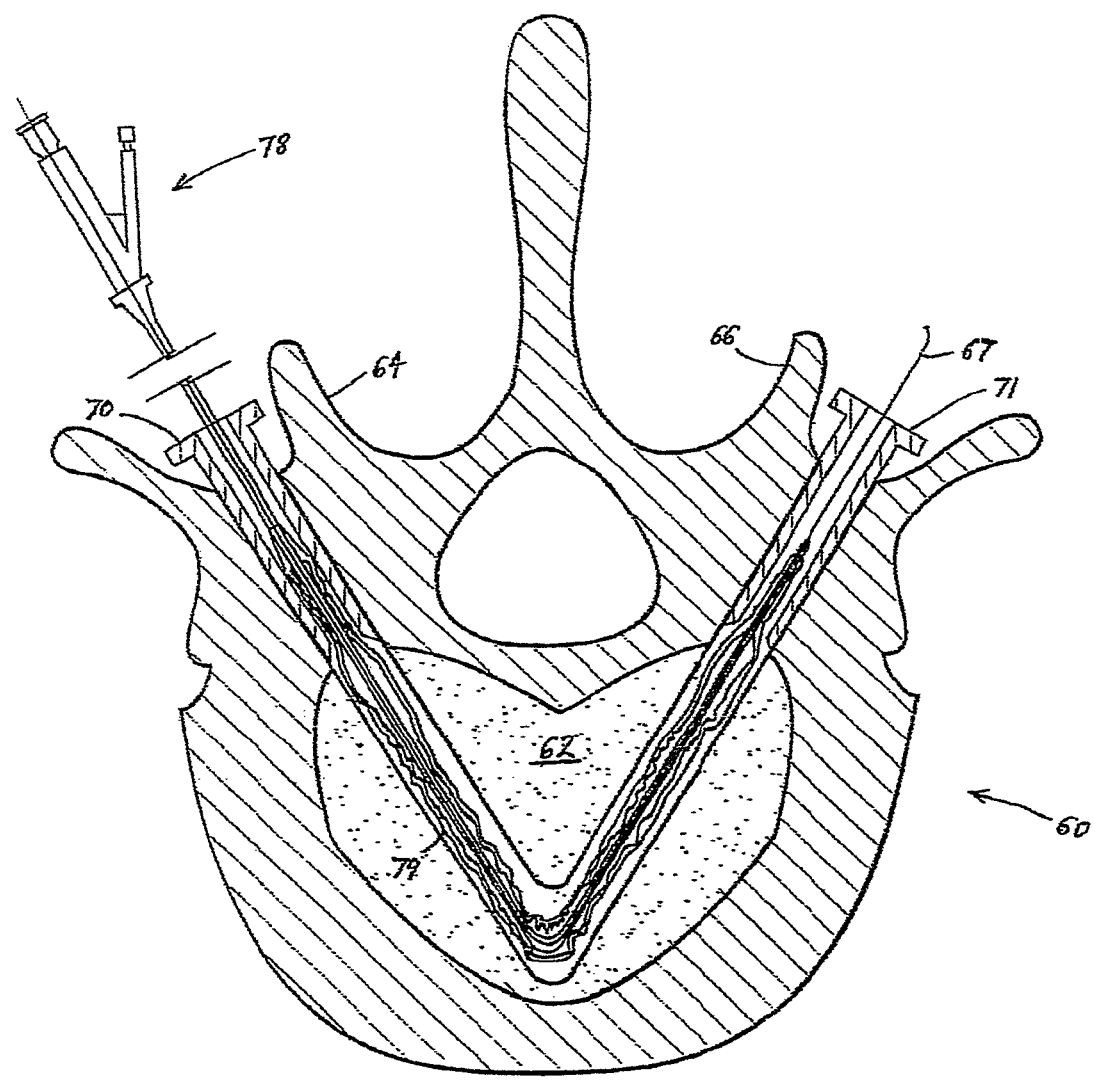
Figure 27D:
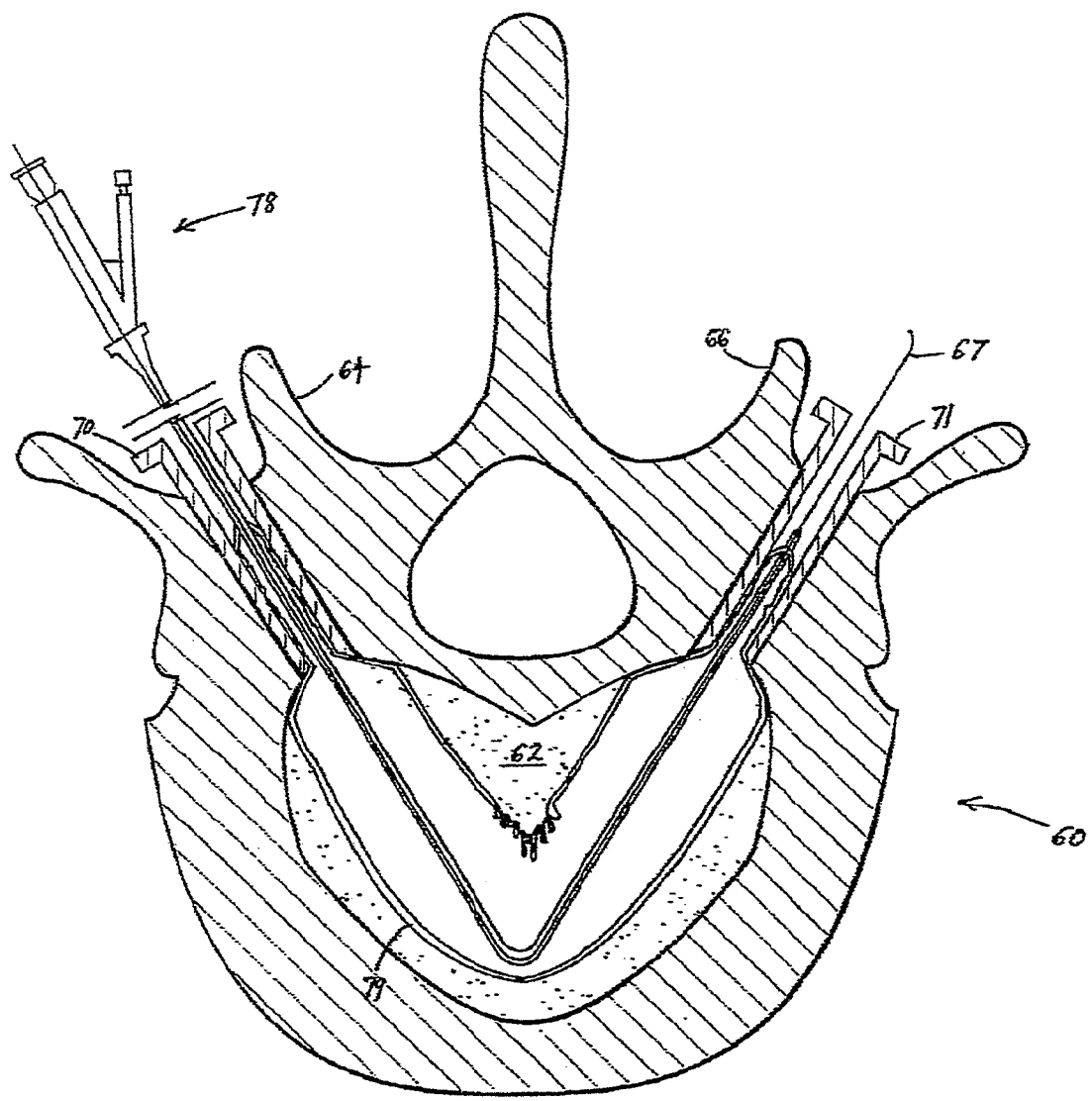

FIGS. 27A-27D generally correspond respectively to FIGS. 26A-26D, as described above, except that in FIGS. 27A-27D, after the V-shaped passageway is created through vertebral segment 60, cannula elements 70 and 71 are inserted respectively into the passages through pedicle portions 64 and 66. As seen in FIG. 27C, the catheter apparatus 78 used with this embodiment of the invention includes a balloon element 79 which is longer than the length of the V-shaped passageway through interior region 62. As a result, a proximal-end portion of balloon element 79 remains in cannula 70 and a distal-end portion of balloon element 79 is in cannula 71. As seen in FIG. 27D, when balloon element 79 is inflated, only the middle portion of the balloon which is inside region 62 can fully inflate. The inflation of the proximal and distal ends of balloon element 79 is constrained by the inner walls respectively of cannula elements 70 and 71. The cannula elements 70 and 71 prevent the expansion forces exerted by the inflated balloon inside the passages through pedicle portions 64 and 66 from rupturing these relatively fragile bones.

Figure 28A:
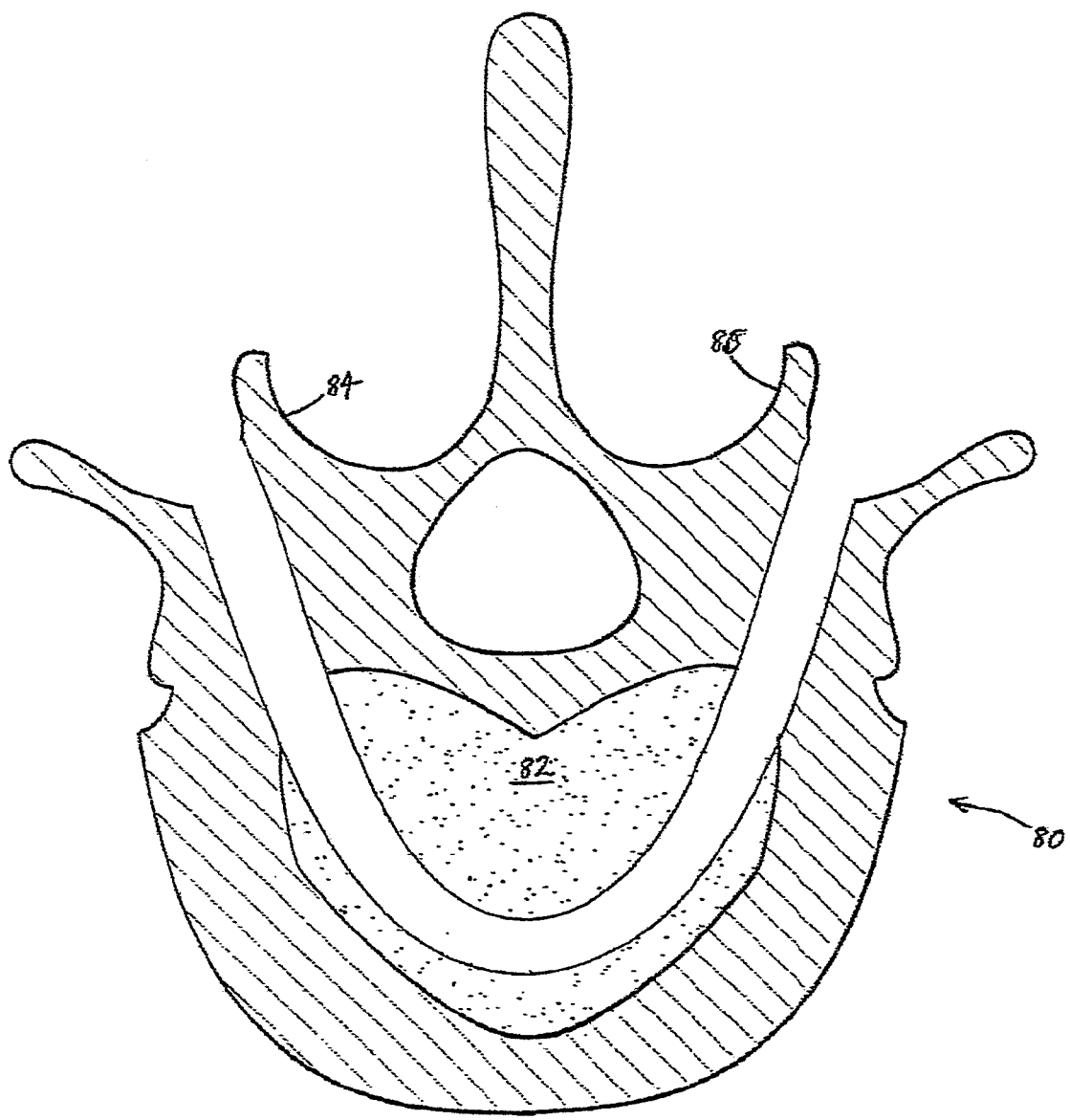

FIGS. 28A-28E schematically illustrate a cross-section of a vertebral segment 80 comprising an interior region 82 filled with cancellous bone, and left and right pedicle portions 84 and 86 respectively. As seen in FIG. 28A, a curved passageway has been created through left pedicle portion 84, through the cancellous bone in region 82, and through the right pedicle portion 86 to form a U-shaped channel from the exterior of vertebral segment 80 through interior region 82.

Figure 28B:
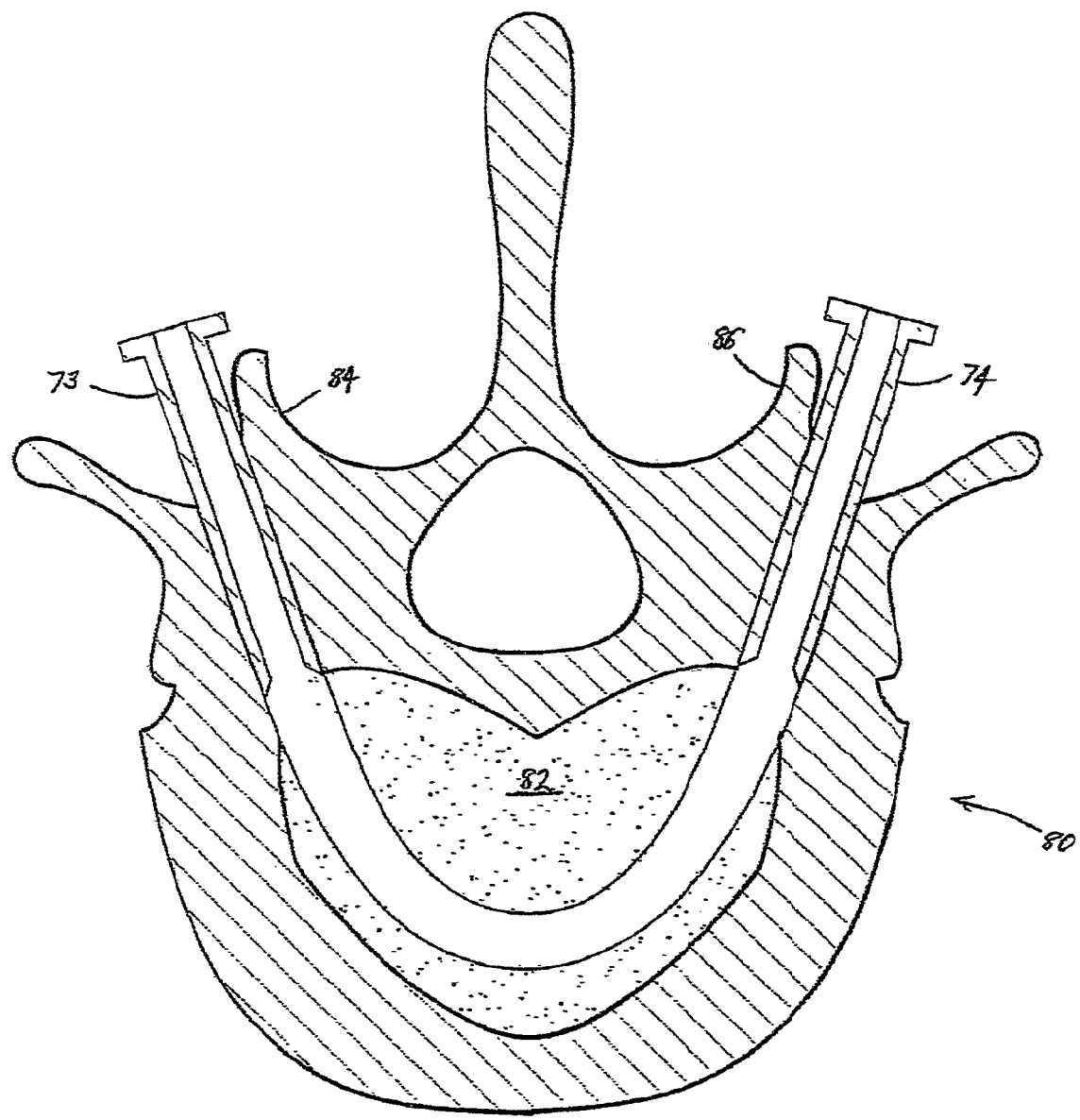
Figure 28C:
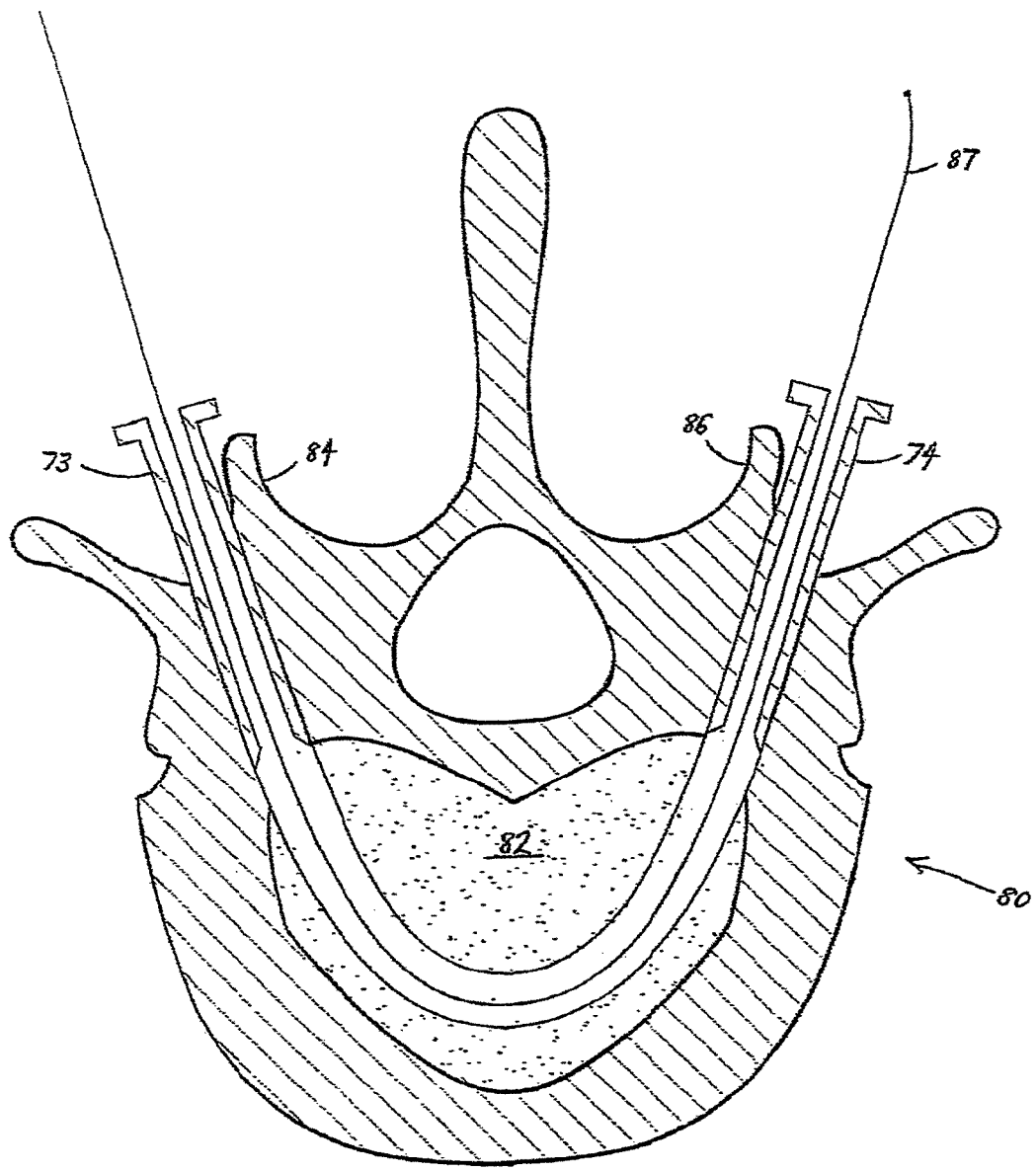
Figure 28D:
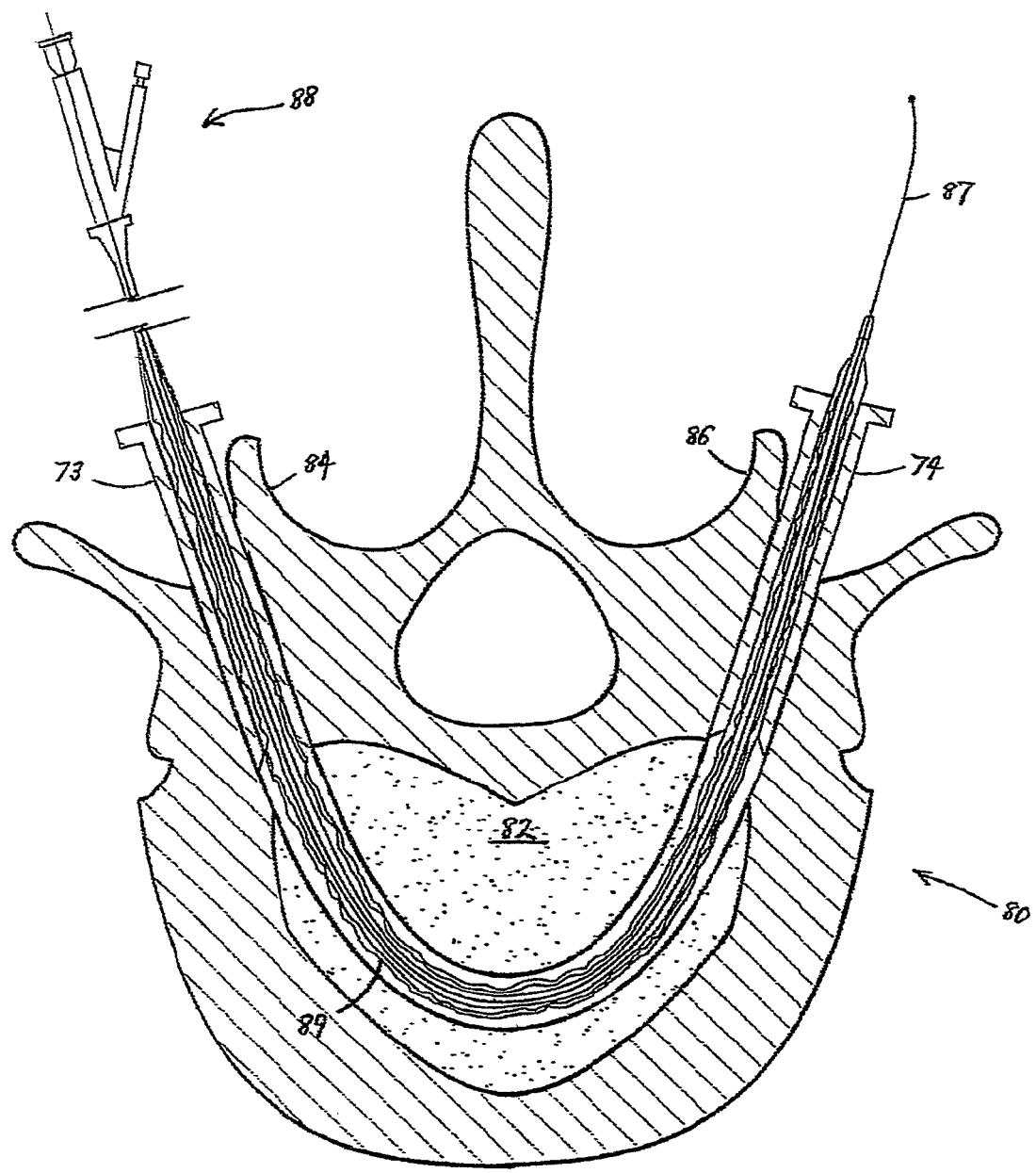

As shown in FIG. 28B, cannula elements 73 and 74 are positioned respectively in the passages through left pedicle portion 84 and right pedicle portion 86. As seen in FIG. 28C, a guidewire 87 may then be positioned in the passageway through the vertebral segment 80. As seen in FIG. 28D, a catheter 88 in accordance with the present invention, having a balloon element 89, may then be positioned along guidewire 87 such that a middle portion of balloon element 89 is in interior region 82. Balloon element 89 is shown longer than the entire passageway through vertebral segment 80. As a result, when balloon element 89 is in place, a proximal-end portion of balloon element 89 extends completely through cannula element 73 in left pedicle portion 84 and a distal-end portion of balloon element 89 extends completely through cannula element 74 in right pedicle portion 86. In a variation of this embodiment, balloon element 89 may be fabricated so as to be pre-curved for easier placement and better fit when inflated inside the U-shaped channel.

Figure 28E:
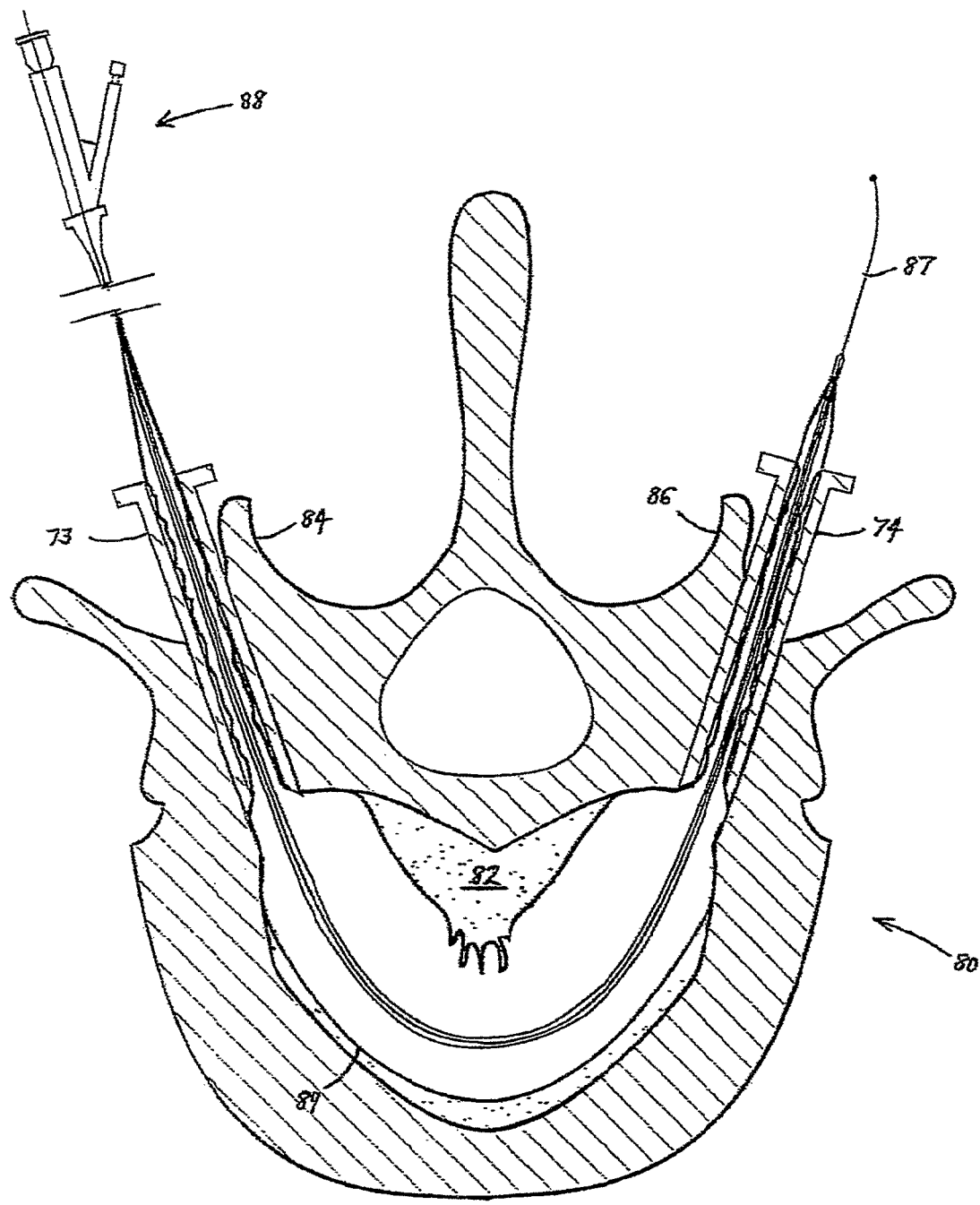

As seen in FIG. 28E, upon inflation of balloon element 89, only the middle portion inside interior region 82 can fully expand. As seen in FIG. 29, while balloon element 89 is in place and inflated, the proximal and distal ends of balloon element 89 are outside vertebral segment 80 and therefore accessible to the surgeon's hands 81 or to instruments.

FIG. 30 schematically illustrates a cross section of a vertebral segment 160 being treated with a catheter apparatus 162 which utilizes a pre-curved internal guidewire 163 but without a spring tensioning element according to another embodiment of the present invention. The pre-curved guidewire 163, fabricated for example from nitinol or other material having "memory" properties, assists in properly positioning the balloon element 169 in the preformed channel through the cancellous bone.

In one variation of this invention embodiment, balloon element 169 may be fabricated as a relatively thinner, more flexible balloon which can be fully inflated at relatively lower pressures inside vertebral segment 160. A more flexible balloon will have more uniform contact with the surrounding cancellous bone resulting in more surface area for expansion during inflation and the application of inflation forces at the interior locations where such forces are needed for expanding the bone mass.

In another variation of this invention embodiment, following a balloon inflation cycle, balloon element 169 can be deflated and guidewire 163 can be utilized similar to the push rods previously described for applying tension to the deflated balloon element to assist with removal through the small-diameter cannula 165. If the balloon element 169 is of a thinner, more flexible construction than those previously described, less tensioning is required for removal. In addition, in the embodiment illustrated in FIG. 30, external tensioning can be applied to the distal end of the catheter, for example by simply pulling on the distal end, to assist in reducing the profile of the deflated balloon element for easier withdrawal. Alternatively or additionally, tensioning could be applied to the distal end of the catheter by twisting it.

In still another variation in accordance with this invention, balloon element 169 could be left in place in the interior of vertebral segment 160, and the cavity inside the balloon could be inflated and filled with cement for permanent support of the damaged vertebral element. During this procedure the push rod, if hollow, could be used as a vent tube that is removed after the balloon is filled with cement. The balloon walls would contain the liquid cement during the setting period thereby preventing leakage through bone fractures causing medical problems. Even after the cement is set, the balloon walls would prevent direct contact between the cement and the surrounding bone or tissue. For this embodiment, the long proximal neck of the balloon would be cut off after filling the balloon with cement and after removing the cannula.

FIG. 31 schematically illustrates a pre-curved balloon element specially designed for use with a catheter apparatus according to this invention.

FIG. 32 schematically illustrates a cross section of a vertebral segment 170 being treated with a catheter apparatus 172 utilizing a pre-curved guidewire 173 according to another embodiment of the present invention.

FIG. 33 schematically illustrates a cross section of a vertebral segment 180 being treated with two catheter apparatuses 182 and 192 according to another embodiment of the present invention.

In still another embodiment of this invention, the catheter balloon element for expanding a damaged bone region may be a multi-lumen balloon as described in U.S. Pat. Nos. 5,342,301 and 5,569,195, which patents are incorporated herein by reference. Use of a multi-lumen balloon can be of particular value where even using the spring tension or manual wrapping techniques described above will not allow production of a desired size and/or pressure balloon because the balloon profile is simply too large to fit in the cannula.

Instead, by using a multi-lumen balloon, one can achieve both large diameters and higher pressures because each individual balloon can hold higher pressures with thinner walls. Even more important is that the cone or transition regions of the multi-lumen balloons are much thinner and much more flexible. For example, one could utilize a balloon element comprising four balloons/lumens with or without a central lumen for the shaft. Alternatively, with a 5-lumen multi-lumen balloon configuration, the shaft can pass through the central fifth lumen created by the four outside lumens or the shaft can pass through one of the four outside lumens.

As an alternative to a true multi-lumen catheter balloon construction, this embodiment of the invention could be practiced with many of the benefits of a multi-lumen balloon using several individual balloons in a side-by-side multiple balloon configuration. The individual balloons could be bonded together or, preferably, one could put an elastomeric or non-elastomeric sleeve over the group of individual balloons to keep them aligned during placement at the intended site, inflation and removal after the inflation cycle.

The multi-lumen and multiple balloon embodiments of this invention as described above may be practiced with straight balloons or with pre-curved balloons configured for easier placement and better fit inside a curved catheter access channel.

FIGS. 34A-34C illustrate yet another embodiment of the present invention. FIG. 34A is a schematic elevation view of a balloon dilatation apparatus 610 in some respects comparable to the balloon dilatation apparatus 210 of FIG. 10A. As best seen in the sectional view of FIG. 34B, this embodiment of the invention utilizes a stationary inner shaft or rod element 634 secured at its distal end to the tip 628 of inflation or balloon element 616 and a rotatable outer shaft 614. Rod element 634 runs through a central longitudinal channel in the catheter to the tip 628 of balloon element 616. Outer shaft 614 is connected at its distal end to inflation or balloon element 616 and at its proximal end to a rotatable sleeve element 612, which may advantageously include outward projections 615 to assist with manual rotation of the sleeve element and the connected outer shaft 614.

The proximal end of sleeve element 612 is designed with a lip portion 613 to receive and rotatably hold the distal end of a catheter inlet conduit 624 through which a fluid 640 can be introduced to inflate the balloon element 616. A gasket, seal, or O-ring 629, or a similar fluid-sealing element, having a centrally-located aperture, is seated between the end of conduit 624 and the lip portion 613 of sleeve element 612.

This embodiment of the present invention is especially useful in duct dilatation applications, for example in treating the lacrimal duct. In such applications, the inflation or balloon element 616 of apparatus 610 is positioned inside a duct that requires dilatation, for example to improve fluid drainage. Prior to insertion into the duct, the balloon element 616 can be tightly wrapped around the rod element 634 to reduce its profile and to facilitate insertion with minimal tissue damage or trauma. Once properly positioned, the balloon can be unwrapped by rotating sleeve element 612, for example using projections 615, either clockwise or counterclockwise as appropriate.

After it is positioned and unwrapped, balloon element 616 can be inflated with fluid 640 supplied from a pressurized fluid source through the hollow central channel running from the proximal end of inlet conduit 624 to the interior of the balloon element 616. The balloon element may be inflated to a desired size and/or a desired inflation pressure, depending on the elastic or inelastic nature of the balloon material, maintained fully inflated for a desired length of time, such as one to ten minutes, and then deflated by disconnecting the fluid source and/or withdrawing the fluid, for example by applying a vacuum. This inflation cycle may be repeated two or more times as appropriate for treating the duct dysfunction.

Following this medical procedure, the balloon or dilatation element is deflated and sleeve element 612 is again rotated either clockwise or counterclockwise in order to rewrap the deflated balloon element 616 tightly around rod element 634 to reduce its profile for removal from the duct. Projections 615 can be especially useful during this step to put additional twisting (rotational) forces on the deflated balloon element to obtain a tight wrap. Projections 615 can be held manually to maintain a tight wrap of the deflated balloon element or they can be used to secure this wrapped position such as with an elastic or other holding element. The rewrapped balloon element can then be relatively easily withdrawn from the duct with little or no trauma to surrounding tissue.

FIGS. 35A to 35E illustrate various aspects of another embodiment of a catheter/expandable element assembly 10X according to this invention. The assembly of FIGS. 35A to 35E is specially designed and adapted, as explained below, to fit through the interior of a very narrow gauge (e.g., an 11-gauge) medical cannula without the use or presence of any lubricants.

The assembly 10X of FIG. 35A comprises a single lumen catheter shaft 12X of suitable dimensions typically fabricated from a thermoplastic material using conventional fabrication techniques, as are well-known in this art. The catheter shaft 12X would be of a suitable length (or would be trimmed to a suitable length) to extend from a location outside a human body to the site of a bone or other body part to be treated. The catheter shaft 12X would ordinarily have a generally uniform wall thickness of suitable dimensions to insure structural integrity, while leaving the maximum possible open cross-sectional interior region to accommodate a mandrel element (as described hereinafter) and for flowing an inflation fluid to and from the expandable element that is bonded to the distal end of the catheter shaft. Catheter shaft 12X is a "conforming" catheter shaft, which is defined herein as a shaft fabricated to meet all existing relevant medical standards in this field.

At the same time, the outer diameter (O.D.) of catheter shaft 12X must be approximately equal to or preferably at least slightly smaller than the inside diameter (I.D.) of the narrow gauge cannula through which apparatus 10X needs to pass. For a standard 11-gauge (11G) cannula, the I.D. is 0.094 inches with a tolerance of ±0.002 inches, meaning that the O.D. of catheter 12X should not be greater than 0.092 inches for use in an 11G system. In a specific embodiment of the present invention, for example, the outer diameter of the catheter shaft is 0.080 inches, the outer diameter of the proximal neck portion of the expandable element is about 0.085 inches (so that the outer diameter at the butt-joined juncture between the distal end of the catheter shaft and the proximal neck portion of the expandable element is also about 0.085 inches), and the diameter of the conforming balloon (when folded) is about 0.087 to 0.089 inches. Thus, this assembly according to this invention would pass through the interior of a standard 11G cannula (with a minimum inside diameter of 0.092 inches) even without the use of any lubricant. No existing catheter assembly for these applications has or can achieve these small diameter sizes.

FIG. 35A additionally shows a conforming expandable element 14X (shown in an inflated state) at the distal end of the assembly 10X and a bifurcation apparatus 40X at the proximal end of the assembly 10X. These features are described in greater detail below with reference to FIGS. 35B, 35C, 35D and 35E.

FIG. 35B is an exploded sectional view of the expandable element 14X (in an inflated state) at the distal end of the assembly 10X in FIG. 35A. As seen in FIG. 35B, expandable element 14X comprises an inflatable balloon portion 16X having a proximal balloon neck portion 18X and a distal balloon neck portion 20X. A mandrel 22X extends from the proximal end of assembly 10X (FIG. 35A), through the catheter shaft 12X, and through expandable element 14X to the interior distal end of the distal balloon neck portion 20X. In a preferred invention embodiment, the distal end of mandrel 22X is bonded to the interior distal end of the distal balloon neck portion 20X.

The inflatable balloon portion 16X of expandable element 14X is a conforming full-sized balloon made of a suitable elastomeric material according to current medical protocols in this field, and the balloon 16X has a wall thickness and design that also satisfies all current medical protocols in this field. For purposes of this invention, such balloons will be referred to herein as "conforming balloons." Although the balloon 16X as seen in FIGS. 35A and 35B is shown in an inflated state for illustration purposes, it will be understood by those skilled in this art that the balloon 16X would be deflated and folded or wrapped to realize a smaller cross-sectional profile for insertion into and withdrawal from a bone or body treatment site through a cannula.

In a preferred invention embodiment, the proximal neck portion 18X of the expandable element 14X is "butt-jointed" to the distal end of the catheter shaft 12X at a juncture location 24X with a suitable adhesive, or by solvent bonding, or by thermal bonding or any other bonding procedure. As discussed earlier, this is a structural and fabrication innovation that in part distinguishes the catheter/expandable element assembly of this invention from prior art apparatus intended for similar applications. As a result of this butt jointed bond between the catheter shaft 12X and proximal neck 18X of expandable element 14X, the outer diameter of assembly 10X at juncture 24X is substantially identical to the O.D. of catheter shaft 12X at its distal end, which is also substantially identical to the O.D. of proximal neck portion 18X of expandable element 14X. This structure facilitates maximizing the O.D. and I.D. of catheter shaft 12X, which is advantageous, while maintaining the minimum possible cross-sectional profile at every location (including at juncture 24X) along assembly 10X that needs to fit through the interior of, for example, an 11G or other narrow gauge cannula.

As seen in FIG. 35B, the I.D. of catheter shaft 12X at juncture 24X, the I.D. of proximal neck portion 18X at juncture 24X, and the O.D. of mandrel 22X need to be sized such that a fluid connection 26X exists between the interior of catheter shaft 12X and the interior of expandable element 14X at juncture 24X so that an inflation fluid can be introduced to, and subsequently removed from, balloon 16X when the balloon is properly positioned in the bone or body location that is being treated.

In alternative invention embodiments, the mandrel 22X may or may not be bonded at its distal end to the expandable element 14X. In one embodiment, the distal end of mandrel 22X can be directly bonded with a suitable adhesive or bonding material to the inside of distal neck portion 20X of element 14X. As shown in FIGS. 35B and 35E, however, in a preferred invention embodiment a mandrel bonding spring element 28X of a suitable size is bonded at a spring proximal end to the distal end of mandrel 22X and the distal end of the spring is bonded to neck portion 20X. The mandrel bonding spring element is one preferred approach to more securely bonding the distal end of mandrel 22X to the inside of distal neck portion 20X of expandable element 14X.

In this embodiment, which is best seen in FIG. 35E, mandrel bonding spring element 28X may have spring coils of an inner diameter sized to fit around the distal end of mandrel 22X. As better seen in FIG. 35E, mandrel 22X can be formed to have a reduced diameter at its distal end 23X so as to accommodate spring 28X while the outer diameter of the spring coils can be substantially the same as the outer diameter of the more proximal portion 25X of mandrel 22X. Mandrel bonding spring element 28X can be positioned such that a proximal portion of spring 28X (e.g., a spring portion about 1 mm long) surrounds the distal end 23X of mandrel 22X and a distal portion of spring 28X (e.g., a spring portion about 1 mm long) extends beyond the end of mandrel 22X into the interior of neck portion 20X (FIG. 35B). The spring 28X can then be securely bonded (e.g., by an adhesive, by welding, by soldering, etc.) to both the end of mandrel 22X and to the interior of neck portion 20X. For example, the spring 28X can be impregnated with 75 D polyurethane on its interior and exterior to enable it to bond securely to the mandrel and the inside of neck portion 20X. The impregnated polyurethane holds the mandrel's distal end in place in the balloon bond even if the distal balloon bond should fail and rupture.

As shown in the invention embodiment of FIG. 35B, there are no radiopaque markings inside balloon 16X. This is another important distinction between some embodiments of the catheter/expandable element assembly of this invention and prior art apparatus. As discussed above, the conventional practice of placing one or more radiopaque markings inside balloon 16X has been found (in at least some instances) to impair the ability to wrap or fold a conforming balloon as tightly as needed to reduce its profile sufficiently to pass through the interior of an 11-gauge cannula. Instead, assembly 10X as seen in FIGS. 35A and 35B includes a radiopaque material at the sealed distal tip 30X of expandable element 14X for purposes of assisting a physician in properly positioning the balloon 16X at a treatment site. For example, the polyurethane seal that comprises distal tip 30X may contain a radiopaque material such as tungsten.

In some embodiments of this invention, however, it has been found possible to place one or two very thin radiopaque bands (e.g., a 0.003 inch thick platinum marker band) under the balloon and still wrap or fold it tightly enough to fit through a standard 11-gauge cannula. Thus, in alternative invention embodiments, radiopaque markings may be limited to the distal tip of the expandable element 14X as shown in FIG. 35B, or there may be a radiopaque band near the proximal end of the balloon portion 16X with or without a radiopaque element at the tip (not shown in the drawings), or there may be radiopaque bands under each of the proximal and distal ends of the balloon portion 16X, again either with or without a radiopaque element at the tip (not shown in the drawings).

FIGS. 35C and 35D illustrate in greater detail the features of the proximal end of assembly 10X as seen in FIG. 35A. FIG. 35C shows a first form of a catheter bifurcation assembly 40X that is specially adapted for the preferred "floating" mandrel embodiment of the present invention. As seen in FIG. 35C, the catheter bifurcation assembly 40X consists of an inflation fluid side arm 42X and a mandrel retention arm 44X which is substantially in axial alignment with the catheter shaft. The catheter bifurcation assembly 40X is bonded or otherwise connected to the catheter shaft along juncture 46X. The inflation fluid arm 42X functions in a conventional manner and is used to add or withdraw inflation fluid from the device for alternatively inflating or deflating the balloon.

The mandrel retention arm 44X, however, is designed and operates differently than the second arm of conventional catheter bifurcation assemblies. In contrast to catheter assemblies where the mandrel is fully axially moveable along the catheter axis (toward or away from the distal end) and, in fact, can be completely withdrawn from the proximal end of the mandrel arm, mandrel 22X of the present invention is only capable of restricted axial movement and is maintained inside arm 44X and catheter shaft 12X during normal operation of the device.

An embodiment of the "floating" mandrel feature of this invention is illustrated in FIG. 35C. The proximal end of mandrel retention arm 44X is sealed by means of a male cap 48X which may, for example, be internally threaded to mate with external threads at the proximal end of arm 44X. Male cap 48X has a centrally-located recess portion 50X extending from the proximal end exterior of the cap into the interior of arm 44X. At the distal end of recess 50X, an aperture 52X sized to just accommodate mandrel 22X extends through the wall portion of male cap 48X at the distal end of recess 50X into the interior of arm 44X. The open proximal end of recess 50X is sealed by suitable means, such as a plug 56X, after the mandrel 22X has been inserted. The length of recess 50X will define the allowable axial movement of mandrel 22X.

The proximal end of mandrel 22X comprises a geometric feature that is larger than aperture 52X, for example a ball end 54X, but which is smaller than the inside diameter of recess 50X such that the proximal end of mandrel 22X can slide in recess 50X but cannot slide through aperture 52X. Thus, in this configuration of elements, recess 50X of male cap 48X forms a sleeve of a limited length in which mandrel 22X can slide without exiting from arm 44X.

In a preferred design feature of this invention embodiment, as seen in FIG. 35C, the wall defining the interior of the proximal end of arm 44X has a slight inward taper in the distal direction, and, correspondingly, the wall defining the outside and the inside of recess 50X has a similar inward taper. This configuration facilitates obtaining a tight seal between the male cap 48X and the interior of arm 44X under the pressurized conditions that exist during a balloon inflation procedure. In another preferred design feature of this invention embodiment, as shown in FIG. 35C, the open proximal end of recess 50X is sealed (after inserting mandrel 22X) by means of a dome-ended tubular sealing member or plug 56X sized to fit securely inside recess 50X. Such a tubular sealing member 56X can be retained in place by compression fitting (utilizing the inward taper of recess 50X), or by bonding, or by other suitable means.

FIG. 35D is generally comparable to FIG. 35C, except that FIG. 35D uses a modified design for the combination of cap 48X/plug 56X of FIG. 35C. As seen in FIG. 35D, capping element 57X replaces plug 56X. Capping element 57X does not extend into the recess 50X. Capping element 57X may be formed separate from cap 48X and it may lock or screw into place or otherwise mate with cap 48X.

FIGS. 36A and 36B illustrate alternative invention embodiments of mandrel 22X. As in the embodiment of FIGS. 35A to 35E, at its distal end mandrel 22X is bonded to a mandrel bonding spring element 28X to assist in more securely fixing the distal end of the mandrel to the distal neck 20X of expandable element 14X (FIG. 35B). In FIG. 36A, the proximal end of mandrel 22X is a ball-shaped feature 54X that is larger than the diameter of mandrel 22X (as seen in FIGS. 35C and 35D). In FIG. 36B however, in place of the ball element 54X of FIG. 36A, the geometric feature that prevents the proximal end of mandrel 22X from passing through aperture 52X (FIGS. 35C and 35D) is a hook-shaped end 61X. Other types of geometric features could similarly be substituted for ball element 54X or hook element 61X.

FIG. 37 illustrates a narrow gauge (e.g., an 11G) medical cannula system 70X suitable for use in the medical device systems of this invention. FIG. 37 shows a view in which the expandable element 14X (shown in a wrapped or folded state) of catheter assembly 10X has completely passed through the interior of cannula 71X. FIG. 38 is an expanded, partially cutaway view of the cannula 71X as seen in FIG. 37 with an expandable element 14X (again shown in a wrapped or folded state) having a distal tip 20X and the associated catheter shaft 12X located inside cannula 71X. System 70X includes narrow gauge cannula 71X, which may be an 11-gauge cannula, having a standardized I.D. of 0.094 inches±0.002 inches in combination with catheter assembly 10X, as previously described. System 70X may also advantageously include a handle element 7X to assist a physician in maneuvering the device. Cannula 71X has been specially adapted for use in this invention by not applying any lubricant to the interior wall 72X of cannula 71X. Similarly, as seen in FIG. 38, no lubricant has been applied to the exterior of expandable element 14X. As discussed above, the specialized design and fabrication features of this invention (which reduce the cross-sectional profile of the catheter/expandable element assemblies of this invention), enable the catheter shaft 12X and expandable element 14X of catheter assembly 10X to fit through the interior of cannula 71X without the use of any lubricants or similar substances.

Table 1 below presents comparative size data for three differently sized medical cannulas: a standard 8-gauge (8G) cannula; a thin-walled 10-gauge (10G) cannula; and a standard 11-gauge (11G) cannula. As previously discussed, the standard 8G and thin-walled 10G cannulas have been used for bone treatment procedures. Prior to the present invention, however, size constraints have essentially made it impossible to utilize 11G cannulas for the type of bone treatment procedures that require positioning an expandable element inside a bone structure. The data in Tables 1 and 2 below help to illustrate how size constraints have impeded use of standard 11G cannulas in this type of bone treatment procedure prior to the innovations of this invention.

TABLE 1

| Cannula Size Gauge # | Inner Diameter (ID) inches | Cross-sectional Area of cannula opening sq. inches | Outer Diameter (OD) inches | Cross-sectional Area of body aperture needed to accommodate the cannula sq. inches |
| --- | --- | --- | --- | --- |
| Standard 8G (Prior Art) | 0.135 | 0.014314 | 0.165 | 0.021383 |
| Thin-walled 10G | 0.114 | 0.010207 | 0.134 | 0.014103 |

TABLE 1-continued

| Cannula Size Gauge # | Inner Diameter (ID) inches | Cross-sectional Area of cannula opening sq. inches | Outer Diameter (OD) inches | Cross-sectional Area of body aperture needed to accommodate the cannula sq. inches |
|---|---|---|---|---|
| (Prior Art) 11G (Present Invention) | 0.094 | 0.006940 | 0.120 | 0.011310 |

For "standard" cannulas, the gauge number assures a standardized inner diameter (ID) within very narrow tolerances and a standardized wall thickness for required structural integrity. For example, for a standard 11G cannula, the ID is set at 0.094 inches±0.002 inches. This assures that the ID of a standard 11G cannula will fall between 0.092 and 0.096 inches. The corresponding OD for a standard gauge cannula is established by adding to the standardized ID the necessary cannula wall thickness required for structural integrity.

Table 1 illustrates for example that the cross-sectional area of the cannula opening for a standard 11G cannula is only about 68% as large as the cross-sectional area of the cannula opening for a thin-walled 10G cannula, which correspondingly requires a much smaller diameter catheter/expandable element assembly in order to fit through that smaller cannula opening. But, there is also a corresponding reduction in the outer diameter (OD) of the 11G cannula. Therefore, the 11G cannula can be placed in a much smaller-sized opening in a patient's skin and bone (e.g., in an opening made with an 11-gauge needle) that has a cross-sectional area that is 20% smaller than the cross-sectional area of the opening needed to accommodate the larger 10G cannula. This means that a 20% smaller hole (based on area) needs to be made in a patient's bone structure; 20% less bone/tissue needs to be removed or displaced (which means less patient trauma); and, there is a greatly reduced chance of fracturing a delicate bone structure like a vertebral segment.

Table 2 below presents comparative size data for the folded balloon elements associated with catheter/expandable element assemblies intended for use with three differently sized medical cannulas: a standard 8G cannula; a thin-walled 10G cannula; and a standard 11G cannula.

TABLE 2

| Folded Balloon Size for Corresponding Gauge # | Cross-sectional Area of Folded Balloon (sq. inches) | Cross-sectional Area of cannula opening (sq. inches) |
|---|---|---|
| Standard 8G (Prior Art) | 0.01458 | 0.014314 |
| Thin-walled 10G (Prior Art) | 0.008012 | 0.010207 |
| 11G (Present Invention) | 0.006225 (average of low of 0.005945 sq. in. and high of 0.006504 sq. in.) | 0.006940 (0.094 ID) 0.006648 (0.092 ID) |

Table 2 shows the measured cross-sectional areas of three folded balloon elements compared with the cross-sectional areas of the cannula openings for the associated cannulas. Each of the three balloon elements has the same wall thickness as mandated by existing medical protocols in this field. Table 2 illustrates that an 11G cannula has an opening that can clearly accommodate the folded balloon of an expandable element/catheter assembly according to this invention, but not the folded balloon of current 10G systems.

In particular, Table 2 shows that balloon elements fabricated according to the present invention can be folded to a size that is about 52% smaller in cross-sectional area than the comparable measurement for a balloon used for a conventional 8G device (i.e., the folded balloon elements of this invention will fit through a cannula interior having a cross-sectional area that is about 52% smaller than the balloons used for an 8G device). Table 2 further shows that balloon elements according to the present invention can be folded to a size that is about 22% smaller in cross-sectional area than the comparable measurement for a balloon used for a conventional 10G device (i.e., the folded balloon elements of this invention will fit through a cannula interior having a cross-sectional area that is about 22% smaller than the balloon used for a 10G device).

The criticality of these size differences becomes even more apparent when comparing the data of Tables 1 and 2. Neither of the 8G or the 10G folded balloons would be expected to fit through the interior of a standard 11G cannula because the cross-sectional areas of these folded balloons is greater than the cross-sectional area of the cannula opening for an 11G cannula. On the other hand, a folded balloon element and catheter assembly in accordance with this invention (having an average diameter of about 0.089 inches and a cross-sectional area of about 0.006225 sq. in.) would fit through the interior of an 11G cannula, even at the lower I.D. tolerance limit of 0.092 inches (a cannula opening of 0.006648 sq. in.).

Other advantageous embodiments of this invention will now be described with reference to FIGS. 39-42B. In some invention embodiments, it may be desirable to provide for added flexibility, or to provide for active deflectability, along the distal portion of the catheter/expandable element assembly, particularly the mandrel. The distal portion of the mandrel in this context refers to at least the portion of the mandrel that is located inside the expandable element of the catheter assembly. The distal portion of the mandrel as used in connection with the embodiments of FIGS. 39-42B may more broadly refer to a portion of the mandrel that begins inside the catheter shaft and extends through the proximal neck portion of the expandable element, through the balloon, to the distal neck portion of the expandable element. In some of these embodiments, a combination of a proximally located tube or rod element in conjunction with a distally located flexibility and/or deflection spring element are provided inside the catheter shaft to add the desired flexibility/deflectability functionality.

FIG. 39 illustrates a modified mandrel configuration that provides added flexibility at the distal end of the catheter/expandable element assembly. Expandable element 14X is shown in an inflated state. A proximal portion 82X of the mandrel is of normal size in FIG. 39, while a distal portion 83X of the mandrel, beginning inside catheter shaft 12X and extending through expandable element 14X, is of a reduced diameter. The reduced diameter of mandrel section 83X provides additional flexibility that can facilitate maneuvering the expandable element 14X. In other respects, however, the embodiment of FIG. 39 is comparable to that shown in FIG. 35B.

FIGS. 40A to 40D and 41A to 41C illustrate invention embodiments that provide for active deflection of the distal end of the mandrel and of the distal end of the expandable element to which the distal end of the mandrel is bonded. Such active deflection can provide additional maneuverability that can facilitate optimizing placement of the expandable element for a treatment procedure.

FIG. 40A is an exploded, schematic sectional view of the distal end of a catheter/expandable element assembly showing a balloon element 16X, a proximal neck portion 18X and a distal neck portion 20X (as in FIG. 35B). In FIG. 40A, however, the distal end of mandrel 63X tapers to a taper point 64X, and the portion 65X of the mandrel that is distal of taper point 64X is flattened (as better seen in FIG. 41C), ending in a curved or hooked end 66X. As also seen in FIG. 40A, at a distal end of the assembly, a deflectability spring 61X surrounds mandrel 63X (inside the catheter shaft) and extends into the distal tip of the assembly where it is bonded (comparable to the configuration seen in FIG. 35B). In this respect, deflectability spring 61X serves a function comparable to mandrel bonding spring 28X in FIG. 35B.

As also seen in FIG. 40A, the hooked end 66X of mandrel 63X engages one or more coils of deflectability spring 61X near, but proximal of, the point where spring 61X is bonded to distal tip 20X. Because of this feature, applying axial tensioning to the proximal end of mandrel 63X in a proximal direction results in actively deflecting the distal end of the mandrel (as seen in FIG. 41A) with the result of also deflecting the distal end of the expandable element.

In a preferred embodiment, the entire length of spring 61X is enveloped in a protective sheath, such as a polymer coating 62X (best seen in FIG. 40D). Also in a preferred embodiment, a distal portion of spring 61X, for example a spring portion distal of the taper point 64X, comprises coils having a spaced relationship (as better seen in FIG. 40C) relative to the more closely spaced coils along a proximal portion of spring 61X. The greater spacing of spring coils along a more distal part of the spring adds greater flexibility/deflectability to the distal end of the assembly and also facilitates hooking the hooked end 66X of the mandrel between the coils.

FIG. 40B is an exploded, schematic sectional view of the proximal end of a catheter/expandable element assembly corresponding to the actively deflectable assembly tip embodiment of FIG. 40A. FIG. 40B is comparable to the configuration seen in FIGS. 35C and 35D showing a bifurcation assembly comprising an inflation arm 42X and a mandrel arm 44X with a male cap 48X. FIG. 40B, however, shows a mandrel tensioning assembly 90X mounted proximally of the end of mandrel arm 44X. Mandrel tensioning assembly 90X comprises two threadably-engaged tensioning elements—a cap extension element 91X and a mandrel pull screw 92X.

As better seen in the blow-up of FIG. 41B, proximal end 93X of the mandrel extends proximally through an axially aligned aperture in the cap 48X (see FIG. 40B), through an open channel in the center of the internally threaded cap extension 91X, and along the hollow center axis of pull screw 92X, and terminates in a geometrically enlarged feature, such as a ball end 94X, beyond the proximal end of pull screw 92X. As seen in FIGS. 40B and 41B, the proximal end of pull screw 9X2 may comprise a small central recess 97X to accommodate the enlarged proximal end of the mandrel. Pull screw 92X is sized and externally threaded to mate with internal threads in a recessed portion 95X of cap extension 91X. As a result of this configuration, rotating pull screw 92X in an appropriate clockwise or counterclockwise direction (illustrated by a rotation arrow in FIG. 40B) results in withdrawing pull screw 92X from the threaded interior 95X of cap extension 91X.

As pull screw 92X retracts from cap extension 91X in a proximal direction, it applies axial tensioning to the proximal end 93X of the mandrel and simultaneously to the distal end 63X (FIG. 40A) of the mandrel. The result of pulling the mandrel in a proximal direction by rotating pull screw 92X is to cause the hooked end 66X of the mandrel to deflect the end of the mandrel and of the spring 61X, as indicated by the dotted lines in FIG. 41A. As a consequence, the entire distal tip of the catheter/expanded element assembly is caused to deflect.

Rotating the pull screw 92X in an opposite direction (so as to advance pull screw 92X into the recessed internally-threaded section 95X of cap extension 91X) releases the axial tensioning of the mandrel and allows the deflected tip portion of the assembly to return (under action of spring 61X) to its pre-deflected axial alignment. Because the proximal end 93X of the mandrel is not attached to cap extension 91X or to pull screw 92X, but rather rests freely in the axial channel running through these elements, the mandrel is not rotated by rotation of pull screw 92X. At the same time, because the enlarged head 94X of the mandrel is larger than the diameter of the axial channel, the proximal end of the mandrel cannot be pulled into the interior of pull screw 92X.

FIG. 40C is an isolated, schematic sectional blow-up of the mandrel 63X and spring 61X inside the balloon 16X as shown in FIG. 40A. FIG. 40C provides a better illustration of the tapering mandrel, tapering to taper point 64X, and the hooked end 66X engaging the distal coils of spring 61X.

FIG. 40D is an isolated, schematic partial-sectional blow-up of the interior of the catheter shaft 12X at the point where a proximally-located tube or rod element 67X inside the catheter shaft forms a tube-spring juncture 69X with the distally-located deflection spring 61X. In a preferred embodiment, element 67X and spring 61X are housed in a polymeric sheath 62X that separates these elements from inflation fluid passing through the catheter shaft. The tube element 67X and spring 61X may be maintained in adjacent axial alignment at juncture 69X because both are encased in the polymeric sheath 62X, and also because of the axial tensioning caused by the hooked end 66X of the mandrel engaging the coils of spring 61X.

FIGS. 42A and 42B illustrate an alternative invention embodiment designed to improve the flexibility of the distal end of a catheter/expandable element assembly, but without the active deflectability of the embodiment shown in FIGS. 40A to 40D and FIGS. 41A to 41C. FIG. 43A is generally comparable to FIG. 40A, except in FIG. 42A there is no reason to have a coil separation in the spring coils along the distal portion of spring 61X, as was preferred in FIG. 40A. The preference for a coil separation in the embodiment of FIG. 40A was to better accommodate active deflectability of the tip, which is not a feature of the embodiment of FIG. 42A.

FIG. 42B shows the proximal end of an assembly corresponding to FIG. 42A. FIG. 42B is generally comparable to FIG. 40B, except the embodiment of FIGS. 42A and 42B does not require the mandrel tensioning mechanism 90X of FIG. 40B. Instead, FIG. 42B more closely resembles FIG. 35D, the main difference from FIG. 35D being in the configuration that includes the proximal end of the sheath-covered tube (see FIG. 40D) that forms a juncture with the distally-located spring 61X, as described more completely above with reference to FIGS. 40C and 40D.

It will be apparent to those skilled in the art that other changes and modifications may be made in the above-described systems, apparatus and methods without departing from the scope of the invention herein, and it is intended that all matter contained in the above description shall be interpreted in an illustrative and not a limiting sense.

The invention claimed is:

1. A catheter/expandable element assembly with proximal and distal assembly ends for medical applications comprising:
a single catheter shaft having a long axis and proximal and distal catheter portions;
an expandable element comprising a balloon portion suitable for treating vertebral fractures and related Kyphoplasty-type procedures with a balloon interior and also comprising a proximal neck portion butt-jointed and bonded at a bond juncture to the distal catheter portion wherein the balloon portion and the bond juncture can be passed through an 11-gauge or smaller diameter medical cannula before inflation of the balloon portion and after deflation of the balloon portion after a treatment procedure;
a fluid passageway extending from the proximal catheter portion to the balloon interior; and,
a mandrel element extending through the distal catheter portion and the expandable element wherein a distal mandrel portion beginning inside the catheter shaft and extending through the expandable element is of a reduced diameter relative to a proximal mandrel portion.

2. An assembly according to claim 1 further comprising a passive balloon tensioning and/or balloon wrapping device.

3. An assembly according to claim 1 further comprising an 11-gauge or smaller diameter cannula wherein at least one end of the balloon portion extends into or completely through said cannula when the balloon portion is positioned in a cavity to be dilated.

4. A catheter/expandable element assembly according to claim 1 additionally wherein the proximal neck portion is butt-jointed by a bonding procedure selected from the group consisting of an adhesive bonding procedure, a solvent bonding procedure and a thermal bonding procedure to the distal catheter portion.

5. A catheter/expandable element assembly according to claim 1 wherein the assembly has a maximum diameter of less than 0.092 inches at the bond juncture.

6. A catheter/expandable element assembly according to claim 1 wherein the fluid passageway has a generally circular cross-section with a fluid passageway diameter defined by an inner wall of the catheter shaft and wherein the fluid passageway diameter on either side of the bond juncture is substantially the same size as an inner diameter of the distal catheter portion at the bond juncture.

7. A catheter/expandable element assembly according to claim 1 wherein an outer diameter of the distal catheter portion and an outer diameter of the proximal neck portion at the bond juncture are substantially the same size so as to form a smooth, uninterrupted outer surface at the bond juncture.

8. A catheter/expandable element assembly according to claim 7 wherein an inner diameter of the distal catheter portion, a diameter of the fluid passageway, and an inner diameter of the proximal neck portion at the bond juncture are substantially the same size.

9. A catheter/expandable element assembly according to claim 1 wherein the only catheter shaft is a single lumen catheter.

10. A catheter/expandable element assembly according to claim 1 wherein an inner diameter of the distal catheter portion, a diameter of the fluid passageway, and an inner diameter of the proximal neck portion at the bond juncture are substantially the same size, and also wherein an outer diameter of the distal catheter portion and an outer diameter of the proximal neck portion at the bond juncture are substantially the same size so as to form a smooth, uninterrupted outer surface at the bond juncture.

11. A catheter/expandable element assembly according to claim 1 wherein the mandrel element is a floating mandrel that extends through the distal catheter portion and through the expandable element to a distal portion of the expandable element, wherein the floating mandrel comprises a distal mandrel end bonded to the expandable element and a free, unbonded proximal mandrel end.

12. An assembly according to claim 1 further comprising an active balloon tensioning and/or balloon wrapping device.

13. A system for carrying out a medical dilatation and/or a cavity creation, enlargement or treatment procedure at an internal body site comprising a catheter/expandable element assembly according to claim 1 in combination with an 11-gauge or smaller diameter cannula having a cannula interior for delivering the expandable element from outside the body, through the cannula interior, to the desired internal body site and, following a treatment procedure, for withdrawing the deflated expandable element from the body site through the cannula interior.

14. A system according to claim 13 wherein the cannula interior is free of any lubricant and also wherein no lubricant is applied to the catheter/expandable element assembly.

15. A method for carrying out a medical treatment that includes a dilatation and/or a cavity creation, enlargement or treatment procedure using a system according to claim 13, the method comprising the steps of: (A) positioning the cannula in a body location so that a distal end of the cannula is proximate to the intended treatment site; (B) inserting at least the expandable element portion of the assembly through the cannula interior to position the expandable element in the interior of a bone or body site without the use of any lubricants; (C) inflating the balloon portion of the expandable element inside the interior of the bone or body site to a size and/or inflation pressure and for a time sufficient to complete the treatment; (D) deflating the balloon portion of the expandable element; and, (E) withdrawing the expandable element including the deflated balloon portion of the assembly through the cannula interior without the use of any lubricants.

16. A method for carrying out a medical treatment that includes a dilatation and/or a cavity creation, enlargement or treatment procedure that is performed with an expandable conforming balloon using a catheter/expandable element assembly according to claim 1, the method comprising the steps of: (A) inserting at least the expandable element portion of the assembly through the interior of a previously-placed 11-gauge or smaller diameter cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and (D) withdrawing the expandable element including the deflated balloon portion of the assembly through the interior of the 11-gauge or smaller diameter cannula.

17. A method according to claim 16 additionally comprising a step of stretching, folding and/or wrapping the expandable element following step (B) and prior to step (D).

18. A catheter/expandable element assembly with proximal and distal assembly ends for medical applications comprising a catheter shaft having a long axis and proximal and distal catheter portions, an expandable element comprising a balloon suitable for treating vertebral fractures and related Kyphoplasty-type procedures with a balloon interior and also comprising a proximal neck portion butt-jointed at a bond juncture to the distal catheter portion, and a fluid passageway extending from the proximal catheter portion to the balloon interior, the assembly being characterized by:

(A) a balloon having the following properties:
  (i) the balloon has expansion properties that enable the expansion of the balloon inside a targeted bone region to press against and compress surrounding cancellous bone, or to move cortical bone to a prefracture or other desired condition, or both, prior to failure of the balloon wall, when the balloon is expanded to an elongation at least 50% greater than before expansion;
  (ii) the balloon has shape properties that enable the balloon to predictably deform during expansion to an expanded shape whereby a desired expanded shape inside the targeted bone region can be selected based on prior analysis of the morphology of the targeted bone region; and,
  (iii) the balloon has toughness properties that enable the balloon to resist surface abrasion, tearing and puncture when it is expanded and in contact with cancellous bone, including the properties of: a Taber Abrasion value of less than approximately 200 mg loss; and/or an Elmendorf Tear Strength of at least approximately 150 lb.-ft./in.; and/or a Shore Hardness of less than approximately 75 D; and, (B) the assembly also being characterized by one or more of the following features:
(a) the expandable element comprises a balloon which can be stretched, folded and/or wrapped to a maximum diameter of less than 0.092 inches before inflation of the balloon and after deflation of the balloon after a treatment procedure;
(b) the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure;
(c) the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure without the use of any lubricant or similar friction-reducing substance;
(d) the expandable element can be stretched, folded and/or wrapped to sufficiently reduce the cross-sectional profile of the assembly before inflation of the balloon and after deflation of the balloon after a treatment procedure to be compatible with the use of a narrow gauge cannula;
(e) the expandable element can be stretched, folded and/or wrapped to sufficiently reduce the cross-sectional profile of the assembly before inflation of the balloon and after deflation of the balloon after a treatment procedure to be compatible with the use of an 11-gauge or smaller-diameter cannula;
(f) the catheter shaft is a single lumen catheter shaft and the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure;
(g) the proximal neck portion is butt jointed to the distal end of the distal catheter portion by a bonding procedure selected from the group consisting of an adhesive bonding procedure, a solvent bonding procedure and a thermal bonding procedure;
(h) the expandable element comprises a distal neck portion having a sealed tip, and the sealed tip contains the only radiopaque marker along the expandable element;
(i) the expandable element comprises one or more bands of a radiopaque material under the balloon with or without radiopaque material at a distal tip of the expandable element;
(j) the assembly comprises a feature selected from features (a) to (g), and additionally comprises a floating mandrel element that extends through the distal catheter portion, and through the expandable element to an interior distal portion of the expandable element;
(k) the assembly comprises a feature selected from features (a) to (g), and additionally comprises a floating mandrel element that extends through the distal catheter portion, and through the expandable element to an interior distal portion of the expandable element and further wherein the mandrel element has a free, unbonded proximal mandrel end and a distal mandrel end bonded to an interior distal portion of the expandable element;
(l) the assembly comprises a feature selected from features (a) to (g), and additionally comprises a sleeve section of the distal catheter portion that accommodates limited axial movement of a mandrel inside the sleeve section and a free, unbonded proximal end of the mandrel is of an enlarged size such that the proximal end of the mandrel is retained in the sleeve section;
(m) the assembly comprises a feature selected from features (a) to (g), and additionally comprises a floating mandrel element that extends through the distal catheter portion, and through the expandable element to an interior distal portion of the expandable element, and further wherein a distal end of the mandrel is bonded to a distal portion of the expandable element and an unbonded proximal end of the mandrel has an enlarged geometrical feature that can move axially along or parallel to the axis of the catheter shaft but only within a sleeve section bounded by a mandrel retaining structure;
(n) the assembly comprises a feature selected from features (a) to (g), and additionally comprises a mandrel that extends through the distal catheter portion, and through the expandable element to an interior distal portion of the expandable element, wherein a distal portion of the mandrel beginning inside the catheter shaft and extending through the expandable element is of a reduced diameter relative to a proximal portion of the mandrel;
(o) the assembly additionally comprises a mandrel element that extends through the distal catheter portion, and into the expandable element, wherein at least a portion of the mandrel inside the expandable element tapers to a flattened distal mandrel end that terminates in an unbonded angled or hooked mandrel tip at a location proximate to the distal end of the balloon portion;
(p) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils;

(q) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein there is greater spacing between adjacent spring coils along a distal spring portion than along a proximal spring portion;

(r) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the spring is covered by a polymeric sleeve;

(s) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the mandrel can be axially tensioned to compress the spring where the hooked mandrel tip engages the spring coils causing the distal end of the expandable element to deflect from an axial orientation while the mandrel is axially tensioned; and, (t) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements whereby the threadably-engaged tensioning elements provide an axial channel in which one of the mandrel tensioning elements can slide such that rotating one tensioning element relative to the other causes one of the tensioning elements to move in a proximal direction relative to the second tensioning element thereby applying axial tensioning to the mandrel while the axial tensioning is applied.

19. An assembly according to claim 18 further including a mandrel element wherein active and/or passive forces can be applied to the mandrel element for tensioning and/or wrapping the balloon portion.

20. An assembly according to claim 19 wherein the distal end of the balloon portion is sealed, and the mandrel element extends to the sealed distal end of the balloon portion.

21. An assembly according to claim 19 wherein the mandrel element is not attached to the balloon portion.

22. An assembly according to claim 19 wherein the mandrel element is attached to or otherwise engages the balloon portion.

23. An assembly according to claim 19 further wherein rotational force can be applied manually or automatically to rotate the mandrel element causing the balloon portion at least in part to wrap around the mandrel element.

24. An assembly according to claim 19 wherein said mandrel element is positioned sufficiently in a distal direction to cause axial tensioning and elongation of the balloon portion.

25. An assembly according to claim 19 wherein said mandrel element is rotated sufficiently to cause wrapping and rotational tensioning of the balloon portion.

26. An assembly according to claim 19 wherein said mandrel element is positioned sufficiently in a distal direction and is rotated sufficiently to cause both axial and rotational tensioning of the balloon portion.

27. An assembly according to claim 19 wherein said mandrel element comprises a knob at the proximal end of the mandrel element.

28. An assembly according to claim 19 wherein the mandrel element is hydraulically or pneumatically actuated.

29. An assembly according to claim 19 wherein said mandrel element is adjustable in length.

30. A catheter/expandable element assembly according to claim 18 wherein the assembly comprises a mandrel element that has a distal mandrel portion beginning inside the catheter shaft and extending through the expandable element of a reduced diameter relative to a proximal mandrel portion and also wherein the balloon portion can be stretched, folded and/or wrapped to a maximum diameter of less than 0.092 inches before inflation of the balloon portion and after deflation of the balloon portion after a treatment procedure.

31. A catheter/expandable element assembly according to claim 30 additionally wherein the mandrel element has a free, unbonded proximal mandrel end and a distal mandrel end bonded to an interior distal portion of the expandable element.

32. A catheter/expandable element assembly according to claim 31 additionally wherein the fluid passageway has a generally circular cross-section with a fluid passageway diameter defined by an inner wall of the catheter shaft and wherein the fluid passageway diameter on either side of the bond juncture is substantially the same size as an inner diameter of the distal catheter portion at the bond juncture.

33. A catheter/expandable element assembly according to claim 31 additionally wherein an outer diameter of the distal catheter portion and an outer diameter of the proximal neck portion at the bond juncture are substantially the same size so as to form a smooth, uninterrupted outer surface at the bond juncture.

34. A catheter/expandable element assembly according to claim 33 additionally wherein an inner diameter of the distal catheter portion, a diameter of the fluid passageway, and an inner diameter of the proximal neck portion at the bond juncture are substantially the same size.

35. A catheter/expandable element assembly according to claim 34 additionally wherein the only catheter shaft is a single lumen catheter.

36. A catheter/expandable element assembly according to claim 30 additionally wherein the proximal neck portion is butt-jointed by a bonding procedure selected from the group consisting of an adhesive bonding procedure, a solvent bonding procedure and a thermal bonding procedure to the distal catheter portion.

37. A catheter/expandable element assembly according to claim 30 additionally wherein the fluid passageway has a generally circular cross-section with a fluid passageway diameter defined by an inner wall of the catheter shaft and wherein the fluid passageway diameter on either side of the bond juncture is substantially the same size as an inner diameter of the distal catheter portion at the bond juncture.

38. A catheter/expandable element assembly according to claim 30 additionally wherein an outer diameter of the distal catheter portion and an outer diameter of the proximal neck portion at the bond juncture are substantially the same size so as to form a smooth, uninterrupted outer surface at the bond juncture.

39. A catheter/expandable element assembly according to claim 38 additionally wherein an inner diameter of the distal catheter portion, a diameter of the fluid passageway, and an inner diameter of the proximal neck portion at the bond juncture are substantially the same size.

40. A catheter/expandable element assembly according to claim 39 additionally wherein the only catheter shaft is a single lumen catheter.

41. A system for carrying out a medical dilatation and/or a cavity creation, enlargement or treatment procedure at an internal body site comprising a catheter/expandable element assembly according to any combination of characterizing features of claim 18 in combination with a narrow gauge cannula having a cannula interior for delivering the expandable element from outside the body, through the cannula interior, to the desired internal body site and, following a treatment procedure, for withdrawing the deflated expandable element from the body site through the cannula interior.

42. A system according to claim 41 wherein the cannula interior is free of any lubricant and also wherein no lubricant is applied to the catheter/expandable element assembly.

43. A method for carrying out a medical treatment that includes a dilatation and/or a cavity creation, enlargement or treatment procedure using a system according to claim 41, the method comprising the steps of: (A) positioning the cannula in a body location so that a distal end of the cannula is proximate to the intended treatment site; (B) inserting at least the expandable element portion of the assembly through the cannula interior to position the expandable element in the interior of a bone or body site without the use of any lubricants; (C) inflating the balloon portion of the expandable element inside the interior of the bone or body site to a size and/or inflation pressure and for a time sufficient to complete the treatment; (D) deflating the balloon portion of the expandable element; and, (E) withdrawing the expandable element including the deflated balloon portion of the assembly through the cannula interior without the use of any lubricants.

44. A method for carrying out a medical treatment that includes a dilatation and/or a cavity creation, enlargement or treatment procedure that is performed with an expandable conforming balloon using a catheter/expandable element assembly according to any combination of characterizing features of claim 18, the method comprising the steps of: (A) inserting at least the expandable element portion of the assembly through the interior of a previously-placed narrow gauge cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and, (D) withdrawing the expandable element including the deflated balloon portion of the assembly through the interior of the narrow gauge cannula.

45. A method according to claim 44 additionally comprising a step of stretching, folding and/or wrapping the expandable element following step (B) and prior to step (D).

46. A system for carrying out a medical dilatation and/or a cavity creation, enlargement or treatment procedure at an internal body site comprising a catheter/expandable element assembly according to any combination of characterizing features of claim 18 in combination with an 11-gauge or smaller diameter cannula having a cannula interior for delivering the expandable element from outside the body, through the cannula interior, to the desired internal body site and, following a treatment procedure, for withdrawing the deflated expandable element from the body site through the cannula interior.

47. A method for carrying out a medical treatment that includes a dilatation and/or a cavity creation, enlargement or treatment procedure that is performed with an expandable balloon using a catheter/expandable element assembly according to any combination of characterizing features of claim 18, the method comprising the steps of: (A) inserting at least the expandable element portion of the assembly through the interior of a previously-placed 11-gauge or smaller diameter cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and (D) withdrawing the expandable element including the deflated balloon portion of the assembly through the interior of the 11-gauge or smaller diameter cannula.

48. A method for carrying out a medical treatment that includes a dilatation and/or a cavity creation, enlargement or treatment procedure that is performed with an expandable balloon using a catheter/expandable element assembly according to any combination of characterizing features of claim 18, the method comprising the steps of: (A) inserting at least the expandable element portion of the assembly through the interior of a previously-placed narrow gauge cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and, (D) withdrawing the expandable element including the deflated balloon portion of the assembly through the interior of the narrow gauge cannula.

49. A catheter/expandable element assembly with proximal and distal assembly ends for medical applications comprising a catheter shaft having a long axis and proximal and distal catheter portions, an expandable element comprising a balloon suitable for treating vertebral fractures and related Kyphoplasty-type procedures with a balloon interior and also comprising a proximal neck portion butt-jointed at a bond juncture to the distal catheter portion, and a fluid passageway extending from the proximal catheter portion to the balloon interior, the assembly being characterized by:
  (A) a balloon having the following properties:
    (i) the balloon has expansion properties that enable the expansion of the balloon inside a targeted bone region to press against and compress surrounding cancellous bone, or to move cortical bone to a prefracture or other desired condition, or both, prior to failure of the balloon wall, when the balloon is expanded to an elongation at least 50% greater than before expansion;
    (ii) the balloon has shape properties that enable the balloon to predictably deform during expansion to an expanded shape whereby a desired expanded shape inside the targeted bone region can be selected based on prior analysis of the morphology of the targeted bone region; and,
    (iii) the balloon has toughness properties that enable the balloon to resist surface abrasion, tearing and puncture when it is expanded and in contact with cancellous bone, including the properties of: a Taber Abrasion value of less than approximately 200 mg loss; and/or an Elmendorf Tear Strength of at least approximately 150 lb.-ft./in.; and/or a Shore Hardness of less than approximately 75 D;
  (B) a floating mandrel element that extends through the distal catheter portion and through the expandable element to an interior distal portion of the expandable element and further wherein the mandrel element has a free, unbonded proximal mandrel end and a distal mandrel end bonded to an interior distal portion of the expandable element and
  (C) the assembly also being characterized by one or more of the following features:
    (a) the expandable element comprises a balloon which can be stretched, folded and/or wrapped to a maximum diameter of less than 0.092 inches before inflation of the balloon and after deflation of the balloon after a treatment procedure;
    (b) the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure;
    (c) the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure without the use of any lubricant or similar friction-reducing substance;
    (d) the expandable element can be stretched, folded and/or wrapped to sufficiently reduce the cross-sectional profile of the assembly before inflation of the balloon and after deflation of the balloon after a treatment procedure to be compatible with the use of a narrow gauge cannula;
    (e) the expandable element can be stretched, folded and/or wrapped to sufficiently reduce the cross-sectional profile of the assembly before inflation of the balloon and after deflation of the balloon after a treatment procedure to be compatible with the use of an 11-gauge or smaller-diameter cannula;
    (f) the catheter shaft is a single lumen catheter shaft and the assembly includes both a stretched, folded and/or wrapped balloon and a bond juncture between the catheter shaft and the proximal neck portion that will fit through the interior of a standard 11-gauge medical cannula before inflation of the balloon and after deflation of the balloon after a treatment procedure;
    (g) the proximal neck portion is butt jointed to the distal end of the distal catheter portion by a bonding procedure selected from the group consisting of an adhesive bonding procedure, a solvent bonding procedure and a thermal bonding procedure;
    (h) the expandable element comprises a distal neck portion having a sealed tip, and the sealed tip contains the only radiopaque marker along the expandable element;
    (i) the expandable element comprises one or more bands of a radiopaque material under the balloon with or without radiopaque material at a distal tip of the expandable element;
    (j) the assembly comprises a feature selected from features (a) to (g), and additionally comprises a sleeve section of the distal catheter portion that accommodates limited axial movement of a mandrel inside the sleeve section and a free, unbonded proximal end of the mandrel is of an enlarged size such that the proximal end of the mandrel is retained in the sleeve section;
    (k) the assembly comprises a feature selected from features (a) to (g), and additionally comprises a floating mandrel element that extends through the distal catheter portion, and through the expandable element to an interior distal portion of the expandable element, and further wherein a distal end of the mandrel is bonded to a distal portion of the expandable element and an unbonded proximal end of the mandrel has an enlarged geometrical feature that can move axially along or parallel to the axis of the catheter shaft but only within a sleeve section bounded by a mandrel retaining structure;
    (l) the assembly comprises a feature selected from features (a) to (g), and additionally comprises a mandrel that extends through the distal catheter portion, and through the expandable element to an interior distal portion of the expandable element, wherein a distal portion of the mandrel beginning inside the catheter shaft and extending through the expandable element is of a reduced diameter relative to a proximal portion of the mandrel;

(m) the assembly additionally comprises a mandrel element that extends through the distal catheter portion, and into the expandable element, wherein at least a portion of the mandrel inside the expandable element tapers to a flattened distal mandrel end that terminates in an unbonded angled or hooked mandrel tip at a location proximate to the distal end of the balloon;

(n) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils;

(o) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein there is greater spacing between adjacent spring coils along a distal spring portion than along a proximal spring portion;

(p) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the spring is covered by a polymeric sleeve;

(q) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the mandrel can be axially tensioned to compress the spring where the hooked mandrel tip engages the spring coils causing the distal end of the expandable element to deflect from an axial orientation while the mandrel is axially tensioned; and, (r) the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements whereby the threadably-engaged tensioning elements provide an axial channel in which one of the mandrel tensioning elements can slide such that rotating one tensioning element relative to the other causes one of the tensioning elements to move in a proximal direction relative to the second tensioning element thereby applying axial tensioning to the mandrel while the axial tensioning is applied.

50. An assembly according to claim 49 wherein the assembly additionally comprises a mandrel element that extends through the distal catheter portion, and into the expandable element, wherein at least a portion of the mandrel inside the expandable element tapers to a flattened distal mandrel end that terminates in an unbonded angled or hooked mandrel tip at a location proximate to the distal end of the balloon.

51. An assembly according to claim 49 wherein the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils.

52. An assembly according to claim 49 wherein the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein there is greater spacing between adjacent spring coils along a distal spring portion than along a proximal spring portion.

53. An assembly according to claim 49 wherein the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the spring is covered by a polymeric sleeve.

54. An assembly according to claim 49 wherein the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also wherein the mandrel can be axially tensioned to compress the spring where the hooked mandrel tip engages the spring coils causing the distal end of the expandable element to deflect from an axial orientation while the mandrel is axially tensioned.

55. An assembly according to claim 49 wherein the assembly additionally comprises a mandrel element that extends through the distal portion of the catheter shaft, and into the expandable element, wherein at least a portion of the mandrel element inside the expandable element tapers to a flattened distal mandrel end that terminates in an unbonded angled or hooked mandrel tip at a location proximate to the distal end of the balloon, and additionally comprising an elongated spring element with spring coils that surround the mandrel element beginning at a location proximal of the expandable element and extending into the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements whereby the threadably-engaged tensioning elements provide an axial channel in which one of the mandrel tensioning elements can slide such that rotating one tensioning element relative to the other causes one of the tensioning elements to move in a proximal direction relative to the second tensioning element thereby applying axial tensioning to the mandrel while the axial tensioning is applied.

56. A system for carrying out a medical dilatation and/or a cavity creation, enlargement or treatment procedure at an internal body site comprising a catheter/expandable element assembly according to any combination of characterizing features of claim 49 in combination with an 11-gauge or smaller diameter cannula having a cannula interior for delivering the expandable element from outside the body, through the cannula interior, to the desired internal body site and, following a treatment procedure, for withdrawing the deflated expandable element from the body site through the cannula interior.

57. A method for carrying out a medical treatment that includes a dilatation and/or a cavity creation, enlargement or treatment procedure that is performed with an expandable balloon using a catheter/expandable element assembly according to any combination of characterizing features of claim 49, the method comprising the steps of: (A) inserting at least the expandable element portion of the assembly through the interior of a previously-placed 11-gauge or smaller diameter cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and (D) withdrawing the expandable element including the deflated balloon portion of the assembly through the interior of the 11-gauge or smaller diameter cannula.

58. A method for carrying out a medical treatment that includes a dilatation and/or a cavity creation, enlargement or treatment procedure that is performed with an expandable balloon using a catheter/expandable element assembly according to any combination of characterizing features of claim 49, the method comprising the steps of: (A) inserting at least the expandable element portion of the assembly through the interior of a previously-placed narrow gauge cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and, (D) withdrawing the expandable element including the deflated balloon portion of the assembly through the interior of the narrow gauge cannula.

59. A catheter/expandable element assembly with proximal and distal assembly ends for medical applications comprising:
 a catheter shaft having a long axis and proximal and distal catheter portions;
 an expandable element comprising a balloon portion suitable for treating vertebral fractures and related Kyphoplasty-type procedures with a balloon interior and also comprising a proximal neck portion bonded at a bond juncture to the terminal end of the distal catheter portion, wherein the balloon portion and the bond juncture can be passed through an 11-gauge or smaller diameter medical cannula before inflation of the balloon portion and after deflation of the balloon portion after a treatment procedure, and also wherein the distal catheter portion and the proximal neck portion are butt-jointed and bonded to each other at the bond juncture;

a fluid passageway extending from the proximal catheter portion through the distal catheter portion to the balloon interior; and, a floating mandrel that extends through the distal catheter portion and through the expandable element to a distal portion of the expandable element, wherein the floating mandrel comprises a distal mandrel portion beginning inside the catheter shaft and extending through the expandable element of a reduced diameter relative to a proximal mandrel portion, a distal end of the mandrel is bonded to the expandable element and a proximal end of the mandrel is a free, unbonded end, and the floating mandrel can move axially within a limited range of axial movement along or parallel to the long axis of the catheter shaft.

60. A system for carrying out a medical dilatation and/or a cavity creation, enlargement or treatment procedure at an internal body site comprising a catheter/expandable element assembly according to claim 59 in combination with an 11-gauge or smaller diameter cannula having a cannula interior for delivering the expandable element from outside the body, through the cannula interior, to the desired internal body site and, following a treatment procedure, for withdrawing the deflated expandable element from the body site through the cannula interior.

61. A method for carrying out a medical treatment that includes a dilatation and/or a cavity creation, enlargement or treatment procedure that is performed with an expandable balloon using a catheter/expandable element assembly according to claim 59, the method comprising the steps of: (A) inserting at least the expandable element portion of the assembly through the interior of a previously-placed 11-gauge or smaller diameter cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and (D) withdrawing the expandable element including the deflated balloon portion of the assembly through the interior of the 11-gauge or smaller diameter cannula.

62. A catheter/expandable element assembly with proximal and distal assembly ends for medical applications comprising:

a single catheter shaft having a long axis and proximal and distal catheter portions;

an expandable element comprising a balloon portion suitable for treating vertebral fractures and related Kyphoplasty-type procedures with a balloon interior and also comprising a proximal neck portion butt-jointed and bonded at a bond juncture to the distal catheter portion wherein the balloon portion and the bond juncture can be passed through an 11-gauge or smaller diameter medical cannula before inflation of the balloon portion and after deflation of the balloon portion after a treatment procedure;

a fluid passageway extending from the proximal catheter portion to the balloon interior; and, a mandrel element extending through the distal catheter portion and the expandable element wherein a distal mandrel portion beginning inside the catheter shaft and extending through the expandable element is of a reduced diameter relative to a proximal mandrel portion;

and further wherein an inner diameter of the distal catheter portion, a diameter of the fluid passageway, and an inner diameter of the proximal neck portion at the bond juncture are substantially the same size, and also wherein an outer diameter of the distal catheter portion and an outer diameter of the proximal neck portion at the bond juncture are substantially the same size so as to form a smooth, uninterrupted outer surface at the bond juncture.

63. A catheter/expandable element assembly with proximal and distal assembly ends for medical applications comprising:

a single catheter shaft having a long axis and proximal and distal catheter portions;

an expandable element comprising a balloon portion suitable for treating vertebral fractures and related Kyphoplasty-type procedures with a balloon interior and also comprising a proximal neck portion butt-jointed and bonded at a bond juncture to the distal catheter portion wherein the balloon portion and the bond juncture can be passed through an 11-gauge or smaller diameter medical cannula before inflation of the balloon portion and after deflation of the balloon portion after a treatment procedure;

a fluid passageway extending from the proximal catheter portion to the balloon interior; and, a mandrel element extending through the distal catheter portion and the expandable element wherein a distal mandrel portion beginning inside the catheter shaft and extending through the expandable element is of a reduced diameter relative to a proximal mandrel portion;

and further wherein the mandrel element is a floating mandrel that comprises a distal mandrel end bonded to the expandable element and a free, unbonded proximal mandrel end.

64. A method for carrying out a medical treatment that includes a dilatation and/or a cavity creation, enlargement or treatment procedure that is performed with an expandable balloon using a catheter/expandable element assembly according to claim 63, the method comprising the steps of: (A) inserting at least the expandable element portion of the assembly through the interior of a previously-placed narrow gauge cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and, (D) withdrawing the expandable element including the deflated balloon portion of the assembly through the interior of the narrow gauge cannula.

\* \* \* \* \*